US009056899B2

(12) United States Patent
Collins et al.

(10) Patent No.: US 9,056,899 B2
(45) Date of Patent: Jun. 16, 2015

(54) ENGINEERED BACTERIOPHAGES AS ADJUVANTS FOR ANTIMICROBIAL AGENTS AND COMPOSITIONS AND METHODS OF USE THEREOF

(75) Inventors: James J Collins, Newton Center, MA (US); Timothy Kuan-Ta Lu, Boston, MA (US)

(73) Assignees: Trustees of Boston University, Boston, MA (US); Massachusetts Institute of Technology, Cambridge, MA (US)

( * ) Notice: Subject to any disclaimer, the term of this patent is extended or adjusted under 35 U.S.C. 154(b) by 744 days.

(21) Appl. No.: 12/812,212

(22) PCT Filed: Jan. 12, 2009

(86) PCT No.: PCT/US2009/030755
§ 371 (c)(1),
(2), (4) Date: Aug. 31, 2010

(87) PCT Pub. No.: WO2009/108406
PCT Pub. Date: Sep. 3, 2009

(65) Prior Publication Data
US 2010/0322903 A1 Dec. 23, 2010

Related U.S. Application Data

(60) Provisional application No. 61/020,197, filed on Jan. 10, 2008.

(51) Int. Cl.
*A01N 63/00* (2006.01)
*C12N 7/01* (2006.01)
*C07K 14/005* (2006.01)
*A61K 35/76* (2015.01)
*C12N 15/113* (2010.01)

(52) U.S. Cl.
CPC .............. *C07K 14/005* (2013.01); *A61K 35/76* (2013.01); *C12N 15/113* (2013.01); *C12N 2320/32* (2013.01); *C12N 2330/30* (2013.01); *C12N 2795/14122* (2013.01); *C12N 2795/14132* (2013.01)

(58) Field of Classification Search
None
See application file for complete search history.

(56) References Cited

U.S. PATENT DOCUMENTS

| 4,559,078 A | 12/1985 | Maier |
| 4,677,217 A | 6/1987 | Maier |
| 4,678,750 A | 7/1987 | Vandenbergh et al. |
| 6,335,012 B1 | 1/2002 | Fischetti et al. |
| 6,699,701 B1 | 3/2004 | Sulakvelidze et al. |
| 2005/0004030 A1 | 1/2005 | Fischetti et al. |
| 2012/0301433 A1* | 11/2012 | Lu et al. ........................ 424/93.2 |

FOREIGN PATENT DOCUMENTS

EP 0112803 4/1984

OTHER PUBLICATIONS

Alekshun et al. Molecular mechanisms of antibacterial multidrug resistance. Cell 128, 1037-1050 (2007).
Avery, S.V. Microbial cell individuality and the underlying sources of heterogeneity. Nat Rev Microbiol 4, 577-587 (2006).
Balaban et al. Bacterial persistence as a phenotypic switch. Science 305, 1622-1625 (2004).
Beaber et al. SOS response promotes horizontal dissemination of antibiotic resistance genes. Nature 427, 72-74 (2004).
Bergstrom et al. Ecological theory suggests that antimicrobial cycling will not reduce antimicrobial resistance in hospitals. Proc Natl Acad Sci U S A 101, 13285-13290 (2004).
Bonhoeffer et al. Evaluating treatment protocols to prevent antibiotic resistance. Proc Natl Acad Sci U S A 94, 12106-12111 (1997).
Brown et al., Antibiotic cycling or rotation: a systematic review of the evidence of efficacy. Journal of Antimicrobial Chemotherapy, 55, 6-9 (2005).
Brüssow, H. Phage therapy: the *Escherichia coli* experience. Microbiology 151, 2133-2140 (2005).
Chait et al. Antibiotic interactions that select against resistance. Nature 446, 668-671 (2007).
Chang et al. Infection with vancomycin-resistant *Staphylococcus aureus* containing the vanA resistance gene, NE Journal of Medicine 348, 1342-1347 (2003).
Curtin et al., Using Bacteriophages to reduce formation of catheter-associated biofilms by *Staphylococcus* epidermis, (2006) Antimicrob. Agents Chemother. 50; 1268-1275.
Dwyer, D.J., Kohanski, M.A., Hayete, B. & Collins, J.J. Gyrase inhibitors induce an oxidative damage cellular death pathway in *Escherichia coli*. Mol Syst Biol 3, 91 (2007).
From the Centers for Disease Control and Prevention. Four pediatric deaths from community-acquired methicillin-resistant *Staphylococcus aureus*—Minnesota and North Dakota, 1997-1999. JAMA.
Hagens et al. Genetically modified filamentous phage as bactericidal agents: a pilot study. Lett. Appl. Microbiol. 37, 318-323 (2003).
Hagens et al. Augmentation of the antimicrobial efficacy of antibiotics by filamentous phage. Microb Drug Resist 12, 164-168 (2006).

(Continued)

*Primary Examiner* — Michael Burkhart
(74) *Attorney, Agent, or Firm* — Nixon Peabody, LLP

(57) ABSTRACT

The present invention relates to the treatment and prevention of bacteria and bacterial infections. In particular, the present invention relates to engineered bacteriophages used in combination with antimicrobial agents to potentiate the antimicrobial effect and bacterial killing by the antimicrobial agent. The present invention generally relates to methods and compositions comprising engineered bacteriophages and antimicrobial agents for the treatment of bacteria, and more particularly to bacteriophages comprising agents that inhibit antibiotic resistance genes and/or cell survival genes, and/or bacteriophages comprising repressors of SOS response genes or inhibitors of antimicrobial defense genes and/or expressing an agent which increases the sensitivity of bacteria to an antimicrobial agent in combination with at least one antimicrobial agent, and their use thereof.

20 Claims, 28 Drawing Sheets

(56) References Cited

OTHER PUBLICATIONS

Hagens et al. Therapy of experimental pseudomonas infections with a nonreplicating genetically modified phage. Antimicrob. Agents Chemother. 48, 3817-3822 (2004).
Hall, B.G. Predicting the evolution of antibiotic resistance genes. Nat Rev Microbiol 2, 430-435 (2004).
Hall-Stoodley et al. Bacterial biofilms: from the natural environment to infectious diseases. Nat Rev Microbiol 2, 95-108 (2004).
Heitman et al. Phage Trojan horses: a conditional expression system for lethal genes. Gene 85, 193-197 (1989).
Huff et al., Therapeutic Efficacy of Bacteriophage and Baytril (Enrofloxacin) Individually and in Combination to Treat Colibacillosis in Broilers, Poultry Science, 83,1994-1947 (2004).
Klevens et al. Invasive methicillin-resistant *Staphylococcus aureus* infections in the United States. JAMA 298, 1763-1771 (2007).
Kohanski et al. A common mechanism of cellular death induced by bactericidal antibiotics. Cell 130, 797-810 (2007).
Korch et al. Ectopic overexpression of wild-type and mutant hipA genes in *Escherichia coli*: effects on macromolecular synthesis and persister formation. J. Bacteriol. 188, 3826-3836 (2006).
Levin et al. Cycling antibiotics may not be good for your health. Proc Natl Acad Sci U S A 101, 13101-13102 (2004).
Levy et al. Antibacterial resistance worldwide: causes, challenges and responses. Nat. Med. 10, S122-S129 (2004).
Lewis, K. Persister cells and the riddle of biofilm survival. Biochemistry (Mosc). 70, 267-274 (2005).
Lewis, K. Persister cells, dormancy and infectious disease. Nat Rev Microbiol (2006).
Loose et al. A linguistic model for the rational design of antimicrobial peptides. Nature 443, 867-869 (2006).
Lorch, A. "Bacteriophages: An alternative to antibiotics?" Biotechnology and Development Monitor, No. 39, pp. 14-17 (1999).
Martinez et al. Mutation frequencies and antibiotic resistance. Antimicrob. Agents Chemother. 44, 1771-1777 (2000).
Morens et al. The challenge of emerging and re-emerging infectious diseases. Nature 430, 242-249 (2004).
Projan, S. Phage-inspired antibiotics? Nat. Biotechnol. 22, 167-168 (2004).
Salyers et al. Human intestinal bacteria as reservoirs for antibiotic resistance genes. Trends Microbiol. 12, 412-416 (2004).
Schoolnik et al. Phage offer a real alternative. Nat. Biotechnol. 22, 505-507 (2004).
Shah et al. Persisters: a distinct physiological state of *E. coli*. BMC Microbiol. 6, 53 (2006).
Soulsby, E.J. Resistance to antimicrobials in humans and animals. BMJ 331, 1219-1220 (2005).
Soulsby, L. Antimicrobials and animal health: a fascinating nexus. J. Antimicrob. Chemother. 60 Suppl 1, i77-i78 (2007).
Summers, W.C. Bacteriophage therapy. Annu. Rev. Microbiol. 55, 437-451 (2001).
Ubeda et al. Antibiotic-induced SOS response promotes horizontal dissemination of pathogenicity island-encoded virulence factors in staphylococci. Mol. Microbiol. 56, 836-844 (2005).
Vandenesch et al. Community-acquired methicillin-resistant *Staphylococcus aureus* carrying Panton-Valentine leukocidin genes: worldwide emergence. Emerg. Infect. Dis. 9, 978-984 (2003).
Vázquez-Laslop et al. Increased persistence in *Escherichia coli* caused by controlled expression of toxins or other unrelated proteins. J. Bacteriol. 188, 3494-3497 (2006).
Walsh, C. Where will new antibiotics come from? Nat Rev Microbiol 1, 65-70 (2003).
Wang et al. Platensimycin is a selective FabF inhibitor with potent antibiotic properties. Nature 441, 358-361 (2006).
Wise, R. The relentless rise of resistance? J. Antimicrob. Chemother. 54, 306-310 (2004).
Wiuff et al. Phenotypic tolerance: antibiotic enrichment of noninherited resistance in bacterial populations. Antimicrob. Agents Chemother. 49, 1483-1494 (2005).
Yacoby et al., Targeting antibacterial agents by using drug-carrying filamentous bacteriophages, Antimicrobial Agents and Chemotherapy, 50, 2087-2097 (2006).
Yacoby et al., Targeted drug-carrying bacteriophages as antibacterial nanomedicines, Antimicrobial Agents and Chemotherapy, 51, 2156-2163 (2007).
Hummel, A et al., "Characterisation and transfer of antibiotic resistance genes from enterococci isolated from food." Systematic and Applied Microbiology 30:1-7, 2006.
Kwon, NH et al., "Staphylococcal cassette chromosome mec (SCCmec) characterization and molecular analysis for methicillin-resistant *Staphylococcus aureus* and novel SCCmec subtype IVg isolated from bovine milk in Korea." Journal of Antimicrobial Chemotherapy 56:624-632, 2005.
Westwater, C et al., "Use of Genetically Engineered Phage to Deliver Antimicrobial Agents to Bacteria: an Alternative Therapy for Treatment of Bacterial Infections." Antimicrobial Agents and Chemotherapy 47(4):1301-1307, 2003.
Lu, T Combating Biofilms and Antibiotic Resistance Using Synthetic Biology. DSPACE@MIT, Dec. 11, 2008.
Lu, TK "Curriculum Vitae." Internet Article, pp. 1-8.
Yanisch-Perron C et al., "Improved M-13 Phage Cloning Vectors and Host Strains Nucleotide Sequence of the M-13MP-18 and PUC-19 Vectors." Database Biosis, Biosciences Information Service, Philadelphia, PA, Database Accession No. PREV198580021779, Gene 33(1):103-119, 1985 (Abstract).
Lu, TK and JJ Collins, "Dispersing biofilms with engineered enzymatic bacteriophage." PNAS 104 (27):11197-11202, 2007.
Lu, TK and JJ Collins, "Engineered bacteriophage targeting gene networks as adjuvants for antibiotic therapy." PNAS 106(12):4629-4634, 2009.

* cited by examiner

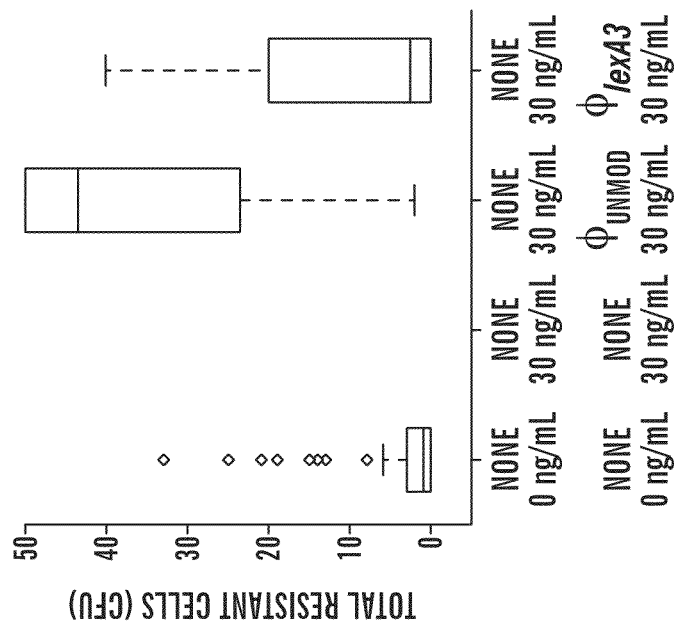
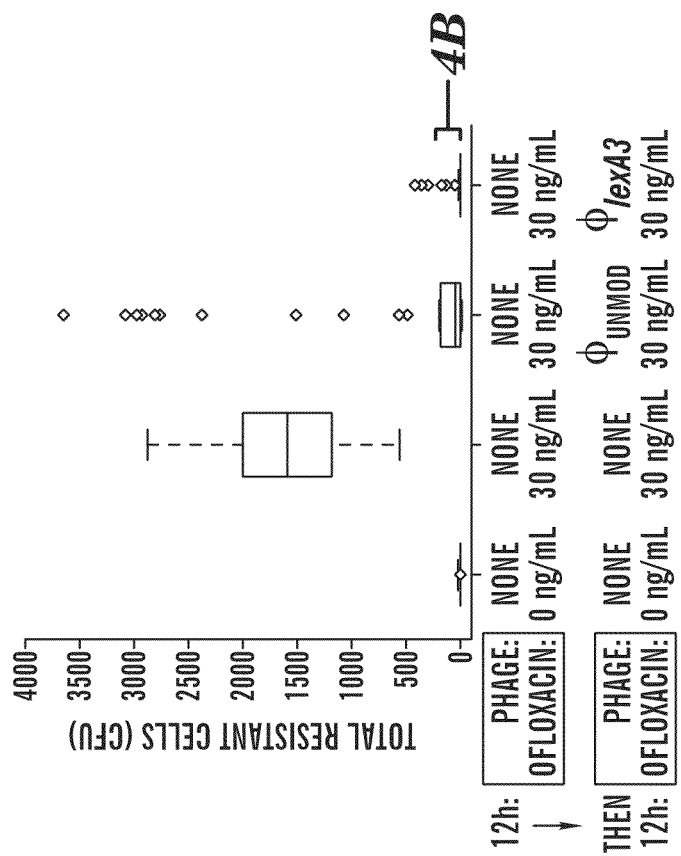
FIG. 4A
FIG. 4B

ENGINEERED BACTERIOPHAGES AS ADJUVANTS FOR ANTIMICROBIAL AGENTS AND COMPOSITIONS AND METHODS OF USE THEREOF

CROSS REFERENCE TO RELATED APPLICATIONS

This application is a National Phase Entry Application under 35 U.S.C. §371 of co-pending International Application PCT/US2009/030755, filed 12 Jan. 2009, which claims benefit under 35 U.S.C. 119(e) of U.S. Provisional Patent Application Ser. No. 61/020,197 filed 10 Jan. 2008, the contents of which are incorporated herein by reference in their entirety.

GOVERNMENT SUPPORT

This invention was made with the Government support under Contract No. EF-0425719 awarded by the National Science Foundation (NSF) and Contract No. OD003644 awarded by the National Institutes of Health (NIH). The Government has certain rights in the invention.

FIELD OF THE INVENTION

The present invention relates to the field of treatment and prevention of bacteria and bacterial infections. In particular, the present invention relates to engineered bacteriophages used in combination with antimicrobial agents to potentiate the antimicrobial effect and bacterial killing of the antimicrobial agent.

BACKGROUND

Bacteria rapidly develop resistance to antibiotic drugs within years of first clinical use[1]. Antibiotic resistance can be acquired by horizontal gene transfer or result from persistence, in which a small fraction of cells in a population exhibits a non-inherited tolerance to antimicrobials[2]. Since antimicrobial drug discovery is increasingly lagging behind the evolution of antibiotic resistance, there is a pressing need for new antibacterial therapies[3].

Bacterial infections are responsible for significant morbidity and mortality in clinical settings[3]. Though the advent of antibiotics has reduced the impact of bacterial diseases on human health, the constant evolution of antibiotic resistance poses a serious challenge to the usefulness of today's antibiotic drugs[3-7]. Infections that would have been easily cured by antibiotics in the past are now able to survive to a greater extent, resulting in sicker patients and longer hospitalizations[5,8,9]. The economic impact of antibiotic-resistant infections is estimated to be between US $5 billion and US $24 billion per year in the United States alone[10]. Resistance to antibiotic drugs develops and spreads rapidly, often within a few years of first clinical use[1]. However, the drug pipelines of pharmaceutical companies have not kept pace with the evolution of antibiotic resistance[1,3].

Acquired antibiotic resistance results from mutations in antibacterial targets or from genes encoding conjugative proteins that pump antibiotics out of cells or inactivate antibiotics[11]. Horizontal gene transfer, which can occur via transformation, conjugative plasmids, or conjugative transposons, is a major mechanism for the spread of antibiotic resistance genes[12,13]. For example, Staphylococcus aureus became quickly resistant to sulpha drugs in the 1940s, penicillin in the 1950s, and methicillin in the 1980s[12]. In 2002, staphylococci developed resistance to vancomycin, the only uniformly effective antibiotic against staphylococci, by receiving vancomycin-resistance genes via conjugation from co-infecting Enterococcus faecalis, which itself became completely resistant to vancomycin in nosocomial settings by 1988[12,14]. Drugs such as ciprofloxacin that induce the SOS response can even promote the horizontal dissemination of antibiotic resistance genes by mobilizing genetic elements[15,16]. For example, Streptococcus pneumoniae and Neisseria gonorrhoeae have also obtained resistance to antibiotics (Morens, et al., (2004) Nature 430: 242-249). Sub-inhibitory concentrations or incomplete treatment courses can present evolutionary pressures for the development of antibiotic resistance[17]. Use of antibiotics outside of clinical settings, for example in livestock for the agricultural industry, has contributed to the emergence of resistant organisms such as methicillin-resistant staphylococci and is unlikely to abate due to economic reasons and modern farming practices[12,18]. Resistance genes that develop in non-clinical settings may be subsequently transmitted to bacterial populations which infect humans, worsening the antibiotic resistance problem[12].

In addition to acquiring antibiotic-resistance genes, a small subpopulation of cells known as persisters can survive antibiotic treatment by entering a metabolically-dormant state[2,19,20]. Persister cells do not typically carry genetic mutations but rather exhibit phenotypic resistance to antibiotics[21]. In Escherichia coli, the fraction of a population which represents persister cells increases dramatically in late-exponential and stationary phases. Chromosomally-encoded toxins may be important contributors to the persister phenotype but the underlying mechanisms that control the stochastic persistence phenomena are not well understood[22-25]. Persisters constitute a reservoir of latent cells that can begin to regrow once antibiotic treatment ceases and may be responsible for the increased antibiotic tolerance observed in bacterial biofilms[20]. By surviving treatment, persisters may play an important role in the development of mutations or acquisition of genes that confer antibiotic resistance.

Several strategies have been proposed for controlling antibiotic resistant infections. New classes of antibiotics would improve the arsenal of drugs available to fight antibiotic-resistant bacteria but few are in pharmaceutical pipelines[3,26]. Surveillance and containment measures have been instituted in government and hospitals so that problematic infections are rapidly detected and isolated but do not address the fundamental evolution of resistance[12]. Cycling antibiotics is one method of controlling resistant organisms but is costly and may not be efficacious[27,28]. Reducing the overprescribing of antibiotics has only moderately reduced antibiotic resistance[29]. Efforts have been also made to lessen the use of antibiotics in farming but some use is inevitable[30]. Using bacteriophage to kill bacteria has been in practice since the early 20th century, particularly in Eastern Europe[16,17]. Bacteriophage can be chosen to lyse and kill bacteria or can be modified to express lethal genes to cause cell death[31-35]. However, bacteriophage which are directly lethal to their bacterial hosts can also produce phage-resistant bacteria in short amounts of time[6,7,31,32,36]. In addition to the aforementioned approaches, novel methods for designing antimicrobial drugs are becoming more important to extending the lifespan of the antibiotic era[37]. Combination therapy with different antibiotics or antibiotics with phage may enhance bacterial cell killing and thus reduce the incidence of antibiotic resistance, and reduce persisters[38-41]. Unmodified filamentous bacteriophage have been shown to augment antibiotic efficacy[42]. Systems biology analysis can be employed to identify pathways to target and followed by synthetic biology to devise methods to attack those pathways[38,43,44].

Bacterial biofilms are sources of contamination that are difficult to eliminate in a variety of industrial, environmental and clinical settings. Biofilms are polymer structures secreted by bacteria to protect bacteria from various environmental attacks, and thus result also in protection of the bacteria from disinfectants and antibiotics. Biofilms can be found on any environmental surface where sufficient moisture and nutrients are present. Bacterial biofilms are associated with many human and animal health and environmental problems. For instance, bacteria form biofilms on implanted medical devices, e.g., catheters, heart valves, joint replacements, and damaged tissue, such as the lungs of cystic fibrosis patients. Bacteria in biofilms are highly resistant to antibiotics and host defenses and consequently are persistent sources of infection.

Biofilms also contaminate surfaces such as water pipes and the like, and render also other industrial surfaces hard to disinfect. For example, catheters, in particular central venous catheters (CVCs), are one of the most frequently used tools for the treatment of patients with chronic or critical illnesses and are inserted in more than 20 million hospital patients in the USA each year. Their use is often severely compromised as a result of bacterial biofilm infection which is associated with significant mortality and increased costs. Catheters are associated with infection by many biofilm forming organisms such as *Staphylococcus epidermidis, Staphylococcus aureus, Pseudomonas aeruginosa, Enterococcus faecalis* and *Candida albicans* which frequently result in generalized blood stream infection. Approximately 250,000 cases of CVC-associated bloodstream infections occur in the US each year with an associated mortality of 12%-25% and an estimated cost of treatment per episode of approximately $25,000. Treatment of CVC-associated infections with conventional antimicrobial agents alone is frequently unsuccessful due to the extremely high tolerance of biofilms to these agents. Once CVCs become infected the most effective treatment still involves removal of the catheter, where possible, and the treatment of any surrounding tissue or systemic infection using antimicrobial agents. This is a costly and risky procedure and re-infection can quickly occur upon replacement of the catheter.

Bacteriophages (often known simply as "phages") are viruses that grow within bacteria. The name translates as "eaters of bacteria" and reflects the fact that as they grow, the majority of bacteriophages kill the bacterial host in order to release the next generation of bacteriophages. Naturally occurring bacteriophages are incapable of infecting anything other than specific strains of the target bacteria, undermining their potential for use as control agents.

Bacteriophages and their therapeutic uses have been the subject of much interest since they were first recognized early in the 20th century. Lytic bacteriophages are viruses that infect bacteria exclusively, replicate, disrupt bacterial metabolism and destroy the cell upon release of phage progeny in a process known as lysis. These bacteriophages have very effective antibacterial activity and in theory have several advantages over antibiotics. Most notably they replicate at the site of infection and are therefore available in abundance where they are most required; no serious or irreversible side effects of phage therapy have yet been described and selecting alternative phages against resistant bacteria is a relatively rapid process that can be carried out in days or weeks.

Bacteriophage have been used in the past for treatment of plant diseases, such as fireblight as described in U.S. Pat. No. 4,678,750. Also, Bacteriophages have been used to destroy biofilms (e.g., U.S. Pat. No. 6,699,701). In addition, systems using natural bacteriophages that encode biofilm destroying enzymes in general have been described. Art also provides a number of examples of lytic enzymes encoded by bacteriophages that have been used as enzyme dispersion to destroy bacteria (U.S. Pat. No. 6,335,012 and U.S. Patent Application Publication No. 2005/0004030). The Eastern European research and clinical trials, particularly in treating human diseases, such as intestinal infections, has apparently concentrated on use of naturally occurring phages and their combined uses (Lorch, A. (1999), "Bacteriophages: An alternative to antibiotics?" Biotechnology and Development Monitor, No. 39, p. 14-17).

For example, non-engineered bacteriophages have been used as carriers to deliver antibiotics (such as chloroamphenicol) (Yacoby et al., Antimicrobial agents and chemotherapy, 2006; 50; 2087-2097). Non-engineered bacteriophages have also had aminoglycosides antibiotics, such as chloroamphenicol, attached to the outside of filamentous non-engineered bacteriophage (Yacoby et al., Antimicrobial agents and chemotherapy, 2007; 51; 2156-2163). M13 non-lytic bacteriophages have also been engineered to carry lethal cell death genes Gef and ChpBK. However, these phages have not been used, or suggested to be useful in combination with antimicrobial or antibiotic agents (Westwater et al., 2003, Antimicrobial agents and chemotherapy, 47; 1301-1307). Non-engineered filamentous Pf3 bacteriophages have also been administered with low concentration of gentamicin, where neither the filamentous Pf3 or the gentamicin could eliminate the bacterial infection alone (Hagens et al, Microb. Drug resistance, 2006; 12; 164-8). The non-engineered bacteriophage and the antibiotic enrofloxacin have been administered simultaneously, although the use of the antibiotic was more effective than the combination of the antibiotic and bacteriophage (see Table 1 in Huff et al., 2004; Poltry Sci, 83; 1994-1947).

Constant evolutionary pressure will ensure that antibiotic resistance bacteria will continue to grow in number. The dearth of new antibacterial agents being developed in the last 25-30 years certainly bodes poorly for the future of the antibiotic era (Wise, R (2004) J Antimicrob Chemother 54: 306-310). Thus, new methods for combating bacterial infections are needed in order to prolong the antibiotic age. For example, bacteriophage therapy or synthetic antibacterial peptides have been proposed as potential solutions (Loose et al., (2006) Nature 443: 867-869; Curtin, et al., (2006) Antimicrob Agents Chemother 50: 1268-1275).

Because antibiotic resistance in treating bacterial infections and biofilms poses a significant hurdle to eliminating or controlling or inhibiting bacteria and biofilms with conventional antimicrobial drugs, new anti-biofilm strategies, such as phage therapy, should be explored. Novel synthetic biology technologies are needed to enable the engineering of natural phage with biofilm-degrading enzymes to produce libraries of enzymatically-active phage, which can complement efforts to screen for new biofilm-degrading bacteriophages in the environment.

SUMMARY

The inventors have discovered a two pronged strategy to significantly reduce or eliminate a bacterial infection. In particular, the inventors have engineered bacteriophages to be used in combination with an antimicrobial agent, such that the engineered bacteriophage functions as an adjuvant to the antimicrobial agent. In particular, the inventors have engineered bacteriophages to specifically disable (or deactivate) the bacteria's natural resistance mechanisms to the antimicrobial agents and/or phage infection. Accordingly, one aspect of the present invention generally relates to engineered bacteriophages which have been modified or engineered to (i) inhibit at least one bacterial resistance gene, or (ii) to inhibit at least one SOS response gene or bacterial defense gene in bacteria, or (iii) to express a protein which increases the susceptibility of a bacterial cell to an antimicrobial agent. Any one of these engineered bacteriophages, used alone, or in any combination can be used with an antimicrobial agent. Accordingly, the inventors have discovered a method to prevent the development of bacterial resistance to antimicrobial agents and the generation of persistent bacteria by inhibiting the local bacterial synthetic machinery which normally circumvents the antimicrobial effect, by engineering bacteriophages to be used in conjunction (or in combination with) an antimicrobial agent, where an engineered bacteriophage can inhibit an antimicrobial resistance gene, or inhibit a SOS response gene or a non-SOS bacterial defense gene, or express a protein to increase the susceptibility of a bacterial cell to an antimicrobial agent.

Accordingly, one aspect of the present invention relates to the engineered bacteriophages as discussed herein for use in conjunction with (i.e. in combination with) at least one antimicrobial agent, and that the engineered bacteriophages serve as adjuvants to such antimicrobial agents. Another aspect of the present invention relates to a method for inhibiting bacteria and/or removing bacterial biofilms in environmental, industrial, and clinical settings by administering a composition comprising at least one engineered bacteriophages as discussed herein with at least one antimicrobial agent.

One aspect of the present invention relates to methods of using engineered bacteriophages in combination with antimicrobial agents to potentiate the antimicrobial effect of bacterial killing (i.e. eliminating or inhibiting the growth or controlling the bacteria) by the antimicrobial agent. Accordingly, the present invention relates to the discovery of an engineered bacteriophage as an antibiotic adjuvant. In some embodiments, an engineered bacteriophage as discussed herein functions as an antibiotic adjuvant for an aminglycoside antimicrobial agent, such as but not limited to, gentamicin, as an antibiotic adjuvant for β-lactam antibiotics, such as but not limited to, ampicillin, and as antibiotic adjuvants for quinolones antimicrobial agents, such as but not limited to, ofloxacin.

Another aspect of the present invention relates to an engineered bacteriophage which comprises a nucleic acid encoding an agent which inhibits at least one gene involved in antibiotic resistance. In such and embodiment of this aspect of the invention, an engineered bacteriophage can comprise at least 2, 3, 4,5 or even more, for example 10 different nucleic acids which inhibit at least one gene involved in antibiotic resistance. In an alternative embodiment, an engineered bacteriophage can comprise a nucleic acid encoding an agent which inhibits at least one gene involved in cell survival repair. In another embodiment, an engineered bacteriophage can comprise at least 2, 3, 4, 5 or even more, for example 10 different nucleic acids which inhibit at least one gene involved in cell survival repair. Such engineered bacteriophages as disclosed herein which comprise a nucleic acid encoding an agent which inhibits at least one gene involved in bacterial antibiotic resistance and/or cell survival gene are referred to herein as "inhibitor-engineered bacteriophages". In some embodiments, the agent inhibits the gene expression and/or protein function of antibiotic resistance genes such as, but not limited to cat, vanA or mecD. In some embodiments, the agent inhibits the gene expression and/or protein function of a cell survival repair gene such as, but not limited to RecA, RecB, RecC, Spot or RelA. In another embodiment, an inhibitor-engineered bacteriophages can comprise at least 2, 3, 4, 5 or more, for example 8 different nucleic acids encoding inhibitors to antibiotic resistance genes or cell survival repair genes, such as at least 2, 3, 4, 5 or more selected from the group, but not limited to, cat, vanA, mecD, RecA, RecB, RecC, Spot or RelA and other antibiotic resistance genes or cell survival repair genes. In some embodiments of this aspect and all aspects described herein, an agent encoded by the nucleic acid of an inhibitor-engineered bacteriophage is a protein which inhibits an antibiotic resistance gene and/or cell survival gene or encodes an RNA-inhibitor (RNAi) agent which inhibits the translation and expression of an antibiotic resistance gene and/or cell survival gene.

Another aspect of the present invention relates to an engineered bacteriophage which comprises a nucleic acid encoding a repressor protein, or fragment thereof of a bacterial SOS response gene, or an agent (such as a protein) which inhibits a non-SOS pathway bacterial defense gene and are referred to herein as "repressor-engineered bacteriophages." In some embodiments, the repressor of an SOS response gene is, for example but not limited to, lexA, or modified version thereof. In some embodiments, the SOS response gene is, for example but is not limited to marRAB, arcAB and lexO. In some embodiments of this aspect and all other aspects described herein, an inhibitor of a non-SOS pathway bacterial defense gene is soxR, or modified version thereof. In some embodiments of this aspect and all other aspects described herein, an inhibitor of a non-SOS pathway bacterial defense gene is selected from the group of: marR, arc, soxR, fur, crp, icdA or craA or ompA or modified version thereof. In other embodiments of this aspect of the invention, an agent encoded by the nucleic acid of a repressor engineered bacteriophage which inhibits a non-SOS defense gene can inhibit any gene listed in Table 2. In some embodiments, a repressor-engineered bacteriophage which inhibits a non-SOS defense gene can be used in combination with selected antimicrobial agents, for example, where the repressor-engineered bacteriophage encodes an agent which inhibits a gene listed in Table 2A, such a repressor-engineered bacteriophage can be used in combination with a ciprofloxacin antimicrobial agent or a variant or analogue thereof. Similarly, in other embodiments a repressor-engineered bacteriophage which inhibits a non-SOS defense gene can encode an agent which inhibits a gene listed in Table 4B can be used in combination with a vancomycin antimicrobial agent or a variant or analogue thereof. Similarly, in other embodiments a repressor-engineered bacteriophage which inhibits a non-SOS defense gene can encode an agent which inhibits a gene listed in Table 2C, 2D, 2E, 2F and 2G can be used in combination with a rifampicin antimicrobial agent, or a ampicillin antimicrobial agent or a sulfmethaxazone antimicrobial agent or a gentamicin antimicrobial agent or a metronidazole antimicrobial agent, respectively, or a variant or analogue thereof.

Another aspect of the present invention relates to an engineered bacteriophage which comprises a nucleic acid encoding an agent, such as but not limited to a protein, which increases the susceptibility of a bacteria to an antimicrobial agent. Such herein engineered bacteriophage which comprises a nucleic acid encoding an agent which increases the susceptibility of a bacteria to an antimicrobial agent can be referred to herein as an "susceptibility agent-engineered bacteriophage" but are also encompassed under the definition of a "repressor-engineered bacteriophage" In some embodiments of this aspect, and all other aspects described herein, such an agent which increases the susceptibility of a bacteria to an antimicrobial agent is referred to as a "susceptibility agent" and refers to any agent which increases the bacteria's susceptibility to the antimicrobial agent by at least about 10% or at least about 15%, or at least about 20% or at least about 30% or at least about 50% or more than 50%, or any integer between 10% and 50% or more, as compared to the use of the antimicrobial agent alone. In one embodiment, a susceptibility agent is an agent which specifically targets a bacteria cell. In another embodiment, a susceptibility agent modifies (i.e. inhibits or activates) a pathway which is specifically expressed in bacterial cells. In one embodiment, a susceptibility agent is an agent which has an additive effect of the efficacy of the antimicrobial agent (i.e. the agent has an additive effect of the killing efficacy or inhibition of growth by the antimicrobial agent). In a preferred embodiment, a susceptibility agent is an agent which has a synergistic effect on the efficacy of the antimicrobial agent (i.e. the agent has a synergistic effect of the killing efficacy or inhibition of growth by the antimicrobial agent).

In one embodiment, a susceptibility agent increases the entry of an antimicrobial agent into a bacterial cell, for example, a susceptibility agent is a porin or porin-like protein, such as but is not limited to, protein OmpF, and Beta barrel porins, or other members of the outer membrane porin (OMP)) functional superfamily which include, but are not limited to those disclosed in world wide web site: "//biocyc.org/ECOLI/NEW-IMAGE?object=BC-4.1.B", or a OMP family member listed in Table 3 as disclosed herein, or a variant or fragment thereof. In another embodiment, a susceptibility agent is an agent, such as but not limited to a protein, which increases iron-sulfur clusters in the bacteria cell and/or increases oxidative stress or hydroxyl radicals in the bacteria. Examples of a susceptibility agent which increases the iron-sulfur clusters include agents which modulate (i.e. increase or decrease) the Fenton reaction to form hydroxyl radicals, as disclosed in Kahanski et al., Cell, 2007, 130; 797-810, which is incorporated herein by reference in its entirety. Examples of a susceptibility agent to be expressed by a susceptibility-engineered bacteriophage include, for example, those listed in Table 4, or a fragment or variant thereof or described in world-wide-web site "biocyc.org/ECOLI/NEW-IMAGE?type=COMPOUND&object=CPD-7"

In some embodiments, a susceptibility agent is not a chemotherapeutic agent. In another embodiment, a susceptibility agent is not a toxin protein, and in another embodiment, a susceptibility agent is not a bacterial toxin protein or molecule.

Accordingly, the inventors have developed a modular design strategy in which bacteriophages are engineered to have enhanced capacity to kill bacteria to disable or deactivate the bacteria's natural resistance genes to antimicrobial agents or phage infection. In some embodiments, the bacteriophages can be engineered or modified to express (i) at least one inhibitor to at least one bacterial resistance gene and/or cell survival gene, or (ii) at least one inhibitor (such as, but not limited to a repressor) at least one SOS response gene or bacterial defense gene in bacteria, or (iii) a susceptibility agent which increases the susceptibility of a bacterial cell to an antimicrobial agent.

In some embodiments, any one of these engineered bacteriophages, used alone, or in any combination can be used with at least one antimicrobial agent. For example, one aspect discussed herein relates to an engineered bacteriophage which expresses a nucleic acid inhibitor, such as an antisense nucleic acid inhibitor or antisense RNA (asRNA) which inhibits at least one, or at least two or at least three antibiotic genes and/or a cell survival gene, such as, but not limited to cat, vanA, mecD, RecA, RecB, RecC, Spot or RelA. In another aspect, an engineered bacteriophage can express an repressor, or fragment thereof, of at least one, or at least two or at least three SOS response genes, such as, but not limited to lexA, marR, arc, soxR, fur, crp, icdA, craA or ompA.

The inventors also demonstrated that a repressor-engineered bacteriophage and/or an inhibitor-engineered bacteriophage and/or a susceptibility agent-engineered bacteriophage can reduce the number of antibiotic-resistant bacteria in a population and act as a strong adjuvant for a variety of other bactericidal antibiotics, such as for example, but not limited to gentamicin and ampicillin.

In some embodiments of all aspects of the invention, any engineered bacteriophage disclosed herein, such as repressor-engineered bacteriophage and/or an inhibitor-engineered bacteriophage and/or a susceptibility agent-engineered bacteriophage as discussed herein can additionally comprise a least one of the degrading enzymes effective at degrading bacteria biofilms, such as effective EPS-degrading enzymes specific to the target biofilm, particularly, for example, dispersin B (DspB) which is discussed in PCT application PCT/US2005/032365 and U.S. application Ser. No. 12/337,677, which are incorporated herein by reference.

Also discussed herein is the generation of a diverse library of engineered bacteriophages described herein, such as a library of repressor-engineered bacteriophage and/or an inhibitor-engineered bacteriophage and/or a susceptibility agent-engineered bacteriophages which are capable of acting as adjuvants or to enhance antimicrobial agents, which is advantageous than trying to isolate such bacteriophages that function as adjuvants from the environment. By multiplying within the bacterial colony or biofilm and hijacking the bacterial machinery, inhibitor engineered bacteriophages achieves high local concentrations of both enzyme and lytic phage to target multiple biofilm components, even with small initial phage inoculations.

Rapid bacteriophage (also referred to as "phage" herein) replication with subsequent bacterial lysis and expression of inhibitors of SOS genes renders this a two-pronged attack strategy for use in combination with antimicrobial agents for an efficient, autocatalytic method for inhibiting bacteria and/or removing bacterial biofilms in environmental, industrial, and clinical settings.

Also disclosed herein is a method for the combined use of an inhibitor-engineered bacteriophage and/or a repressor-engineered bacteriophage and/or susceptibility agent-engineered bacteriophage with at least one antimicrobial agent. The inventors have demonstrated that the combined use of an inhibitor-engineered bacteriophage and/or a repressor-engineered bacteriophage and/or susceptibility agent-engineered bacteriophage is at least 4.5 orders of magnitude more efficient than use of the antimicrobial agent alone, and at least two orders of magnitude more efficient at killing or eliminating the bacteria as compared to use of an antimicrobial agent with a non-engineered bacteriophage alone (i.e. an antimicrobial agent in the presence of a bacteriophage which is not an inhibitor-engineered bacteriophage or a repressor-engineered bacteriophage or susceptibility agent-engineered bacteriophage). Thus, the inventors have demonstrated a significant and surprising improvement over the combined use of non-engineered bacteriophages and antimicrobial agents as therapies described in prior art. The inventors have also demonstrated that use of such engineered bacteriophages as disclosed herein, such as the inhibitor-engineered bacteriophages or repressor-engineered bacteriophages are very effective at reducing the number of antibiotic resistant bacterial cells which can develop in the presence of sub-inhibitory antimicrobial drug concentrations.

Also, one significant advantage of the present invention as compared to methods using non-engineered bacteriophages in combination with antimicrobial agents is that the use of the engineered bacteriophages as disclosed herein with antimicrobial agents allows one to significantly reduce or eliminate a population of persister cells. For example, the administration or application of an engineered bacteriophage as disclosed herein after initial treatment with an antimicrobial agent can reduce or eliminate a population of persister cells. Furthermore, the inventors have discovered that an engineered bacteriophage as disclosed herein, such as an inhibitor-engineered bacteriophage or a repressor-engineered bacteriophage or susceptibility agent-engineered bacteriophage can reduce the number of antibiotic resistant mutant bacteria that survive in a bacterial population exposed to one or more antimicrobial agents, and therefore the engineered bacteriophages described herein are effective at reducing the number of antibiotic resistant cells which develop in the presence of sub-inhibitory antimicrobial agent drug concentrations.

Another advantage of the present invention is that it allows one to reduce or eliminate multiple applications of the composition during the treatment of a surface having a bacterial biofilm.

One aspect of the present invention relates to engineering or modification of any bacteriophage strain or species to generate the engineered bacteriophages disclosed herein. For example, an inhibitor-engineered bacteriophage or a repressor-engineered bacteriophage or susceptibility agent-engineered bacteriophage can be any bacteriophage known by a skilled artisan. For example, in one embodiment, the bacteriophage is a lysogenic bacteriophage, for example but not limited to a M13 bacteriophage. In another embodiment, the bacteriophage is a lytic bacteriophage such as, but not limited to T7 bacteriophage. In another embodiment, the bacteriophage is a phage K or a *Staphylococcus* phage K for use against bacterial infections of methicillin-resistant *S. aureus*.

One aspect of the present invention relates to an engineered lysogenic M13 bacteriophage comprising a nucleic acid operatively linked to a M13 promoter, wherein the nucleic acid encodes at least one agent that inhibits an antibiotic resistance gene and/or a cell survival repair gene.

Another aspect of the present invention relates to an engineered lysogenic M13 bacteriophage comprising a nucleic acid operatively linked to a M13 promoter, wherein the nucleic acid encodes at least one repressor of a SOS response gene and/or an inhibitor to a non-SOS bacterial defense gene.

Another aspect of the present invention relates to an engineered lysogenic M13 bacteriophage comprising a nucleic acid operatively linked to a M13 promoter, wherein the nucleic acid encodes at least one agent that increases the susceptibility of a bacterial cell to an antimicrobial gene.

Another aspect of the present invention relates to an engineered lytic T7 bacteriophage comprising a nucleic acid operatively linked to a T7 promoter, wherein the nucleic acid encodes at least one agent that inhibits at least one antibiotic resistance gene and/or at least one cell survival repair gene.

Another aspect of the present invention relates to an engineered lytic T7 bacteriophage comprising a nucleic acid operatively linked to a T7 promoter, wherein the nucleic acid encodes at least one repressor of a SOS response gene and/or an inhibitor to a non-SOS bacterial defense gene.

Another aspect of the present invention relates to an engineered lytic T7 bacteriophage comprising a nucleic acid operatively linked to a T7 promoter, wherein the nucleic acid encodes at least one agent that increases the susceptibility of a bacterial cell to an antimicrobial gene.

In some embodiments, an antibiotic resistance gene is selected from the group comprising cat, vanA or mecD or variants thereof. In some embodiments, a cell survival gene is selected from the group comprising RecA, RecB, RecC, spot, RelA or variants thereof.

In some embodiments of all aspects described herein, a bacteriophage can comprise an agent which is selected from a group comprising, siRNA, antisense nucleic acid, asRNA, RNAi, miRNA and variants thereof. In some embodiments, the bacteriophage comprises an as RNA agent.

In some embodiments, the bacteriophage comprises a nucleic acid encoding at least two agents that inhibit at least two different cell survival repair genes, for example but not limited to, at least two agents that inhibit at least two of RecA, RecB or RecC.

In some embodiments, the repressor of a SOS response gene is selected from the group comprising lexA, marR, arcR, soxR, fur, crp, icdA, craA, ompF or variants or fragments thereof. In some embodiments, the repressor is LexA and in some embodiments, the repressor is csrA or omF, and in some embodiments the bacteriophage can comprise the nucleic acid encoding a mixture of LexA, csrA or omF in any combination. For example, in some embodiments, the bacteriophage can comprise the nucleic acid encoding at least two different repressors of at least one SOS response gene, such as, but not limited to the bacteriophage can comprise the repressors csrA and ompF or variants or homologues thereof.

Another aspect of the present invention relates to a method to inhibit or eliminate a bacterial infection comprising administering to a surface infected with bacteria; (i) a bacteriophage comprising a nucleic acid operatively linked to a bacteriophage promoter, wherein the nucleic acid encodes at least one agent that inhibits an antibiotic resistance gene and/or a cell survival repair gene, and (ii) at least one antimicrobial agent.

Another aspect of the present invention relates to a method to inhibit or eliminate a bacterial infection comprising administering to a surface infected with bacteria; (i) a bacteriophage comprising a nucleic acid operatively linked to a bacteriophage promoter, wherein the nucleic acid encodes at least one repressor of a SOS response gene, and (ii) at least one antimicrobial agent.

Another aspect of the present invention relates to a method to inhibit or eliminate a bacterial infection comprising administering to a surface infected with bacteria; (i) a bacteriophage comprising a nucleic acid operatively linked to a bacteriophage promoter, wherein the nucleic acid encodes at least one agent which increases the susceptibility of a bacterial cell to a antimicrobial agent, and (ii) at least one antimicrobial agent.

In some embodiments of all aspects described herein, a bacteriophage useful in the methods disclosed herein and used to generate an engineered bacteriophage, such as a inhibitor-engineered bacteriophage or a repressor-engineered bacteriophage or a susceptibility-engineered bacteriophage is any bacteriophage know by a skilled artisan. A non-limiting list of examples of bacteriophages which can be used are disclosed in Table 5 herein. In one embodiment, the bacteriophage is a lysogenic bacteriophage such as, for example a M13 lysogenic bacteriophage. In alternative embodiments, a bacteriophage useful in all aspects disclosed herein is a lytic bacteriophage, for example but not limited to a T7 lytic bacteriophage. In one embodiment, a bacteriophage useful in all aspects disclosed herein is a SP6 bacteriophage or a phage K, or a *staphylococcus* phage K bacteriophage.

In some embodiments, administration of any engineered-bacteriophage as disclosed herein and the antimicrobial agent occurs simultaneously, and in alternative embodiments, the administration of a engineered-bacteriophage occurs prior to the administration of the antimicrobial agent. In other embodiments, the administration of an antimicrobial agent occurs prior to the administration of a engineered-bacteriophage.

In some embodiments, antimicrobial agents useful in the methods as disclosed herein are quinolone antimicrobial agents, for example but not limited to, antimicrobial agents selected from a group comprising ciprofloxacin, levofloxacin, and ofloxacin, gatifloxacin, norfloxacin, lomefloxacin, trovafloxacin, moxifloxacin, sparfloxacin, gemifloxacin, pazufloxacin or variants or analogues thereof. In some embodiments, an antimicrobial agents useful in the methods as disclosed herein is ofloxacin or variants or analogues thereof.

In some embodiments, antimicrobial agents useful in the methods as disclosed herein are aminoglycoside antimicrobial agents, for example but not limited to, antimicrobial agents selected from a group consisting of amikacin, gentamycin, tobramycin, netromycin, streptomycin, kanamycin, paromomycin, neomycin or variants or analogues thereof. In some embodiments, an antimicrobial agent useful in the methods as disclosed herein is gentamicin or variants or analogues thereof.

In some embodiments, antimicrobial agents useful in the methods as disclosed herein are β-lactam antibiotic antimicrobial agents, such as for example but not limited to, antimicrobial agents selected from a group consisting of penicillin, ampicillin, penicillin derivatives, cephalosporins, monobactams, carbapenems, β-lactamase inhibitors or variants or analogues thereof. In some embodiments, an antimicrobial agent useful in the methods as disclosed herein is ampicillin or variants or analogues thereof.

Another aspect of the present invention relates to a composition comprising a lysogenic M13 bacteriophage comprising a nucleic acid operatively linked to a M13 promoter, wherein the nucleic acid encodes at least one agent that inhibits an antibiotic resistance gene and/or a cell survival repair gene and at least one antimicrobial agent. Another aspect of the present invention relates to a composition comprising a lysogenic M13 bacteriophage comprising a nucleic acid operatively linked to a M13 promoter, wherein the nucleic acid encodes at least one repressor of a SOS response gene and at least one antimicrobial agent.

Another aspect of the present invention relates to a composition comprising a lytic T7 bacteriophage comprising a nucleic acid operatively linked to a T7 promoter, wherein the nucleic acid encodes at least one agent that inhibits an antibiotic resistance gene and/or a cell survival repair gene and at least one antimicrobial agent. Another aspect of the present invention relates to a composition a lytic T7 bacteriophage comprising a nucleic acid operatively linked to a T7 promoter, wherein the nucleic acid encodes at least one repressor of a SOS response gene and at least one antimicrobial agent.

In some embodiments, the composition comprises antimicrobials agents such as, for example but not limited to, quinolone antimicrobial agents and/or aminoglycoside antimicrobial agents and/or β-lactam antimicrobial agent, for example, but not limited to, antimicrobial agents selected from a group comprising ciprofloxacin, levofloxacin, and ofloxacin, gatifloxacin, norfloxacin, lomefloxacin, trovafloxacin, moxifloxacin, sparfloxacin, gemifloxacin, pazufloxacin, amikacin, gentamycin, tobramycin, netromycin, streptomycin, kanamycin, paromomycin, neomycin, penicillin, ampicillin, penicillin derivatives, cephalosporins, monobactams, carbapenems, β-lactamase inhibitors or variants or analogues thereof.

In some embodiments, the composition comprises at least one inhibitor-engineered bacteriophage and/or at least one repressor-engineered bacteriophage as disclosed herein.

Another aspect of the present invention relates to a kit comprising a lysogenic M13 bacteriophage comprising the nucleic acid operatively linked to a M13 promoter, wherein the nucleic acid encodes at least one agent that inhibits an antibiotic resistance gene and/or a cell survival repair gene. Another aspect of the present invention relates a kit comprising a lysogenic M13 bacteriophage comprising the nucleic acid operatively linked to a M13 promoter, wherein the nucleic acid encodes at least one repressor of a SOS response.

Another aspect of the present invention relates a kit comprising a lytic T7 bacteriophage comprising the nucleic acid operatively linked to a T7 promoter, wherein the nucleic acid encodes at least one agent that inhibits an antibiotic resistance gene and/or a cell survival repair gene. Another aspect of the present invention relates a kit comprising a lytic T7 bacteriophage comprising the nucleic acid operatively linked to a T7 promoter, wherein the nucleic acid encodes at least one repressor of a SOS response.

In some embodiments, the methods and compositions as disclosed herein are administered to a subject. In some embodiments, the methods to inhibit or eliminate a bacterial infection comprising administering the compositions as disclosed herein to a subject, wherein the bacteria are present in the subject. In some embodiments, the subject is a mammal, for example but not limited to a human.

In some embodiments, any of the bacteriophages as disclosed herein are useful in combination with at least one antimicrobial agent to reduce the number of bacteria as compared to use of the antimicrobial agent alone. In some embodiments, any of the bacteriophages as disclosed herein are useful in combination with at least one antimicrobial agent to inhibit or eliminate a bacterial infection, such as for example inhibit or eliminate a bacteria present a biofilm.

In some embodiments, the present invention relates to methods to inhibit or eliminate a bacterial infection comprising administering to a surface infected with bacteria; (i) a bacteriophage comprising a nucleic acid operatively linked to a bacteriophage promoter, wherein the nucleic acid encodes at least one repressor of a SOS response gene, and (ii) at least one antimicrobial agent. In some embodiments, the bacteria is in a biofilm.

BRIEF DESCRIPTION OF FIGURES

FIG. 1A shows a schematic of combination therapy with engineered phage and antibiotics. Bactericidal antibiotics induce DNA damage via hydroxyl radicals, leading to induction of the SOS response. SOS induction results in DNA repair and can lead to survival (Kohanski et al., 2007, Cell 130, 797-8108). Engineered phage carrying the lexA3 gene ($\phi_{lexA3}$) under the control of the synthetic promoter PLtetO and a ribosome-binding sequence (Lutz et al., 1997, Nucleic Acids Res 25, 1203-121027) acts as an antibiotic adjuvant by suppressing the SOS response and increasing cell death. FIG. 1B shows a killing curves for no phage (diamonds), unmodified phage $\phi_{unmod}$ (squares), and engineered phage $\phi_{lexA3}$ (circles) with 60 ng/mL ofloxacin [oflox] (solid lines, closed symbols). $10^8$ PFU/mL phage was used. A growth curve for E. coli EMG2 with no treatment is shown for comparison (dotted line, open symbols). $\phi_{lexA3}$ greatly enhanced killing by ofloxacin by 4 hours of treatment. FIG. 1C is a ofloxacin dose response showing that $\phi_{lexA3}$ (circles with solid line) increases killing even at low levels of drug compared with no phage (diamonds with dash-dotted line) and φunmod (squares with dashed line). $10^8$ PFU/mL phage was used. FIG. 1D shows killing curves for no phage (diamonds), $\phi_{unmod}$(squares), and $\phi_{lexA3}$ (circles) with 5 μg/mL gentamicin [gent]. $10^9$ PFU/mL phage was used. $\phi_{lexA3}$ phage greatly increases killing by gentamicin. FIG. 1E shows killing curves for no phage (diamonds), $\phi_{unmod}$ (squares), and $\phi_{lexA3}$ (circles) with 5 μg/mL ampicillin [amp]. $10^9$ PFU/mL phage was used. $\phi_{lexA3}$ phage greatly increases killing by ampicillin.

FIG. 3A shows a schematic of a female Charles River CD-1 mice inoculated with intraperitoneal injections of $8.8\times10^7$ CFU/mouse *E. coli* EMG2 bacteria. After 1 hour, the mice received either no treatment or intravenous treatment with no phage, unmodified phage $\phi_{unmod}$, or engineered phage $\phi_{lexA3}$ with 0.2 mg/kg ofloxacin. $10^9$ PFU/mouse phage was used. The mice were observed for 5 days and deaths were recorded at the end of each day to generate survival curves. FIG. 3B shows survival curves for infected mice treated with phage and/or ofloxacin demonstrate that engineered phage $\phi_{lexA3}$ plus ofloxacin (closed circles with solid line) significantly increases survival of mice compared with unmodified phage funmod plus ofloxacin (closed squares with solid line), no phage plus ofloxacin (closed diamonds with solid line), and no treatment (open diamonds with dashed line).

FIGS. 4A-4B show box-and-whisker plot of the total number of *E. coli* EMG2 cells in 60 observations that were resistant to 100 ng/mL ofloxacin after growth under various conditions (bars indicate medians, diamonds represent outliers). FIG. 4A shows cells grown with no phage and no ofloxacin for 24 hours had very low numbers of antibiotic-resistant cells. Cells grown with no phage and 30 ng/mL ofloxacin for 24 hours had high numbers of resistant cells due to growth in subinhibitory drug concentrations (Martinez et al., 2000, Antimicrob. Agents Chemother. 44, 1771-177730). Cells grown with no phage and 30 ng/mL ofloxacin for 12 hours followed by $10^9$ PFU/mL unmodified phage funmod and 30 ng/mL ofloxacin for 12 hours exhibited a modest level of antibiotic-resistant bacteria. Cells grown with no phage and 30 ng/mL ofloxacin for 12 hours followed by $10^9$ PFU/mL $\phi_{lexA}$ and 30 ng/mL ofloxacin for 12 hours exhibited a low level of antibiotic-resistant bacteria, close to the numbers seen with no ofloxacin and no phage. FIG. 4B shows a zoomed-in version of box-and-whisker plot in (a) for increased resolution around low total resistant cell counts confirms that $\phi_{lexA3}$ with 30 ng/mL ofloxacin treatment reduced the number of resistant cells to levels similar to that of no ofloxacin with no phage.

FIG. 5A show Ofloxacin stimulates superoxide generation, which is normally countered by the oxidative stress response, coordinated by SoxR (Kohanski et al., 2007, Cell 130, 797-8108). Engineered phage producing SoxR ($\phi_{soxR}$) enhances ofloxa- cin-based killing by disrupting regulation of the oxidative stress response. FIG. 5B show killing curves for no phage (diamonds), unmodified phage $\phi_{unmod}$ (squares), and engineered phage $\phi_{soxR}$ (downwards-facing triangles) with 60 ng/mL ofloxacin (solid lines, closed symbols). $10_8$ PFU/mL phage was used. The killing curve for funmod and a growth curve for *E. coli* EMG2 with no treatment (dotted line, open symbols) are reproduced from FIG. 1B for comparison and show that $\phi_{soxR}$ enhances killing by ofloxacin. FIG. 5C CsrA suppresses the biofilm state in which bacterial cells tend to be more resistant to antibiotics (Jackson et al., 2002, J. Bacteriol. 184, 290-30135). OmpF is a porin used by quinolones to enter bacterial cells (Hirai K, et al., 1986, Antimicrob. Agents Chemother. 29, 535-53837). Engineered phage producing both CsrA and OmpF simultaneously ($\phi_{csrA-ompF}$) enhances antibiotic penetration via OmpF and represses biofilm formation and antibiotic tolerance via CsrA to produce an improved dual targeting adjuvant for ofloxacin. FIG. 5D shows killing curves for $\phi_{csrA}$ (diamonds), $\phi_{ompF}$ (squares), and $\phi_{csrA-ompF}$ (upwards-facing triangles) with 60 ng/mL ofloxacin. $10^8$ PFU/mL phage was used. Phage expressing both csrA and ompF ($\phi_{csrA-ompF}$) is a better adjuvant for ofloxacin than phage expressing csrA ($\phi_{csrA}$) or ompF alone ($\phi_{ompF}$).

FIG. 6A shows a killing curves for no phage (black diamonds), $10^8$ PFU/mL unmodified M13mp18 (i.e. $\phi_{unmod}$) (squares), and $10^8$ PFU/mL M13mp18-soxR (i.e. $\phi_{SoxR}$) (downwards-facing triangles) without ofloxacin (dotted lines, open symbols) or with 60 ng/mL ofloxacin (solid lines, closed symbols). Killing curves for no phage and unmodified m13mp18 phage ($\phi_{unmod}$) are reproduced from FIG. 1B for comparison and demonstrate that M13mp18-soxR (i.e. $\phi_{soxR}$) enhances killing by ofloxacin. $10^8$ PFU/mL represents an MOI of approximately 1:10. FIG. 6B shows a killing curves for $10^8$ PFU/mL M13 mp18-csrA ($\phi_{csrA}$) (black diamonds), $10^8$ PFU/mL M13mp18-ompF ($\phi_{ompF}$) (squares), and $10^8$ PFU/mL M13mp18-csrA-ompF ($\phi_{csrA-ompF}$) (upwards-facing triangles) without ofloxacin (dotted lines, open symbols) or with 60 ng/mL ofloxacin (solid lines, closed symbols). Phage expressing both csrA and ompF (M13mp18-csrA-ompF or $\phi_{csrA-ompF}$) is a better adjuvant for ofloxacin than phage expressing csrA alone (M13mp18-csrA; $\phi_{csrA}$) or ompF alone (M13mp18-ompF; $\phi_{ompF}$). $10^8$ PFU/mL represents an MOI of approximately 1:10. FIG. 6C shows a phage dose response which demonstrates that both M13mp18-soxR (downwards-facing triangles with solid line) and M13mp18-csrA-ompF (upwards-facing triangles with solid line) are effective as adjuvants for ofloxacin (60 ng/mL) over a wide range of initial inoculations. Phage dose response curves for no phage (dash-dotted line) and unmodified M13mp18 phage (squares with dashed line) are reproduced from FIG. 1c for comparison. FIG. 6D shows a Ofloxacin dose response with $10^8$ PFU/mL that shows that both M13mp18-soxR (downwards-facing triangles with solid line) and M13mp18-csrA-ompF (upwards-facing triangles with solid line) improve killing throughout a range of drug concentrations. Ofloxacin dose response curves for no phage (diamonds with dash-dotted line) and unmodified M13mp18 phage (squares with dashed line) are reproduced from FIG. 1D for comparison.

FIG. 7A shows cells grown with no phage and no ofloxacin for 24 hours had very low numbers of antibiotic-resistant cells. Inset of FIG. 8A shows the distribution of observations with total resistant cells between 0 and 50 for increased resolution and demonstrates that many observations were devoid of antibiotic-resistant bacteria. FIG. 7B shows cells grown with no phage and 30 ng/mL ofloxacin for 24 hours had high numbers of resistant cells, demonstrating a large increase in antibiotic resistance due to growth in subinhibitory drug concentrations[17]. No inset is shown because no observations had less than 50 resistant cells. FIG. 7C shows cells grown with no phage and 30 ng/mL ofloxacin for 12 hours followed by $10^9$ PFU/mL unmodified M13mp18 phage and 30 ng/mL ofloxacin for 12 hours exhibited a modest level of antibiotic-resistant bacteria. Inset of FIG. 7C shows the distribution of observations with total resistant cells between 0 and 50 for increased resolution and demonstrates that no observations were devoid of antibiotic-resistant bacteria. FIG. 7D shows cells grown with no phage and 30 ng/mL ofloxacin for 12 hours followed by $10^9$ PFU/mL M13mp18-lexA3 and 30 ng/mL ofloxacin for 12 hours exhibited a low level of antibiotic-resistant bacteria compared to no phage and 30 ng/mL ofloxacin in FIG. 7D, and unmodified M13mp18 and 30 ng/mL ofloxacin in FIG. 8C. Inset of FIG. 7D shows the distribution of observations with total resistant cells between 0 and 50 for increased resolution and demonstrates that M13mp18-lexA3 treatment reduced the number of resistant cells under 30 ng/mL ofloxacin to levels similar to that of 0 ng/mL ofloxacin in FIG. 8A.

FIG. 8A shows killing curves for no phage (diamonds), $10^9$ PFU/mL unmodified M13mp18 (squares), and $10^9$ PFU/mL M13mp18-lexA3 (circles) with 5 µg/mL gentamicin [gent]. Engineered M13mp18-lexA3 phage greatly improved killing by gentamicin. $10^9$ PFU/mL represents an MOI of approximately 1:1. FIG. 8B shows a killing curves for no phage (diamonds), $10^9$ PFU/mL unmodified M13mp18 (squares), and $10^9$ PFU/mL M13mp18-lexA3 (circles) with 5 µg/mL ampicillin [amp]. Engineered M13mp18-lexA3 phage greatly improved killing by ampicillin $10^9$ PFU/mL represents an MOI of approximately 1:1.

FIG. 9A shows unmodified M13mp18 ($\phi_{unmod}$) contains lacZ to allow blue-white screening of engineered bacteriophage. FIG. 9B shows engineered M13mp18 bacteriophage expressing lexA3 ($\phi_{lexA3}$). FIG. 9C shows engineered M13mp18 bacteriophage expressing soxR ($\phi_{soxR}$). FIG. 9D shows engineered M13mp18 bacteriophage expressing csrA ($\phi_{csrA}$). FIG. 9E shows engineered M13mp18 bacteriophage expressing ompF ($\phi_{ompF}$). FIG. 9F shows engineered M13mp18 bacteriophage expressing csrA and ompF ($\phi_{csrA-ompF}$).

FIG. 10A shows 0 ng/mL ofloxacin treatment. FIG. 10B shows 20 ng/mL ofloxacin treatment. FIG. 10C show 60 ng/mL ofloxacin treatment. FIG. 10D show 100 ng/mL ofloxacin treatment. FIG. 10E shows 200 ng/mL ofloxacin treatment.

FIG. 19 shows a $P_{LtetO-1}$ (SEQ ID NO: 32), $P_{LlacO-1}$ (SEQ ID NO: 33), $P_{AlacO-1}$ (SEQ ID NO: 34) and $P_{lac/ara-1}$ (SEQ ID NO: 35) promoters which can be used.

DETAILED DESCRIPTION

Figure 1A:
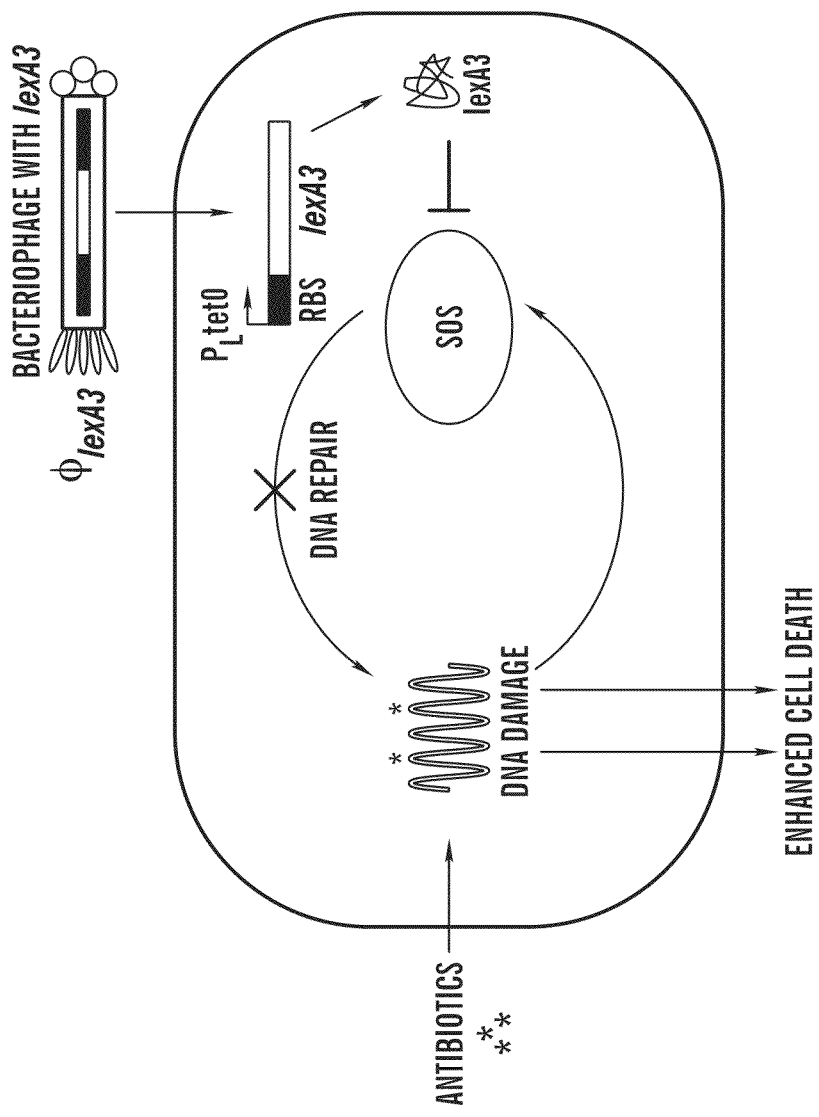
FIGS. 1A-1E show engineered $\phi_{lexA3}$ bacteriophage enhances killing of wild-type E. coli EMG2 bacteria by bactericidal antibiotics.

As disclosed herein, the inventors have discovered a two pronged strategy to significantly reduce or eliminate a bacterial infection. In particular, the inventors have engineered bacteriophages to be used in combination with an antimicrobial agent, such that the engineered bacteriophage functions as an adjuvant to the antimicrobial agent. Thus, the inventors have engineered bacteriophages to be used in combination with an antimicrobial agent, such that the engineered bacteriophage functions as an adjuvant to at least one antimicrobial agent. In particular, the inventors have engineered bacteriophages to specifically disable (or deactivate) the bacteria's natural resistance mechanisms to the antimicrobial agents and/or phage infection. Accordingly, one aspect of the present invention generally relates to engineered bacteriophages which have been modified or engineered to (i) inhibit at least one bacterial resistance gene, or (ii) to inhibit at least one SOS response gene or bacterial defense gene in bacteria, or (iii) to express a protein which increases the susceptibility of a bacterial cell to an antimicrobial agent. Any one of these engineered bacteriophages, used alone, or in any combination can be used with an antimicrobial agent. Accordingly, the inventors have discovered a method to prevent the development of bacterial resistance to antimicrobial agents and the generation of persistent bacteria by inhibiting the local bacterial synthetic machinery which normally circumvents the antimicrobial effect, by engineering bacteriophages to be used in conjunction (or in combination with) an antimicrobial agent, where an engineered bacteriophage can inhibit an antimicrobial resistance gene, or inhibit a SOS response gene or a non-SOS bacterial defense gene, or express a protein to increase the susceptibility of a bacterial cell to an antimicrobial agent.

Accordingly, one aspect of the present invention relates to the engineered bacteriophages as discussed herein for use in conjunction with (i.e. in combination with) at least one antimicrobial agent, and that the engineered bacteriophages serve as adjuvants to such antimicrobial agents.

One aspect of the present invention relates to a method to potentiate the bacterial killing effect of an antimicrobial agent. In particular, one aspect of the present invention relates to methods and compositions comprising engineered bacteriophages for use in combination with an antimicrobial agent to potentiate the antimicrobial effect and bacterial killing of the antimicrobial agent. Another aspects relates to the use of an engineered bacteriophage as an antibiotic adjuvant. In some embodiments of this and all aspects described herein, an engineered bacteriophage can be used as an antibiotic adjuvant for an aminglycoside antimicrobial agent, such as but not limited to, gentamicin, as antibiotic adjuvants for a β-lactam antibiotic, such as but not limited to, ampicillin, and as an antibiotic adjuvant for a quinolone antimicrobial agent, such as but not limited to, ofloxacin. In one embodiment of this aspect and all aspects described herein, an engineered bacteriophage can function as an antimicrobial adjuvant or antibiotic adjuvant for at least 2, at least 3, at least 4, at least 5, least 6, at least 7, at least 8, at least 9 or at least 10 or more different antimicrobial agents at any one time. In some embodiments, any of the engineered bacteriophages as disclosed herein can used in combination with at least one or more antimicrobial agent, for example an engineered bacteriophage as disclosed herein can used in combination with at least 2, 3, 4, 5, 6, 7, 8, 9 or 10 or more different antimicrobial agents.

In one aspect of the present invention, an engineered bacteriophage as disclosed herein can comprise a nucleic acid encoding an agent which inhibits at least one bacterial gene involved in the development of antibiotic resistance. In another embodiment of this aspect and all aspects described herein, an engineered bacteriophage can comprise a nucleic acid encoding an agent which inhibits at least one gene involved in bacterial cell survival repair. As discussed previously, such engineered bacteriophages which comprise a nucleic acid encoding an agent which inhibits at least one bacterial gene involved in antibiotic resistance and/or at least one bacterial gene involved in cell survival are referred to herein as "inhibitor-engineered bacteriophages". In some embodiments of this aspect and all aspects discussed herein, an agent which inhibits an antibiotic resistance bacterial gene can inhibit the gene expression and/or protein function of antibiotic resistance genes such as, but not limited to, cat, vanA or mecD. In some embodiments of this aspect and all aspects discussed herein, an agent which inhibits a bacterial cell survival gene can inhibit the gene expression and/or protein function of a cell survival repair gene such as, but not limited to RecA, RecB, RecC, Spot or RelA.

In some embodiments of this aspect and all aspects described herein, an inhibitor-engineered bacteriophage can comprise a nucleic acid encoding an agent which inhibits at least one gene involved in antibiotic resistance and/or cell survival repair. In one embodiment of this aspect and all aspect described herein, an inhibitor-engineered bacteriophage can comprise at least 2, 3, 4, 5 or even more, for example 10 different nucleic acids which inhibit at least one gene, for example, 2, 3, 4, 5 or up to 10 genes involved in antibiotic resistance and/or cell survival repair. In some embodiment of this aspect, an inhibitor-engineered bacteriophage can comprise at least 2, 3, 4, 5 or more, for example 8 different nucleic acids encoding inhibitors to at least one antibiotic resistance gene or to at least one cell survival repair gene, such as at least 2, 3, 4, 5 or more selected from the group, but not limited to, cat, vanA, mecD, RecA, RecB, RecC, Spot or RelA and other antibiotic resistance genes or cell survival repair genes. In some embodiments, any or all different combinations of inhibitors of antibiotic resistance genes and/or cell survival repair genes can be present in an inhibitor-engineered bacteriophage.

In another aspect of the present invention, an engineered bacteriophage can comprise at least one nucleic acid encoding a repressor protein, or fragment thereof of a bacterial SOS response gene, or an agent (such as a protein) which inhibits a non-SOS pathway bacterial defense gene and are referred to herein as "repressor-engineered bacteriophages." In some embodiments, the repressor of an SOS response gene is, for example but not limited to, lexA, or modified version thereof. In some embodiments, the SOS response gene is, for example but is not limited to marRAB, arcAB and lexO. In some embodiments of this aspect and all other aspects described herein, an inhibitor of a non-SOS pathway bacterial defense gene can be any agent, such as but not limited to a protein or an RNAi agent, such as antisense to a non-SOS gene such as, for example but not limited to soxR, or modified version thereof. In some embodiments of this aspect and all other aspects described herein, an repressor, such as an agent which inhibits a non-SOS pathway bacterial defense gene inhibits, for example genes selected from the group of: marR, arc, soxR, fur, crp, icdA or craA or ompA or modified version thereof. In other embodiments of this aspect of the invention, a nucleic acid of a repressor engineered bacteriophage is an agent which inhibits a non-SOS defense gene, for example the repressor agent can inhibit any gene, or any combination of genes listed in Table 2. In some embodiments, a repressor-engineered bacteriophage which inhibits a non-SOS defense gene can be used in combination with selected antimicrobial agents, for example, where the repressor-engineered bacteriophage encodes an agent which inhibits a gene listed in Table 2A, such a repressor-engineered bacteriophage can be used in combination with a ciprofloxacin antimicrobial agent or a variant or analogue thereof. Similarly, in other embodiments a repressor-engineered bacteriophage which inhibits a non-SOS defense gene can encode an agent which inhibits a gene listed in Table 4B can be used in combination with a vancomycin antimicrobial agent or a variant or analogue thereof. Similarly, in other embodiments a repressor-engineered bacteriophage which inhibits a non-SOS defense gene can encode an agent which inhibits a gene listed in Table 2C, 2D, 2E, 2F and 2G can be used in combination with a rifampicin antimicrobial agent, or a ampicillin antimicrobial agent or a sulfmethaxazone antimicrobial agent or a gentamicin antimicrobial agent or a metronidazole antimicrobial agent, respectively, or a variant or analogue thereof.

In some embodiments of this aspect an all other aspects discussed herein, a repressor is, for example but not limited to, lexA, marR, arc, soxR, fur, crp, icdA, craA or ompA or a modified version thereof. In some embodiments, the SOS response gene is, for example but is not limited to marRAB, arcAB and lexO.

In some embodiments of this aspect and all other aspects described herein, a repressor-engineered bacteriophage can comprise at least 2, 3, 4, 5 or more, for example 8 different nucleic acids encoding different repressors of SOS response genes, such as at least 2, 3, 4, 5 or more selected from the group, but not limited to, lexA, marRAB, arcAB and lexO and other repressors of SOS response genes, or least 2, 3, 4, 5 or more, for example 8 different nucleic acids encoding different repressors (i.e. inhibitors) of non-SOS defense genes. In some embodiments, a repressor engineered bacteriophage can comprise any or all different combinations of repressors of SOS genes described herein and/or any and all different combinations of inhibitors non-SOS defense genes listed in Tables 2 and 2A-2G can be present in a repressor-engineered bacteriophage.

In another aspect of the present invention, an engineered bacteriophage can comprise at least one nucleic acid encoding an agent, such as but not limited to a protein, which increases the susceptibility of a bacteria to an antimicrobial agent. Such herein engineered bacteriophage which comprises a nucleic acid encoding an agent which increases the susceptibility of a bacteria to an antimicrobial agent can be referred to herein as an "susceptibility agent-engineered bacteriophage" but are also encompassed under the definition of a "repressor-engineered bacteriophage" In some embodiments of this aspect, and all other aspects described herein, such an agent which increases the susceptibility of a bacteria to an antimicrobial agent is referred to as a "susceptibility agent" and refers to any agent which increases the bacteria's susceptibility to the antimicrobial agent by at least about 10% or at least about 15%, or at least about 20% or at least about 30% or at least about 50% or more than 50%, or any integer between 10% and 50% or more, as compared to the use of the antimicrobial agent alone. In one embodiment, a susceptibility agent is an agent which specifically targets a bacteria cell. In another embodiment, a susceptibility agent modifies (i.e. inhibits or activates) a pathway which is specifically expressed in bacterial cells. In one embodiment, a susceptibility agent is an agent which has an additive effect of the efficacy of the antimicrobial agent (i.e. the agent has an additive effect of the killing efficacy or inhibition of growth by the antimicrobial agent). In a preferred embodiment, a susceptibility agent is an agent which has a synergistic effect on the efficacy of the antimicrobial agent (i.e. the agent has a synergistic effect of the killing efficacy or inhibition of growth by the antimicrobial agent).

Accordingly, another aspect of the invention relates to the use of an inhibitor-engineered bacteriophage and/or a repressor-engineered bacteriophage and/or a susceptibility-engineered bacteriophage to potentiate the killing effect of antimicrobial agents or stated another way, to enhance the efficacy of antimicrobial agents. An inhibitor-engineered bacteriophages and/or a repressor engineered bacteriophage and/or a susceptibility-engineered bacteriophage is considered to potentiate the effectiveness of an antimicrobial agent if the amount of antimicrobial agent used in combination with an engineered bacteriophage as disclosed herein is reduced by at least about 10% without adversely affecting the result, for example, without adversely effecting the level of antimicrobial activity. In another embodiment, the criteria used to select an inhibitor-engineered bacteriophage and/or a repressor engineered bacteriophage and/or a susceptibility-engineered bacteriophage that potentiates the activity of an antimicrobial agent is a reduction of at least about 10%, . . . or at least about 15%, . . . or at least about 20%, . . . or at least about 25%, . . . or at least about 35%, . . . or at least about 50%, . . . or at least about 60%, . . . or at least about 90% and all integers in between 10-90% of the amount of the antimicrobial agent without adversely effecting the antimicrobial effect when compared to the similar amount without the addition of an inhibitor-engineered bacteriophage and/or repressor engineered bacteriophage and/or a susceptibility-engineered bacteriophage. Stated another way, an inhibitor-engineered bacteriophage and/or repressor engineered bacteriophage and/or a susceptibility-engineered bacteriophage is effective as an adjuvant to an antimicrobial agent when the combination of the antimicrobial agent and the engineered bacteriophage results in about the same level (i.e. within about 10%) of antimicrobial effect at reducing the bacterial infection or killing the bacteria with the reduction in the dose (i.e. the amount) of the antimicrobial agent. Such a reduction in antimicrobial dose can be, for example by about 10%, or about 15%, . . . or about 20%, . . . or about 25%, . . . or about 35%, . . . or about 50%, . . . or about 60%, . . . or more than 60% with the same level of antimicrobial efficacy.

The inventors herein have demonstrated that the engineered bacteriophage can target gene networks that are not directly attacked by antibiotics and by doing so, greatly enhanced the efficacy of antibiotic treatment in bacteria, such as *Escherichia coli*. The inventors demonstrated that suppressing or inhibiting the bacterial SOS response network with a repressor-engineered bacteriophage can enhance killing by an antimicrobial agent such as an antibiotic, for example but not limited to, ofloxacin, a quinolone drug, by over 2.7 orders of magnitude as compared with a control bacteriophage (i.e. non-engineered bacteriophages) plus ofloxacin, and over 4.5 orders of magnitude compared with ofloxacin alone.

The inventors have also demonstrated herein in Examples 6-8 that a repressor-engineered bacteriophage, which comprises at least one inhibitor to one or more non-SOS genetic networks are also effective antibiotic adjuvants. The inventors also demonstrated that repressor-engineered bacteriophage and/or inhibitor-engineered bacteriophage can reduce the number of antibiotic-resistant bacteria in a population and act as a strong adjuvant for a variety of other bactericidal antibiotics, such as for example, but not limited to gentamicin and ampicillin Thus, the inventors have demonstrated that by selectively targeting gene networks with bacteriophage, one can enhance killing by antibiotics, thus discovering a highly effective new antimicrobial strategy.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

As used herein, the term "adjuvant" as used herein refers to an agent which enhances the pharmaceutical effect of another agent. As used herein, the bacteriophages as disclosed herein function as adjuvants to antimicrobial agents, such as, but not limited to antibiotic agents, by enhancing the effect of the antimicrobial agents by at least . . . 5%, . . . at least 10%, . . . at least 15%, . . . at least 20%, . . . at least 25%, . . . at least 35%, . . . at least 50%, . . . at least 60%, . . . at least 90% and all amounts in-between as compared to use of the antimicrobial agent alone. Accordingly, the engineered bacteriophages as disclosed herein, such as the inhibitor-engineered bacteriophage and/or repressor engineered bacteriophage function as antimicrobial agent adjuvants.

As used herein, the term "inhibitor-engineered bacteriophage" refers to a bacteriophage that have been genetically engineered to comprise a nucleic acid which encodes an agent which inhibits at least one gene involved in antibiotic resistance and/or cell survival. Such engineered bacteriophages as disclosed herein are termed "inhibitor-engineered bacteriophages" as they comprise a nucleic acid which encodes at least one inhibitor genes, such as but not limited to antibiotic resistance genes such as, but not limited to cat, vanA or mecD, or cell survival repair gene such as, but not limited to RecA, RecB, RecC, Spot or RelA. Naturally, one can engineer a bacteriophage to comprise at least one nucleic acid which encodes more than one inhibitor, for example, two or more inhibitors to the same gene or to at least two different genes which can be used in the methods and compositions as disclosed herein.

As used herein, the term "repressor-engineered bacteriophage" refers to bacteriophages that have been genetically engineered to comprise at least one nucleic acid which encodes a repressor protein, or fragment thereof, where the repressor protein function to prevent activation of a gene involved in a SOS response. Alternatively, the term repressor-engineered bacteriophage refers to a bacteriophage which has been genetically engineered to comprise at least one nucleic acid which encodes a repressor protein, such as an inhibitors (including but not limited to RNAi agents) which inhibits a non-SOS bacterial defense. Such engineered bacteriophages as disclosed herein are referred to herein as "repressor-engineered bacteriophages" as they comprise a nucleic acid encoding a repressor protein, for example, but not limited to, lexA, or soxR, or modified version thereof. In some embodiments, a SOS response gene is, for example but is not limited to marRAB, arcAB and lexO. One can engineer a repressor-engineered bacteriophage to comprise at least one nucleic acid which encodes more than one repressor, for example at least 2, 3, 4 or more repressors to the same or different SOS response gene, in any combination, can be used in the methods and compositions as disclosed herein. Similarly, one can also engineer a repressor-engineered bacteriophage to comprise at least one nucleic acid which encodes more than one repressor, for example at least 2, 3, 4 or more repressors, such as inhibitors which inhibits any number and any combination of non-SOS bacterial defense genes listed in Table 2, and can be used in any combination, can be used in the methods and compositions as disclosed herein. The term "repressor-engineered bacteriophage" also encompasses susceptibility-engineered bacteriophages as that term is defined herein.

As used herein, the term "susceptibility-engineered bacteriophage" refers to a bacteriophage that has been genetically engineered to comprise at least one nucleic acid which encodes at least one agent which increases the susceptibility of a bacterial cell to an antimicrobial agent. An agent which increases the susceptibility of a bacteria to an antimicrobial agent is referred to herein as a "susceptibility agent" and includes any agent (such as a protein or RNAi agent) which increases the bacteria's susceptibility to the antimicrobial agent by at least about 10% or at least about 15%, or at least about 20% or at least about 30% or at least about 50% or more than 50%, or any integer between 10% and 50% or more, as compared to the use of the antimicrobial agent alone. In one embodiment, a susceptibility agent is an agent which specifically targets a bacteria cell. In another embodiment, a susceptibility agent modifies (i.e. inhibits or activates) a pathway which is specifically expressed in bacterial cells. In one embodiment, a susceptibility agent is an agent which has an additive effect of the efficacy of the antimicrobial agent (i.e. the agent has an additive effect of the killing efficacy or inhibition of growth by the antimicrobial agent). In a preferred embodiment, a susceptibility agent is an agent which has a synergistic effect on the efficacy of the antimicrobial agent (i.e. the agent has a synergistic effect of the killing efficacy or inhibition of growth by the antimicrobial agent).

The term "engineered bacteriophage" as used herein refer to any one, or a combination of an inhibitor-engineered bacteriophage or a repressor-engineered bacteriophage or a susceptibility-engineered bacteriophage as these phrases are defined herein.

The term "additive" when used in reference to a susceptibility agent, or an engineered bacteriophage such as an susceptibility-bacteriophage having an additive effect of the efficacy of the antimicrobial agent refers to refers to a total increase in antimicrobial efficacy (i e killing, or reducing the viability of a bacterial population or inhibiting growth of a bacterial population) with the combination of the antimicrobial agent and the susceptibility-engineered bacteriophage components of the invention, over their single efficacy of each component alone. An additive effect to increase total antimicrobial effectiveness can be a result of an increase in antimicrobial effect of both components (i.e. the antimicrobial agent and the susceptibility-engineered bacteriophage) or alternatively, it can be the result of the increase in activity of only one of the components (i.e. the antimicrobial agent or the susceptibility-engineered bacteriophage). For clarification by way of a non-limiting illustrative example of a additive effect, if an antimicrobial agent is effective at reducing a bacterial population by 30%, and a susceptibility-engineered bacteriophage was effective at reducing a bacterial population by 20%, an additive effect of a combination of the antimicrobial agent and the susceptibility-engineered bacteriophage could be, for example 35%. Stated another way, in this example, any total effect greater than 30% (i.e. greater than the highest antimicrobial efficacy (i.e. 30% which, in this example is displayed by the antimicrobial agent) would be indicative of an additive effect. In some embodiments of the present invention, the antimicrobial agent and susceptibility-engineered bacteriophage component show at least some additive anti-pathogenic activity. An additive effect of the combination of an antimicrobial agent with an engineered bacteriophage can be an increase in at least about 10% or at least about 20% or at least about 30% or at least about 40% or at least about 50% or more anti-pathogenic (or antimicrobial) efficacy as compared to the highest antimicrobial effect achieved with either the antimicrobial agent alone or the engineered bacteriophage alone.

The term "synergy" or "synergistically" are used interchangeably herein, and when used in reference to a susceptibility agent, or an engineered bacteriophage such as an susceptibility-bacteriophage having a synergistic effect of the efficacy of the antimicrobial agent refers to a total increase in antimicrobial efficacy (i.e. killing, or reducing the viability of a bacterial population or inhibiting growth of a bacterial population) with the combination of the antimicrobial agent and the susceptibility-engineered bacteriophage components of the invention, over their single and/or additive efficacy of each component alone. A synergistic effect to increase total antimicrobial effectiveness can be a result of an increase in antimicrobial effect of both components (i.e. the antimicrobial agent and the susceptibility-engineered bacteriophage) or alternatively, it can be the result of the increase in activity of only one of the components (i.e. the antimicrobial agent or the susceptibility-engineered bacteriophage). For clarification by way of a non-limiting illustrative example of a synergistic effect, if an antimicrobial agent is effective at reducing (i.e. killing) a bacterial population by 15%, and a susceptibility-engineered bacteriophage was effective at reducing a bacterial population by 10%, a synergistic effect of a combination of the antimicrobial agent and the susceptibility-engineered bacteriophage could be 50%. Stated another way, in this example, any total effect greater than 25% (i.e. greater than the sum of the antibacterial agent alone (i.e. 15%) and the susceptibility agent alone (i.e. 10%) would be indicative of a synergistic effect. In some embodiments of the present invention, the antimicrobial agent and susceptibility-engineered bacteriophage component show at least some synergistic antipathogenic activity. A synergistic effect of the combination of an antimicrobial agent with an engineered bacteriophage can be an increase in at least about 10% or at least about 20% or at least about 30% or at least about 40% or at least about 50% or more anti-pathogenic (or antimicrobial) efficacy as compared to the sum of the antimicrobial effect achieved with use of the antimicrobial agent alone or the engineered bacteriophage alone.

The term "bidirectional synergy" refers to the increase in activity of each component (i.e. the antimicrobial agent and the engineered bacteriophage) when used in combination with each other, and not merely an increase in activity of one of the antimicrobial components. In some embodiments, an antimicrobial agent and engineered bacteriophage show at least synergistic antimicrobial activity. In some embodiments, an antimicrobial agent and engineered bacteriophage show bidirectional synergistic antimicrobial activity. Stated in other words, for example, bidirectional synergy means an engineered bacteriophage enhances the activity of an antimicrobial agent and vice versa, an antimicrobial agent can be used to enhance the activity of the engineered bacteriophage.

The term "SOS" used in the context of "SOS response" or "SOS response genes" as used herein refers to an inducible DNA repair system that allows bacteria to survive sudden increases in DNA damage. SOS response genes are repressed to differ rent degrees under normal growth conditions. Without being bound by theory, the SOS response is a postreplication DNA repair system that allows DNA replication to bypass lesions or errors in the DNA. One example is the SOS repressor RecA protein. The RecA protein, stimulated by single-stranded DNA, is involved in the inactivation of the LexA repressor thereby inducing the response. The bacterial SOS response, studied extensively in *Escherichia coli*, is a global response to DNA damage in which the cell cycle is arrested and DNA repair and mutagenesis are induced. SOS is the prototypic cell cycle check-point control and DNA repair system. A central part of the SOS response is the de-repression of more than 20 genes under the direct and indirect transcriptional control of the LexA repressor. The LexA regulon includes recombination and repair genes recA, recN, and ruvAB, nucleotide excision repair genes uvrAB and uvrD, the error-prone DNA polymerase (pol) genes dinB (encoding pol IV) and umuDC (encoding pol V), and DNA polymerase II in addition to many other genes functions. In the absence of a functional SOS response (i.e. in the presence of repressors as disclosed herein), cells are sensitive to DNA damaging agents. McKenzie et al., PNAS, 2000; 6646-6651; Michel, PLos Biology, 2005; 3; e255, and which are incorporated in their entirety herein by reference. A "non-SOS gene" also includes a "bacterial defense gene" and refers to genes expressed by a bacteria or a microorganism which serve protect the bacteria or microorganism from cell death, for example from being killed or growth suppressed by an antimicrobial agent. Typically, inhibition or knocking out such non-SOS defense genes increases the susceptibility of a microorganism such as bacteria to an antimicrobial agent. A non-SOS gene" or "bacterial defense gene" is not part of the SOS-response network, but still serve as protective functions to prevent microorganism cell death. In certain conditions, some non-SOS genes and/or bacterial defense genes can be expressed (i.e. upregulated) on DNA damage or in stressful conditions. Examples of a non-SOS gene is soxS, which is repressed by soxR, and examples of defense genes are any gene listed in Table 2.

The term "repressor" as used herein, refers to a protein that binds to an operator of a gene preventing the transcription of the gene. Accordingly, a repressor can effectively "suppress" or inhibit the transcription of a gene. The binding affinity of repressors for the operator can be affected by other molecules, such as inducers, which bind to repressors and decrease their binding to the operator, while co-repressors increase the binding. The paradigm of repressor proteins is the lactose repressor protein that acts on the lac operon and for which the inducers are β- galactosides such as lactose, it is a polypeptide of 360 amino acids that is active as a tetramer. Other examples are the lambda repressor protein of lambda bacteriophage that prevents the transcription of the genes required for the lytic cycle leading to lysogeny and the cro protein, also of lambda, which represses the transcription of the lambda repressor protein establishing the lytic cycle. Both of these are active as dimers and have a common structural feature the helix turn helix motif that is thought to bind to DNA with the helices fitting into adjacent major grooves. Useful repressors according to the present invention include, but are not limited to lexA, marR, arc, soxR, fur, crp, icdA, or craA or modified version thereof.

The term "antimicrobial agent" as used herein refers to any entity with antimicrobial activity, i.e. the ability to inhibit the growth and/or kill bacterium, for example gram positive- and gram negative bacteria. An antimicrobial agent is any agent which results in inhibition of growth or reduction of viability of a bacteria by at least about 30% or at least about 40%, or at least about 50% or at least about 60% or at least about 70% or more than 70%, or any integer between 30% and 70% or more, as compared to in the absence of the antimicrobial agent. Stated another way, an antimicrobial agent is any agent which reduces a population of antimicrobial cells, such as bacteria by at least about 30% or at least about 40%, or at least about 50% or at least about 60% or at least about 70% or more than 70%, or any integer between 30% and 70% as compared to in the absence of the antimicrobial agent. In one embodiment, an antimicrobial agent is an agent which specifically targets a bacteria cell. In another embodiment, an antimicrobial agent modifies (i.e. inhibits or activates or increases) a pathway which is specifically expressed in bacterial cells. In some embodiments, an antimicrobial agent does not include the following agents; chemotherapeutic agent, a toxin protein expressed by a bacteria or other microorganism (i.e. a bacterial toxin protein) and the like. An antimicrobial agent can include any chemical, peptide (i.e. an antimicrobial peptide), peptidomimetic, entity or moiety, or analogues of hybrids thereof, including without limitation synthetic and naturally occurring non-proteinaceous entities. In some embodiments, an antimicrobial agent is a small molecule having a chemical moiety. For example, chemical moieties include unsubstituted or substituted alkyl, aromatic or heterocyclyl moieties including macrolides, leptomycins and related natural products or analogues thereof. Antimicrobial agents can be any entity known to have a desired activity and/or property, or can be selected from a library of diverse compounds.

The term "agent" as used herein and throughout the application is intended to refer to any means such as an organic or inorganic molecule, including modified and unmodified nucleic acids such as antisense nucleic acids, RNAi, such as siRNA or shRNA, peptides, peptidomimetics, receptors, ligands, and antibodies, aptamers, polypeptides, nucleic acid analogues or variants thereof.

The term "antimicrobial peptide" as used herein refers to any peptides with antimicrobial activity, i.e. the ability to inhibit the growth and/or kill bacterium, for example gram positive- and gram negative bacteria. The term antimicrobial peptides encompasses all peptides that have antimicrobial activity, and are typically, for example but not limited to, short proteins, generally between 12 and 50 amino acids long, however larger proteins with such as, for example lysozymes are also encompassed as antimicrobial peptides in the present invention. Also included in the term antimicrobial peptide are antimicrobial peptidomimetics, and analogues or fragments thereof. The term "antimicrobial peptide" also includes all cyclic and non-cyclic antimicrobial peptides, or derivatives or variants thereof, including tautomers, see Li et al. JACS, 2006, 128: 5776-85 and world-wide-web at //aps.unmc.edu, at /AP/main.php for examples, which are incorporated herein in their entirety by reference. In some embodiments, the antimicrobial peptide is a lipopeptide, and in some embodiments the lipopeptide is a cyclic lipopeptide. The lipopeptides include, for example but not limited to, the polymyxin class of antimicrobial peptides.

The term "microorganism" includes any microscopic organism or taxonomically related macroscopic organism within the categories algae, bacteria, fungi, yeast and protozoa or the like. It includes susceptible and resistant microorganisms, as well as recombinant microorganisms. Examples of infections produced by such microorganisms are provided herein. In one aspect of the invention, the antimicrobial agents and enhancers thereof are used to target microorganisms in order to prevent and/or inhibit their growth, and/or for their use in the treatment and/or prophylaxis of an infection caused by the microorganism, for example multi-drug resistant microorganisms and gram-negative microorganisms. In some embodiments, gram-negative microorganisms are also targeted.

The anti-pathogenic aspects of the invention target the broader class of "microorganism" as defined herein. However, given that a multi-drug resistant microorganism is so difficult to treat, the antimicrobial agent and inhibitor-engineered bacteriophage and/or repressor-engineered bacteriophage in the context of the anti-pathogenic aspect of the invention is suited to treating all microorganisms, including for example multi-drug resistant microorganisms, such as bacterium and multi-drug resistant bacteria.

Unless stated otherwise, in the context of this specification, the use of the term "microorganism" alone is not limited to "multi-drug resistant organism", and encompasses both drug-susceptible and drug-resistant microorganisms. The term "multi-drug resistant microorganism" refers to those organisms that are, at the very least, resistant to more than two antimicrobial agents such as antibiotics in different antibiotic classes. This includes those microorganisms that have more resistance than those that are resistant to three or more antibiotics in a single antibiotic class. This also includes microorganisms that are resistant to a wider range of antibiotics, i.e. microorganisms that are resistant to one or more classes of antibiotics.

The term "persistent cell" or "persisters" are used interchangeably herein and refer to a metabolically dormant subpopulation of microorganisms, typically bacteria, which are not sensitive to antimicrobial agents such as antibiotics. Persisters typically are not responsive (i.e. are not killed by the antibiotics) as they have non-lethally downregulated the pathways on which the antimicrobial agents act i.e. the persister cells have down regulated the pathways which are normally inhibited or corrupted by the antimicrobial agents, such as the transcription, translation, DNA replication and cell wall biosynthesis pathways. Persisters can develop at non-lethal (or sub-lethal) concentrations of the antimicrobial agent.

The term "analog" as used herein refers to a composition that retains the same structure or function (e.g., binding to a receptor) as a polypeptide or nucleic acid herein. Examples of analogs include peptidomimetics, peptide nucleic acids, small and large organic or inorganic compounds, as well as derivatives and variants of a polypeptide or nucleic acid herein. The term "analog" as used herein refers to a composition that retains the same structure or function (e.g., binding to a receptor) as a polypeptide or nucleic acid herein.

The term "infection" or "microbial infection" which are used interchangeably herein refers to in its broadest sense, any infection caused by a microorganism and includes bacterial infections, fungal infections, yeast infections and protozomal infections.

The term "treatment and/prophylaxis" refers generally to afflicting a subject, tissue or cell to obtain a desired pharmacologic arid/or physiologic effect, which in the case of the methods of this invention, include reduction or elimination of microbial infections or prevention of microbial infections. The methods as disclosed herein can be used prophylactically for example in instances where an individual is susceptible for infections or re-infection with a particular bacterial strain or a combination of such strains. For example, microbial infections such as bacterial infections such as biofilms can occur on any surface where sufficient moisture and nutrients are present. One such surface is the surface of implanted medical devices, such as catheters, heart valves and joint replacements. In particular, catheters are associated with infection by many biofilm forming organisms such as *Staphylococcus epidermidis, Staphylococcus aureus, Pseudomonas aeruginosa, Enterococcus faecalis* and *Candida albicans* which frequently result in generalized blood stream infection. In a subject identified to have a catheter infected with bacterial, such as for example, a bacterial infected central venous catheter (CVC), the subject can have the infected catheter removed and can be treated by the methods and compositions as disclosed herein comprising an engineered bacteriophage and antimicrobial agent to eliminate the bacterial infection. Furthermore, on removal of the infected catheter and its replacement with a new catheter, the subject can also be administered the compositions comprising engineered bacteriophages and antimicrobial agents as disclosed herein on a prophylaxis basis to prevent re-infection or the re-occurrence of the bacterial infection. Alternatively, a subject can be administered the compositions as disclosed herein comprising engineered bacteriophages and antimicrobial agents on a prophylaxis basis on initial placement of the catheter to prevent any antimicrobial infection such as a bacterial biofilm infection. The effect can be prophylactic in terms of completely or partially preventing a disease or sign or symptom thereof, and/or can be therapeutic in terms of a partial or complete cure of a disease.

As used herein, the term "effective amount" is meant an amount of antimicrobial agent and/or inhibitor-engineered bacteriophages or repressor-engineered bacteriophages effective to yield a desired decrease in bacteria or increase to increase the efficacy of antimicrobial agent as compared to the activity of the antimicrobial agent alone (i.e. without the engineered bacteriophages as disclosed herein). The term "effective amount" as used herein refers to that amount of composition necessary to achieve the indicated effect, i.e. a reduction of the number of viable microorganisms, such as bacteria, by at reduction of least 5%, at least 10%, by at least 20%, by at least 30% . . . at least 35%, . . . at least 50%, . . . at least 60%, . . . at least 90% or any reduction of viable microorganism in between. As used herein, the effective amount of the bacteriophage as disclosed herein is the amount sufficient to enhance the effect of the antimicrobial agents by at least . . . 5%, at least 10%, . . . at least 15%, . . . at least 20%, . . . at least 25%, . . . at least 35%, . . . at least 50%, . . . at least 60%, . . . at least 90% and all amounts in-between as compared to use of the antimicrobial agent alone. Or alternatively result in the same efficacy of the antimicrobial effect with less (i.e. for example by about 10%, or about 15%, . . . or about 20%, . . . or about 25%, . . . or about 35%, . . . or about 50%, . . . or about 60%, . . . or more than 60% less) amount or dose of the antimicrobial agents as compared to its use alone to achieve the same efficacy of antimicrobial effect. The "effective amount" or "effective dose" will, obviously, vary with such factors, in particular, the strain of bacteria being treated, the strain of bacteriophage being used, the genetic modification of the bacteriophage being used, the antimicrobial agent, as well as the particular condition being treated, the physical condition of the subject, the type of subject being treated, the duration of the treatment, the route of administration, the type of antimicrobial agent and/or enhancer of antimicrobial agent, the nature of concurrent therapy (if any), and the specific formulations employed, the ratio of the antimicrobial agent and/or enhancers antimicrobial agent components to each other, the structure of each of these components or their derivatives. The term "effective amount" when used in reference to administration of the compositions comprising an antimicrobial agent and a engineered bacteriophage as disclosed herein to a subject refers to the amount of the compositions—to reduce or stop at least one symptom of the disease or disorder, for example a symptom or disorder of the microorganism infection, such as bacterial infection. For example, an effective amount using the methods as disclosed herein would be considered as the amount sufficient to reduce a symptom of the disease or disorder of the bacterial infection by at least 10%. An effective amount as used herein would also include an amount sufficient to prevent or delay the development of a symptom of the disease, alter the course of a symptom disease (for example but not limited to, slow the progression of a symptom of the disease), or reverse a symptom of the disease.

As used herein, a "pharmaceutical carrier" is a pharmaceutically acceptable solvent, suspending agent or vehicle for delivering the combination of antimicrobial agent and/or inhibitor-engineered bacteriophages or repressor-engineered bacteriophages to the surface infected with bacteria or to a subject. The carrier can be liquid or solid and is selected with the planned manner of administration in mind. Each carrier must be pharmaceutically "acceptable" in the sense of being compatible with other ingredients of the composition and non injurious to the subject.

As used herein, "gene silencing" or "gene silenced" in reference to an activity of in RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein).

As used herein an "siRNA" refers to a nucleic acid that forms a double stranded RNA, which double stranded RNA has the ability to reduce or inhibit expression of a gene or target gene when the siRNA is present or expressed in the same cell as the target gene, for example Lp-PLA$_2$. The double stranded RNA siRNA can be formed by the complementary strands. In one embodiment, a siRNA refers to a nucleic acid that can form a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNA are small RNAs naturally present in the genome which are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116: 281-297), comprises a dsRNA molecule.

The terms "patient", "subject" and "individual" are used interchangeably herein, and refer to an animal, particularly a human, to whom treatment including prophylaxis treatment is provided. The term "subject" as used herein refers to human and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model. Suitable mammals also include members of the orders Primates, Rodentla, Lagomorpha, Cetacea, Homo sapiens, Carnivora, Perissodactyla and Artiodactyla. Members of the orders Perissodactyla and Artiodactyla are included in the invention because of their similar biology and economic importance, for example but not limited to many of the economically important and commercially important animals such as goats, sheep, cattle and pigs have very similar biology and share high degrees of genomic homology.

The term "gene" used herein can be a genomic gene comprising transcriptional and/or translational regulatory sequences and/or a coding region and/or non-translated sequences (e.g., introns, 5'- and 3'-untranslated sequences and regulatory sequences). The coding region of a gene can be a nucleotide sequence coding for an amino acid sequence or a functional RNA, such as tRNA, rRNA, catalytic RNA, siRNA, miRNA and antisense RNA. A gene can also be an mRNA or cDNA corresponding to the coding regions (e.g. exons and miRNA) optionally comprising 5'- or 3' untranslated sequences linked thereto. A gene can also be an amplified nucleic acid molecule produced in vitro comprising all or a part of the coding region and/or 5'- or 3'-untranslated sequences linked thereto.

The term "gene product(s)" as used herein refers to include RNA transcribed from a gene, or a polypeptide encoded by a gene or translated from RNA.

The term "inhibit" or "reduced" or "reduce" or "decrease" as used herein generally means to inhibit or decrease the expression of a gene or the biological function of the protein (i.e. an antibiotic resistance protein) by a statistically significant amount relative to in the absence of an inhibitor. The term "inhibition" or "inhibit" or "reduce" when referring to the activity of an antimicrobial agent or composition as disclosed herein refers to prevention of, or reduction in the rate of growth of the bacteria. Inhibition and/or inhibit when used in the context to refer to an agent that inhibits an antibiotic resistance gene and/or cell survival refers to the prevention or reduction of activity of a gene or gene product, that when inactivated potentiates the activity of an antimicrobial agent. However, for avoidance of doubt, "inhibit" means statistically significant decrease in activity of the biological function of a protein by at least about 10% as compared to in the absence of an inhibitor, for example a decrease by at least about 20%, at least about 30%, at least about 40%, at least about 50%, or least about 60%, at least about 70%, or least about 80%, at least about 90% or more, up to and including a 100% inhibition (i.e. complete absence of an antibiotic resistance gene protein in the presence of an inhibitor), or any decrease in biological activity of the protein (i.e. of an antibiotic resistance gene protein) between 10-100% as compared to a in the absence of an inhibitor.

The terms "activate" or "increased" or "increase" as used in the context of biological activity of a protein (i.e. activation of a SOS response gene) herein generally means an increase in the biological function of the protein (i.e. SOS response protein) by a statically significant amount relative to in a control condition. For the avoidance of doubt, an "increase" of activity, or "activation" of a protein means a statistically significant increase of at least about 10% as compared to the absence of an agonist or activator agent, including an increase of at least about 20%, at least about 30%, at least about 40%, at least about 50%, at least about 60%, at least about 70%, at least about 80%, at least about 90%, at least about 100% or more, including, for example at least 2-fold, at least 3-fold, at least 4-fold, at least 5-fold, at least 10-fold increase or greater as compared to in a control condition.

The term "nucleic acid" or "oligonucleotide" or "polynucleotide" used herein can mean at least two nucleotides covalently linked together. As will be appreciated by those in the art, the depiction of a single strand also defines the sequence of the complementary strand. Thus, a nucleic acid also encompasses the complementary strand of a depicted single strand. As will also be appreciated by those in the art, many variants of a nucleic acid can be used for the same purpose as a given nucleic acid. Thus, a nucleic acid also encompasses substantially identical nucleic acids and complements thereof. As will also be appreciated by those in the art, a single strand provides a probe for a probe that can hybridize to the target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo- nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

A nucleic acid will generally contain phosphodiester bonds, although nucleic acid analogs can be included that can have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog can be located for example at the 5'-end and/or the 3'-end of the nucleic acid molecule. Representative examples of nucleotide analogs can be selected from sugar- or backbone-modified ribonucleotides. It should be noted, however, that also nucleobase-modified ribonucleotides, i.e. ribonucleotides, containing a non naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8- bromo guanosine; deaza nucleotides, e.g. 7 deaza-adenosine; O- and N-alkylated nucleotides, e.g. N6-methyl adenosine are suitable. The 2'OH-group can be replaced by a group selected from H. OR, R. halo, SH, SR, $NH_2$, NHR, $NR_2$ or CN, wherein R is C-C6 alkyl, alkenyl or alkynyl and halo is F, Cl, Br or I. Modifications of the ribose-phosphate backbone can be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs can be made.

As used herein, the terms "administering," and "introducing" are used interchangeably and refer to the placement of the bacteriophages and/or antimicrobial agents as disclosed herein onto the surface colonized by bacteria or into a subject, such as a subject with a bacterial infection or other microorganism infection, by any method or route which results in at least partial localization of the engineered-bacteriophages and/or antimicrobial agents at a desired site. The compositions as disclosed herein can be administered by any appropriate route which results in the effective killing, elimination or control of the growth of the bacteria.

The term "vectors" is used interchangeably with "plasmid" to refer to a nucleic acid molecule capable of transporting another nucleic acid to which it has been linked A vector can be a plasmid, bacteriophage, bacterial artificial chromosome or yeast artificial chromosome. A vector can be a DNA or RNA vector. A vector can be either a self replicating extrachromosomal vector or a vector which integrate into a host genome. Vectors capable of directing the expression of genes and/or nucleic acid sequence to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. Other expression vectors can be used in different embodiments of the invention, for example, but are not limited to, plasmids, episomes, bacteriophages or viral vectors, and such vectors can integrate into the host's genome or replicate autonomously in the particular cell. Other forms of expression vectors known by those skilled in the art which serve the equivalent functions can also be used. Expression vectors comprise expression vectors for stable or transient expression encoding the DNA.

The term "analog" as used herein refers to a composition that retains the same structure or function (e.g., binding to a receptor) as a polypeptide or nucleic acid herein. Examples of analogs include peptidomimetics, peptide nucleic acids, small and large organic or inorganic compounds, as well as derivatives and variants of a polypeptide or nucleic acid herein. The term "analog" as used herein refers to a composition that retains the same structure or function (e.g., binding to a receptor) as a polypeptide or nucleic acid herein.

The term "derivative" or "variant" as used herein refers to a peptide, chemical or nucleic acid that differs from the naturally occurring polypeptide or nucleic acid by one or more amino acid or nucleic acid deletions, additions, substitutions or side-chain modifications. Amino acid substitutions include alterations in which an amino acid is replaced with a different naturally-occurring or a non-conventional amino acid residue. Such substitutions may be classified as "conservative", in which case an amino acid residue contained in a polypeptide is replaced with another naturally occurring amino acid of similar character either in relation to polarity, side chain functionality or size.

Substitutions encompassed by the present invention may also be "non conservative", in which an amino acid residue which is present in a peptide is substituted with an amino acid having different properties, such as naturally-occurring amino acid from a different group (e.g., substituting a charged or hydrophobic amino; acid with alanine), or alternatively, in which a naturally-occurring amino acid is substituted with a non-conventional amino acid. In some embodiments amino acid substitutions are conservative.

The articles "a" and "an" are used herein to refer to one or to more than one (i.e., at least one) of the grammatical object of the article. By way of example, "an element" means one element or more than one element. Thus, in this specification and the appended claims, the singular forms "a," "an," and "the" include plural references unless the context clearly dictates otherwise. Thus, for example, reference to a pharmaceutical composition comprising "an agent" includes reference to two or more agents.

As used herein, the term "comprising" means that other elements can also be present in addition to the defined elements presented. The use of "comprising" indicates inclusion rather than limitation. The term "consisting of" refers to compositions, methods, and respective components thereof as described herein, which are exclusive of any element not recited in that description of the embodiment. As used herein the term "consisting essentially of" refers to those elements required for a given embodiment. The term permits the presence of elements that do not materially affect the basic and novel or functional characteristic(s) of that embodiment of the invention.

Other than in the operating examples, or where otherwise indicated, all numbers expressing quantities of ingredients or reaction conditions used herein should be understood as modified in all instances by the term "about." The term "about" when used in connection with percentages can mean ±1%.

This invention is further illustrated by the following examples which should not be construed as limiting. The contents of all references cited throughout this application, as well as the figures and tables are incorporated herein by reference.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Other features and advantages of the invention will be apparent from the following Detailed Description, the drawings, and the claims.

Inhibitor-engineered Bacteriophages

One aspect of the present invention relates to an engineered bacteriophage which comprise a nucleic acid which encodes an agent which inhibits at least one antibiotic resistance gene or at least one cell survival gene, thereby gene silencing such genes and preventing the development of antibiotic resistance and/or increased cell viability of the bacteria in the presence of the antimicrobial agent. As discussed herein, such engineered bacteriophages which comprise a nucleic acid encoding an agent which inhibits at least one gene involved in antibiotic resistance and/or at least one cell survival gene as disclosed herein are referred to herein as "inhibitor-engineered bacteriophages".

In some embodiments, an inhibitor-engineered bacteriophage can comprise a nucleic acid encoding any type of inhibitor, such as a nucleic acid inhibitor. Nucleic acid inhibitors include, for example but are not limited to antisense nucleic acid inhibitors, oligonucleosides, RNA interference (RNAi) and paired termini (PT) antisense and variants thereof.

In some embodiments of this aspect of the invention, an inhibitor-engineered bacteriophage can encode an agent which inhibits the gene expression and/or protein function of any bacterial antibiotic resistance genes commonly known by persons of ordinary skill in the art, such as, but not limited to cat (SEQ ID NO:1), vanA (SEQ ID NO:2) or mecD (SEQ ID NO:3). In alternative embodiments, an agent can inhibit the gene expression and/or protein function of any bacterial cell survival repair gene commonly known by persons of ordinary skill in the art such as, but not limited to RecA, RecB, RecC, Spot or RelA.

For reference, RecA (recombinase A) can be identified by Accession number: P03017 and Gene ID Seq ID GI:132224.

Table 1 provides the accession numbers and Gene ID numbers for examples of antibiotic resistance genes and cell survival genes which can be inhibited in the methods of the present invention, as well examples of as repressors which one can use in repressor-engineered bacteriophages.

TABLE 1

Gene ID numbers and SEQ ID

| Gene | SEQ ID NO: | Other Aliases: | Annotation | Gene ID: | Other Designations: |
|---|---|---|---|---|---|
| ptsG (cat) | 1 | b1101, CR, ECK1087, JW1087, car, cat, glcA, tgl, umg, umgC | NC_000913.2 (1157092 . . . 1158525) | 945651 | fused glucose-specific PTS enzymes: IIB component/IIC component |
| vanA | 2 | | M97297 | 479085 | Vancomycin-resistant protein |
| mecA | 3 | | X52593 | 46610 | Penicillin binding protein II |
| recA | 4 | b2699, ECK2694, JW2669, lexB, recH, rnmB, srf, tif, umuB, umuR, zab | NC_000913.2 (2820730 . . . 2821791, complement) | 947170 | |
| recB | 5 | b2820, ECK2816, JW2788, ior, rorA | NC_000913.2 (2950483 . . . 2954025, complement) | 947286 | exonuclease V (RecBCD complex), beta subunit |
| recC | 6 | b2822, ECK2818, JW2790 | NC_000913.2 (2957082 . . . 2960450, complement) | 947294 | exonuclease V (RecBCD complex), gamma chain |
| spoT | 7 | b3650, ECK3640, JW3625 | NC_000913.2 (3820423 . . . 3822531) | 948159 | bifunctional (p)ppGpp synthetase II/guanosine-3',5'-bis pyrophosphate 3'-pyrophosphohydrolase |
| relA | 8 | b2784, ECK2778, JW2755, RC | NC_000913.2 (2909439 . . . 2911673, complement) | 947244 | (p)ppGpp synthetase I/GTP pyrophosphokinase |
| lexA | 9 | b4043, ECK4035, JW4003, exrA, recA, spr, tsl, umuA | NC_000913.2 (4255138 . . . 4255746) | 948544 | DNA-binding transcriptional repressor of SOS regulon |
| marR | 10 | b1530, ECK1523, JW5248, cfxB, inaR, soxQ | NC_000913.2 (1617144 . . . 1617578) | 945825 | DNA-binding transcriptional repressor of multiple antibiotic resistance |
| arc | 11 | P22gp18 | NC_002371.2 (14793 . . . 15022) | 1262795 | Arc; transcriptional repressor |
| soxR | 12 | b4063, ECK4055, JW4024, marC | NC_000913.2 (4275492 . . . 4275956) | 948566 | DNA-binding transcriptional dual regulator, Fe—S center for redox-sensing |
| fur | 13 | b0683, ECK0671, JW0669 | NC_000913.2 (709423 . . . 709869, complement) | 945295 | DNA-binding transcriptional dual regulator of siderophore biosynthesis and transport |
| crp | 14 | b3357, ECK3345, JW5702, cap, csm | NC_000913.2 (3484142 . . . 3484774) | 947867 | DNA-binding transcriptional dual regulator |
| icd | 15 | b1136, ECK1122, JW1122, icdA, icdE | NC_000913.2 (1194346 . . . 1195596) | 945702 | e14 prophage; isocitrate dehydrogenase, specific for NADP+ |
| csrA | 16 | b2696, ECK2691, JW2666, zfiA | NC_000913.2 (2816983 . . . 2817168, complement) | 947176 | pleiotropic regulatory protein for carbon source metabolism |
| ompA | 17 | b0957, ECK0948, JW0940, con, tolG, tut | NC_000913.2 (1018236 . . . 1019276, complement) | 945571 | outer membrane protein A (3a; II*; G; d) |

In some embodiments, one can use a modular design strategy in which bacteriophage kill bacteria in a species-specific manner are engineered to express at least one inhibitor of at least one antibiotic gene and/or a cell survival gene, or express at least one repressor of a SOS response gene. For example, in some embodiments, the bacteriophage can express an nucleic acid inhibitor, such as an antisense nucleic acid inhibitor or antisense RNA (asRNA) which inhibits at least one, or at least two or at least three antibiotic genes and/or a cell survival gene, such as, but not limited to cat (SEQ ID NO:1), vanA (SEQ ID NO:2) mecD (SEQ ID NO:3), RecA (SEQ ID NO:4), RecB (SEQ ID NO:5), RecC (SEQ ID NO:6), Spot (SEQ ID NO:7) or RelA (SEQ ID NO:8).

Some aspects of the present invention are directed to use of a inhibitor-engineered bacteriophage as an adjuvants to an antimicrobial agent, where an inhibitor-engineered bacteriophage encodes at least one inhibitor to an antimicrobial or antibacterial resistance gene in the bacteria. Previous uses of antibiotic resistance genes have been used to increase the susceptibility of bacteria to antimicrobial agents. For example, US patent application US2002/0076722 discusses a method of improving susceptibility of bacteria to antibacterial agents by identifying gene loci which decrease the bacterium's susceptibility to antibacterial agents, and identify OftX, WbbL, Slt, and Wza as such loci. However, in contrast to the present application, US2002/0076722 does not teach method to inhibit the loci to increase the bacterial susceptibility to antibacterial agents. Similarly, U.S. Pat. No. 7,125,622 discusses a method to identify bacterial antibiotic resistance genes by analyzing pools of bacterial genomic fragments and selecting those fragments which hybridize or have high homology (using computer assisted in silico methodologies) to numerous known bacterial resistance genes. The U.S. Pat. No. 7,125,622 discloses a number of bacterial resistance genes, including; katG, rpoB, rpsL, ampC, beta-lactamases, aminoglycoside kinases, mexA, mexB, oprM, ermA, carA, ImrA, ereA, vgbA, InvA, mphA, tetA, tetB, pp-cat, vanA, vanH, vanR, vanX, vanY, vanZ, folC, folE, folP, and folk, which are encompassed as targets for the inhibitors in an inhibitor-engineered bacteriophage as discussed herein. However, in contrast to the present application, U.S. Pat. No. 7,125,622 does not teach method to inhibit the bacterial resistance genes using an inhibitor-engineered bacteriophage of the present invention, or their inhibition by such an inhibitor-engineered bacteriophage in combination with an antimicrobial agent. Similarly, International Application WO2008/110840 discusses the use of six different bacteriophages (NCIMB numbers 41174-41179) to increase sensitivity of bacteria to antibiotics. However, WO2008/110840 but does not teach genetically modifying such bacteriophages to inhibit bacterial resistance genes or repressing SOS genes. While there are some reports of modifying bacteriophages to increase their effectiveness of killing bacteria, previous studies have mainly focused on optimizing method to degrade bacteria biofilms, such as, for example introducing a lysase enzyme such as alginate lyse (discussed in International Application WO04/062677); or modifying bacteriophages to inhibit the cell which propagates the bacteriophage, such introducing a KIL gene such as the Holin gene in the bacteriophage (discussed in International Application WO02/034892 and WO04/046319), or introducing bacterial toxin genes such as pGef or ChpBK and Toxin A (discussed in U.S. Pat. No. 6,759,229 and Westwater et al., Antimicrobial agents and Chemotherapy, 2003., 47: 1301-1307). However, unlike the present invention the modified bacteriophages discussed in WO04/062677, WO02/034892, WO04/046319, U.S. Pat. No. 6,759,229 and Westwater et al., have not been modified to target and disable the bacteria's antimicrobial resistance mechanism by inhibiting the bacterial resistance genes or expressing a repressor to a SOS gene.

An inhibitor to any antimicrobial resistance genes known to one or ordinary skill in the art is encompassed for use in the inhibitor-engineered bacteriophages disclosed herein. In addition to the antibiotic resistance genes discussed herein, other such antibiotic resistance genes which can be used include, for example, are katG, rpoB, rpsL, ampC, beta-lactamases, aminoglycoside kinases, mexA, mexB, oprM, ermA, carA, ImrA, ereA, vgbA, InvA, mphA, tetA, tetB, vanH, vanR, vanX, vanY, vanZ, folC, folE, folP, and folk which are disclosed in U.S. Pat. No. 7,125,622, which is incorporated herein in its entity by reference.

Repressor-engineered Bacteriophages

In another aspect of the present invention, an engineered bacteriophage can comprise a nucleic acid encoding a repressor, or fragment thereof, of a SOS response gene or a non-SOS defense gene and as discussed previously, are referred to herein as "repressor-engineered bacteriophages."

In some embodiments of this aspect and all aspects described herein, a repressor-engineered bacteriophage can comprises a nucleic acid encoding a repressor protein, or fragment thereof of a bacterial SOS response gene, or an agent (such as a protein) which inhibits a non-SOS pathway bacterial defense gene.

Without wishing to be limited to theory, the SOS response in bacteria is an inducible DNA repair system which allows bacteria to survive sudden increases in DNA damage. For instance, when bacteria are exposed to stress they produce can defense proteins from genes which are normally in a repressed state and allow repair of damaged DNA and reactivation of DNA synthesis. The SOS response is based upon the paradigm that bacteria play an active role in the mutation of their own genomes by inducing the production of proteins during stressful conditions which facilitate mutations, including Pol II (PolB), Pol IV (dinB) and Pol V (umuD and umuC). Inhibition of these proteins, such as Pol II, Pol IV and Pol V or prevention of their derepression by inhibition of LexA cleavage is one strategy to prevent the development of antibiotic-resistant bacteria. The SOS response is commonly triggered by single-stranded DNA, which accumulates as a result of either DNA damage or problematic replication or on bacteriophage infection. In some situations antibiotics trigger the SOS response, as some antibiotics, such as fluoroquinolones and β-lactams induce antibiotic-mediated DNA damage. The SOS response is discussed in Benedicte Michel, PLos Biology, 2005; 3; 1174-1176; Janion et al., Acta Biochemica Polonica, 2001; 48; 599-610 and Smith et al., 2007, 9; 549-555, and Cirz et al., PLoS Biology, 2005; 6; 1024-1033, and are incorporated herein in their entirety by reference.

In some embodiments, the repressor of an SOS response gene is, for example but not limited to, lexA (SEQ ID NO:9), or modified version thereof. In other embodiments of this aspect of the invention, a SOS response gene is, for example but is not limited to marRAB (SEQ ID NO:18), arcAB (SEQ ID NO:19) and lexO (SEQ ID NO:20).

In some embodiments of this aspect and all other aspects described herein, an inhibitor of a non-SOS pathway bacterial defense gene is soxR (SEQ ID NO: 12), or modified version thereof. In some embodiments of this aspect and all other aspects described herein, an inhibitor of a non-SOS pathway bacterial defense gene is selected from the group of: marR (SEQ ID NO:10), arc (SEQ ID NO:11), soxR (SEQ ID NO:12), fur (SEQ ID NO:13), crp (SEQ ID NO:14), icdA (SEQ ID NO:15), craA (SEQ ID NO:16) or ompA (SEQ ID NO:17) or modified version thereof. In some embodiments, a non-SOS repressor expressed by a repressor-engineered bacteriophage is soxR (SEQ ID NO: 12) which represses soxS and protects against oxidative stress.

In other embodiments of this aspect of the invention, a repressor-engineered bacteriophage can express an repressor, or fragment thereof, of at least one, or at least two or at least three or more SOS response genes, such as, but not limited to lexA, marR, arc, soxR, fur, crp, icdA, craA or ompA. Other repressors known by a skilled artisan are also encompassed for use in repressor-engineered bacteriophages. In some embodiments, repressor-engineered bacteriophages are used in combination with antimicrobial agents which trigger the SOS response, or trigger DNA damage, such as, for example fluoroquinolones, ciprofloxacin and β-lactams.

In other embodiments of this aspect of the invention, an agent encoded by the nucleic acid of a repressor engineered bacteriophage which inhibits a non-SOS defense gene can inhibit any gene listed in Table 2.

TABLE 2

Examples of non-SOS defense genes which can be inhibited by a repressor or an inhibitor expressed by a repressor-engineered bacteriophage.
Table 2: Examples of non-SOS defense genes which can be inhibited by an repressor or inhibitor expressed by a repressor-engineered bacteriophage acrA
acrB
atpA
bdm
BW25113
cedA
cysB
dacA
dapF
dcd
ddlB
dedD
degP
deoT
dinB
dksA
dnaK
elaD
emtA
envC
envZ
fabF
fepC
fis
fkpB
folB
gntY
gor
gpmB
gpmM
gshA
gshB
hflK
hfq
hns
hrpA
hscA
hscB
ihfA
JW5115
JW5360
JW5474
lon
lpdA
lpp
lptB
mrcB
msbB
nagA TABLE 2-continued Examples of non-SOS defense genes which can be inhibited by a repressor or an inhibitor expressed by a repressor-engineered bacteriophage.
Table 2: Examples of non-SOS defense genes which can be inhibited by an repressor or inhibitor expressed by a repressor-engineered bacteriophage nudB
oxyR
pal
pal
pgmB
phoP
plsX
ppiB
prfC
proW
pstA
pstS
qmcA
recA
recB
recC
recG
recN
recO
resA
rfaC
rfaD
rfaE
rfaG
rfaH
rffA
rimK
rluB
rnt
rpe
rpiA
rplI
rpmE
rpmF
rpmJ
rpoN
rpsF
rpsU
rrmJ
rseA
ruvA
ruvC
sapC
secG
skp
smpA
sufI
surA
tatB
tatC
tolC
tolR
tonB
trxA
tusC
tusD
typA
ubiG
uvrA
uvrC
uvrD
xapR
xseA
xseB
ybcN
ybdN
ybeD
ybeY
ybgC
ybgF
ybhT
ybjL
ycbR TABLE 2-continued Examples of non-SOS defense genes which can be inhibited by a repressor or an inhibitor expressed by a repressor-engineered bacteriophage.
Table 2: Examples of non-SOS defense genes which can be inhibited by an repressor or inhibitor expressed by a repressor-engineered bacteriophage yceD
ychJ
yciM
yciS
ydfP
ydhT
ydjI
yfgC
yfgL
yfiH
ygcO
ygdD
yhdP
yidD
yiiU
yjjY
ylcG
ymfI
yneE In some embodiments, a repressor-engineered bacteriophage which inhibits a non-SOS defense gene can be used in combination with selected antimicrobial agents, for example, where the repressor-engineered bacteriophage encodes an agent which inhibits a gene listed in Table 2A, such a repressor-engineered bacteriophage can be used in combination with a ciprofloxacin antimicrobial agent or a variant or analogue thereof. Similarly, in other embodiments a repressor-engineered bacteriophage which inhibits a non-SOS defense gene can encode an agent which inhibits a gene listed in Table 2B can be used in combination with a vancomycin antimicrobial agent or a variant or analogue thereof. Similarly, in other embodiments a repressor-engineered bacteriophage which inhibits a non-SOS defense gene can encode an agent which inhibits a gene listed in Table 2C, 2D, 2E, 2F and 2G can be used in combination with a rifampicin antimicrobial agent, or a ampicillin antimicrobial agent or a sulfmethaxazone antimicrobial agent or a gentamicin antimicrobial agent or a metronidazole antimicrobial agent, respectively, or a variant or analogue thereof. In some embodiments, other non-SOS response genes which can be inhibited or repressed in a repressor-engineered bacteriophage includes, for example, but not limited to genes induced by DNA damage, such as DinD, DinF, DinG, DinI, DinP, OraA, PolB, RecA, RecN, RuvA, RuvB, SbmC, Ssb, SulA, UmuC, UmuD, UvrA, UvrB, and Uvr D, as discussed in Dwyer et al., Mol Systems Biology, 2007; 3; 1-15, which is incorporated herein in its entirety by reference. In another embodiment, other non-SOS response genes which can be inhibited or repressed in a repressor-engineered bacteriophage includes, for example, but not limited to genes induced by oxidative damage, such as MarA, MarB, MarR, SodA and SoxS, as discussed in Dwyer et al., Mol Systems Biology, 2007; 3; 1-15, which is incorporated herein in its entirety by reference.

Susceptibility Agent-engineered Bacteriophages

Another aspect of the present invention relates to an engineered bacteriophage which comprises a nucleic acid encoding an agent, such as but not limited to a protein, which increases the susceptibility of a bacteria to an antimicrobial agent. Such herein engineered bacteriophage which comprises a nucleic acid encoding an agent which increases the susceptibility of a bacteria to an antimicrobial agent can be referred to herein as an "susceptibility agent-engineered bacteriophage" or "susceptibility-engineered bacteriophage" but are also encompassed under the definition of a "repressor-engineered bacteriophage" In some embodiments of this aspect, and all other aspects described herein, such an agent which increases the susceptibility of a bacteria to an antimicrobial agent is referred to as a "susceptibility agent" and refers to any agent which increases the bacteria's susceptibility to the antimicrobial agent by about at least 10% or about at least 15%, or about at least 20% or about at least 30% or about at least 50% or more than 50%, or any integer between 10% and 50% or more, as compared to the use of the antimicrobial agent alone. In one embodiment, a susceptibility agent is an agent which specifically targets a bacteria cell. In another embodiment, a susceptibility agent modifies (i.e. inhibits or activates) a pathway which is specifically expressed in bacterial cells. In one embodiment, a susceptibility agent is an agent which has an additive effect of the efficacy of the antimicrobial agent (i.e. the agent has an additive effect of the killing efficacy or inhibition of growth by the antimicrobial agent). In a preferred embodiment, a susceptibility agent is an agent which has a synergistic effect on the efficacy of the antimicrobial agent (i.e. the agent has a synergistic effect of the killing efficacy or inhibition of growth by the antimicrobial agent).

In one embodiment, a susceptibility agent increases the entry of an antimicrobial agent into a bacterial cell, for example, a susceptibility agent is a porin or porin-like protein, such as but is not limited to, protein OmpF, and Beta barrel porins, or other members of the outer membrane porin (OMP)) functional superfamily which include, but are not limited to those disclosed in world wide web site: "//biocyc.org/ECOLI/NEW-IMAGE?object=BC-4.1.B", or a OMP family member listed in Table 3 as disclosed herein, or a variant or fragment thereof.

TABLE 3

Examples of members of the Outer Membrane Porin (OMP) Superfamily which can be expressed as a susceptibility agent by a susceptibility-agent engineered bacteriophage.
Table 3: Members of The Outer Membrane Porin (OMP) Functional Superfamily bglH (carbohydrate-specific outer membrane porin, cryptic),
btuB (outer membrane receptor for transport of vitamin B12, E colicins, and bacteriophage BF23),
fadL (long-chain fatty acid outer membrane transporter; sensitivity to phage T2),
fecA (outer membrane receptor; citrate-dependent iron transport, outer membrane receptor),
fepA (FepA, outer membrane receptor for ferric enterobactin (enterochelin) and colicins B and D),
fhuA (FhuA outer membrane protein receptor for ferrichrome, colicin M, and phages T1, T5, and phi80),
fhuE (outer membrane receptor for ferric iron uptake),
fiu (putative outer membrane receptor for iron transport),
lamB,
mdtQ (putative channel/filament protein),
ompA (outer membrane protein 3a (II*; G; d)),
ompC,
ompF,
ompG (outer membrane porin OmpG),
ompL (predicted outer membrane porin L),
ompN (outer membrane pore protein N, non-specific),
ompW (OmpW, outer membrane protein),
pgaA (partially N-deacetylated poly-?-1,6-N-acetyl-D-glucosamine outer membrane porin),
phoE
tolB
tolC (TolC outer membrane channel),
tsx (nucleoside channel; receptor of phage T6 and colicin K),
yncD (probable TonB-dependent receptor In another embodiment, a susceptibility agent is an agent, such as but not limited to a protein, which increases iron-sulfur clusters in the bacteria cell and/or increases oxidative stress or hydroxyl radicals in the bacteria. Examples of a susceptibility agent which increases the iron-sulfur clusters include agents which modultate (i.e. increase or decrease) the Fenton reaction to form hydroxyl radicals, as disclosed in Kahanski et al., Cell, 2007, 130; 797-810, which is incorporated herein by reference in its entirety. Examples of a susceptibility agent to be expressed by a susceptibility-engineered bacteriophage include, for example, those listed in Table 4, or a fragment or variant thereof or described in world-wide-web site "biocyc.org/ECOLI/NEW-IMAGE?type=COMPOUND&object=CPD-7". Examples of susceptibility agents which increases iron-sulfur clusters in the bacteria cell include, for example but not limited to IscA, IscR, IscS and IscU. Examples of susceptibility agents which increase iron uptake and utilization and can be used as susceptibility agents include, for example but not limited to EntC, ExbB, ExbD, Fecl, FecR, FepB, FepC, Fes, FhuA, FhuB, FhuC, FhuF, NrdH, Nrdl, SodA and TonB, as discussed in Dwyer et al., Mol Systems Biology, 2007; 3; 1-15, which is incorporated herein in its entirety by reference.

TABLE 4

Examples of genes which can be expressed as a susceptibility agent by a susceptibility-engineered bacteriophage to increase iron cluster formation in bacteria.
Table 4: Example of susceptibility agents which increase iron clusters Cofactor of: serine deaminase, L-serine deaminase, L-serine deaminase, pyruvate formate-lyase activating enzyme, 2,4-dienoyl-CoA reductase
Prosthetic Group of: biotin synthase, dihydroxy-acid dehydratase, dihydroxy-acid dehydratase, lysine 2,3-aminomutase, NADH: ubiquinone oxidoreductase, sulfite reductase-(NADPH), aconitase B, fumarase A, aconitase, fumarase B, anaerobic coproporphyrinogen III oxidase, succinate dehydrogenase, nitrate reductase, flavin reductase, aconitase B, fumarate reductase
Cofactor or Prosthetic Group of: quinolinate synthase, ribonucleoside triphosphate reductase activase, 23S ribosomal RNA 5-methyluridine methyltransferase In some embodiments, a susceptibility agent is an agent such as CsrA, which is described in world-wide web site: "biocyc.org/ECOLI/NEW-IMAGE?type=ENZYME&object=CPLX0-1041.

In some embodiments, a susceptibility agent is not a chemotherapeutic agent. In another embodiment, a susceptibility agent is not a toxin protein, and in another embodiment, a susceptibility agent is not a bacterial toxin protein or molecule.

Modification of Inhibitor-engineered Bacteriophages, Repressor-engineered Bacteriophages and Susceptibility-agent Engineered Bacteriophages In another embodiment, an inhibitor-engineered bacteriophage and/or a repressor-engineered bacteriophage and/or a susceptibility-engineered bacteriophage can be further be modified to comprise nucleic acids which encode phage resistant genes, for example any phage resistant gene known by persons of ordinary skill in the art, such as, but not limited to AbiZ (as disclosed in U.S. Pat. No. 7,169,911 which is incorporated herein by reference), sie$_{2009}$, sie$_{IL409}$, sie$_{F7/24}$, orf2, orf258, orf2(M), olfD, orf304, orfB, orf142, orf203, orf3 ψ, orf2 ψ gp34, gp33, gp32, gp25, glo, orfl, SieA, SieB, imm, sim, rexB (McGrath et al., Mol Microbiol, 2002; 43; 509-520).

In another embodiment, the inhibitor-engineered bacteriophages and/or repressor-engineered bacteriophages and/or a susceptibility-engineered bacteriophage can be further be modified to comprise nucleic acids which encode enzymes which assist in breaking down or degrading the biofilm matrix, for example any phage resistant gene known as a biofilm degrading enzyme by persons of ordinary skill in the art, such as, but not limited to Dispersin D aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, xylanase or lyase. In other embodiments, the enzyme is selected from the group consisting of cellulases, such as glycosyl hydroxylase family of cellulases, such as glycosyl hydroxylase 5 family of enzymes also called cellulase A; polyglucosamine (PGA) depolymerases; and colonic acid depolymerases, such as 1,4-L-fucodise hydrolase (see, e.g., Verhoef R. et al., Characterization of a 1,4-beta-fucoside hydrolase degrading colanic acid, Carbohydr Res. 2005 Aug. 15; 340(11):1780-8), depolymerazing alginase, and DNase I, or combinations thereof, as disclosed in the methods as disclosed in U.S. patent application Ser. No. 11/662,551 and International Patent Application Wo2006/137847 and provisional patent application 61/014,518, which are specifically incorporated herein in their entirety by reference.

In another embodiment, the inhibitor-engineered bacteriophages and/or repressor-engineered bacteriophages and/or a susceptibility-engineered bacteriophage can be further be modified in a species-specific manner, for example, one can modify or select the bacteriophage on the basis for its infectivity of specific bacteria.

A bacteriophage to be engineered or developed into an inhibitor-engineered bacteriophage or repressor-engineered bacteriophage or a susceptibility-engineered bacteriophage can be any bacteriophage as known by a person of ordinary skill in the art. In some embodiments, an inhibitor-engineered bacteriophage or a repressor-engineered bacteriophage or a susceptibility-engineered bacteriophage is derived from any or a combination of bacteriophages listed in Table 5.

In some embodiments, a bacteriophage which is engineered to become an engineered bacteriophage as disclosed herein is a lytic bacteriophage or lysogenic bacteriophage, or any bacteriophage that infects *E. coli*, *P. aeriginosa*, *S. aureaus*, *E. facalis* and the like. Such bacteriophages are well known to one skilled in the art and are listed in Table 5, and include, but are not limited to, lambda phages, M13, T7, T3, and T-even and T-even like phages, such as T2, and T4, and RB69; also phages such as Pfl, Pf4, *Bacteroides fragilis* phage B40-8 and coliphage MS-2 can be used. For example, lambda phage attacks *E. coli* by attaching itself to the outside of the bacteria and injecting its DNA into the bacteria. Once injected into its new host, a bacteriophage uses *E. coli*'s genetic machinery to transcribe its genes. Any of the known phages can be engineered to express an agent that inhibits an antibiotic resistance gene or cell survival gene, or alternatively express a repressor agent or an inhibitor of a non-SOS defense gene for a repressor-engineered bacteriophage, or express a susceptibility agent for a susceptibility-engineered bacteriophage as described herein.

In some embodiments, bacteriophages which have been engineered to be more efficient cloning vectors or naturally lack a gene important in infecting all bacteria, such as male and female bacteria can be used to generate engineered bacteriophages as disclosed herein. Typically, bacteriophages have been engineered to lack genes for infecting all variants and species of bacteria can have reduced capacity to replicate in naturally occurring bacteria thus limiting the use of such phages in degradation of biofilm produced by the naturally occurring bacteria.

For example, the capsid protein of phage T7, gene 10, comes in two forms, the major product 10A (36 kDa) and the minor product 10B (41 kDa) (Condron, B. G., Atkins, J. F., and Gesteland, R. F. 1991. Frameshifting in gene 10 of bacteriophage T7. J. Bacteriol. 173:6998-7003). Capsid protein 10B is produced by frameshifting near the end of the coding region of 10A. NOVAGEN® modified gene 10 in T7 to remove the frameshifting site so that only 10B with the attached user-introduced peptide for surface display is produced (U.S. Pat. No. 5,766,905. 1998. Cytoplasmic bacteriophage display system, which is incorporated in its entirety herein by reference). The 10B-enzyme fusion product is too large to make up the entire phage capsid because the enzymes that are typically introduced into phages, such as T7, are large (greater than a few hundred amino acids). As a result, T7select 10-3b must be grown in host bacterial strains that produce wild-type 10A capsid protein, such as BLT5403 or BLT5615, so that enough 10A is available to be interspersed with the 10B-enzyme fusion product to allow replication of phage (U.S. Pat. No. 5,766,905. 1998. Cytoplasmic bacteriophage display system, which is incorporated in its entirety herein by reference). However, because most biofilm-forming *E. coli* do not produce wild-type 10A capsid protein, this limits the ability of T7select 10-3b displaying large enzymes on their surface to propagate within and lyse some important strains of *E. coli*. Accordingly, in some embodiments, the present invention provides genetically engineered phages that in addition to comprising inhibitors to cell survival genes or antibiotic resistance genes, or nucleic acids encoding repressor proteins, also express all the essential genes for virus replication in naturally occurring bacterial strains. In one embodiment, the invention provides an engineered T7select 10-3b phage that expresses both cellulase and 10A capsid protein.

It is known that wild-type T7 does not productively infect male (F plasmid-containing) *E. coli* because of interactions between the F plasmid protein PifA and T7 genes 1.2 or 10 (Garcia, L. R., and Molineux, I. J. 1995. Incomplete entry of bacteriophage T7 DNA into F plasmid-containing *Escherichia coli*. J. Bacteriol. 177:4077-4083.). F plasmid-containing *E. coli* infected by T7 die but do not lyse or release large numbers of T7 (Garcia, L. R., and Molineux, I. J. 1995. Incomplete entry of bacteriophage T7 DNA into F plasmid-containing *Escherichia coli*. J. Bacteriol. 177:4077-4083). Wild-type T3 grows normally on male cells because of T3's gene 1.2 product (Garcia, L. R., and Molineux, I. J. 1995, Id.). When T3 gene 1.2 is expressed in wild-type T7, T7 is able to productively infect male cells (Garcia, L. R., and Molineux, I. J. 1995. Id).

Because many biofilm-producing *E. coli* contain the F plasmid (Ghigo, et al., 2001. Natural conjugative plasmids induce bacterial biofilm development. Nature. 412:442-445), it is important, although not necessary, for an engineered bacteriophage to be able to productively infect also male cells. Therefore, in addition to engineering the phage to display a biofilm degrading enzyme on its surface, one can also engineer it to express the gene necessary for infecting the male bacteria. For example, one can use the modification described by Garcia and Molineux (Garcia, L. R., and Molineux, I. J. 1995. Incomplete entry of bacteriophage T7 DNA into F plasmid-containing *Escherichia coli*. J. Bacteriol. 177:4077-4083) to express T3 gene 1.2 in T7.

Nucleic Acid Inhibitors of Antibiotic Resistance Genes and/or Cell Survival Genes for Inhibitor-engineered Bacteriophages or Nucleic Acid Inhibitors of Non-SOS Defense Genes in Repressor-engineered Bacteriophages.

In some embodiments of aspects of the invention involving inhibitor-engineered bacteriophages, agents that inhibit an antibiotic resistance gene and/or a cell survival gene is a nucleic acid. In another embodiments, repressor-engineered bacteriophages comprise nucleic acids which inhibit non-SOS defense genes, such as those listed in Table 2, and Tables 2A-2F. An antibiotic resistance gene and/or cell survival gene and/or non-SOS defense gene can be inhibited by inhibition of the expression of such antibiotic resistance proteins and/or cell survival polypeptide or non-SOS defense gene or by "gene silencing" methods commonly known by persons of ordinary skill in the art. A nucleic acid inhibitor of an antibiotic resistance gene and/or a cell survival gene or non-SOS defense gene, includes for example, but is not limited to, RNA interference-inducing (RNAi) molecules, for example but are not limited to siRNA, dsRNA, stRNA, shRNA, miRNA and modified versions thereof, where the RNA interference molecule gene silences the expression of the antibiotic resistance gene and/or cell survival gene non SOS-defense gene. In some embodiments, the nucleic acid inhibitor of an antibiotic resistance gene and/or cell survival gene and/or non-SOS defense gene is an anti-sense oligonucleic acid, or a nucleic acid analogue, for example but are not limited to DNA, RNA, peptide-nucleic acid (PNA), pseudo-complementary PNA (pc-PNA), or locked nucleic acid (LNA) and the like. In alternative embodiments, the nucleic acid is DNA or RNA, and nucleic acid analogues, for example PNA, pcPNA and LNA. A nucleic acid can be single or double stranded, and can be selected from a group comprising nucleic acid encoding a protein of interest, oligonucleotides, PNA, etc. Such nucleic acid inhibitors include for example, but are not limited to, a nucleic acid sequence encoding a protein that is a transcriptional repressor, or an antisense molecule, or a ribozyme, or a small inhibitory nucleic acid sequence such as a RNAi, an shRNAi, an siRNA, a micro RNAi (miRNA), an antisense oligonucleotide etc.

In some embodiments, a nucleic acid inhibitor of an antibiotic resistance gene and/or a cell survival gene and/or non-SOS defense gene can be for example, but are not limited to, paired termini antisense, an example of which is disclosed in FIG. 8 and disclosed in Nakashima, et al., (2006) Nucleic Acids Res 34: e138, which in incorporated herein in its entirety by reference.

In some embodiments of this aspect and all aspects described herein, a single-stranded RNA (ssRNA), a form of RNA endogenously found in eukaryotic cells can be used to form an RNAi molecule. Cellular ssRNA molecules include messenger RNAs (and the progenitor pre-messenger RNAs), small nuclear RNAs, small nucleolar RNAs, transfer RNAs and ribosomal RNAs. Double-stranded RNA (dsRNA) induces a size-dependent immune response such that dsRNA larger than 30 bp activates the interferon response, while shorter dsRNAs feed into the cell's endogenous RNA interference machinery downstream of the Dicer enzyme.

RNA interference (RNAi) provides a powerful approach for inhibiting the expression of selected target polypeptides. RNAi uses small interfering RNA (siRNA) duplexes that target the messenger RNA encoding the target polypeptide for selective degradation. siRNA-dependent post-transcriptional silencing of gene expression involves cutting the target messenger RNA molecule at a site guided by the siRNA.

RNA interference (RNAi) is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) *J. of Virology* 76(18):9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of a target genes, such an antibiotic resistance gene and/or cell survival gene and/or non-SOS defense gene. As used herein, "inhibition of target gene expression" includes any decrease in expression or protein activity or level of the target gene (i.e. antibiotic resistance gene) or protein encoded by the target gene (i.e. antibiotic resistance protein) as compared to the level in the absence of an RNA interference (RNAi) molecule. The decrease in expression or protein level as result of gene silencing can be of at least 30%, 40%, 50%, 60%, 70%, 80%, 90%, 95% or 99% or more as compared to the expression of a target gene or the activity or level of the protein (i.e. expression of the antibiotic resistance gene or antibiotic resistance protein) encoded by a target gene which has not been targeted and gene silenced by an RNA interfering (RNAi) agent.

As used herein, the term "short interfering RNA" (siRNA), also referred to herein as "small interfering RNA" is defined as an agent which functions to inhibit expression of a target gene, e.g., by RNAi. An siRNA can be chemically synthesized, can be produced by in vitro transcription, or can be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and can contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. In some embodiments, the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand can precede the nucleotide loop structure and the antisense strand can follow. These shRNAs can be contained in plasmids, retroviruses, and lentiviruses and expressed from, for example, the pol III U6 promoter, or another promoter (see, e.g., Stewart, et al. (2003) RNA Apr; 9(4):493-501, incorporated by reference herein in its entirety).

Typically a target gene or sequence targeted by gene silencing by an RNA interfering (RNAi) agent can be a cellular gene or genomic sequence encoding an antibiotic resistant protein or a cell survival protein. In some embodiments, an siRNA can be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target.

The siRNA preferably targets only one sequence. Each of the RNA interfering agents, such as siRNAs, can be screened for potential off-target effects by, for example, expression profiling. Such methods are known to one skilled in the art and are described, for example, in Jackson et al, Nature Biotechnology 6:635-637, 2003. In addition to expression profiling, one can also screen the potential target sequences for similar sequences in the sequence databases to identify potential sequences which can have off-target effects. For example, according to Jackson et al. (Id.) 15, or perhaps as few as 11 contiguous nucleotides of sequence identity are sufficient to direct silencing of non-targeted transcripts. Therefore, one can initially screen the proposed siRNAs to avoid potential off-target silencing using the sequence identity analysis by any known sequence comparison methods, such as BLAST (Basic Local Alignment Search Tool available from or at NIBI).

siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. For example, siRNA containing D-arabinofuranosyl structures in place of the naturally-occurring D-ribonucleosides found in RNA can be used in RNAi molecules according to the present invention (U.S. Pat. No. 5,177,196, which is incorporated herein by reference). Other examples include RNA molecules containing the o-linkage between the sugar and the heterocyclic base of the nucleoside, which confers nuclease resistance and tight complementary strand binding to the oligonucleotidesmolecules similar to the oligonucleotides containing 2'-O-methyl ribose, arabinose and particularly D-arabinose (U.S. Pat. No. 5,177,196, which is incorporated herein in its entirety by reference).

The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatized with a variety of groups.

Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases can also be modified. Any modified base useful for inhibiting or interfering with the expression of a target sequence can be used. For example, halogenated bases, such as 5-bromouracil and 5-iodouracil can be incorporated. The bases can also be alkylated, for example, 7-methylguanosine can be incorporated in place of a guanosine residue. Non-natural bases that yield successful inhibition can also be incorporated.

The most preferred siRNA modifications include 2'-deoxy-2'-fluorouridine or locked nucleic acid (LNA) nucleotides and RNA duplexes containing either phosphodiester or varying numbers of phosphorothioate linkages. Such modifications are known to one skilled in the art and are described, for example, in Braasch et al., Biochemistry, 42: 7967-7975, 2003. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA.

siRNA and miRNA molecules having various "tails" covalently attached to either their 3'- or to their 5'-ends, or to both, are also known in the art and can be used to stabilize the siRNA and miRNA molecules delivered using the methods of the present invention. Generally speaking, intercalating groups, various kinds of reporter groups and lipophilic groups attached to the 3' or 5' ends of the RNA molecules are well known to one skilled in the art and are useful according to the methods of the present invention. Descriptions of syntheses of 3'-cholesterol or 3'-acridine modified oligonucleotides applicable to preparation of modified RNA molecules useful according to the present invention can be found, for example, in the articles: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993).

Other siRNAs useful for targeting Lp-PLA$_2$ expression can be readily designed and tested. Accordingly, siRNAs useful for the methods described herein include siRNA molecules of about 15 to about 40 or about 15 to about 28 nucleotides in length. Preferably, the siRNA molecules have a length of about 19 to about 25 nucleotides. More preferably, the siRNA molecules have a length of about 19, 20, 21, or 22 nucleotides. The siRNA molecules can also comprise a 3' hydroxyl group. The siRNA molecules can be single-stranded or double stranded; such molecules can be blunt ended or comprise overhanging ends (e.g., 5', 3'). In specific embodiments, the RNA molecule is double stranded and either blunt ended or comprises overhanging ends.

In one embodiment, at least one strand of the RNA molecule has a 3' overhang from about 0 to about 6 nucleotides (e.g., pyrimidine nucleotides, purine nucleotides) in length. In other embodiments, the 3' overhang is from about 1 to about 5 nucleotides, from about 1 to about 3 nucleotides and from about 2 to about 4 nucleotides in length. In one embodiment the RNA molecule is double stranded—one strand has a 3' overhang and the other strand can be blunt-ended or have an overhang. In the embodiment in which the RNA molecule is double stranded and both strands comprise an overhang, the length of the overhangs can be the same or different for each strand. In a particular embodiment, the RNA of the present invention comprises about 19, 20, 21, or 22 nucleotides which are paired and which have overhangs of from about 1 to about 3, particularly about 2, nucleotides on both 3' ends of the RNA. In one embodiment, the 3' overhangs can be stabilized against degradation. In a preferred embodiment, the RNA is stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

In some embodiments, assessment of the expression and/or knock down of antibiotic resistance gene and/or cell survival gene protein and/or non-SOS defense genes using such RNAi agents such as antisense RNA can be determined by a person of ordinary skill in the art determining the viability of a bacteria expressing such a RNAi agent in the presence of an antimicrobial agent. In some embodiments, bacterial cell viability can be determined by using commercially available kits. Others can be readily prepared by those of skill in the art based on the known sequence of the target mRNA. To avoid doubt, the nucleic acid sequence which can be used to design nucleic acid inhibitors for inhibitor-engineered bacteriophages as disclosed herein can be based on any antibiotic resistance gene or any SOS gene or any non-SOS defense gene listed in Tables 2 or 2A-2F as disclosed herein.

siRNA sequences are chosen to maximize the uptake of the antisense (guide) strand of the siRNA into RISC and thereby maximize the ability of the inhibitor to target RISC to target antibiotic resistance gene or cell survival gene mRNA for degradation. This can be accomplished by scanning for sequences that have the lowest free energy of binding at the 5'-terminus of the antisense strand. The lower free energy leads to an enhancement of the unwinding of the 5'-end of the antisense strand of the siRNA duplex, thereby ensuring that the antisense strand will be taken up by RISC and direct the sequence-specific cleavage of the targeted mRNA.

RNA interference molecules and nucleic acid inhibitors useful in the methods as disclosed herein can be produced using any known techniques such as direct chemical synthesis, through processing of longer double stranded RNAs by exposure to recombinant Dicer protein or *Drosophila* embryo lysates, through an in vitro system derived from S2 cells, using phage RNA polymerase, RNA-dependant RNA polymerase, and DNA based vectors. Use of cell lysates or in vitro processing can further involve the subsequent isolation of the short, for example, about 21-23 nucleotide, siRNAs from the lysate, etc. Chemical synthesis usually proceeds by making two single stranded RNA-oligomers followed by the annealing of the two single stranded oligomers into a double stranded RNA. Other examples include methods disclosed in WO 99/32619 and WO 01/68836, which are incorporated herein by reference, teach chemical and enzymatic synthesis of siRNA. Moreover, numerous commercial services are available for designing and manufacturing specific siRNAs (see, e.g., QIAGEN Inc., Valencia, Calif. and AMBION Inc., Austin, Tex.)

In one embodiment, the nucleic acid inhibitors of antibiotic resistance genes and/or cell survival genes can be obtained synthetically, for example, by chemically synthesizing a nucleic acid by any method of synthesis known to the skilled artisan. The synthesized nucleic acid inhibitors of antibiotic resistance genes and/or cell survival genes can then be purified by any method known in the art. Methods for chemical synthesis of nucleic acids include, but are not limited to, in vitro chemical synthesis using phosphotriester, phosphate or phosphoramidite chemistry and solid phase techniques, or via deoxynucleoside H-phosphonate intermediates (see U.S. Pat. No. 5,705,629 to Bhongle).

In some circumstances, for example, where increased nuclease stability is desired, nucleic acids having nucleic acid analogs and/or modified internucleoside linkages can be preferred. Nucleic acids containing modified internucleoside linkages can also be synthesized using reagents and methods that are well known in the art. For example, methods of synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide ($-CH_2-S-CH_2-$), diinethylene-sulfoxide ($-CH_2-SO-CH_2-$), dimethylene-sulfone ($-CH_2-SO_2CH_2-$), 2'-O-alkyl, and 2'-deoxy-2'-fluoro' phosphorothioate internucleoside linkages are well known in the art (see Uhlmann et al., 1990, Chem. Rev. 90:543-584; Schneider et al., 1990, Tetrahedron Lett. 31:335 and references cited therein). U.S. Pat. Nos. 5,614,617 and 5,223,618 to Cook, et al., U.S. Pat. No. 5,714,606 to Acevedo, et al, U.S. Pat. No. 5,378,825 to Cook, et al., U.S. Pat. Nos. 5,672,697 and 5,466,786 to Buhr, et al., U.S. Pat. No. 5,777,092 to Cook, et al., U.S. Pat. No. 5,602,240 to De Mesmacker, et al., U.S. Pat. No. 5,610,289 to Cook, et al. and U.S. Pat. No. 5,858,988 to Wang, also describe nucleic acid analogs for enhanced nuclease stability and cellular uptake.

Synthetic siRNA molecules, including shRNA molecules, can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. (2001) Nature 411:494-498; Elbashir, S. M., W. Lendeckel and T. Tuschl (2001) Genes & Development 15:188-200; Harborth, J. et al. (2001) J. Cell Science 114:4557-4565; Masters, J. R. et al. (2001) Proc. Natl. Acad. Sci., USA 98:8012-8017; and Tuschl, T. et al. (1999) Genes & Development 13:3191-3197). Alternatively, several commercial RNA synthesis suppliers are available including, but not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses (Paddison, P. J. et al. (2002) Genes Dev. 16:948-958; McManus, M. T. et al. (2002) RNA 8:842-850; Paul, C. P. et al. (2002) Nat. Biotechnol. 20:505-508; Miyagishi, M. et al. (2002) Nat. Biotechnol. 20:497-500; Sui, G. et al. (2002) Proc. Natl. Acad. Sci., USA 99:5515-5520; Brummelkamp, T. et al. (2002) Cancer Cell 2:243; Lee, N. S., et al. (2002) Nat. Biotechnol. 20:500-505; Yu, J. Y., et al. (2002) Proc. Natl. Acad. Sci., USA 99:6047-6052; Zeng, Y., et al. (2002) Mol. Cell. 9:1327-1333; Rubinson, D. A., et al. (2003) Nat. Genet. 33:401-406; Stewart, S. A., et al. (2003) RNA 9:493-501). These vectors generally have a polIII promoter upstream of the dsRNA and can express sense and antisense RNA strands separately and/or as a hairpin structures. Within cells, Dicer processes the short hairpin RNA (shRNA) into effective siRNA.

The targeted region of the siRNA molecule of the present invention can be selected from a given target gene sequence, e.g., an antibiotic resistance genes and/or cell survival genes coding sequence, beginning from about 25 to 50 nucleotides, from about 50 to 75 nucleotides, or from about 75 to 100 nucleotides downstream of the start codon. Nucleotide sequences can contain 5' or 3' UTRs and regions nearby the start codon. One method of designing a siRNA molecule of the present invention involves identifying the 23 nucleotide sequence motif AA(N19)TT (where N can be any nucleotide), and selecting hits with at least 25%, 30%, 35%, 40%, 45%, 50%, 55%, 60%, 65%, 70% or 75% G/C content. The "TT" portion of the sequence is optional. Alternatively, if no such sequence is found, the search can be extended using the motif NA(N21), where N can be any nucleotide. In this situation, the 3' end of the sense siRNA can be converted to TT to allow for the generation of a symmetric duplex with respect to the sequence composition of the sense and antisense 3' overhangs. The antisense siRNA molecule can then be synthesized as the complement to nucleotide positions 1 to 21 of the 23 nucleotide sequence motif. The use of symmetric 3' TT overhangs can be advantageous to ensure that the small interfering ribonucleoprotein particles (siRNPs) are formed with approximately equal ratios of sense and antisense target RNA-cleaving siRNPs (Elbashir et al. (2001) supra and Elbashir et al. 2001 supra). Analysis of sequence databases, including but are not limited to the NCBI, BLAST, Derwent and GenSeq as well as commercially available oligosynthesis software such as OLIGOENGINE®, can also be used to select siRNA sequences against EST libraries to ensure that only one gene is targeted.

Accordingly, the RNAi molecules functioning as nucleic acid inhibitors of antibiotic resistance genes and/or cell survival genes as disclosed herein are for example, but are not limited to, unmodified and modified double stranded (ds) RNA molecules including short-temporal RNA (stRNA), small interfering RNA (siRNA), short-hairpin RNA (shRNA), microRNA (miRNA), double-stranded RNA (dsRNA), (see, e.g. Baulcombe, Science 297:2002-2003, 2002). The dsRNA molecules, e.g. siRNA, also can contain 3' overhangs, preferably 3'UU or 3'TT overhangs. In one embodiment, the siRNA molecules of the present invention do not include RNA molecules that comprise ssRNA greater than about 30-40 bases, about 40-50 bases, about 50 bases or more. In one embodiment, the siRNA molecules of the present invention are double stranded for more than about 25%, more than about 50%, more than about 60%, more than about 70%, more than about 80%, more than about 90% of their length. In some embodiments, a nucleic acid inhibitor of antibiotic resistance genes and/or cell survival genes is any agent which binds to and inhibits the expression of antibiotic resistance genes and/or cell survival gene mRNA, where the expression of the antibiotic resistance genes and/or cell survival mRNA or a product of transcription of nucleic acid encoded by antibiotic resistance genes and/or cell survival gene is inhibited.

In another embodiment of the invention, agents inhibiting antibiotic resistance genes and/or cell survival genes are catalytic nucleic acid constructs, such as, for example ribozymes, which are capable of cleaving RNA transcripts and thereby preventing the production of wildtype protein. Ribozymes are targeted to and anneal with a particular sequence by virtue of two regions of sequence complementary to the target flanking the ribozyme catalytic site. After binding, the ribozyme cleaves the target in a site specific manner. The design and testing of ribozymes which specifically recognize and cleave sequences of the gene products described herein, for example for cleavage of antibiotic resistance genes and/or cell survival genes or homologues or variants thereof can be achieved by techniques well known to those skilled in the art (for example Lleber and Strauss, (1995) Mol Cell Biol 15:540.551, the disclosure of which is incorporated herein by reference).

Promoters of the Engineered Bacteriophages

In some embodiments of all aspects described herein, an engineered bacteriophage comprises a nucleic acid which expresses an inhibitor to an antibiotic resistance gene (such as in inhibitor-engineered bacteriophages) or a repressor to a SOS gene or a repressor (or inhibitor) to a non-SOS defense gene (in the case of repressor-engineered bacteriophages) or a susceptibility agent (in a case of a susceptibility-agent engineered bacteriophage). In each instance, gene expression from the nucleic acid is regulated by a promoter to which the nucleic acid is operatively linked to. In some embodiments, a promoter is a bacteriophage promoter. One can use any bacteriophage promoter known by one of ordinary skill in the art, for example but not limited to, any promoter listed in Table 6 or disclosed in world-wide web site "partsregistry.org/cgi/partsdb/pgroup.cgi?pgroup=other_regulator&show=1".

In some embodiments, an agent is protein or polypeptide or RNAi agent that inhibits expression of antibiotic resistance genes and/or cell survival gene, or a non-SOS defense genes. In such embodiments bacteriophage cells can be modified (e.g., by homologous recombination) to provide increased expression of such an agent, for example by replacing, in whole or in part, the naturally occurring bacteriophage promoter with all or part of a heterologous promoter so that the bacteriophage and/or the bacteriophage infected-host cell expresses a high level of the inhibitor agent of antibiotic resistance genes and/or cell survival gene or a repressor or an inhibitor to a non-SOS defense gene or a susceptibility agent. In some embodiments, a heterologous promoter is inserted in such a manner that it is operatively linked to the desired nucleic acid encoding the agent. See, for example, PCT International Publication No. WO 94/12650 by Transkaryotic Therapies, Inc., PCT International Publication No. WO 92/20808 by Cell Genesys, Inc., and PCT International Publication No. WO 91/09955 by Applied Research Systems, which are incorporated herein in their entirety by reference.

In some embodiments, bacteriophages can be engineered as disclosed herein to express an endogenous gene, such as a repressor protein, or a nucleic acid inhibitor of an antibiotic resistance gene or cell survival gene comprising the agent under the control of inducible regulatory elements, in which case the regulatory sequences of the endogenous gene can be replaced by homologous recombination. Gene activation techniques are described in U.S. Pat. No. 5,272,071 to Chappel; U.S. Pat. No. 5,578,461 to Sherwin et al.; PCT/US92/09627 (WO93/09222) by Selden et al.; and PCT/US90/06436 (WO91/06667) by Skoultchi et al, which are all incorporated herein in their entirety by reference.

Other exemplary examples of promoter which can be used include, for example but not limited, Anhydrotetracycline (aTc) promoter, PLtetO-1 (Pubmed Nucleotide# U66309), Arabinose promoter (PBAD), IPTG inducible promoters PTAC (in vectors such as Pubmed Accession #EU546824), PTrc-2, Plac (in vectors such as Pubmed Accession #EU546816), PLlacO-1, PAllacO-1, and Arabinose and IPTG promoters, such as Plac/ara-a. Examples of these promoters are as follows:

Anhydrotetracycline (aTc) promoter, such as PLtetO-1 (Pubmed Nucleotide# U66309): GCATGCTCCCTAT-CAGTGATAGAGATTGACATCCCTAT-CAGTGATAGAGATACTGAGCAC ATCAGCAGGACG-CACTGACCAGGA (SEQ ID NO: 36); Arabinose promoter (PBAD): or modified versions which can be found at worldwide web site: partsregistry.org/wiki/index.php?title=Part:BBa_I13453" AAGAAACCAATTGTCCATATTGCATCA-GACATTGCCGTCACTGCGTCTTTTACTGGCTCTT CTCGCTAACCAAACCGGTAACCCCGCT-TATTAAAAGCATTCTGTAACAAAGCGGGACCAA AGCCATGACAAAAACGCGTAACAAAAGT-GTCTATAATCACGGCAGAAAAGTCCACATTG ATTATTTGCACGGCGTCACACTTTGC-TATGCCATAGCATTTTTATCCATAAGATTAGCGGA TCCTACCTGACGCTTTTTATCG-CAACTCTCTACTGTTTCTCCATA (SEQ ID NO: 37); IPTG promoters: (i) PTAC (in vectors such as Pubmed Accession #EU546824, which is incorporated herein by reference), (ii) PTrc-2: CCATCGAATGGCTGAAATGAGCTGTTGA-CAATTAATCATCCGGCTCGTATAATGTGTGGA ATTGTGAGCGGATAACAATTTCACACAGGA (SEQ ID NO: 38) and temperature sensitive promoters such as PLs1con, GCATGCACAGATAACCATCTGCGGT-GATAAATTATCTCTGGCGGTGTTGACATAAATACC ACTGGCGGTtATAaTGAGCACATCAGCAGG//GTATG-CAAAGGA (SEQ ID NOS: 39-40) and modified variants thereof.

Modification of Engineered Bacteriophages.

In some embodiments of all aspects described herein, an engineered bacteriophage can also be designed for example, for optimal enzyme activity or to delay cell lysis or using multiple phage promoters to allow for increased enzyme production, or targeting multiple biofilm EPS components with different proteins. In some embodiments, one can also target multi-species biofilm with a cocktail of different species-specific engineered enzymatically-active phage, and combination therapy with other agents other than antimicrobial agent that are well known to one skilled in the art and phage to improve the efficacy of both types of treatment.

In some embodiments of all aspects described herein, an engineered bacteriophage can also be used together with other antibacterial or bacteriofilm degrading agents or chemicals such as EGTA, a calcium-specific chelating agent, effected the immediate and substantial detachment of a P. aeruginosa biofilm without affecting microbial activity, NaCl, CaCl$_2$ or MgCl$_2$, surfactants and urea.

Phage therapy or bacteriophage therapy has begun to be accepted in industrial and biotechnological settings. For example, the FDA has previously approved the use of phage targeted at Listeria monocytogenes as a food additive. Phage therapy has been used successfully for therapeutic purposes in Eastern Europe for over 60 years. The development and use of phage therapy in clinical settings in Western medicine, in particular for treating mammals such as humans has been delayed due to the lack of properly designed clinical trials to date as well as concerns with (i) development of phage resistance, (ii) phage immunogenicity in the human body and clearance by the reticuloendothelial system (RES), (iii) the release of toxins upon bacterial lysis, and (iv) phage specificity. Many of these concerns are currently being studied and addressed, such as the isolation and development of long-circulating phage that can avoid RES clearance for increased in vivo efficacy. Accordingly, in all aspects described herein, the methods of the present invention are applicable to human treatment as the engineered bacteriophages can be designed to prevent the development of phage resistance in bacteria. A skilled artisan can also develop and carry out an appropriate clinical trial for use in clinical applications, such as therapeutic purposes as well as in human subjects. In some instances, a skilled artisan could establish and set up a clinical trial to establish the specific tolerance of the engineered bacteriophage in human subjects. The inventors have already demonstrated herein that inhibitor-engineered bacteriophage and repressor-engineered bacteriophages and susceptibility-engineered bacteriophages are effective at increasing the efficacy of antimicrobial agents, and are effective in dispersing biofilms, including biofilms present in human organs, such as colon or lungs and other organs in a subject prone to bacterial infection such as bacterial biofilm infection.

Another aspect relates to a pharmaceutical composition comprising at least one engineered bacteriophage and at least one antimicrobial agent. In some embodiments of this and all aspects described herein, the composition can be administered as a co-formulation with one or more other non-antimicrobial or therapeutic agents.

In a further embodiment, the invention provides methods of administration of the compositions and/or pharmaceutical formulations of the invention and include any means commonly known by persons skilled in the art. In some embodiments, the subject is any organism, including for example a mammalian, avian or plant. In some embodiments, the mammalian is a human, a domesticated animal and/or a commercial animal.

While clearance issue is not significant in treatment of chronic diseases, the problem of phage clearance is an important one that needs to be solved as it can make phage therapy more useful for treating transient infections rather than chronic ones. Non-lytic and non-replicative phage have been engineered to kill bacteria while minimizing endotoxin release. Accordingly, the present invention encompasses modification of the inhibitor-engineered and/or repressor-engineered bacteriophage and/or susceptibility engineered bacteriophage with minimal endotoxin release or toxin-free bacteriophage preparation.

The specificity of phage for host bacteria is both an advantage and a disadvantage for phage therapy. Specificity allows human cells as well as innocuous bacteria to be spared, potentially avoiding serious issues such as drug toxicity. Antibiotic therapy is believed to alter the microbial flora in the colon due to lack of target specificity, and in some instances allowing resistant *C. difficile* to proliferate and cause disease such as diarrhea and colitis. The inhibitor-engineered bacteriophage and repressor-engineered bacteriophages and/or susceptibility engineered bacteriophage as disclosed herein are capable of inhibiting the local bacterial synthetic machinery which normally circumvent antimicrobial effect to result in persistent bacteria.

For host specificity (i.e. bacteria specific inhibitor or repressor-engineered bacteriophages), a well-characterized library of phage must be maintained so that an appropriate inhibitor-engineered bacteriophage or repressor-engineered bacteriophage and/or susceptibility engineered bacteriophage therapy can be designed for each individual bacterial infection. The diversity of bacterial infections implies that it may be difficult for any one particular engineered phage to be an effective therapeutic solution for a wide range of biofilms. Accordingly, in one embodiment, the invention provides use of a variety of different engineered bacteriophages in combination (i.e. a cocktail of engineered bacteriophages discussed herein) to cover a range of target bacteria.

One skilled in the art can generate a collection or a library of the inhibitor-engineered bacteriophage and/or repressor engineered bacteriophage and/or susceptibility engineered bacteriophage as disclosed herein by new cost-effective, large-scale DNA sequencing and DNA synthesis technologies. Sequencing technologies allows the characterization of collections of natural phage that have been used in phage typing and phage therapy for many years. Accordingly, a skilled artisan can use synthesis technologies as described herein to add different inhibitors to antibiotic resistance genes or cell survival genes, and/or different repressors to different SOS response genes or non-SOS defense genes or susceptibility agents to produce a variety of new inhibitor-engineered bacteriophage and repressor-engineered bacteriophages and/or susceptibility engineered bacteriophage respectively.

In particular embodiments, the engineered bacteriophages as described herein can be engineered to express an endogenous gene, such as a repressor protein, or a nucleic acid inhibitor of an antibiotic resistance gene or cell survival gene comprising the agent under the control of inducible regulatory elements, in which case the regulatory sequences of the endogenous gene can be replaced by homologous recombination. Gene activation techniques are described in U.S. Pat. No. 5,272,071 to Chappel; U.S. Pat. No. 5,578,461 to Sherwin et al.; PCT/US92/09627 (WO93/09222) by Selden et al.; and PCT/US90/06436 (WO91/06667) by Skoultchi et al, which are all incorporated herein in their entirety by reference.

Furthermore, rational engineering methods with new synthesis technologies can be employed to broaden the engineered bacteriophage host range. For example, T7 can be modified to express K1-5 endosialidase, allowing it to effectively replicate in *E. coli* that produce the K1 polysaccharide capsule. In some embodiments, the gene 1.2 from phage T3 can be used to extend the bacteriophages as disclosed herein to be able to transfect a host range to include *E. coli* that contain the F plasmid, thus demonstrating that multiple modifications of a phage genome can be done without significant impairment of the phage's ability to replicate. *Bordetella* bacteriophage use a reverse-transcriptase-mediated mechanism to produce diversity in host tropism which can also be used according to the methods of the present invention to create a phage that encodes an agent which inhibits antibiotic resistance genes and/or cell survival genes, or alternatively encodes repressors of SOS response genes, and is lytic to the target bacterium or bacteria. The many biofilm-promoting factors required by *E. coli* K-12 to produce a mature biofilm are likely to be shared among different biofilm-forming bacterial strains and are thus also targets for engineered enzymatic bacteriophage as disclosed herein.

Antimicrobial Agents

One aspect of the present invention relates to the killing or inhibiting the growth of bacteria using a combination of an inhibitor-engineered bacteriophage and/or a repressor engineered bacteriophage and/or a susceptibility engineered bacteriophage with at least one antimicrobial agent. Accordingly, one aspect of the present invention relates to methods and compositions comprising engineered bacteriophages for use in combination with antimicrobial agents to potentiate the antimicrobial effect and bacterial killing function or inhibition of growth function of the antimicrobial agent.

Accordingly in some embodiments of this aspect of the present invention relates to the use of a inhibitor-engineered bacteriophage and/or a repressor engineered bacteriophage and/or susceptibility engineered bacteriophage to potentiate the killing effect of antimicrobial agents. Stated another way, the inhibitor-engineered or repressor-engineered bacteriophage or susceptibility engineered bacteriophage can be used to enhance the efficacy of at least one antimicrobial agent.

An inhibitor-engineered bacteriophages and/or a repressor engineered bacteriophage and/or a susceptibility engineered bacteriophage is considered to potentiate the effectiveness of the antimicrobial agent if the amount of antimicrobial agent used in combination with the engineered bacteriophages as disclosed herein is reduced by at least 10% without adversely affecting the result, for example, without adversely effecting the level of antimicrobial activity. In another embodiment, the criteria used to select inhibitor-engineered bacteriophages and/or a repressor engineered bacteriophage and/or a susceptibility engineered bacteriophage that can potentiate the activity of an antimicrobial agent is an engineered bacteriophage which enables a reduction of at least about 10%, ... or at least about 15%, ... or at least about 20%, ... or at least about 25%, ... or at least about 35%, ... or at least about 50%, ... or at least about 60%, ... or at least about 90% and all integers inbetween 10-90% of the amount (i.e. dose) of the antimicrobial agent without adversely effecting the antimicrobial effect when compared to the similar amount in the absence of an inhibitor-engineered bacteriophage and/or a repressor engineered bacteriophage and/or a susceptibility engineered bacteriophage.

In some embodiments, any antimicrobial agent can be used which is know by persons of ordinary skill in the art can be used in combination with an inhibitor-engineered bacteriophage or a repressor-engineered bacteriophage and/or a susceptibility engineered bacteriophage. In some embodiments an antimicrobial agent is an antibiotic. Thus, in some embodiments, the engineered bacteriophages as disclosed herein function as antibiotic adjuvants for aminglycoside antimicrobial agents, such as but not limited to, gentamicin, amikacin, gentamycin, tobramycin, netromycin, streptomycin, kanamycin, paromomycin, neomycin. In some embodiments, the engineered bacteriophages as disclosed herein function as antibiotic adjuvants for β-lactam antibiotics, such as but not limited to, ampicillin, penicillin, penicillin derivatives, cephalosporins, monobactams, carbapenems and β-lactamase inhibitors. In some embodiments, the engineered bacteriophages as disclosed herein function as antibiotic adjuvants for quinolones antimicrobial agents, such as, but not limited to, ofloxacin, ciproflaxacin, levofloxacin, gatifloxacin, norfloxacin, lomefloxacin, trovafloxacin, moxifloxacin, sparfloxacin, gemifloxacin, and pazufloxacin.

In alternative embodiments, an antimicrobial agent can be, for example, but not limited to, a small molecule, a peptide, a peptidomimetic, a chemical, a compound and any entity that inhibits the growth and/or kills a microorganism. In some embodiments, an antimicrobial agent can include, but is not limited to; antibodies (polyclonal or monoclonal), neutralizing antibodies, antibody fragments, chimeric antibodies, humanized antibodies, recombinant antibodies, peptides, proteins, peptide-mimetics, aptamers, oligonucleotides, hormones, small molecules, nucleic acids, nucleic acid analogues, carbohydrates or variants thereof that function to inactivate the nucleic acid and/or protein of the gene products identified herein, and those as yet unidentified. Nucleic acids include, for example but not limited to, DNA, RNA, oligonucleotides, peptide nucleic acid (PNA), pseudo-complementary-PNA (pcPNA), locked nucleic acid (LNA), RNAi, microRNAi, siRNA, shRNA etc. The an antimicrobial agent inhibitors can be selected from a group of a chemical, small molecule, chemical entity, nucleic acid sequences, nucleic acid analogues or protein or polypeptide or analogue or fragment thereof.

In some embodiments, an antimicrobial agent is an antimicrobial peptide, for example but not limited to, mefloquine, venturicidin A, antimycin, myxothiazol, stigmatellin, diuron, iodoacetamide, potassium tellurite hydrate, aDL-vinylglycine, N-ethylmaleimide, L-allyglycine, diaryquinoline, betaine aldehyde chloride, acivcin, psicofuraine, buthionine sulfoximine, diaminopemelic acid, 4-phospho-D-erythronhydroxamic acid, motexafin gadolinium and/or xycitrin or modified versions or analogues thereof.

In some embodiments, an antimicrobial agent useful in combination with an inhibitor-engineered or repressor-engineered bacteriophage described herein includes, but are not limited to aminoglycosides, carbapenemes, cephalosporins, cephems, glycoproteins fluoroquinolones/quinolones, oxazolidinones, penicillins, streptogramins, sulfonamides and/or tetracyclines.

Aminoglycosides are a group of antibiotics found to be effective against gram-negative. Aminoglycosides are used to treat complicated urinary tract infections, septicemia, peritonitis and other severe intra-abdominal infections, severe pelvic inflammatory disease, endocarditis, mycobacterium infections, neonatal sepsis, and various ocular infections. They are also frequently used in combination with penicillins and cephalosporins to treat both gram-positive and gram-negative bacteria. Examples of aminoglycosides include amikacin, gentamycin, tobramycin, netromycin, streptomycin, kanamycin, paromomycin, and neomycin.

Carbapenems are a class of broad spectrum antibiotics that are used to fight gram-positive, gram-negative, and anaerobic microorganisms. Carbapenems are available for intravenous administration, and as such are used for serious infections which oral drugs are unable to adequately address. For example, carbapenems are often used to treat serious single or mixed bacterial infections, such as lower respiratory tract infections, urinary tract infections, intra-abdominal infections, gynecological and postpartum infections, septicemia, bone and joint infections, skin and skin structure infections, and meningitis. Examples of carbapenems include imipenem/cilastatin sodium, meropenem, ertapenem, and panipenem/betamipron.

Cephalosporins and cephems are broad spectrum antibiotics used to treat gram-positive, gram-negative, and spirochaetal infections. Cephems are considered the next generation Cephalosporins with newer drugs being stronger against gram negative and older drugs better against gram-positive. Cephalosporins and cephems are commonly substituted for penicillin allergies and can be used to treat common urinary tract infections and upper respiratory infections (e.g., pharyugitis and tonsillitis).

Cephalosporins and cephems are also used to treat otitis media, some skin infections, bronchitis, lower respiratory infections (pneumonia), and bone infection (certain; members), and are a preferred antibiotic for surgical prophylaxis. Examples of Cephalosporins include cefixime, cefpodoxime, ceftibuten, cefdinir, cefaclor, cefprozil, loracarbef, cefadroxil, cephalexin, and cephradineze. Examples of cephems include cefepime, cefpirome, cefataxidime pentahydrate, ceftazidime, ceftriaxone, ceftazidime, cefotaxime, cefteram, cefotiam, cefuroxime, cefamandole, cefuroxime axetil, cefotetan, cefazolin sodium, cefazolin, cefalexin.

Fluoroquinolones/quinolones are antibiotics used to treat gram-negative infections, though some newer agents have activity against gram-positive bacteria and anaerobes. Fluoroquinolones/quinolones are often used to treat conditions such as urinary tract infections, sexually transmitted diseases (e.g., gonorrhea, chlamydial urethritis/cervicitis, pelvic inflammatory disease), gram-negative gastrointestinal infections, soft tissue infections, pphthalmic infections, dermatological infections, sinusitis, and respiratory tract infections (e.g., bronchitis, pneumonia, and tuberculosis). Fluoroquinolones/quinolones are used in combination with other antibiotics to treat conditions, such as multi-drug resistant tuberculosis, neutropenic cancer patients with fever, and potentially anthrax. Examples of fluoroquinolones/quinolones include ciproflaxacin, levofloxacin, and ofloxacin, gatifloxacin, norfloxacin, lomefloxacin, trovafloxacin, moxifloxacin, sparfloxacin, gemifloxacin, and pazufloxacin.

Glycopeptides and streptogramins represent antibiotics that are used to treat bacteria that are resistant to other antibiotics, such as methicillin-resistant *staphylococcus aureus* (MRSA). They are also be used for patients who are allergic to penicillin Examples of glycopeptides include vancomycin, teicoplanin, and daptomycin.

β-lactam antibiotics are a broad class of antibiotics which include penicillin derivatives, cephalosporins, monobactams, carbapenems and β-lactamase inhibitors; basically, any antibioticor agent or antimicrobial agent which contains a β-lactam nucleus in its molecular structure. Without being bound by theory, β-Lactam antibiotics are bactericidal, and act by inhibiting the synthesis of the peptidoglycan layer of bacterial cell walls. The peptidoglycan layer is important for cell wall structural integrity, especially in Gram-positive organisms.

The final transpeptidation step in the synthesis of the peptidoglycan is facilitated by transpeptidases known as penicillin binding proteins (PBPs). β-lactam antibiotics are analogues of D-alanyl-D-alanine—the terminal amino acid residues on the precursor NAM/NAG-peptide subunits of the nascent peptidoglycan layer. The structural similarity between β-lactam antibiotics and D-alanyl-D-alanine facilitates their binding to the active site of penicillin binding proteins (PBPs). The β-lactam nucleus of the molecule irreversibly binds to (acylates) the Ser403 residue of the PBP active site. This irreversible inhibition of the PBPs prevents the final crosslinking (transpeptidation) of the nascent peptidoglycan layer, disrupting cell wall synthesis. Under normal circumstances peptidoglycan precursors signal a reorganization of the bacterial cell wall and consequently trigger the activation of autolytic cell wall hydrolyses. Inhibition of cross-linkage by β-lactams causes a build-up of peptidoglycan precursors which triggers the digestion of existing peptidoglycan by autolytic hydrolases without the production of new peptidoglycan. This as a result further enhances the bactericidal action of β-lactam antibiotics.

Carbapenems are used to treat gram-positive, gram-negative, and/or anaerobes.

Oxazolidinones are commonly administered to treat gram-positive infections. Oxazolidinones are commonly used as an alternative to other antibiotic classes for bacteria that have developed resistance. Examples of oxazolidinones include linezolid.

Penicillins are broad spectrum used to treat gram-positive, gram-negative, and spirochaetal infections. Conditions that are often treated with penicillins include pneumococcal and meningococcal meningitis, dermatological infections, ear infections, respiratory infections, urinary tract infections, acute sinusitis, pneumonia, and Lyme disease. Examples of penicillins include penicillin, amoxicillin, amoxicillin-clavulanate, ampicillin, ticarcillin, piperacillin-tazobactam, carbenicillin, piperacillin, mezocillin, benzathin penicillin G penicillin V potassium, methicillin, nafcillin, oxacillin, cloxacillin, and dicloxacillin.

Streptogramins are antibiotics developed in response to bacterial resistance that diminished effectiveness of existing antibiotics. Streptogramins are a very small class of drugs and are currently very expensive. Examples of streptogramins include quinupristin/dafopristin and pristinamycin.

Sulphonamides are broad spectrum antibiotics that have had reduced usage due to increase in bacterial resistance to them. Sulphonamides are commonly used to treat recurrent attacks of rheumatic fever, urinary tract infections, prevention of infections of the throat and chest, traveler's diarrhea, whooping cough, meningococcal disease, sexually transmitted diseases, toxoplasmosis, and rhinitis. Examples of sulfonamides include co-trimoxazole, sulfamethoxazole trimethoprim, sulfadiazine, sulfadoxine, and trimethoprim.

Tetracyclines are broad spectrum antibiotics that are often used to treat gram-positive, gram-negative, and/or spirochaetal infections. Tetracyclines are often used to treat mixed infections, such as chronic bronchitis and peritonitis, urinary tract infections, rickets, chlamydia, gonorrhea, Lyme disease, and periodontal disease. Tetracyclines are an alternative therapy to penicillin in syphilis treatment and are also used to treat acne and anthrax. Examples of tetracyclines include tetracycline, demeclocycline, minocycline, and doxycycline.

Other antimicrobial agents and antibiotics contemplated herein useful in combination with the engineered bacteriophages as disclosed herein according to the present invention (some of which can be redundant with the list above) include, but are not limited to; abrifam; acrofloxacin; aptecin; amoxicillin plus clavulonic acid; apalcillin; apramycin; astromicin; arbekacin; aspoxicillin; azidozillin; azlocillin; aztreonam; bacitracin; benzathine penicillin; benzylpenicillin; clarithromycin, carbencillin; cefaclor; cefadroxil; cefalexin; cefamandole; cefaparin; cefatrizine; cefazolin; cefbuperazone; cefcapene; cefdinir; cefditoren; cefepime; cefetamet; cefixime; cefinetazole; cefminox; cefoperazone; ceforanide; cefotaxime; cefotetan; cefotiam; cefoxitin; cefpimizole; cefpiramide; cefpodoxime; cefprozil; cefradine; cefroxadine; cefsulodin; ceftazidime; ceftriaxone; cefuroxime; cephalexin; chloramphenicol; chlortetracycline; ciclacillin; cinoxacin; clemizole penicillin; cleocin, cleocin-T, cloxacillin; corifam; daptomycin; daptomycin; demeclocycline; desquinolone; dibekacin; dicloxacillin; dirithromycin; doxycycline; enoxacin; epicillin; ethambutol; gemifloxacin; fenampicin; finamicina; fleroxacin; flomoxef; flucloxacillin; flumequine; flurithromycin; fosfomycin; fosmidomycin; fusidic acid; gatifloxacin; gemifloxaxin; isepamicin; isoniazid; josamycin; kanamycin; kasugamycin; kitasamycin; kalrifam, latamoxef; levofloxacin, levofloxacin; lincomycin; linezolid; lomefloxacin; loracarbaf; lymecycline; mecillinam; methacycline; methicillin; metronidazole; mezlocillin; midecamycin; minocycline; miokamycin; moxifloxacin; nafcillin; nafcillin; nalidixic acid; neomycin; netilmicin; norfloxacin; novobiocin; ofloxacin; oleandomycin; oxacillin; oxolinic acid; oxytetracycline; paromycin; pazufloxacin; pefloxacin; penicillin g; penicillin v; phenethicillin; phenoxymethyl penicillin; pipemidic acid; piperacillin and tazobactam combination; piromidic acid; procaine penicillin; propicillin; pyrimethamine; rifadin; rifabutin; rifamide; rifampin; rifapentene; rifomycin; rimactane; rofact; rokitamycin; rolitetracycline; roxithromycin; rufloxacin; sitafloxacin; sparfloxacin; spectinomycin; spiramycin; sulfadiazine; sulfadoxine; sulfamethoxazole; sisomicin; streptomycin; sulfamethoxazole; sulfisoxazole; quinupristan-dalfopristan; teicoplanin; temocillin; gatifloxacin; tetracycline; tetroxoprim; telithromycin; thiamphenicol; ticarcillin; tigecycline; tobramycin; tosufloxacin; trimethoprim; trimetrexate; trovafloxacin; vancomycin; verdamicin; azithromycin; and linezolid.

Uses of the Engineered Bacteriophages

Accordingly, the inventors have demonstrated that an antimicrobial agent when used in combination with an inhibitor-engineered bacteriophage (which expresses an inhibitor to an antibiotic resistance gene or a cell survival gene) and/or in combination with a repressor-engineered bacteriophage (which expresses at least one repressor to a SOS response gene, or at least one inhibitor or repressor to a non-SOS defense gene) and/or in combination with a susceptibility engineered bacteriophage is effective at killing bacteria, such as a bacterial infection or a bacteria biofilm than use of the antimicrobial alone or the use of the antimicrobial agent used in combination with a non-engineered bacteriophage. The inventors have also discovered that engineered bacteriophages can be adapted to work with a variety of different antimicrobial agents as well as be modified to express other biofilm-degrading enzymes to target a wide range of bacteria and bacteria biofilms. In some embodiments, an antimicrobial agent is used in combination with at least one engineered bacteriophage as disclosed herein, and optionally an addition bacteriophage which is not an inhibitor-engineered or repressor-engineered bacteriophage or a susceptibility engineered bacteriophage, but a bacteriophage which is modified to express a therapeutic gene or a toxin gene or a biofilm degrading gene. Such bacteriophages are well known in the art and are encompassed for use in the methods and compositions as disclosed herein.

Bacterial Infections

One aspect of the present invention relates to the use of the methods and compositions comprising an inhibitor-engineered and/or repressor-engineered bacteriophage and/or a susceptibility engineered bacteriophage in combination with an antimicrobial agent to inhibit the growth and/or kill (or reduce the cell viability) of a microorganism, such as a bacteria. In some embodiments of this aspect and all aspects described herein, a microorganism is a bacterium. In some embodiments, the bacteria are gram positive and gram negative bacteria. In some embodiments, the bacteria are multi-drug resistant bacterium. In further embodiments, the bacteria are polymyxin-resistant bacterium. In some embodiments, the bacterium is a persister bacteria. Examples of gram-negative bacteria are for example, but not limited to *P. aeruginosa, A. bumannii, Salmonella* spp, *Klebsiella pneumonia, Shigeila* spp. and/or *Stenotrophomonas maltophilia*. In one embodiment, the bacteria to be targeted using the phage of the invention include *E. coli, S. epidermidis, Yersina pestis* and *Pseudomonas fluorescens*.

In some embodiments, the methods and compositions as disclosed herein can be used to kill or reduce the viability of a bacterium, for example a bacterium such as, but not limited to: *Bacillus cereus, Bacillus anbhracis, Bacillus cereus, Bacillus anthracia, Clostridium botulinum, Clostridium difficle, Clostridium tetani, Clostridium perfringens, Corynebacteria diptheriae, Enterococcus* (*Streptococcus D*), *Lieteria monocytogenes, Pneumoccoccal infections* (*Streptococcus pneumoniae*), *Staphylococcal infections* and *Streptococcal infections*; Gram-negative bacteria including *Bacteroides, Bordetella pertussis, Brucella, Campylobacter* infections, enterohaemorrhagic *Escherichia coli* (EHEC/*E. coli* 0157:17), enteroinvasive *Escherichia coli* (EIEC), enterotoxigenic *Escherichia coli* (ETEC), *Haemophilus influenzae, Helicobacter pylori, Klebsiella pneumoniae, Legionella* spp., *Moraxella catarrhalis, Neisseria gonnorrhoeae, Neisseria meningitidis, Proteus* spp., *Pseudomonas aeruginosa, Salmonella* spp., *Shigella* spp., *Vibrio cholera* and *Yersinia*; acid fast bacteria including *Mycobacterium tuberculosis, Mycobacterium avium-intracellulars, Myobacterium johnei, Mycobacterium leprae*, atypical bacteria, *Chlamydia, Myoplasma, Rickettsia, Spirochetes, Treponema pallidum, Borrelia recurrentis, Borrelia burgdorfii* and *Leptospira icterohemorrhagiae, Actinomyces, Nocardia, P. aeruginosa, A. bumannii, Salmonella* spp., *Klebsiella pneumonia, Shigeila* spp. and/or *Stenotrophomonas maltophilia* and other miscellaneous bacteria.

Bacterial infections include, but are not limited to, infections caused by *Bacillus cereus, Bacillus* anbhracis, *Bacillus cereus, Bacillus anthracia, Clostridium botulinum, Clostridium difficle, Clostridium tetani, Clostridium perfringens, Corynebacteria diptheriae, Enterococcus* (Streptococcus D), *Lieteria monocytogenes, Pneumoccoccal* infections (*Streptococcus pneumoniae*), *Staphylococcal* infections and *Streptococcal* infections/Gram-negative bacteria including *Bacteroides, Bordetella pertussis, Brucella, Campylobacter* infections, enterohaemorrhagic *Escherichia coli* (EHEC/*E. coli* 0157:17) enteroinvasive *Escherichia coli* (EIEC), enterotoxigenic *Escherichia coli* (ETEC), *Haemophilus influenzae, Helicobacter pylori, Klebsiella pneumoniae, Legionella* spp., *Moraxella catarrhalis, Neisseria gonnorrhoeae, Neisseria meningitidis, Proteus* spp., *Pseudomonas aeruginosa, Salmonella* spp., *Shigella* spp., *Vibrio cholera* and *Yersinia*; acid fast bacteria including *Mycobacterium tuberculosis, Myobacterium avium-intracellulars, Myobacterium johnei, Mycobacterium leprae*, atypical bacteria, *Chlamydia, Myoplasma, Rickettsia, Spirochetes, Treponema pallidum, Borrelia recurrentis, Borrelia burgdorfii* and *Leptospira* icterohemorrhagiae and other miscellaneous bacteria, including *Actinomyces* and *Nocardia*.

In some embodiments, the microbial infection is caused by gram-negative bacterium, for example, *P. aeruginosa, A. bumannii, Salmonella* spp, *Klebsiella pneumonia, Shigeila* spp. and/or *Stenotrophomonas maltophilia*. Examples of microbial infections include bacterial wound infections, mucosal infections, enteric infections, septic conditions, pneumonia, trachoma, onithosis, trichomoniasis and salmonellosis, especially in veterinary practice.

Examples of infections caused by *P. aeruginosa* include: A) *Nosocomial infections;* 1. Respiratory tract infections in cystic fibrosis patients and mechanically-ventilated patients; 2. Bacteraemia and sepsis; 3, Wound infections, particularly in burn wound patients; 4. Urinary tract infections; 5. Post-surgery infections on invasive devises 5. Endocarditis by intravenous administration of contaminated drug solutions; 7, Infections in patients with acquired immunodeficiency syndrome, cancer chemotherapy, steroid therapy, hematological malignancies, organ transplantation, renal replacement therapy, and other situations with severe neutropenia. B) Community-acquired infections; 1. Community-acquired respiratory tract infections; 2. Meningitis; 3. Folliculitis and infections of the ear canal caused by contaminated waters; 4. Malignant otitis externa in the elderly and diabetics; 5. Osteomyelitis of the caleaneus in children; Eye infections commonly associated with contaminated contact lens; 6. Skin infections such as nail infections in people whose hands are frequently exposed to water; 7. Gastrointestinal tract infections; 8. Muscoskeletal system infections.

Examples of infections caused by *A. baumannii* include: A) *Nosocomial infections* 1. Bacteraemia and sepsis, 2. respiratory tract infections in mechanically ventilated patients; 3. Post-surgery infections on invasive devices; 4. wound infectious, particularly in burn wound patients; 5. infection in patients with acquired immunodeficiency syndrome, cancer chemotherapy, steroid therapy, hematological malignancies, organ transplantation, renal replacement therapy, and other situations with severe neutropenia; 6. urinary tract infections; 7. Endocarditis by intravenous administration of contaminated drug solutions; 8. Cellulitis. B) Community-acquired infections; a. community-acquired pulmonary infections; 2. Meningitis; Cheratitis associated with contaminated contact lens; 4. War-zone community-acquired infections. C) Atypical infections: 1. Chronic gastritis.

Examples of infections caused by *Stenotrophomonas maltophilia* include B acteremia, pneumonia, meningitis, wound infections and urinary tract infections. Some hospital breaks are caused by contaminated disinfectant solutions, respiratory devices, monitoring instruments and ice machines. Infections usually occur in debilitated patients with impaired host defense mechanisms.

Examples of infections caused by *Klebsiella pneumoniae* include community-acquired primary lobar pneumonia, particularly in people with compromised pulmonary function and alcoholics. It also caused wound infections, soft tissue infections and urinary tract infections.

Examples of infections caused by *Salmonella* app. are acquired by eating contaminated food products. Infections include enteric fever, enteritis and bacteremia.

Examples of infections caused by *Shigella* spp. include gastroenteritis (shigellosis).

The methods and compositions as disclosed herein comprising an inhibitor-engineered or repressor-engineered bacteriophage and at least one antimicrobial agent can also be used in various fields as where antiseptic treatment or disinfection of materials it required, for example, surface disinfection.

The methods and compositions as disclosed herein comprising an inhibitor-engineered or repressor-engineered bacteriophage and at least one antimicrobial agent can be used to treat microorganisms infecting a cell, group of cells, or a multi-cellular organism.

In one embodiment, an antimicrobial agent and an engineered bacteriophage as described herein can be used to reduce the rate of proliferation and/or growth of microorganisms. In some embodiments, the microorganism are either or both gram-positive or gram-negative bacteria, whether such bacteria are cocci (spherical), rods, *vibrio* (comma shaped), or spiral.

Of the cocci bacteria, *micrococcus* and *staphylococcus* species are commonly associated with the skin, and *Streptococcus* species are commonly associated with tooth enamel and contribute to tooth decay. Of the rods family, bacteria *Bacillus* species produce endospores seen in various stages of development in the photograph and *B. cereus* cause a relatively mild food poisoning, especially due to reheated fried food. Of the *vibrio* species, *V. cholerae* is the most common bacteria and causes cholera, a severe diarrhea disease resulting from a toxin produced by bacterial growth in the gut. Of the spiral bacteria, *rhodospirillum* and *Treponema pallidum* are the common species to cause infection (e.g., *Treponema pallidum* causes syphilis). Spiral bacteria typically grow in shallow anaerobic conditions and can photosynthesize to obtain energy from sunlight.

Moreover, the present invention relates to use of or methods comprising an antimicrobial agent and an engineered bacteriophage as disclosed herein can be used to reduce the rate of growth and/or kill either gram positive, gram negative, or mixed flora bacteria or other microorganisms. In one embodiment, the composition consists essentially of at least one antimicrobial agent and at least one engineered bacteriophage, such as an inhibitor-engineered bacteriophage or repressor-engineered bacteriophage or a susceptibility engineered bacteriophage as disclosed herein for the use to reduce the rate of growth and/or kill either gram positive, gram negative, or mixed flora bacteria or other microorganisms. In another embodiment, the composition contains at least one antimicrobial agent and at least one engineered bacteriophage, such as an inhibitor-engineered bacteriophage or repressor-engineered bacteriophage or a susceptibility engineered bacteriophage as disclosed herein for the use to reduce the rate of growth and/or kill either gram positive, gram negative, or mixed flora bacteria or other microorganisms.

Such bacteria are for example, but are not limited to, listed in Table 7. Further examples of bacteria are, for example but not limited to Baciccis Antracis; *Enterococcus faecalis; Corynebacterium; diphtheriae; Escherichia coli; Streptococcus coelicolor; Streptococcus pyogenes; Streptobacillus moniliformis; Streptococcus agalactiae; Streptococcus pneurmoniae; Salmonella typhi; Salmonella paratyphi; Salmonella schottmulleri; Salmonella hirshieldii; Staphylococcus epidermidis; Staphylococcus aureus; Klebsiella pneumoniae; Legionella pneumophila; Helicobacter pylori; Mycoplasma pneumonia; Mycobacterium tuberculosis; Mycobacterium leprae; Yersinia enterocolitica; Yersinia pestis; Vibrio cholerae; Vibrio parahaemolyticus; Rickettsia prowozekii; Rickettsia rickettsii; Rickettsia akari; Clostridium difficile; Clostridium tetani; Clostridium perfringens; Clostridianz novyii; Clostridianz septicum; Clostridium botulinum; Legionella pneumophila; Hemophilus influenzue; Hemophilus parainfluenzue; Hemophilus aegyptus; Chlamydia psittaci; Chlamydia trachonZatis; Bordetella pertcsis; Shigella* spp.; *Campylobacter jejuni; Proteus* spp.; *Citrobacter* spp.; *Enterobacter* spp.; *Pseudomonas aeruginosa; Propionibacterium* spp.; *Bacillus* anthracia; *Pseudomonas syringae;* Spirrilum minus; *Neisseria meningitidis; Listeria monocytogenes; Neisseria gonorrheae; Treponema pallidum; Francisella tularensis; Brucella* spp.; *Borrelia recurrentis; Borrelia hennsii; Borrelia turicatue; Borrelia burgdorferi; Mycobacterium avium; Mycobacterium smegmatis;* Methicillin-resistant *Staphyloccus aureus;* Vanomycin-resistant *enterococcus;* and multi-drug resistant bacteria (e.g., bacteria that are resistant to more than 1, more than 2, more than 3, or more than 4 different drugs).

TABLE 7

Examples of bacteria.
Table 7: Examples of Bacteria

| *Staphyloccocus aureus* |
| *Bacillus anthracis* |
| *Bacillus cereus* |
| *Bacillus subtillis* |
| *Streptococcus phemonia* |
| *Streptococcus pyogenes* |
| *Clostridium tetani* |
| *Listeria monocytogenes* |
| *Mycobacterium tuberculosis* |
| *Staphyloccocus epidermidis* |
| *Nisseria menigintidis* |
| *Nisseria gonerrhoeae* |
| *Vibrio cholerae* |
| *Escherichia coli* K12 |
| *Bartonella henselae* |
| *Haemophilus influenzae* |
| *Salmonella typhi* |
| *Shigella dysentriae* |
| *Yerinisa pestis* |
| *Pseudomona aeruginosa* |
| *Helicbacter pylori* |
| *Legionella pnemophilia* |
| *Borrelia burgdorferi* |
| *Ehrlichia chaffeensis* |
| *Treponema pallidum* |
| *Chlamydia trachomatis* |

In some embodiments, antimicrobial agent and engineered bacteriophages described herein can be used to treat an already drug resistant bacterial strain such as Methicillin-resistant *Staphylococcus aureus* (MRSA) or Vancomycin-resistant *enterococcus* (VRE) of variant strains thereof.

In some embodiments, the present invention also contemplates the use and methods of use of an antimicrobial agent and an engineered bacteriophage as described herein in all combinations with other antimicrobial agents and/or antibiotics to fight gram-positive bacteria that maintain resistance to certain drugs.

In some embodiments, an antimicrobial agents and an engineered bacteriophage as disclosed herein can be used to treat infections, for example bacterial infections and other conditions such as urinary tract infections, ear infections, sinus infections, bacterial infections of the skin, bacterial infections of the lungs, sexually transmitted diseases, tuberculosis, pneumonia, Lyme disease, and Legionnaire's disease. Thus any of the above conditions and other conditions resulting from a microorganism infection, for example a bacterial infection or a biofilm can be prevented or treated by the compositions of the invention herein.

Biofilms

Another aspect of the present invention relates to the use of an inhibitor-engineered bacteriophage and/or a repressor-engineered bacteriophage and/or a susceptibility engineered bacteriophage in combination with any antimicrobial agent to eliminate or reduce a bacterial biofilm, for example a bacterial biofilm in a medical, or industrial, or biotechnological setting.

For instance, some bacteria, including *P. aeruginosa*, actively form tightly arranged multi-cell structures in vivo known as biofilm. The production of biofilm is important for the persistence of infectious processes such as seen in pseudomonal lung-infections in patients with cystic fibrosis and diffuse panbronchiolitis and many other diseases. A biofilm is typically resistant to phagocytosis by host immune cells and the effectiveness of antibiotics at killing bacteria in biofilm structures can be reduced by 10 to 1000 fold. Biofilm production and arrangement is governed by quorum sensing systems. The disruption of the quorum sensing system in bacteria such as *P. aeruginosa* is an important anti-pathogenic activity as it disrupts the biofilm formation and also inhibits alginate production Selection of Subjects Administered a Composition Comprising an Engineered Bacteriophage In some embodiments, a subject amenable for the method described herein or for the administration with a composition comprising at least one antimicrobial agent and an inhibitor-engineered bacteriophage and/or a repressor-engineered bacteriophage and/or a susceptibility engineered bacteriophage is selected based on the desired treatment regime. For instance, a subject is selected for treatment if the subject has a bacterial infection where the bacteria form a biofilm, or where the subject has been non-responsive to prior therapy or administration with an antimicrobial agent.

Accordingly, in some embodiments, a subjects is administered a combination of at least one antimicrobial agent and at least one inhibitor-engineered bacteriophage and/or a repressor-engineered bacteriophage and/or a susceptibility engineered bacteriophage to potentiate the effect of the antimicrobial agent.

In some embodiments, a subject can be administered a composition comprising at least one antimicrobial agent, for example at least 2, 3, or 4 or as many of 10 different antimicrobial agents and at least one engineered bacteriophage as disclosed herein, for example, for example at least 2, 3, or 4 or as many of 10 different engineered bacteriophages as disclosed herein. In some embodiments, the composition can comprise an antimicrobial agent and at least one or a variety of different repressor-engineered bacteriophages with at least one or a variety of different inhibitor-engineered bacteriophages and/or with at least one or a variety of susceptibility engineered bacteriophages. In alternative embodiments, the composition can comprise at least two, or at least 3, 4, 5 or as many of 10 different inhibitor-engineered bacteriophages, wherein each of the inhibitor-engineered bacteriophages comprise a nucleic acid which encodes at least one inhibitor to a different antibiotic resistance gene and/or cell survival repair gene. In alternative embodiments, the composition can comprise at least two, or at least 3, 4, 5 or as many of 10 different repressor-engineered bacteriophages, wherein each of the repressor-engineered bacteriophages comprise a nucleic acid which encodes at least one repressor to a different SOS response gene and/or at least one repressor or inhibitor to a non-SOS defense gene. Any combination and mixture of antimicrobial agents and mixture of inhibitor-engineered bacteriophages and/or repressor-engineered bacteriophages and/or susceptibility engineered bacteriophages are useful in the compositions and methods of the present invention.

In some embodiments, an antimicrobial agent is administered to a subject at the same time, prior to, or after the administration of an inhibitor-engineered bacteriophage and/or a repressor-engineered bacteriophage and/or susceptibility engineered bacteriophage. In some embodiments, an antimicrobial agent can be formulated to a specific time-release for activity, such as the antimicrobial agent is present in a time-release capsule. In such embodiments, an antimicrobial agent that is formulated for time-release can be administered to a subject at the same time, concurrent with, or prior to, or after the administration of an inhibitor-engineered bacteriophage and/or a repressor-engineered bacteriophage and/or susceptibility engineered bacteriophage. Methods of formulation of an antimicrobial agent for release in a time-dependent manner are disclosed herein as "sustained release pharmaceutical compositions" in the section entitled "pharmaceutical formulations and compositions." Accordingly, in such embodiments, a time-release antimicrobial agent can be administered to a subject at the same time (i.e. concurrent with), prior to or after the administration of an engineered bacteriophage independent to the time to which the antimicrobial agent becomes active. In some embodiments, an antimicrobial agent can be administered prior to the administration of the engineered bacteriophage, and the time at which the antimicrobial agent is released from the time-release capsule coincides with the time of the administration of the engineered bacteriophage.

In some embodiments, an antimicrobial agent can be a pro-drug, where it is activated by a second agent. Accordingly, in such embodiments, an antimicrobial pro-drug agent can be administered to a subject at the same time, concurrent with, or prior to, or after the administration of an inhibitor-engineered bacteriophage and/or repressor-engineered bacteriophage and/or susceptibility engineered bacteriophage, and administration of an agent which activates the pro-drug into its active form can be administered the same time, concurrent with, or prior to, or after the administration of the inhibitor-engineered bacteriophage and/or repressor-engineered bacteriophage and/or susceptibility engineered bacteriophage.

In some embodiments, a subject is selected for the administration with the compositions as disclosed herein by identifying a subject that needs a specific treatment regimen of an antimicrobial agent, and is administered an antimicrobial agent concurrently with, or prior to, or after administration with an inhibitor-engineered bacteriophage and/or a repressor-engineered bacteriophage and/or susceptibility engineered bacteriophage as disclosed herein.

Using a subject with cystic fibrosis as an exemplary example, a subject could be administered an antimicrobial agent to avoid chronic endobronchial infections, such as those caused by *pseudomonas aeruginosis* or *stentrophomonas maltophilia*. One such antimicrobial agent which can be used is colistin, however, administration of colistin at the doses and the duration required to efficiently prevent such endobronchial infections in subjects is highly toxic and in some instances fatal. Accordingly, in some embodiments, such a subject selected for a treatment regimen would be administered compositions as disclosed herein comprising an antimicrobial agent and an inhibitor-engineered bacteriophage and/or a repressor-engineered bacteriophage and/or susceptibility engineered bacteriophage. Thus in such embodiments, an antimicrobial agent can be used at a lower dose when used in combination with an inhibitor-engineered bacteriophage and/or repressor-engineered bacteriophage and/or susceptibility engineered bacteriophage as compared to the use of such an antimicrobial agent alone. Thus one aspect of the invention relates to methods to reduce or decrease the dose of an antimicrobial agent while maintaining efficacy of such an antimicrobial agent, and thus reduce toxic side affects associated with higher doses.

Pharmaceutical Formulations and Compositions

The inhibitor-engineered bacteriophage and repressor-engineered bacteriophages as disclosed herein can be formulated in combination with one or more pharmaceutically acceptable anti-microbial agents. In some embodiments, combinations of different antimicrobial agents can be tailored to be combined with a specific inhibitor-engineered bacteriophage and a repressor-engineered bacteriophage and/or susceptibility engineered bacteriophage, where the inhibitor-engineered bacteriophage and/or repressor-engineered bacteriophages and/or susceptibility engineered bacteriophage are designed to target different (or the same) microorganisms or bacteria, which contribute towards morbidity and mortality. A pharmaceutically acceptable composition comprising an inhibitor-engineered bacteriophage and/or a repressor-engineered bacteriophage and/or susceptibility engineered bacteriophage and an antimicrobial agent as disclosed herein, are suitable for internal administration to an animal, for example human.

In some embodiments, an inhibitor-engineered bacteriophage and/or a repressor-engineered bacteriophage and/or susceptibility engineered bacteriophage as disclosed herein can be used for industrial sterilizing, sterilizing chemicals such as detergents, disinfectants, and ammonium-based chemicals (e.g. quaternary ammonium compounds such as QUATAL, which contains 10.5% N-alkyldimethyl-benzlammonium HCl and 5.5% gluteraldehyde as active ingredients, Ecochimie Ltée, Quebec, Canada), and can be used in concurrently with, or prior to or after the treatment or administration of an antimicrobial agent. Such sterilizing chemicals are typically used in the art for sterilizing industrial work surfaces (e.g. in food processing, or hospital environments), and are not suitable for administration to an animal.

In another aspect of the present invention relates to a pharmaceutical composition comprising an inhibitor-engineered bacteriophage and/or repressor-engineered bacteriophage and/or susceptibility engineered bacteriophage and an antimicrobial agent and a pharmaceutically acceptable excipient. Suitable carriers for the engineered bacteriophages of the invention, and their formulations, are described in Remington's Pharmaceutical Sciences, 16$^{th}$ ed., 1980, Mack Publishing Co., edited by Oslo et al. Typically an appropriate amount of a pharmaceutically acceptable salt is used in the formulation to render the formulation isotonic. Examples of the carrier include buffers such as saline, Ringer's solution and dextrose solution. The pH of the solution is preferably from about 5 to about 8, and more preferably from about 7.4 to about 7.8. Further carriers include sustained release preparations such as semipermeable matrices of solid hydrophobic polymers, which matrices are in the form of shaped articles, e.g. liposomes, films or microparticles. It will be apparent to those of skill in the art that certain carriers can be more preferable depending upon for instance the route of administration and concentration of the an engineered bacteriophage being administered.

Administration to human can be accomplished by means determined by the underlying condition. For example, if the engineered bacteriophage is to be delivered into lungs of an individual, inhalers can be used. If the composition is to be delivered into any part of the gut or colon, coated tablets, suppositories or orally administered liquids, tablets, caplets and so forth can be used. A skilled artisan will be able to determine the appropriate way of administering the phages of the invention in view of the general knowledge and skill in the art.

Compounds as disclosed herein, can be used as a medicament or used to formulate a pharmaceutical composition with one or more of the utilities disclosed herein. They can be administered in vitro to cells in culture, in vivo to cells in the body, or ex vivo to cells outside of a subject that can later be returned to the body of the same subject or another subject. Such cells can be disaggregated or provided as solid tissue in tissue transplantation procedures.

Compositions comprising at least one antimicrobial agent and at least one engineered bacteriophage (i.e. an inhibitor engineered and/or repressor-engineered bacteriophage and/or susceptibility engineered bacteriophage) as disclosed herein can be used to produce a medicament or other pharmaceutical compositions. Use of the compositions as disclosed herein which comprise a combination of at least one antimicrobial agents and an engineered bacteriophage can further comprise a pharmaceutically acceptable carrier. The composition can further comprise other components or agents useful for delivering the composition to a subject are known in the art. Addition of such carriers and other components to the agents as disclosed herein is well within the level of skill in this art.

In some embodiments, the composition is a composition for sterilization of a physical object, that is infected with bacteria, such as sterilization of hospital equipment, industrial equipment, medical devices and food products. In another embodiment, the compositions are a pharmaceutical composition useful to treat a bacterial infection in a subject, for example a human or animal subject.

In some embodiments, a pharmaceutical composition as disclosed herein can be administered as a formulation adapted for passage through the blood-brain barrier or direct contact with the endothelium. In some embodiments, the pharmaceutical compositions can be administered as a formulation adapted for systemic delivery. In some embodiments, the compositions can be administered as a formulation adapted for delivery to specific organs, for example but not limited to the liver, bone marrow, or systemic delivery.

Alternatively, pharmaceutical compositions can be added to the culture medium of cells ex vivo. In addition to the antimicrobial agent and engineered bacteriophages, such compositions can contain pharmaceutically-acceptable carriers and other ingredients or agents known to facilitate administration and/or enhance uptake (e.g., saline, dimethyl sulfoxide, lipid, polymer, affinity-based cell specific-targeting systems). In some embodiments, a pharmaceutical composition can be incorporated in a gel, sponge, or other permeable matrix (e.g., formed as pellets or a disk) and placed in proximity to the endothelium for sustained, local release. The composition can be administered in a single dose or in multiple doses which are administered at different times.

Pharmaceutical compositions can be administered to a subject by any known route. By way of example, the composition can be administered by a mucosal, pulmonary, topical, or other localized or systemic route (e.g., enteral and parenteral). The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, infusion and other injection or infusion techniques, without limitation. The phrases "systemic administration," "administered systemically", "peripheral administration" and "administered peripherally" as used herein mean the administration of the agents as disclosed herein such that it enters the animal's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert.

Suitable choices in amounts and timing of doses, formulation, and routes of administration can be made with the goals of achieving a favorable response in the subject with a bacterial infection or infection with a microorganism, for example, a favorable response is killing or elimination of the microorganism or bacteria, or control of, or inhibition of growth of the bacterial infection in the subject or a subject at risk thereof (i.e., efficacy), and avoiding undue toxicity or other harm thereto (i.e., safety). Therefore, "effective" refers to such choices that involve routine manipulation of conditions to achieve a desired effect or favorable response.

A bolus of the pharmaceutical composition can be administered to a subject over a short time, such as once a day is a convenient dosing schedule. Alternatively, the effective daily dose can be divided into multiple doses for purposes of administration, for example, two to twelve doses per day. Dosage levels of active ingredients in a pharmaceutical composition can also be varied so as to achieve a transient or sustained concentration of the composition in the subject, especially in and around the area of the bacterial infection or infection with a microorganism, and to result in the desired therapeutic response or protection. It is also within the skill of the art to start doses at levels lower than required to achieve the desired therapeutic effect and to gradually increase the dosage until the desired effect is achieved.

The amount of the pharmaceutical compositions to be administered to a subject is dependent upon factors known to a persons of ordinary skill in the art such as bioactivity and bioavailability of the antimicrobial agent (e.g., half-life in the body, stability, and metabolism of the engineered bacteriophage); chemical properties of the antimicrobial agent (e.g., molecular weight, hydrophobicity, and solubility); route and scheduling of administration, and the like. It will also be understood that the specific dose level of the composition comprising antimicrobial agents and engineered bacteriophages as disclosed herein to be achieved for any particular subject can depend on a variety of factors, including age, gender, health, medical history, weight, combination with one or more other drugs, and severity of disease, and bacterial strain or microorganism the subject is infected with, such as infection with multi-resistant bacterial strains.

The term "treatment", with respect to treatment of a bacterial infection or bacterial colonization, inter alia, preventing the development of the disease, or altering the course of the disease (for example, but not limited to, slowing the progression of the disease), or reversing a symptom of the disease or reducing one or more symptoms and/or one or more biochemical markers in a subject, preventing one or more symptoms from worsening or progressing, promoting recovery or improving prognosis, and/or preventing disease in a subject who is free therefrom as well as slowing or reducing progression of existing disease.

In some embodiments, efficacy of treatment can be measured as an improvement in morbidity or mortality (e.g., lengthening of survival curve for a selected population). Prophylactic methods (e.g., preventing or reducing the incidence of relapse) are also considered treatment.

Dosages, formulations, dosage volumes, regimens, and methods for analyzing results aimed at reducing the number of viable bacteria and/or activity can vary. Thus, minimum and maximum effective dosages vary depending on the method of administration. Suppression of the clinical changes associated with bacterial infections or infection with a microorganism can occur within a specific dosage range, which, however, varies depending on the organism receiving the dosage, the route of administration, whether the antimicrobial agents are administered in conjunction with the engineered bacteriophages as disclosed herein, and in some embodiments with other co-stimulatory molecules, and the specific regimen administration. For example, in general, nasal administration requires a smaller dosage than oral, enteral, rectal, or vaginal administration.

For oral or enteral formulations for use with the present invention, tablets can be formulated in accordance with conventional procedures employing solid carriers well-known in the art. Capsules employed for oral formulations to be used with the methods of the present invention can be made from any pharmaceutically acceptable material, such as gelatin or cellulose derivatives. Sustained release oral delivery systems and/or enteric coatings for orally administered dosage forms are also contemplated, such as those described in U.S. Pat. No. 4,704,295, "Enteric Film-Coating Compositions," issued Nov. 3, 1987; U.S. Pat. No. 4,556,552, "Enteric Film-Coating Compositions," issued Dec. 3, 1985; U.S. Pat. No. 4,309,404, "Sustained Release Pharmaceutical Compositions," issued Jan. 5, 1982; and U.S. Pat. No. 4,309,406, "Sustained Release Pharmaceutical Compositions," issued Jan. 5, 1982, which are incorporated herein in their entirety by reference.

Examples of solid carriers include starch, sugar, bentonite, silica, and other commonly used carriers. Further non-limiting examples of carriers and diluents which can be used in the formulations of the present invention include saline, syrup, dextrose, and water.

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. See, for example, Molecular Cloning: A Laboratory Manual, 2nd edition. (Sambrook, Fritsch and Maniatis, eds.), Cold Spring Harbor Laboratory Press, 1989; DNA Cloning, Volumes I and II (D. N. Glover, ed), 1985; Oligonucleotide Synthesis, (M. J. Gait, ed.), 1984; U.S. Pat. No. 4,683,195 (Mullis et al.,); Nucleic Acid Hybridization (B. D. Hames and S. J. Higgins, eds.), 1984; Transcription and Translation (B. D. Hames and S. J. Higgins, eds.), 1984; Culture of Animal Cells (R. I. Freshney, ed). Alan R. Liss, Inc., 1987; Immobilized Cells and Enzymes, IRL Press, 1986; A Practical Guide to Molecular Cloning (B. Perbal), 1984; Methods in Enzymology, Volumes 154 and 155 (Wu et al., eds), Academic Press, New York; Gene Transfer Vectors for Mammalian Cells (J. H. Miller and M. P. Calos, eds.), 1987, Cold Spring Harbor Laboratory; Immunochemical Methods in Cell and Molecular Biology (Mayer and Walker, eds.), Academic Press, London, 1987; Handbook of Experiment Immunology, Volumes I-IV (D. M. Weir and C. C. Blackwell, eds.), 1986; Manipulating the Mouse Embryo, Cold Spring Harbor Laboratory Press, 1986.

In some embodiments of the present invention may be defined in any of the following numbered paragraphs:

1. An engineered bacteriophage comprising a nucleic acid operatively linked to a promoter, wherein the nucleic acid encodes at least one agent that inhibits an antibiotic resistance gene and/or a cell survival repair gene.
2. The bacteriophage of any of paragraph 1, wherein the antibiotic resistance gene is selected from the group comprising cat, vanA or mecD or variants thereof.
3. The bacteriophage of any of paragraphs 1 or 2, wherein the cell survival gene is selected from the group comprising RecA, RecB, RecC, spot, RelA or variants thereof.
4. The bacteriophage of any of paragraphs 1 to 3, wherein the agent is selected from a group comprising, siRNA, antisense nucleic acid, asRNA, RNAi, miRNA and variants thereof.
5. The bacteriophage of any of paragraphs 1 to 4, wherein the agent is an antisense RNA (asRNA).
6. The bacteriophage of any of paragraphs 1 to 5, wherein the bacteriophage comprises a nucleic acid encoding at least two agents that inhibit at least two different cell survival repair genes.
7. The bacteriophage of any of paragraphs 1 to 6, wherein the bacteriophage comprises a nucleic acid encoding at least two agents that inhibit at least two of RecA, RecB or RecC.
8. An engineered bacteriophage comprising a nucleic acid operatively linked to a promoter, wherein the nucleic acid encodes at least one repressor of a SOS response gene and/or bacterial defense gene.
9. The bacteriophage of any of paragraphs 8, wherein the repressor of a SOS response gene is lexA.
10. The bacteriophage of any of paragraphs 8 or 9, wherein the repressor of a defense gene is SoxR.
11. The bacteriophage of any of paragraphs 8 to 10, wherein the repressor is selected from the group consisting of; marR, arcR, fur, crp, icdA or variants or fragments thereof.
12. The bacteriophage any of paragraphs 8 to 11, wherein the bacteriophage comprises a nucleic acid encoding at least two different repressors of at least one SOS response gene.
13. The bacteriophage any of paragraphs 8 to 12, wherein the bacteriophage comprises a nucleic acid encoding at least two different repressors of at least one bacterial defense gene.
14. An engineered bacteriophage comprising a nucleic acid operatively linked to a promoter, wherein the nucleic acid encodes at least one agent which increases the susceptibility of a bacteria cell to an antimicrobial agent.
15. The bacteriophage of paragraph 14, wherein the agent which increases the susceptibility of a bacteria cell to an antimicrobial agent increases the efficacy of the antimicrobial effect of the antimicrobial agent by at least 10%.
16. The bacteriophage any of paragraphs 14 or 15, wherein the agent which increases the susceptibility of a bacteria cell to an antimicrobial agent increases the entry of an antimicrobial agent to a bacterial cell.
17. The bacteriophage of any of paragraphs 14 to 16, wherein the agent which increases the entry of an antimicrobial agent to a bacterial cell is a porin.
18. The bacteriophage of any of paragraphs 14 to 17, wherein the porin is ompF or variants or fragments thereof.
19. The bacteriophage of any of paragraphs 14 to 15, wherein the agent which increases the susceptibility of a bacteria cell to an antimicrobial agent is craA or variants or fragments thereof.
20. The bacteriophage of any of paragraphs 14 to 15, wherein the agent which increases the susceptibility of a bacteria cell to an antimicrobial agent is craA or variants or fragments thereof.
21. The bacteriophage of any of paragraphs 14 to 15, wherein the agent which increases the susceptibility of a bacteria cell to an antimicrobial agent modifies a pathway specifically expressed in a bacterial cell.
22. The bacteriophage of any of paragraphs 14 to 15 or 21, wherein modification is inhibition or activation of a pathway specifically expressed in a bacterial cell.
23. The bacteriophage of any of paragraphs 14 to 15, wherein the agent which increases iron-sulfur clusters in the bacterial cell.
24. The bacteriophage of any of paragraphs 14 to 15, wherein the agent which increases oxidative stress in a bacterial cell or increases hydrozyl radicals in a bacterial cell.
25. The bacteriophage of any of paragraphs 14 to 24, wherein the agent is not substantially toxic a bacterial cell in the absence of an antimicrobial agent.
26. The bacteriophage of any of paragraphs 14 to 25, wherein the agent is not a chemotherapeutic agent or an protein toxin.
27. The bacteriophage of any of paragraphs 14 to 26, wherein the bacteriophage comprises a nucleic acid encoding at least two different proteins which increase the susceptibility of a bacteria cell to an antimicrobial agent.
28. The bacteriophage of any of paragraphs 14 to 27, wherein the proteins are csrA and ompF or variants or fragments thereof.
29. The bacteriophage of any of paragraphs 1 to 28, wherein the bacteriophage is a lysogenic bacteriophage.
30. The bacteriophage of any of paragraphs 1 to 29, wherein the lysogenic bacteriophage is a M13 bacteriophage.
31. The bacteriophage of any of paragraphs 1 to 29, wherein the bacteriophage is a lytic bacteriophage.
32. The bacteriophage of any of paragraphs 1 to 29, or 31 wherein the lytic bacteriophage is a T7 bacteriophage.
33. A method to inhibit or eliminate a bacterial infection comprising administering to a surface infected with bacteria; (a) a bacteriophage comprising a nucleic acid operatively linked to a bacteriophage promoter, wherein the nucleic acid encodes at least one agent that inhibits an antibiotic resistance gene and/or a cell survival repair gene, and (b) at least one antimicrobial agent.
34. A method to inhibit or eliminate a bacterial infection comprising administering to a surface infected with bacteria; (a) a bacteriophage comprising a nucleic acid operatively linked to a bacteriophage promoter, wherein the nucleic acid encodes at least one repressor of a SOS response gene or a bacterial-defense gene, and (b) at least one antimicrobial agent.
35. A method to inhibit or eliminate a bacterial infection comprising administering to a surface infected with bacteria; (a) a bacteriophage comprising nucleic acid operatively linked to a bacteriophage promoter, wherein the nucleic acid a encodes at least one agent which increases the susceptibility of a bacteria cell to an antimicrobial agent, and (b) at least one antimicrobial agent.
36. The method of paragraph 33, wherein the bacteriophage is a bacteriophage according to any of paragraphs 1 to 7 or 29-32.

37. The method of paragraph 34, wherein the bacteriophage is a bacteriophage according to any of paragraphs 8 to 13 or 29-32.
38. The method of paragraph 35, wherein the bacteriophage is a bacteriophage according to any of paragraphs 14 to 32.
39. The method of any of paragraphs 33 to 38, wherein the administration of the bacteriophage and the antimicrobial agent occurs simultaneously.
40. The method of any of paragraphs 33 to 38, wherein the administration of the bacteriophage occurs prior to the administration of the antimicrobial agent.
41. The method of any of paragraphs 33 to 38, wherein the administration of the antimicrobial agent occurs prior to the administration of the bacteriophage.
42. The method of any of paragraphs of any of paragraphs 33 to 38, wherein the antimicrobial agent is a quinolone antimicrobial agent.
43. The method of paragraph 33 to 42, wherein the antimicrobial agent is selected from a group consisting of ciproflaxacin, levofloxacin, and ofloxacin, gatifloxacin, norfloxacin, lomefloxacin, trovafloxacin, moxifloxacin, sparfloxacin, gemifloxacin, pazufloxacin or variants or analogues thereof.
44. The method of any of paragraphs 33 to 38, wherein the antimicrobial agent is ofloxacin or variants or analogues thereof.
45. The method of any of paragraphs 33 to 38, wherein the antimicrobial agent is an aminoglycoside antimicrobial agent.
46. The method of paragraph 45, wherein the antimicrobial agent is selected from a group consisting of amikacin, gentamycin, tobramycin, netromycin, streptomycin, kanamycin, paromomycin, neomycin or variants or analogues thereof.
47. The method of any of paragraphs 33 to 38, wherein the antimicrobial agent is gentamicin or variants or analogues thereof.
48. The method of any of paragraphs 33 to 38, wherein the antimicrobial agent is an β-lactam antibiotic antimicrobial agent.
49. The method of any of paragraphs 33 to 38, wherein the antimicrobial agent is selected from a group consisting of penicillin, ampicillin, penicillin derivatives, cephalosporins, monobactams, carbapenems, β-lactamase inhibitors or variants or analogues thereof.
50. The method of any of paragraphs 33 to 38, wherein the antimicrobial agent is ampicillin or variants or analogues thereof.
51. The method of any of paragraphs 33 to 38, wherein the bacteria is present in a subject.
52. The method of any of paragraphs 33 to 51, wherein the subject is a mammal.
53. The method of any of paragraph 33 to 52, wherein the mammal is a human.
54. The method of any of paragraphs 33 to 53, wherein the bacteria is in a biofilm.
55. A composition comprising a bacteriophage comprising a nucleic acid operatively linked to a promoter, wherein the nucleic acid encodes at least one agent that inhibits an antibiotic resistance gene and/or a cell survival repair gene and at least one antimicrobial agent.
56. A composition comprising a bacteriophage comprising a nucleic acid operatively linked to a promoter, wherein the nucleic acid encodes at least one repressor of a SOS response gene or a antimicrobial defense gene and at least one antimicrobial agent.
57. A composition comprising a bacteriophage comprising a nucleic acid operatively linked to a promoter, wherein the nucleic acid encodes at least one protein which increases the susceptibility of a bacteria cell to an antimicrobial agent and at least one antimicrobial agent.
58. The composition of any of paragraphs 55 to 57, wherein the antimicrobial agent is a quinolone antimicrobial agent, or aminoglycoside antimicrobial agent or β-lactam antimicrobial agent.
59. The composition of any of paragraphs 55 or 58, wherein the bacteriophage is according to any paragraphs 1-7 or 29-32.
60. The composition of paragraphs 56 or 58, wherein the bacteriophage is according to any paragraphs 8 to 13 or 29-32.
61. The composition of paragraphs 57 or 58, wherein the bacteriophage is according to any paragraphs 14 to 32.
62. A kit comprising a bacteriophage comprising the nucleic acid operatively linked to a promoter, wherein the nucleic acid encodes at least one agent that inhibits an antibiotic resistance gene and/or a cell survival repair gene.
63. A kit comprising a bacteriophage comprising the nucleic acid operatively linked to a promoter, wherein the nucleic acid encodes at least one repressor of a SOS response or an antimicrobial defense gene.
64. A kit comprising a bacteriophage comprising the nucleic acid operatively linked to a promoter, wherein the nucleic acid encodes at least one protein which increases the susceptibility of a bacteria cell to an antimicrobial agent and at least one antimicrobial agent.
65. The use of a bacteriophage according to any of paragraphs 1 to 23 in combination with an antimicrobial agent to reduce the number of bacteria as compared to use of the antimicrobial agent alone.
66. The use of any of the paragraphs 62-65, wherein the bacteria is in a biofilm.
67. A combination of at least two bacteriophages of any of paragraphs 1 to 23 with at least one antimicrobial agent.
68. The combination of paragraph 67, wherein the antimicrobial agent is a quinolone antimicrobial agent.
69. The combination of paragraph 67, wherein the antimicrobial agent is selected from a group consisting of ciproflaxacin, levofloxacin, and ofloxacin, gatifloxacin, norfloxacin, lomefloxacin, trovafloxacin, moxifloxacin, sparfloxacin, gemifloxacin, pazufloxacin or variants or analogues thereof.
70. The combination of paragraph 67, wherein the antimicrobial agent is ofloxacin or variants or analogues thereof.
71. The combination of paragraph 67, wherein the antimicrobial agent is an aminoglycoside antimicrobial agent.
72. The combination of paragraph 67, wherein the antimicrobial agent is selected from a group consisting of amikacin, gentamycin, tobramycin, netromycin, streptomycin, kanamycin, paromomycin, neomycin or variants or analogues thereof.
73. The combination of paragraph 67, wherein the antimicrobial agent is gentamicin or variants or analogues thereof.
74. The combination of paragraph 67, wherein the antimicrobial agent is an β-lactam antibiotic antimicrobial agent.
75. The combination of paragraph 67, wherein the antimicrobial agent is selected from a group consisting of penicillin, ampicillin, penicillin derivatives, cephalosporins, monobactams, carbapenems, β-lactamase inhibitors or variants or analogues thereof.
76. The combination of paragraph 67, wherein the antimicrobial agent is ampicillin or variants or analogues thereof.

77. The combination of paragraph 67, wherein the composition comprises a combination of any of the antimicrobial agents according to paragraphs 68-76.
78. Use of a bacteriophage of any of claims 1 to 32 with at least one antimicrobial agent.
79. Use of a combination of at least two of any the bacteriophages of claims 1 to 32 with at least one antimicrobial agent.
80. The use of a bacteriophage of claim 78 or 79 or any to claims 1 to 32 to inhibit or eliminate a bacterial infection.
81. The use of a bacteriophage of claim 78 or 79, wherein the bacteria is present in a subject.
82. The use of a bacteriophage of claim 81, wherein the subject is a mammal.
83. The use of a bacteriophage of claim 82, wherein the mammal is a human.
84. The use of a bacteriophage of claim 78 or 79, wherein the bacteria is in a biofilm.
85. Use of a composition of any of claims 55 to 57 to inhibit or eliminate a bacterial infection.
86. The use of the composition of claim 85, wherein the bacteria is present in a subject.
87. The use of the composition of claim 86, wherein the subject is a mammal.
88. The use of the composition of claim 87, wherein the mammal is a human.
89. The use of the composition of claim 85, wherein the bacteria is in a biofilm.

The following Examples are provided to illustrate the present invention, and should not be construed as limiting thereof.

EXAMPLES

The examples presented herein relate to the methods and compositions comprising inhibitor-engineered bacteriophages, repressor-engineered bacteriophages or susceptibility-agent engineered bacteriophages and antimicrobial agents. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Methods

Bacterial strains, bacteriophage, and chemicals. *E. coli* K-12 EMG2 cells, which lack O antigens, were obtained from the Yale Coli Genetic Stock Center (CGSC #4401). *E. coli* RFS289 cells, which contain a gyrA111 mutation rendering them resistant to quinolones, were obtained from the Yale Coli Genetic Stock Center (CGSC #5742). M13mp18 bacteriophage was purchased from New England Biolabs, Inc. (Ipswich, Mass.). *E. coli* XL-10 cells used for cloning, amplifying phage, and plating phage were obtained from Stratagene (La Jolla, Calif.).

T4 DNA ligase and all restriction enzymes were purchased from New England Biolabs, Inc. (Ipswich, Mass.). PCR reactions were carried out using PCR SUPERMIX HIGH FIDELITY from INVITROGEN (Carlsbad, Calif.) or PHUSION HIGH FIDELITY from New England Biolabs, Inc. (Ipswich, Mass.). Purification of PCR reactions and restriction digests was carried out with the QIAQUICK GEL Extraction or PCR Purification kits (QIAGEN, Valencia, Calif.). Plasmid DNA was isolated using the QIAPREP SPIN Miniprep kit (QIAGEN, Valencia, Calif.). All other chemicals and materials were purchased from Fisher Scientific, Inc. (Hampton, N.H.).

Engineering M13mp18 bacteriophage to target genetic networks. To construct engineered phage, lexA3, soxR, csrA, and ompF genes were first placed under the control of the $P_L$tetO promoter in the pZE11G vector[50,51]. Using PCR with primers 5' ttatca ggtacc atgAAAGCGT TAACGGCC 3' (SEQ ID NO: 18) and 5' atacat aagctt TTACAGCCA GTCGCCG 3' (SEQ ID NO: 19), lexA3 was cloned between the KpnI and HindIII sites of pZE11G to form pZE11-lexA3. Since soxR has an internal KpnI site, the inventors built a synthetic RBS by sequential PCR using 5' agaggagaaa ggtacc atgGAAAAGA AATTACCCCG 3' (SEQ ID NO: 20) and 5' atacat aagctt TTAGT TTTGTTCATC TTCCAG 3' (SEQ ID NO: 21) followed by 5' agtaga gaattc attaaagaggagaaa ggtacc atg 3' (SEQ ID NO: 22) and 5' atacat aagctt TTAGT TTTGTTCATC TTCCAG 3' (SEQ ID NO: 23). The resulting EcoRI-RBS-soxR-HindIII DNA was ligated to an XhoI-$P_L$tetO-EcoRI fragment excised from pZE11G and the entire DNA fragment was ligated into pZE11G between XhoI and HindIII to form pZE11-soxR[50]. Primers for csrA for cloning into pZE11G in between KpnI and HindIII to form pZE11-csrA were 5' agaggagaaa ggtacc atgCTGATTC TGACTCGT 3' (SEQ ID NO: 24) and 5' atacat aagctt TTAGTA ACTGGACTG C TGG 3' (SEQ ID NO: 25); and for ompF to form pZE11-ompF, 5' agaggagaaa ggtacc atgATGAAG C GCAATATTCT 3' (SEQ ID NO: 26) and 5' atacat aagctt TTAGAACTG GTAAACGATA CC 3' (SEQ ID NO: 27). To express csrA and ompF simultaneously under the control of $P_L$tetO, we PCR amplified RBS-ompF DNA from pZE11-ompF using 5' ccagtc aagctt attaaagaggagaaa ggtacc 3' (SEQ ID NO: 28) and 5' atacat GGATCC TTAGAACTG GTAAACGATA CC 3' (SEQ ID NO: 29) and cloned the product in between HindIII and BamHI in pZE11-csrA to form pZE11-csrA-ompF. The resulting plasmids were transformed into *E. coli* XL-10 cells.

All $P_L$tetO-gene constructs followed by terminator T1 of the rrnB operon and preceded by a stop codon were PCR amplified from the respective pZE11 plasmids with primers 5' aataca GAGCTC cTAA tccctatcagtgatagagattg 3' (SEQ ID NO: 30) and 5' taatct CGATCG tctagggcggcggat 3' (SEQ ID NO: 31) and cloned into the SacI and PvuI sites of M13mp18 (FIG. 5)[48,50,51]. Resulting phage genomes were transformed into XL-10 cells, mixed with 200 μL overnight XL-10 cells in 3 mL top agar, 1 mM IPTG, and 40 μL of 20 mg/mL X-gal, and poured onto LB agar+chloramphenicol (30 μg/mL) plates for plaque formation and blue-white screening. After overnight incubation of plates at 37° C., white plaques were scraped and placed into 1:10 dilutions of overnight XL-10 cells and grown for 5 hours. Replicative form (RF) M13mp18 DNA was collected by DNA minipreps of the bacterial cultures. All insertions into M13mp18 were verified by PCR and restriction digests of RF DNA. Infective bacteriophage solutions were obtained by centrifuging infected cultures for 5 minutes at 16,100×g and collecting supernatants followed by filtration through Nalgene #190-2520 0.2 μm filters (Nalge Nunc International, Rochester, N.Y.).

Determination of plaque forming units. To obtain plaque forming units, we added serial dilutions of bacteriophage performed in 1×PBS to 200 μL of overnight XL-10 cells in 3 mL top agar, 1 mM IPTG, and 40 μL of 20 mg/mL X-gal, and poured the mixture onto LB agar+chloramphenicol (30 μg/mL) plates. After overnight incubation at 37° C., plaques were counted.

Determination of colony forming units. To obtain CFU counts, 150 μL of relevant cultures were collected, washed with 1× phosphate-buffered saline (PBS), recollected, and resuspended in 150 μL of 1×PBS. Serial dilutions were performed with 1×PBS and sampled on LB agar plates. LB agar plates were incubated at 37° C. overnight before counting.

Flow cytometer assay of SOS induction. To monitor M13mp18-lexA3's ($\phi_{lexA}$) suppression of the SOS response (FIG. 10), the inventors used a plasmid containing an SOS-response promoter driving gfp expression in EMG2 cells ($P_L$lexO-gfp)[43]. After growing 1:500 dilutions of the overnight cells for 2 hours and 15 minutes at 37° C. and 300 rpm (model G25 incubator shaker, New Brunswick Scientific), the inventors applied ofloxacin and bacteriophage and treated for 6 hours at 37° C. and 300 rpm. Cells were then analyzed for GFP fluorescence using a Becton Dickinson (Franklin Lakes, N.J.) FACS caliber flow cytometer with a 488-nm argon laser and a 515-545 nm emission filter (FL1) at low flow rate. The following photo-multiplier tube (PMT) settings were used for analysis: E00 (FSC), 275 (SSC), and 700 (FL1). Becton Dickinson CALIBRITE Beads were used for instrument calibration. 200,000 cells were collected for each sample and processed with MATLAB (Mathworks, Natick, Mass.).

Figures 1B, 1C:
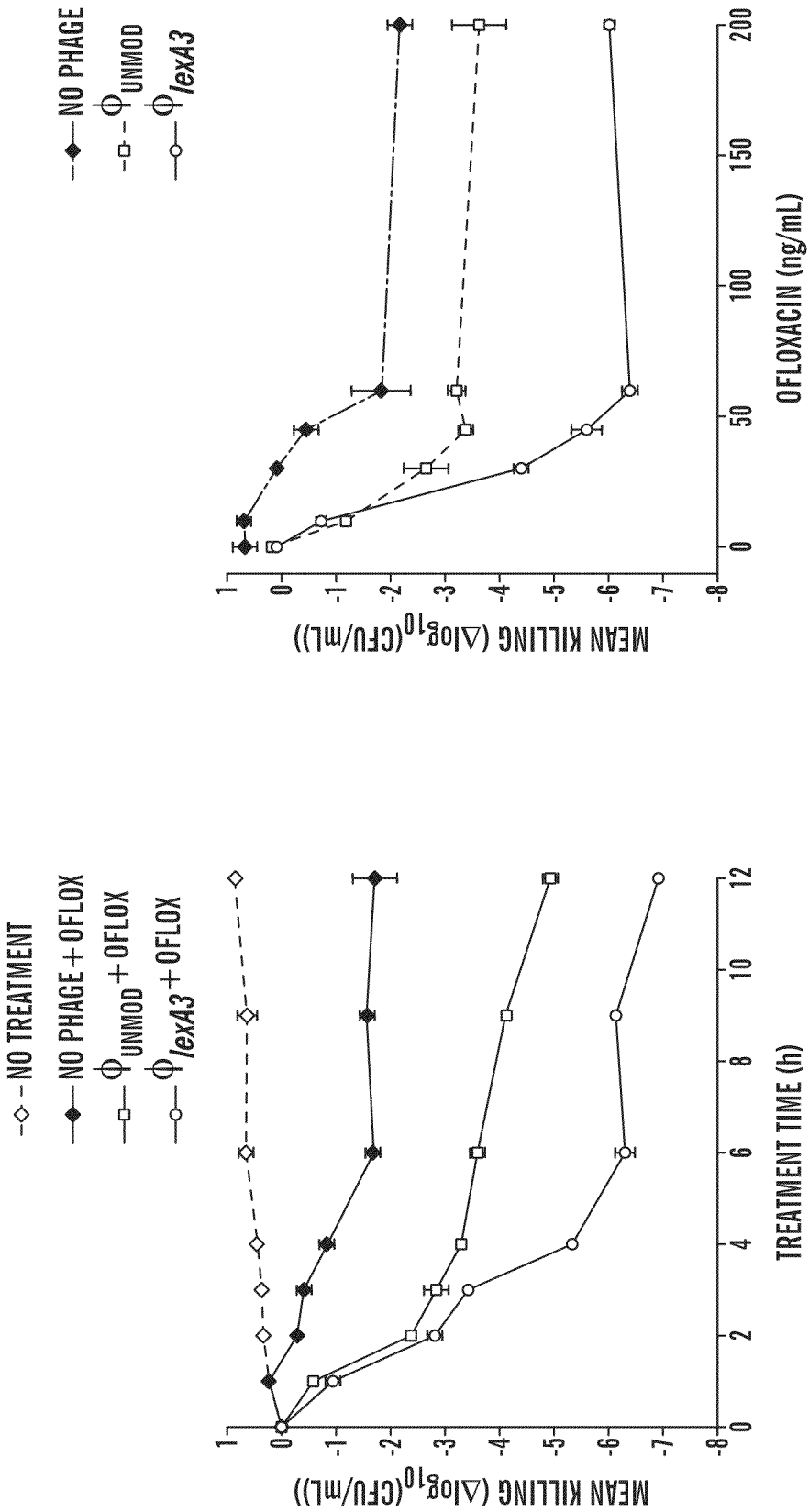
Figure 2:
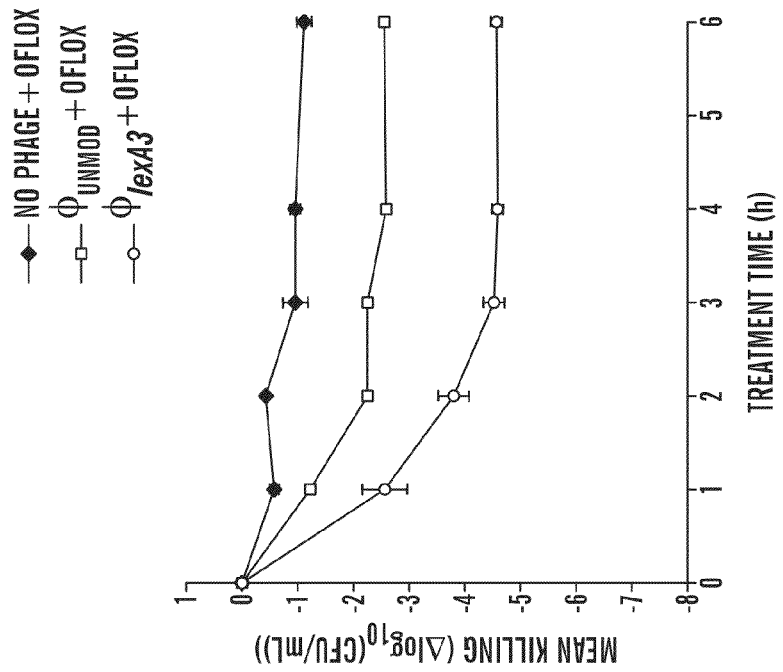
FIG. 2 shows that engineered $\phi_{lexA}$ bacteriophage enhances killing of quinolone-resistant *E. coli* RFS289 bacteria by ofloxacin. Killing curves for no phage (diamonds), unmodified phage funmod (squares), and engineered phage $\phi_{lexA3}$ (circles) with 1 μg/mL ofloxacin [oflox] (solid lines, closed symbols). $10^8$ PFU/mL phage was used. $\phi_{lexA3}$ greatly enhanced killing by ofloxacin by 1 hour of treatment.

Ofloxacin killing assay. To determine the adjuvant effect of engineered phage (FIG. 1B, FIG. 3A and FIG. 3D), the inventors grew 1:500 dilutions of overnight EMG2 cells for 3 hours and 30 minutes at 37° C. and 300 rpm to late-exponential phase and determined initial CFUs. Then, the inventors added 60 ng/mL ofloxacin by itself or in combination with $10^8$ PFU/mL bacteriophage (unmodified $\phi_{unmod}$ or engineered $\phi_{LexA}$, $\phi_{SoxR}$, $\phi_{csr}$, $\phi_{ompF}$, or $\phi_{Csr\text{-}ompF}$ phage) and treated at 37° C. and 300 rpm. At indicated time points, the inventors determined CFUs as described above. Mean killing ($\Delta\log_{10}$ (CFU/mL)) was determined by subtracting mean initial $\log_{10}$ (CFU/mL) from mean $\log_{10}$ (CFU/mL) after treatment in order to compare data from different experiments. This protocol was replicated with E. coli RFS289 to determine the ofloxacin-enhancing effect of engineered $\phi_{lexA3}$ phage against antibiotic-resistant bacteria (FIG. 2). In addition, viable cell counts were obtained for ofloxacin-free EMG2 cultures, ofloxacin-free EMG2 cultures with $\phi_{unmod}$ phage, and ofloxacin-free EMG2 cultures with engineered $\phi_{lexA3}$ phage.

Dose response assays. The initial phage inoculation dose response experiments (FIG. 1c and FIG. 15) were handled using the same protocol as the ofloxacin killing assay except that 60 ng/mL ofloxacin was added with varying concentrations of phage. Cultures were treated for 6 hours before obtaining viable cell counts. The ofloxacin dose response experiments (FIG. 1C) were also obtained using the same protocol as the ofloxacin killing assay except that $10^8$ PFU/mL phage were added with varying concentrations of ofloxacin and viable cell counts were obtained after 6 hours of treatment.

Figure 11:
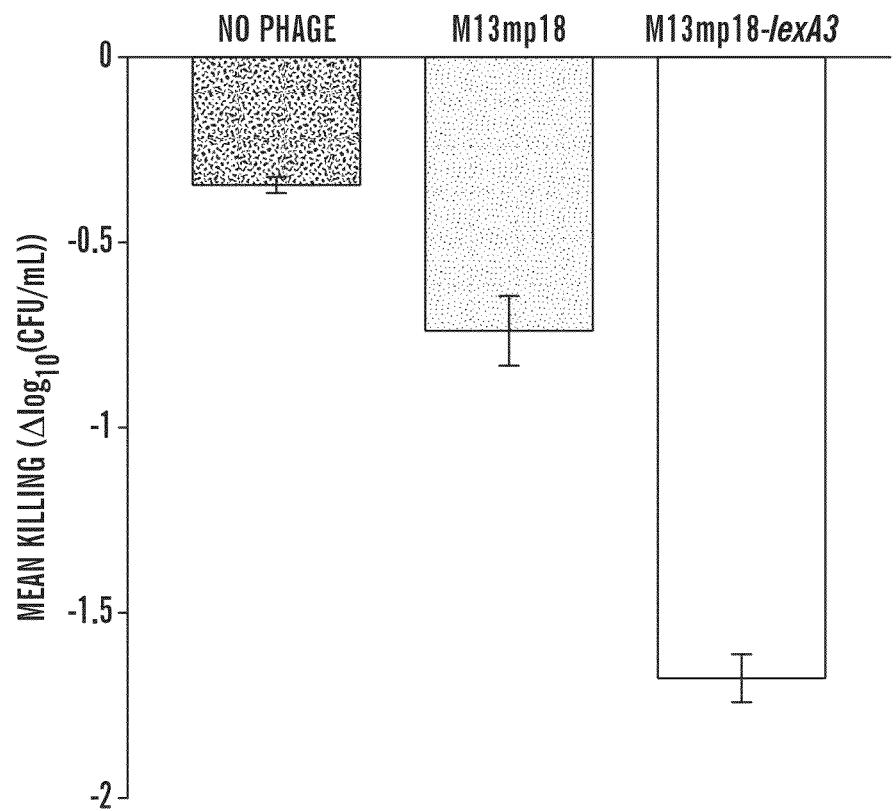
FIG. 11 shows persister killing assay demonstrates that engineered bacteriophage can be applied to a previously drug-treated population to increase killing of surviving persister cells. After 3 hours of 200 ng/mL ofloxacin treatment, no phage, $10^9$ PFU/mL control M13mp18 phage, or $10^9$ PFU/mL engineered M13mp18-lexA3 phage were added to the previously drug-treated cultures. Three additional hours later, viable cell counts were obtained and demonstrated that M13mp18-lexA3 was able to reduce persister cell levels better than no phage or control M13mp8 phage.
Figure 16:
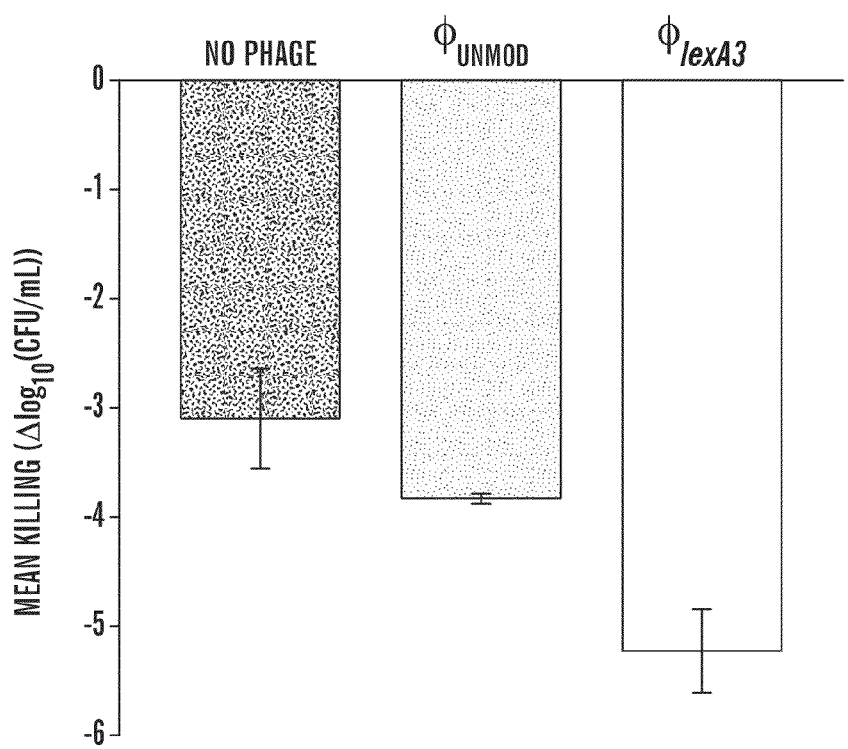
FIG. 16 shows persister killing assay demonstrates that engineered bacteriophage can be applied to a previously drug-treated population to increase killing of surviving persister cells. After 3 hours of 200 ng/mL ofloxacin treatment, no phage (black bar), $10^9$ PFU/mL unmodified phage $\phi_{unmod}$ (red bar), or $10^9$ PFU/mL engineered phage $\phi_{lexA}3$ (blue bar) were added to the previously drug-treated cultures. Three additional hours later, viable cell counts were obtained and demonstrated that $\phi l_{exA3}$ was able to reduce persister cell levels better than no phage or $\phi_{unmod}$.

Persister killing assay. The inventors performed a persister killing assay to determine whether engineered phage could help to kill persister cells in a population which survived initial drug treatment without bacteriophage (FIGS. 11 and 16). The inventors first grew 1:500 dilutions of overnight EMG2 for 3 hours and 30 minutes at 37° C. and 300 rpm followed by treatment with 200 ng/mL ofloxacin for 3 hours to create a population of surviving bacteria. Then, the inventors added either no phage, $10^9$ PFU/mL control $\phi_{unmod}$, or $10^9$ PFU/mL engineered $\phi_{LexA3}$ phage. After 3 hours of additional treatment, the inventors collected the samples and assayed for viable cell counts as described above.

Figure 17:
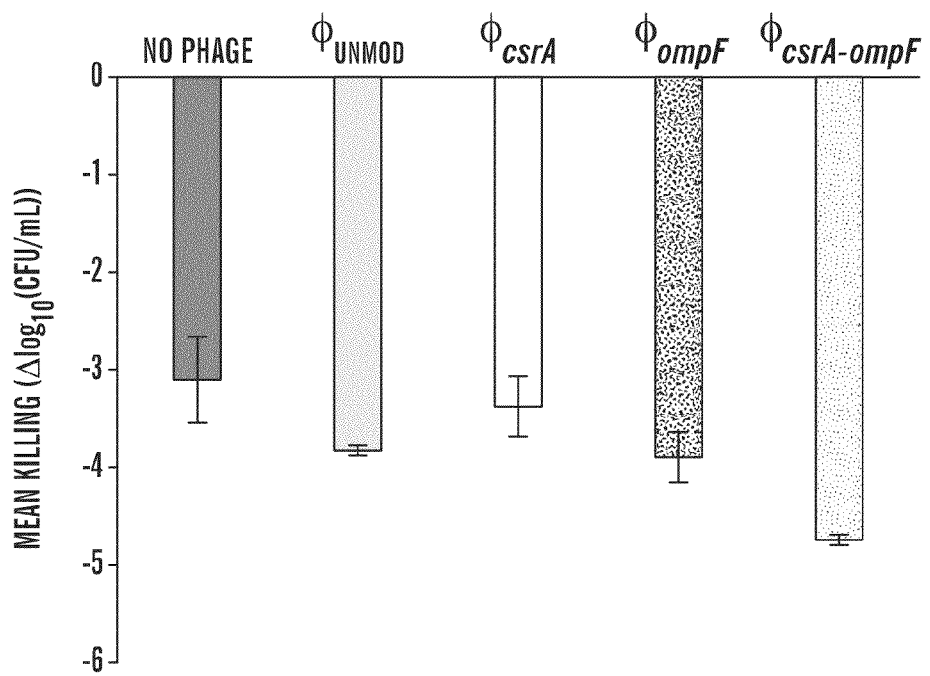
FIG. 17 shows mean killing with 60 ng/mL ofloxacin after 12 hours of treatment of E. coli EMG2 biofilms pregrown for 24 hours. Where indicated, $10^8$ PFU/mL of (r) lexA3 bacteriophage was used.
Figure 18:
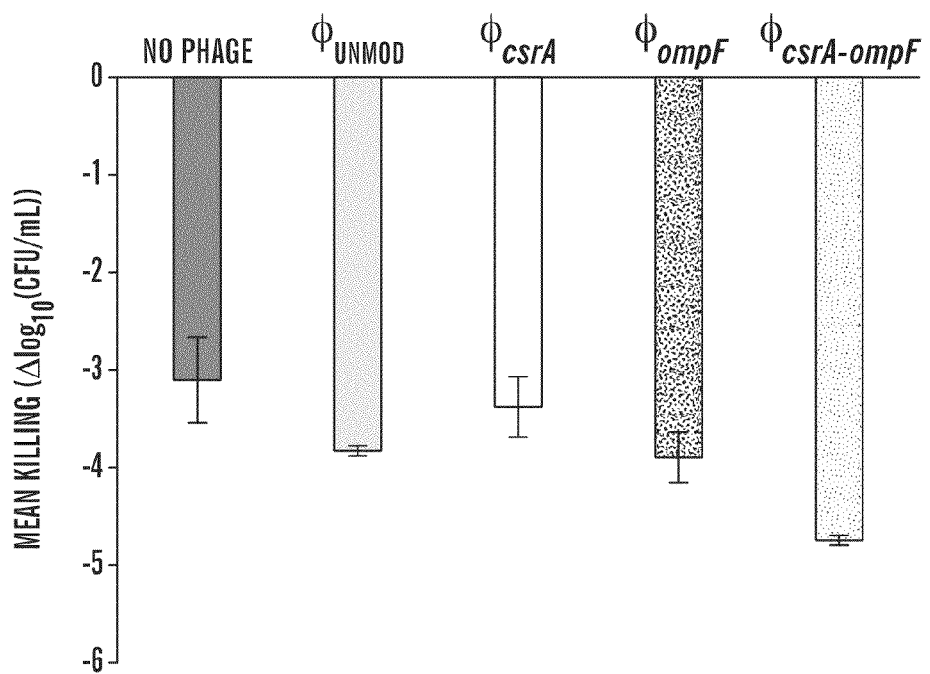
FIG. 18 shows the mean killing with 60 ng/mL ofloxacin after 12 hours of treatment of E. coli EMG2 biofilms pregrown for 24 hours. Where indicated, $10^8$ PFU/mL of $\phi_{csrA}$, $\phi_{ompF}$, or $\phi_{csrA-ompF}$ bacteriophage was used.
Figure 19:
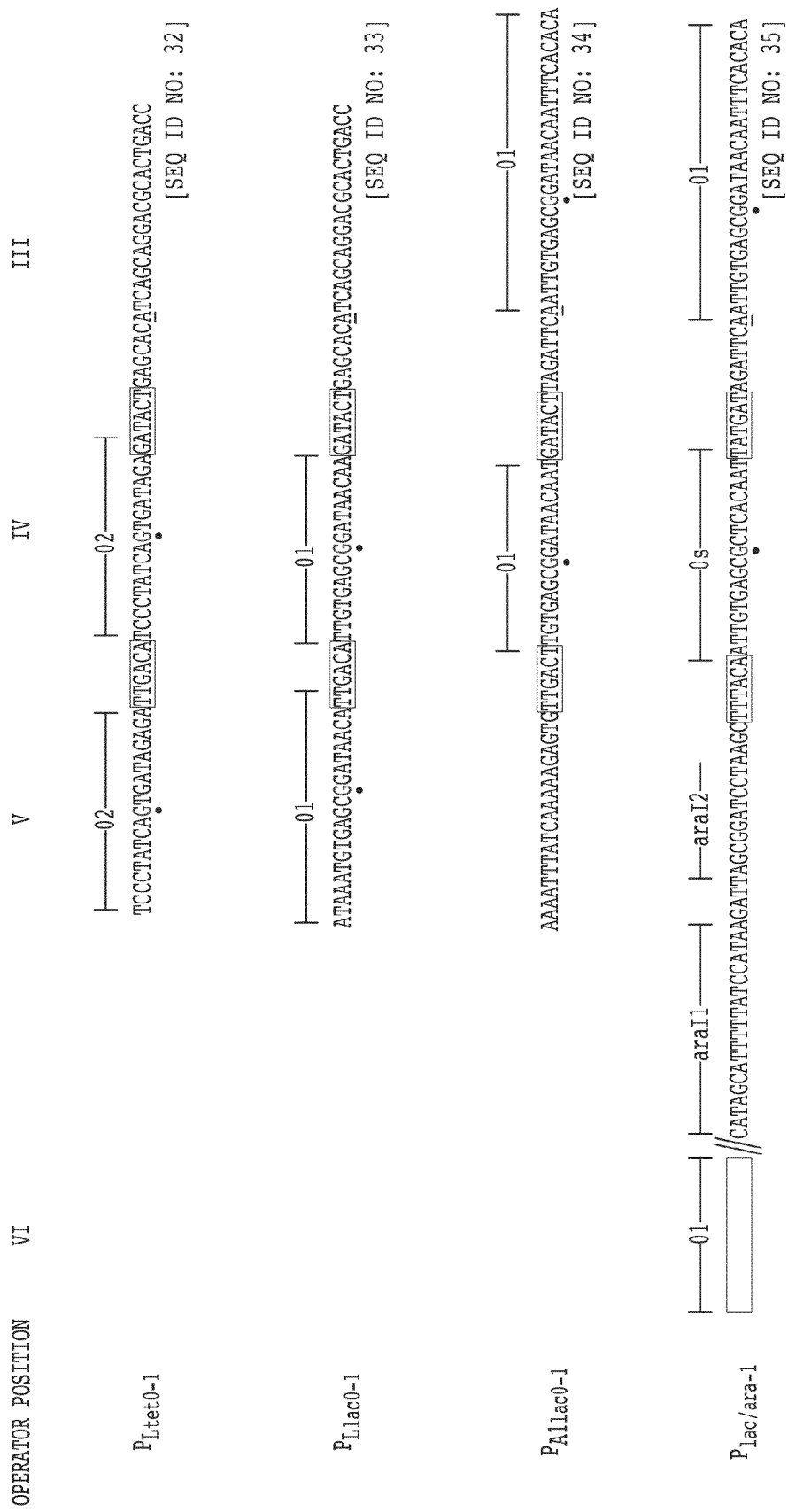
FIG. 19 shows an example of a promoter which can be used to express the nucleic acid in the engineered bacteriophage.

Biofilm killing assay. Biofilms were grown using E. coli EMG2 cells according to a previously-reported protocol (Lu and Collins, 2007). Briefly, lids containing plastic pegs (MBEC Physiology and Genetics Assay, Edmonton, Calif.) were placed in 96-well plates containing overnight cells that were diluted 1:200 in 150 μL LB. Plates were then inserted into plastic bags to minimize evaporation and inserted in a Minitron shaker (Infors HT, Bottmingen, Switzerland). After 24 hours of growth at 35° C. and 150 rpm, lids were moved into new 96-well plates with 200 μL LB with or without $10^8$ PFU/mL of bacteriophage. After 12 hours of treatment at 35° C. and 150 rpm, lids were removed, washed three times in 200 μL of 1×PBS, inserted into Nunc #262162 microtiter plates with 150 μL 1×PBS, and sonicated in an Ultrasonics 5510 sonic water bath (Branson, Danbury, Conn.) at 40 kHz for 30 minutes. Serial dilutions, using the resulting 150 μL 1×PBS, were performed on LB plates and viable cell counts were determined. Mean killing ($\Delta\log_{10}$ (CFU/mL)) was calculated by subtracting mean $\log_{10}$ (CFU/mL) after 24 hours of growth from mean $\log_{10}$ (CFU/mL) after 12 hours of treatment (FIG. 17 and FIG. 18).

Figures 7A, 7B:
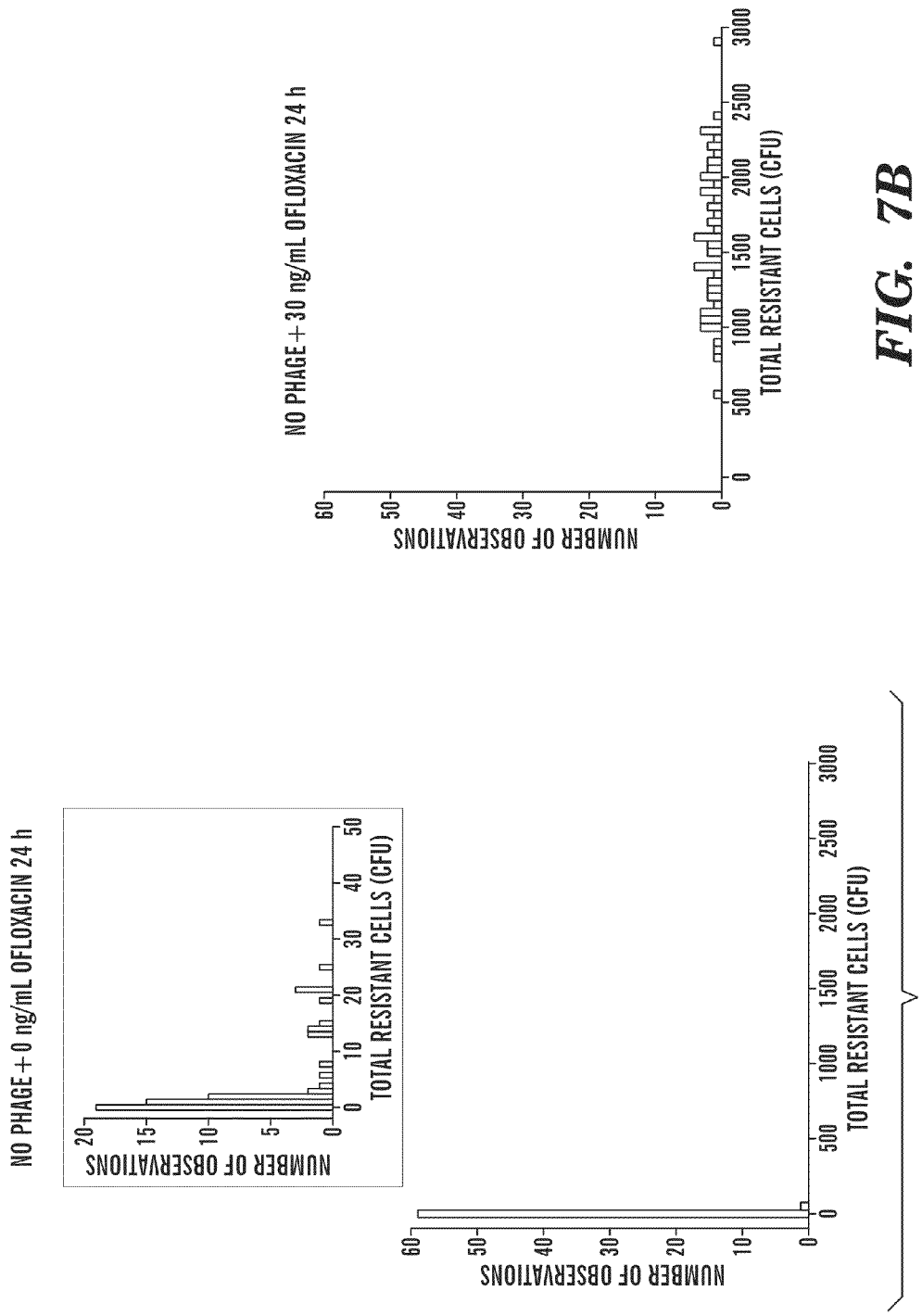
FIGS. 7A-7D show histograms of the total number of *E. coli* cells in 60 observations that were resistant to 100 ng/mL ofloxacin after growth under various conditions.
Figures 7C, 7D:
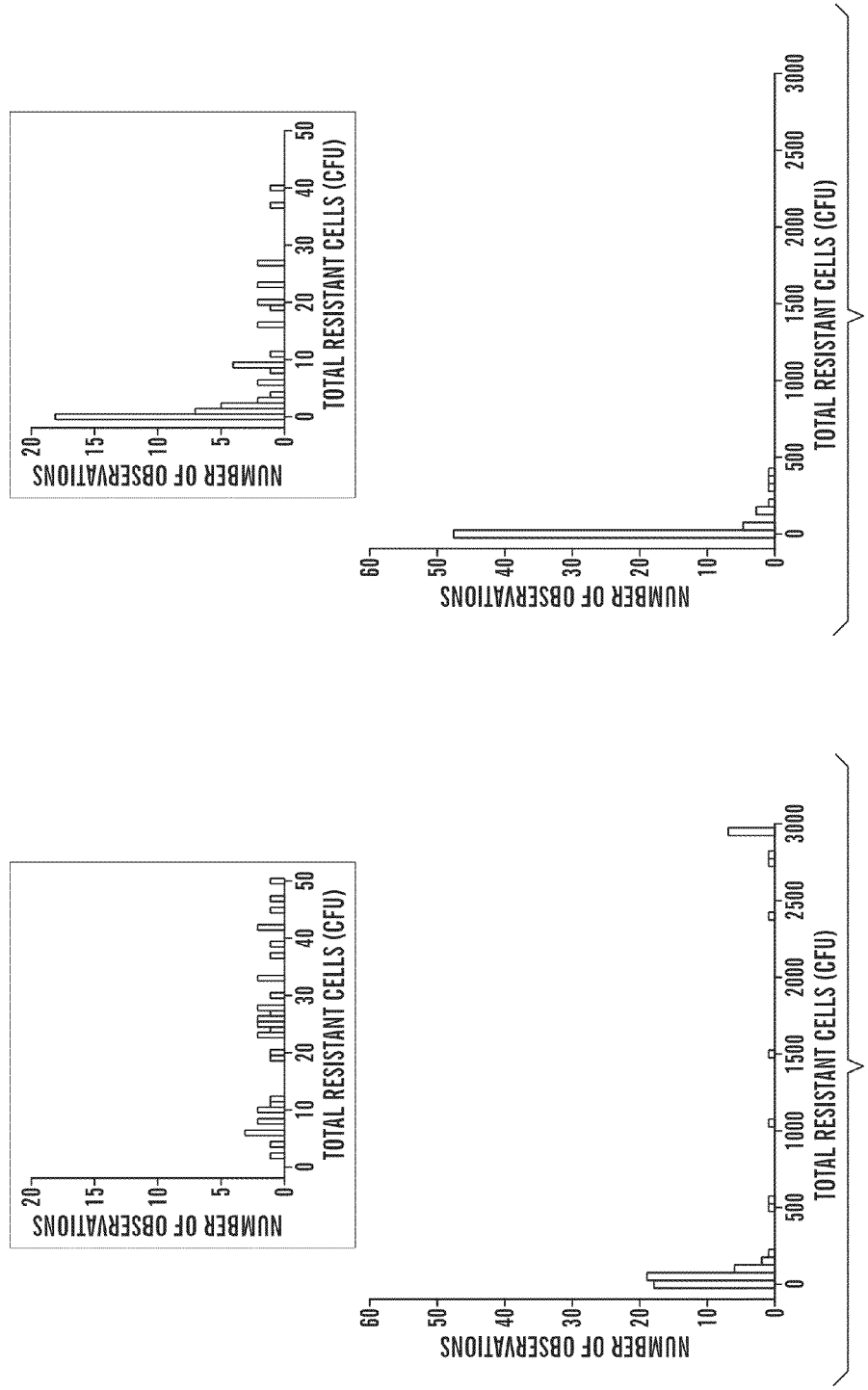

Antibiotic resistance assay. To analyze the effect of subinhibitory concentrations of ofloxacin on the development of antibiotic-resistant mutants, the inventors grew 1:$10^8$ dilutions of overnight EMG2 in LB media containing either no ofloxacin (FIG. 4) or 30 ng/mL ofloxacin (FIG. 7). After 12 hours of growth at 37° C. and 300 rpm, the inventors split the cells grown in no ofloxacin into 100 uL aliquots with no ofloxacin in 60 wells in 96-well plate format (Costar 3370; Fisher Scientific, Pittsburgh, Pa.). The inventors also split the cells grown in 30 ng/mL ofloxacin into 100 uL aliquots in 60 wells with either no phage and 30 ng/mL ofloxacin (FIG. 7B), $\phi_{unmod}$ phage and 30 ng/mL ofloxacin (FIG. 7C), and $\phi_{lexA3}$ and 30 ng/mL ofloxacin (FIG. 7D) in 96-well plate format. The inventors placed the 96-well plates in 37° C. and 300 rpm with plastic bags to minimize evaporation. After 12 hours of treatment, the inventors plated cultures from each well on LB agar+100 ng/mL ofloxacin to select for mutants that developed resistance against ofloxacin. To compare results, the inventors plotted histograms of the number of resistant bacteria found in each well in FIGS. 4 and 8.

Gentamicin and ampicillin killing assays. To determine the antibiotic enhancing or adjuvant effect of engineered bacteriophage for gentamicin and ampicillin, the inventors used the same protocol as the ofloxacin killing assay except that the inventors used $10^9$ PFU/mL initial phage inoculations. 5 μg/mL gentamicin and 5 μg/mL ampicillin were used in FIGS. 1D, 1E, 8A and 8B.

Statistical analysis. All CFU data were $\log_{10}$-transformed prior to analysis. For all data points in all experiments, n=3 samples were collected except where noted. Error bars in figures indicate standard error of the mean.

Example 1

The inventors have engineered synthetic bacteriophage to target genetic networks in order to potentiate bacterial killing in combination therapy with antibiotics. The inventors specifically targeted genetic networks in E. coli which are not directly attacked by antibiotics to avoid imposing additional evolutionary pressures for antibiotic resistance. Instead, the inventors chose proteins that are responsible for repairing cellular damage caused by antibiotics, those that control regulatory networks, or those that modulate sensitivity to antibiotics Unlike conventional antibiotics that act by disrupting protein activity, the inventors designed an engineered phage to overexpress target genes, such as repressors and act as effective antibiotic adjuvants.

Bactericidal antibiotics cause hydroxyl radical formation which leads to DNA, protein, and lipid damage and ultimately, cell death[44]. DNA damage induces the SOS response (Miller et al., (2004) *Science* 305, 1629-1631; Lewin et al., (1989) *J. Med. Microbiol.* 29, 139-144.), which results in DNA repair (FIG. 1A). It has been shown that bacterial killing by bactericidal antibiotics can be enhanced by knocking out recA and disabling the SOS response (Kohanski et al., (2007) *Cell* 130). Here, the inventors used an alternative approach and engineered M13mp8 phage to overexpress lexA3, a repressor of the SOS response (Little et al., (1979) *Proc Natl Acad Sci USA* 76, 6147-51). Overexpression of lexA to suppress the SOS system has been demonstrated to inhibit the emergence of antibiotic resistance (Cirz et al., (2005) in *PLoS Biol, p. e17624*). The inventors used M13mp18, a modified version of M13 phage, as the substrate since it is a non-lytic filamentous phage and can accommodate DNA insertions into its genome (Figure S1) (Yanisch-Perron et al., (1985) *Gene* 33, 103-119).

To repress the SOS response, the inventors placed the lexA3 gene under the control of the synthetic PLtetO promoter followed by a synthetic ribosome-binding sequence (RBS) (Kohanski et al., (2007) *Cell* 130, 797-810; Little et al., (1979) *Proc Natl Acad Sci USA* 76, 6147-51; Walker G C (1984) *Microbiol. Rev.* 48, 60-93; Lutz et al., (1997) *Nucleic Acids Res* 25, 1203-1210.); The inventors named this phage "$\phi_{lexA3}$" (FIG. 1A and Figure S1B) and the unmodified M13mp18 phage $\phi_{unmod}$. PLtetO, which is an inducible promoter in the presence of the TetR repressor, is constitutively on in EMG2 cells, which lack TetR. PLtetO was used for convenience in proof-of-concept experiments as described herein and would not necessarily be the promoter of choice in real-world situations. Accordingly, one of ordinary skill in the art can readily substitute the PLtetO promoter with a different inducible or constitutively active or tissue specific promoter of their choice. The inventors confirmed that $\phi_{lexA3}$ suppressed the SOS response induced by ofloxacin treatment by monitoring GFP fluorescence in *E. coli* K-12 EMG2 cells carrying a plasmid with an SOS-responsive promoter driving gfp expression (Figure S2) (Kohanski et al., (2007) *Cell* 130, 797-810).

To test $\phi_{lexA3}$'s antibiotic-enhancing effect, the inventors obtained time courses for killing of *E. coli* EMG2 bacteria with phage and/or ofloxacin treatment. The inventors calculated viable cell counts by counting colony-forming units (CFUs) during treatment with no phage or $10^8$ plaque-forming units/mL (PFU/mL) of phage and with no ofloxacin or 60 ng/mL ofloxacin (FIG. 1B). Bacteria exposed only to ofloxacin were reduced by about 1.7 $\log_{10}$ (CFU/mL) after 6 hours of treatment, reflecting the presence of persisters not killed by the drug (FIG. 1B). By 6 hours, $\phi_{lexA3}$ improved the bactericidal effect of ofloxacin by 2.7 orders of magnitude compared to unmodified phage $\phi_{unmod}$ (~99.8% additional killing) and by over 4.5 orders of magnitude compared to no phage (~99.998% additional killing) (FIG. 1B). Unmodified phage enhanced ofloxacin's bactericidal effect, which is consistent with previous observations that unmodified filamentous phage augment antibiotic efficacy against *Pseudomonas aeruginosa* (Hagens et al., (2006) *Microb Drug Resist* 12, 164-168). Other researchers have noted that M13-infected *E. coli* exhibited impaired host stress responses to conditions such as acid stress (Karlsson et al., (2005) *Can J Microbiol* 51, 29-35). While wishing not to be bound by theory, the mechanism by which unmodified filamentous phage can augment antibiotic efficacy is not well characterized but can involve membrane disruption or impaired stress responses. No significant bacterial regrowth was apparent with combination phage and antibiotic treatment up to 12 hours (FIG. 1B) (Hagens et al., (2003) *Lett. Appl. Microbiol.* 37, 318-23; Hagens et al., (2004) *Antimicrob. Agents Chemother.* 48, 3817-22; Summers W C (2001) *Annu. Rev. Microbiol.* 55, 437-451). The inventors confirmed that both $\phi_{unmod}$ and $\phi_{lexA3}$ replicated significantly during treatment (data not shown).

Example 2

Figure 15:
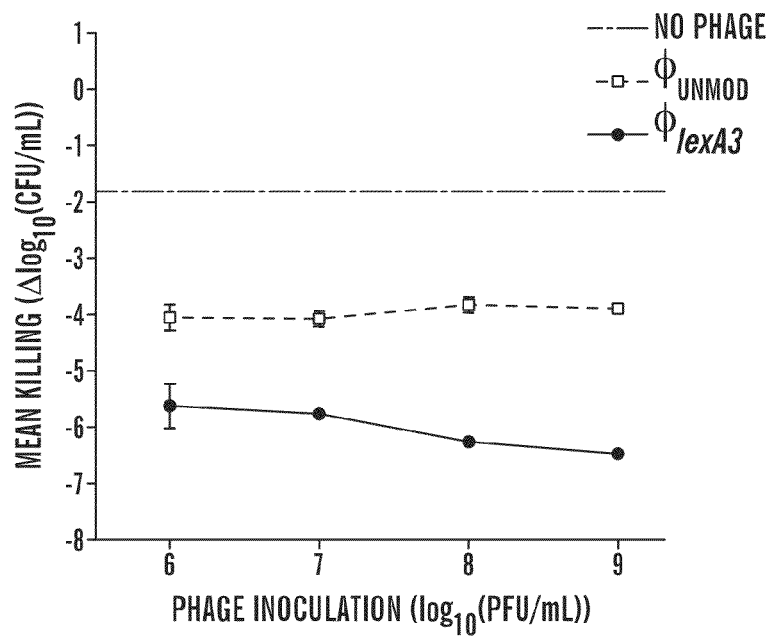
FIG. 15 shows engineered $\phi_{lexA3}$ bacteriophage enhances killing of wild-type E. coli EMG2 bacteria by bactericidal antibiotics. Phage dose response shows that $\phi_{lexA3}$ (blue circles with solid line) is a strong adjuvant for ofloxacin (60 ng/mL) over a wide range of initial inoculations compared with no phage (black dash-dotted line) and $\phi_{unmod}$ (red squares with dashed line). The starting concentration of bacteria was about $10^9$ CFU/mL (data not shown).

To test whether $\phi_{lexA3}$ can act as an antibiotic adjuvant in different situations, the inventors assayed for bacterial killing with varying initial phage inoculation doses (FIG. 15) and varying doses of ofloxacin (FIG. 1C) after 6 hours of treatment, respectively. $\phi_{lexA3}$ enhanced ofloxacin's bactericidal activity over a wide range of multiplicity-of infections (MOIs), from 1:1000 to 1:1 (FIG. 15). $\phi_{lexA3}$'s ability to increase killing by ofloxacin at a low MOI reflects rapid replication and infection by M13 phage. For ofloxacin concentrations of 30 ng/mL and higher, $\phi_{lexA3}$ resulted in much greater killing compared with no phage or unmodified phage $\phi_{unmod}$ (FIG. 1C). Thus, the inventors have demonstrated that $\phi_{lexA3}$ is a strong adjuvant for ofloxacin at doses below and above the minimum inhibitory concentration (60 ng/mL, data not shown).

Figure 1E:
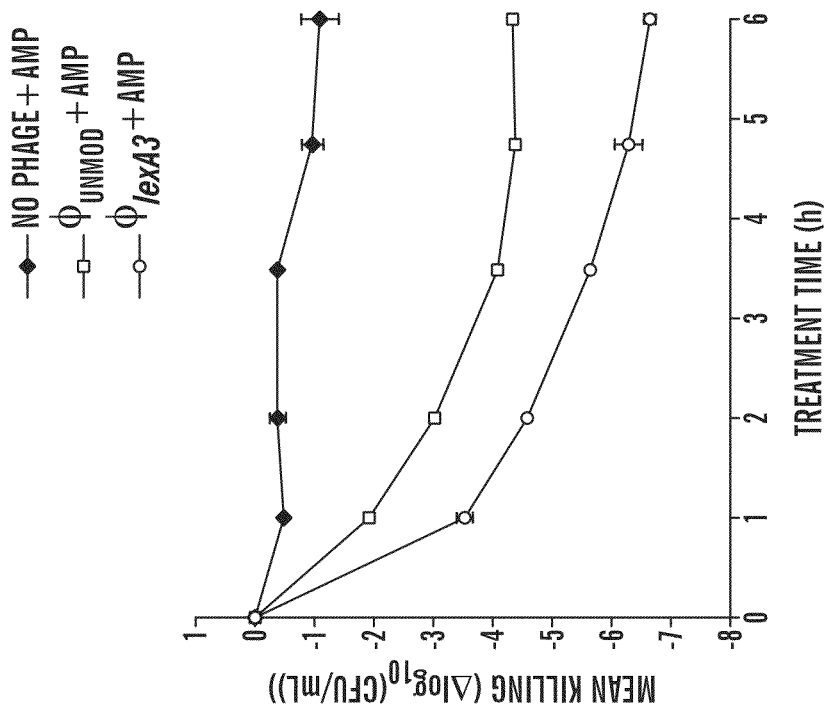
Figure 1D:
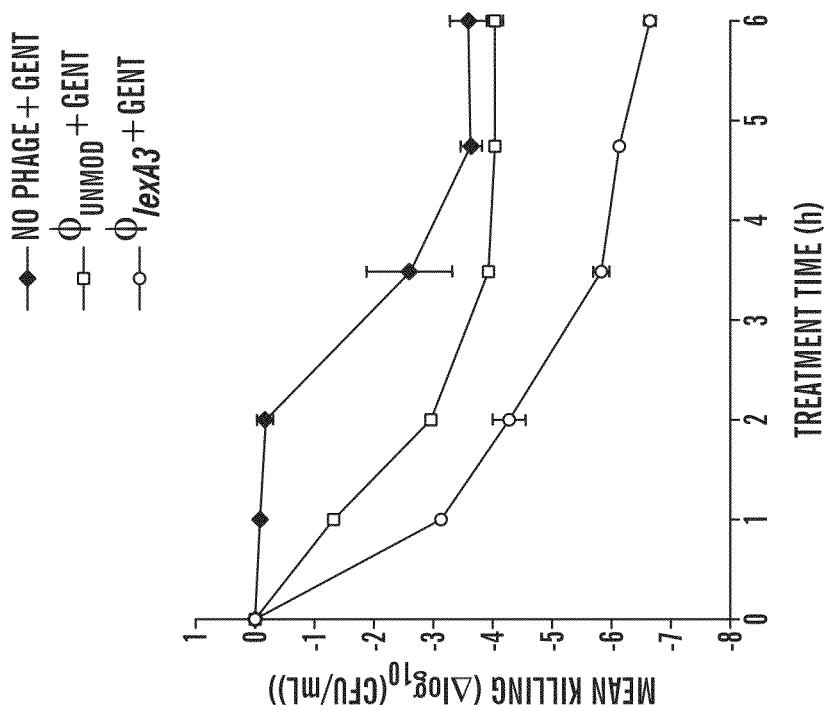

The inventors next determined whether the engineered phage could increase killing by classes of antibiotics other than quinolones. The inventors tested $\phi_{lexA3}$'s antibiotic-enhancing effect for gentamicin, an aminoglycoside, and ampicillin, a β-lactam antibiotic. As demonstrated herein, $\phi_{lexA3}$ increased gentamicin's bactericidal action by over 2.5 and 3 orders of magnitude compared with $\phi_{unmod}$ and no phage, respectively (FIG. 1D). $\phi_{lexA3}$ also improved ampicillin's bactericidal effect by over 2 and 5.5 orders of magnitude compared with $\phi_{unmod}$ and no phage, respectively (FIG. 1E). For both gentamicin and ampicillin, $\phi_{lexA3}$'s strong antibiotic-enhancing effect was noticeable after 1 hour of treatment (FIGS. 1D and 1E). These results are consistent with previous observations that ΔrecA mutants exhibit increased susceptibility to quinolones, aminoglycosides, and β-lactams (Kohanski et al., (2007) *Cell* 130, 797-810), and demonstrate that engineered phages, such as $\phi_{lexA3}$, can act as general adjuvants for the three major classes of bactericidal drugs. The inventors also found that engineered phage $\phi_{lexA3}$ is capable of reducing the number of persister cells in populations already exposed to antibiotics as well as enhancing antibiotic efficacy against bacteria living in biofilms. For example, $\phi_{lexA3}$ added to a population previously treated only with ofloxacin increased the killing of bacteria that survived the initial treatment by approximately 1 and 1.5 orders of magnitude compared with $\phi_{unmod}$ and no phage, respectively (FIG. 16). In addition, simultaneous application of $\phi_{lexA3}$ and ofloxacin improved killing of biofilm cells by about 1.5 and 2 orders of magnitude compared with $\phi_{unmod}$ plus ofloxacin and no phage plus ofloxacin, respectively (FIG. 17).

Since the inventors previous experiments all involved simultaneous application of bacteriophage and drug, the inventors tested whether later addition of engineered $\phi_{lexA3}$ to a previously drug-treated population would also enhance killing Late exponential-phase cells were first exposed to 3 hours of treatment by ofloxacin to generate a population of surviving cells and followed by either no phage, $10^9$ PFU/mL $\phi_{unmod}$, or $10^9$ PFU/mL engineered $\phi_{lexA3}$ phage. After 3 hours of additional treatment, $\phi_{lexA3}$ increased killing by 0.94 $\log_{10}$ (CFU/mL) compared with $\phi_{unmod}$ and by over 1.3 $\log_{10}$ (CFU/mL) compared with no phage (FIG. 11). These results indicate that engineered $\phi_{lexA3}$ bacteriophage increases the killing of bacteria which survive initial antibiotic treatment and reduce the number of persister cells in a given population.

Example 3

Enhancing Killing of Antibiotic-Resistant Bacteria. In addition to killing wild-type bacteria with increased efficacy, the inventors also demonstrate that the engineered phage can enhance killing of bacteria that have already acquired antibiotic resistance. The inventors applied $\phi_{lexA3}$ with ofloxacin against E. coli RFS289, which carries a mutation (gyrA111) that renders it resistant to quinolone antibiotics (Dwyer et al., (2007) Mol Syst Biol 3,917; Schleif R (1972) Proc Natl Acad Sci USA 69, 3479-84). $\phi_{lexA3}$ increased the bactericidal action of ofloxacin by over 2 and 3.5 orders of magnitude compared with $\phi_{unmod}$ and no phage, respectively (FIG. 2). These results demonstrate that antibiotic-enhancing phage, such as $\phi_{lexA3}$ can be used to combat antibiotic-resistant bacteria and therefore can have the potential to bring defunct antibiotics back into clinical use.

Example 4

Figure 3A:
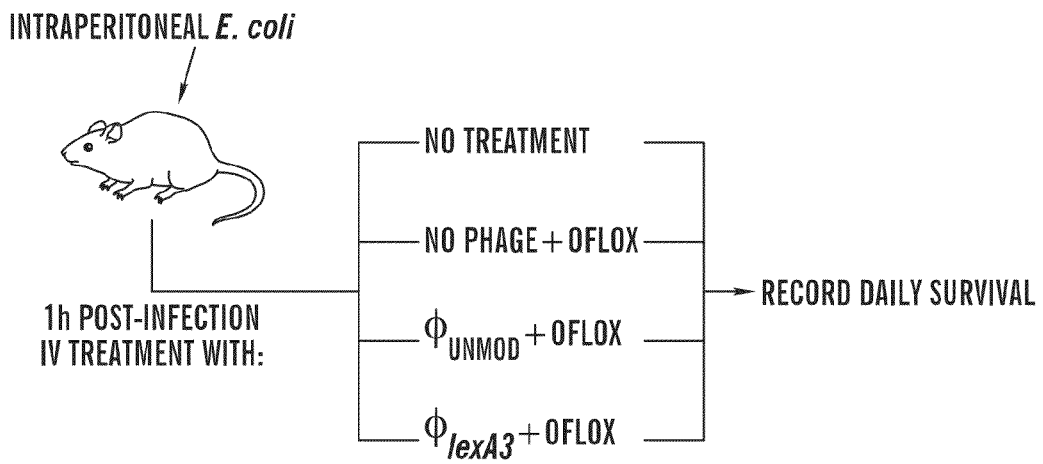
FIGS. 3A-3B show that engineered $\phi_{lexA3}$ bacteriophage increases survival of mice infected with bacteria.
Figure 3B:
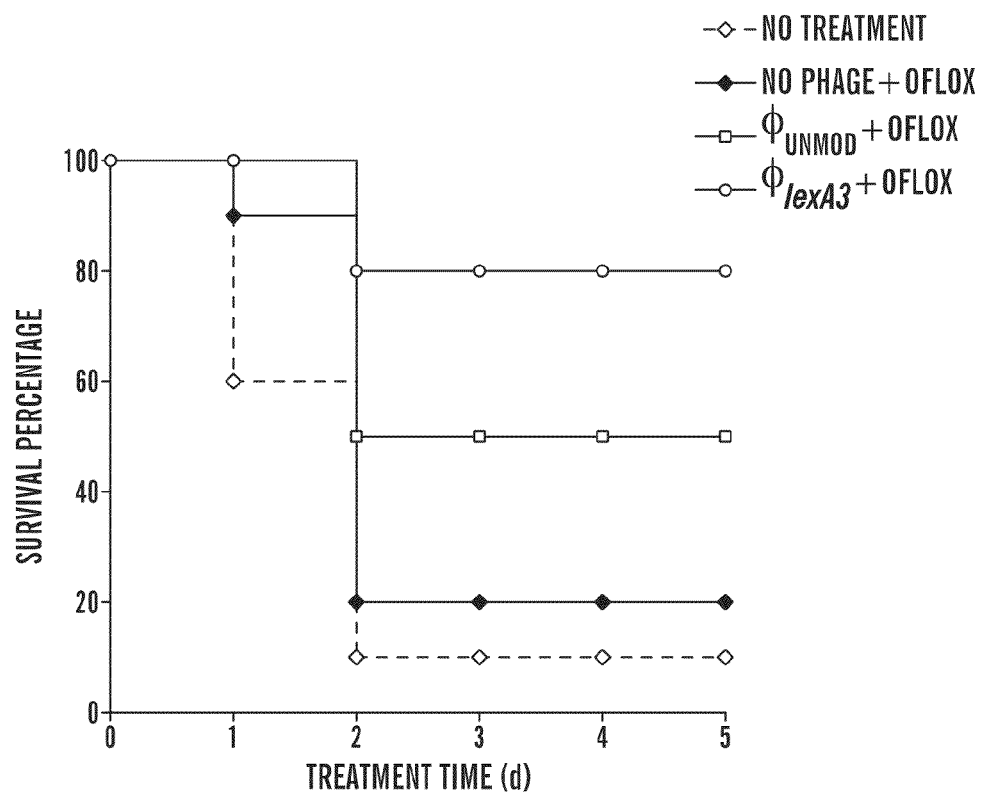

Increasing Survival of Mice Infected with Bacteria. To determine the clinical relevance of antibiotic-enhancing phage in vivo, the inventors applied the engineered phage $\phi_{lexA3}$ with ofloxacin to prevent death in mice infected with bacteria. Mice were injected with E. coli EMG2 intraperitoneally 1 hour prior to receiving different intravenous treatments (FIG. 3A). Eighty percent of mice that received $\phi_{lexA3}$ with ofloxacin survived, compared with 50% and 20% for mice that received $\phi_{unmod}$ plus ofloxacin or ofloxacin alone, respectively (FIG. 3B). The inventors have demonstrated that the engineered phage $\phi_{lexA3}$ with ofloxacin prevents death in vivo of mice with a severe bacterial infection, thus demonstrating that the in vivo efficacy of the antibiotic enhancing phages are effective at rescuing infected mice from death, and demonstrates the feasibility of various embodiments of the invention for clinical use.

Example 5

Reducing the Development of Antibiotic Resistance. Exposure to subinhibitory concentrations of antibiotics can lead to initial mutations which confer low-level antibiotic resistance and eventually more mutations that yield high-level resistance (Martinez et al., (2000) Antimicrob. Agents Chemother. 44, 1771-77). The inventors assessed if the engineered phage, as antibiotic adjuvants, could reduce the number of antibiotic-resistant mutants that result from a bacterial population exposed to antimicrobial drugs. To test this, the inventors grew E. coli EMG2 in media with either no ofloxacin for 24 hours, 30 ng/mL ofloxacin for 24 hours, 30 ng/mL ofloxacin for 12 hours followed by $\phi_{unmod}$ plus ofloxacin treatment for 12 hours, or 30 ng/mL ofloxacin for 12 hours followed by $\phi_{lexA3}$ plus ofloxacin treatment for 12 hours (FIG. 4). Then, the inventors counted the number of mutants resistant to 100 ng/mL ofloxacin for each of the 60 samples under each growth condition. Growth in the absence of ofloxacin yielded very few resistant cells (median=1) (FIG. 4). However, growth with subinhibitory levels of ofloxacin produced a high number of antibiotic-resistant bacteria (median=1592) (FIG. 4). Treatment with unmodified phage $\phi_{unmod}$ decreased the number of resistant cells (median=43.5); however, all samples contained >1 resistant CFU and over half of the samples had >20 resistant CFUs (FIG. 4). In contrast, $\phi_{lexA3}$ treatment dramatically suppressed the level of antibiotic-resistant cells (median=2.5), resulting in a majority of samples with either no resistant CFUs or <20 resistant CFUs (FIG. 4).

Example 6

Figure 5A:
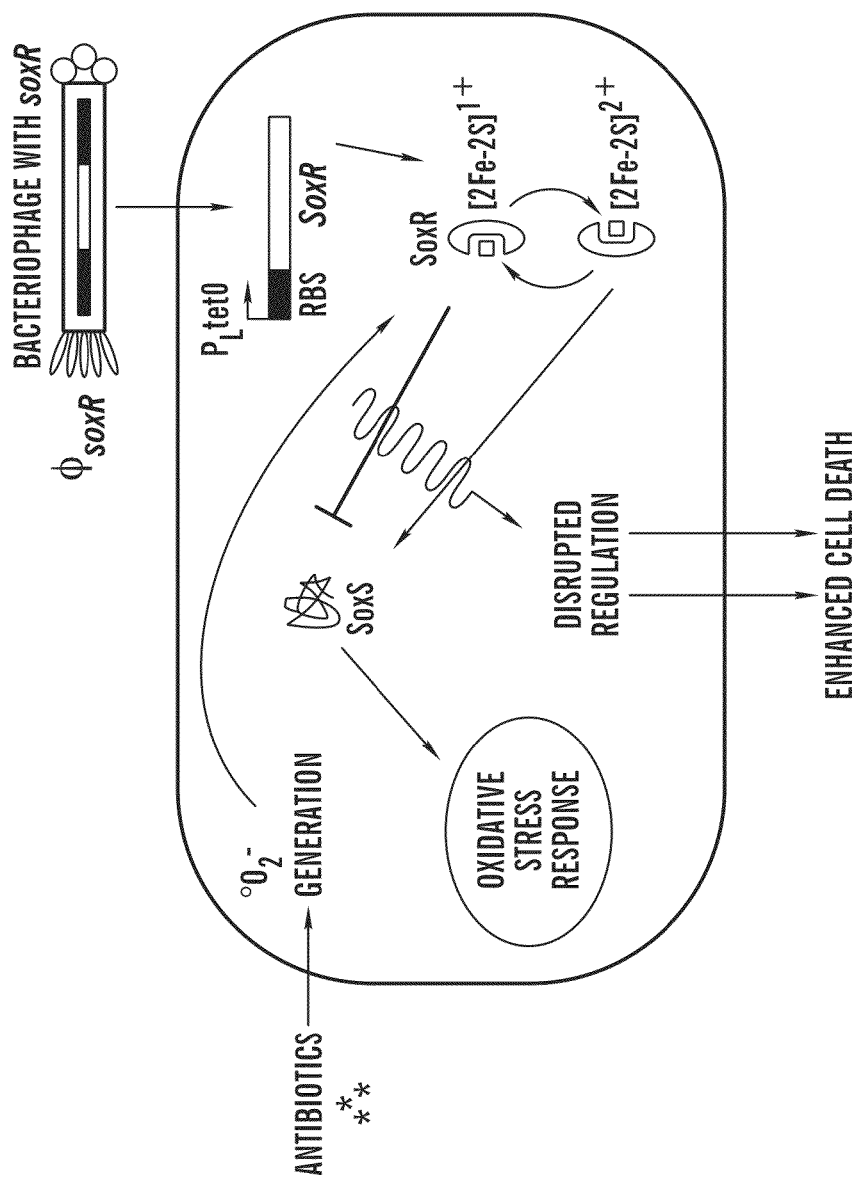
FIGS. 5A-5D show engineered bacteriophage targeting single and multiple gene networks (other than the SOS network) as adjuvants for ofloxacin treatment [oflox].
Figure 5B:
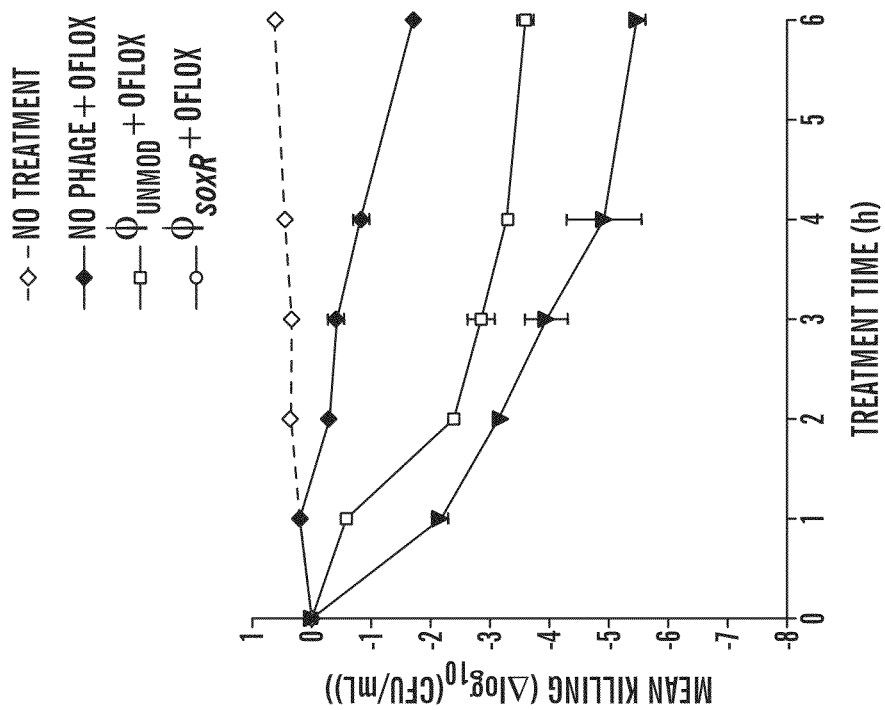

Flexible Targeting of Other Gene Networks. The inventors next demonstrated that the phage platform can be used to target many different gene networks to produce effective antibiotic adjuvants. To demonstrate this, the inventors engineered phage to express proteins that regulate non-SOS gene networks (e.g., SoxR and CsrA) or modulate sensitivity to antibiotics (e.g., OmpF) (FIG. 5 and FIG. 9F) (Lutz et al., (1997) Nucleic Acids Res 25, 1203-10). For example, the soxR-soxS regulon controls a coordinated cellular response to superoxide (Hidalgo et al., (1997) Cell 88, 121-129). SoxR contains a 12Fe-251 cluster that must be oxidized for it to stimulate SoxS production, which then controls the transcription of downstream genes that respond to oxidative stress (Hidalgo et al., (1997) Cell 88, 121-129). As quinolones generate superoxide-based oxidative attack (Dwyer et al., (2007) Mol Syst Biol 3, 91; Kohanski et al., (2007) Cell 130, 797-810), the inventors engineered phage to overexpress wild-type SoxR ($\phi_{soxR}$) to affect this response and improve ofloxacin's bactericidal activity (FIG. 5A). As shown in FIG. 5B, $\phi_{soxR}$ enhanced killing by ofloxacin compared with unmodified phage $\phi_{unmod}$ and no phage (FIG. 5B). The inventors discovered that the overexpression of SoxR may provide additional iron-sulfur clusters that could be destabilized to increase sensitivity to bactericidal antibiotics (Dwyer et al., (2007) Mol Syst Biol 3, 91; Kohanski et al., (2007) Cell 130, 797-810). Alternatively, since SoxR is usually kept at relatively levels in vivo which are unchanged by oxidative stress (Hidalgo et al., (1998) EMBO J. 17, 2629-2636), and the overexpression of large amounts of SoxR may interfere with signal transduction in response to oxidative stress by titrating intracellular iron or oxidizing species or by competing with oxidized SoxR for binding to the soxS promoter (Hidalgo et al., (1998) EMBO J. 17, 2629-36; Meng M et al., (1999) J Bacteriol 181, 4639-4643; Gaudu et al., (1996) Proc Natl Acad Sci USA 93, 10094-98).

Figure 5C:
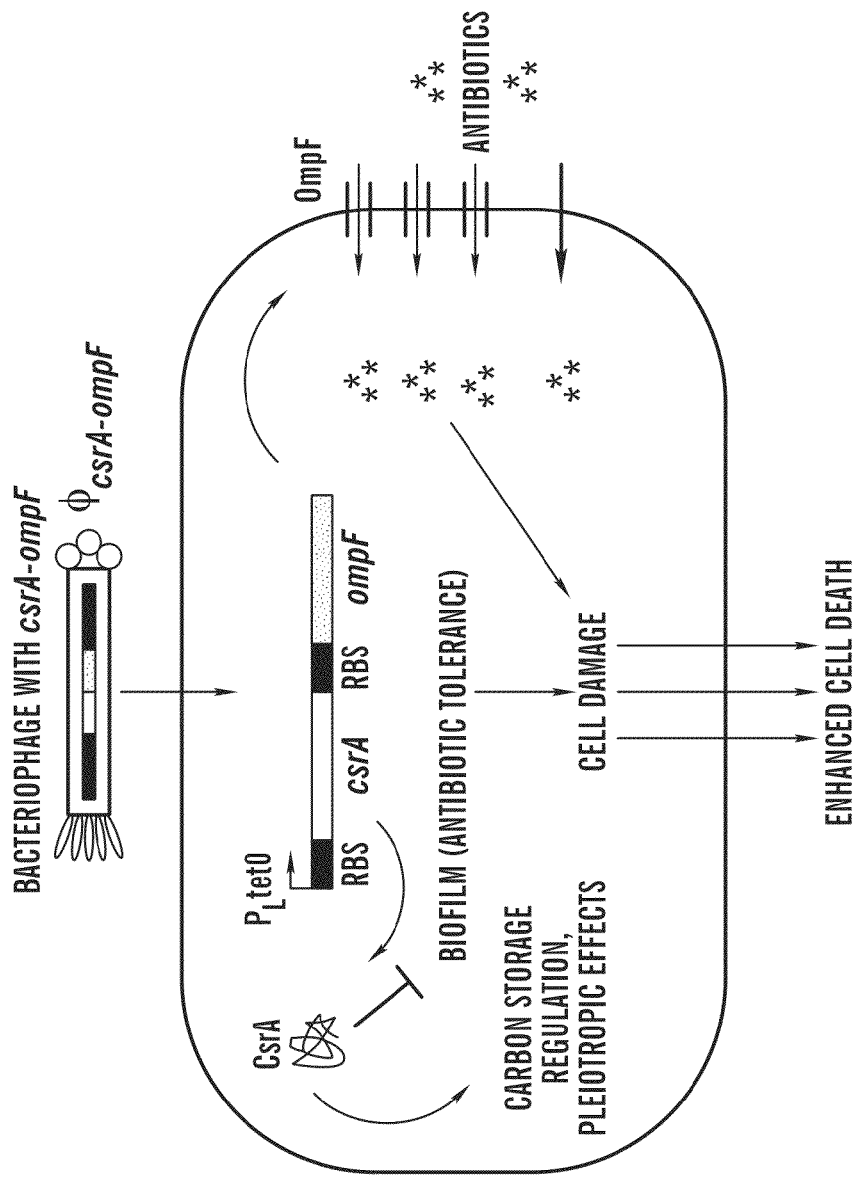
Figure 5D:
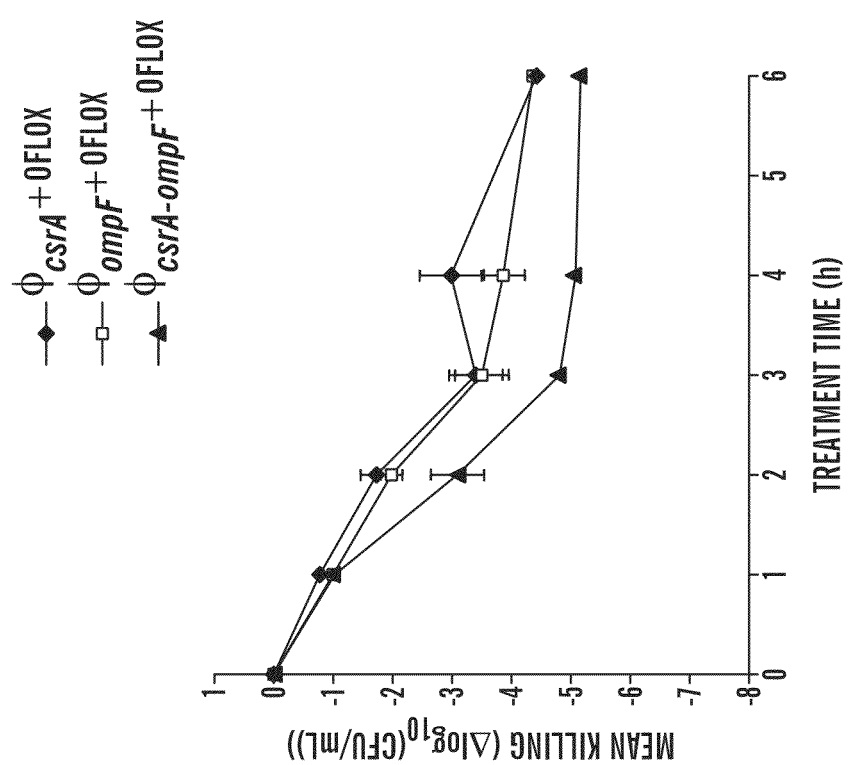

CsrA is a global regulator of glycogen synthesis and catabolism, gluconeogenesis, and glycolysis, and has been shown to represses biofilm formation (Jackson D W et al., (2002) J. Bacteriol. 184, 290-301). As biofilm formation has been linked to antibiotic resistance, the inventors assessed if csrA-expressing phage ($\phi_{csrA}$) would increase susceptibility to antibiotic treatment (Stewart et al., (2001) Lancet 358, 135-138). In addition, since OmpF is a porin used by quinolones to enter bacteria (Hirai et al., (1986) Antimicrob. Agents Chemother. 29, 535-538), the inventors also assessed if ompF-expressing phage ($\phi_{ompF}$) would increase killing by ofloxacin (FIG. 5C). After 6 hours, both $\phi_{csrA}$ and $\phi_{ompF}$ increased ofloxacin's bactericidal effect by approximately 1 and 3 orders of magnitude compared with $\phi_{unmod}$ and no phage, respectively (FIG. 5D).

Example 7

Systems biology analysis often results in the identification of multiple antibacterial targets which are not easily addressed by traditional drug compounds. In contrast, engineered phage are well-suited for incorporating multiple targets into a single antibiotic adjuvant. To demonstrate this capability, the inventors designed an M13mp18 phage to express csrA and ompF simultaneously ($\phi_{csrA-ompF}$) to target csrA-controlled gene networks and increase drug penetration (FIG. 5C). The multi-target phage was constructed by placing RBS and ompF immediately downstream of csrA in $\phi_{csrA}$ (FIG. 9F) (Lutz et al., (1997) *Nucleic Acids Res* 25, 1203-1210). The inventors demonstrated that $\phi_{csrA\text{-}ompF}$ was more effective at enhancing ofloxacin's bactericidal effect compared with its single-target relatives, $\phi_{csrA}$ and $\phi_{ompF}$, in planktonic (FIG. 5D) and biofilm settings (FIG. 18). Together, these results demonstrate that engineering phage to target non-SOS genetic networks such as networks which increase a bacterial cells susceptibility to an antimicrobial agent and/or overexpress multiple factors can produce effective antibiotic adjuvants.

Example 8

Figure 6B:
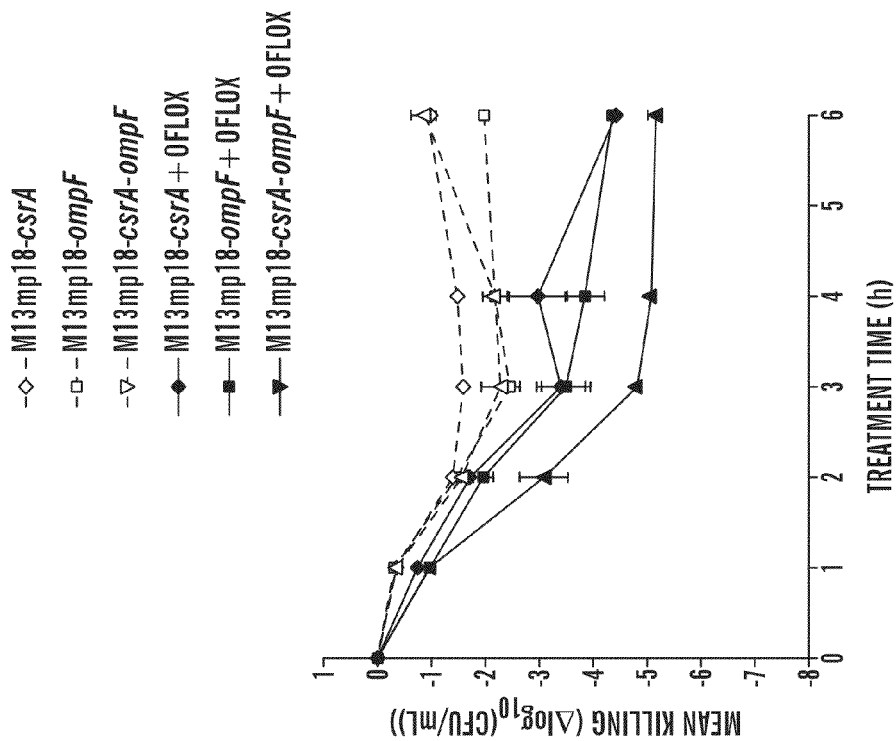
FIGS. 6A-6D show engineered bacteriophage targeting non-SOS systems in *E. coli* as adjuvants for ofloxacin treatment [oflox].
Figure 6A:
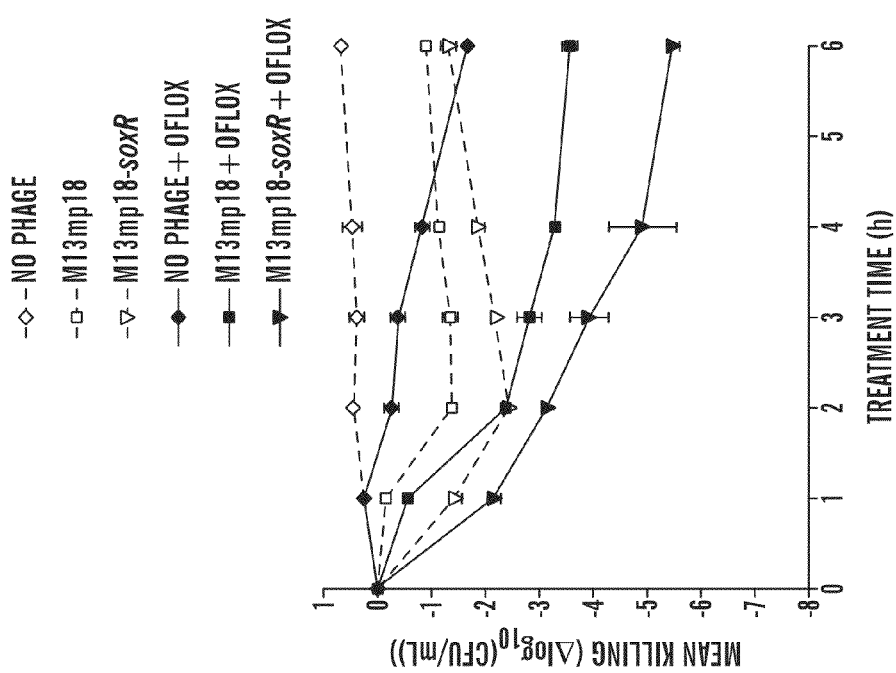
Figure 9B:
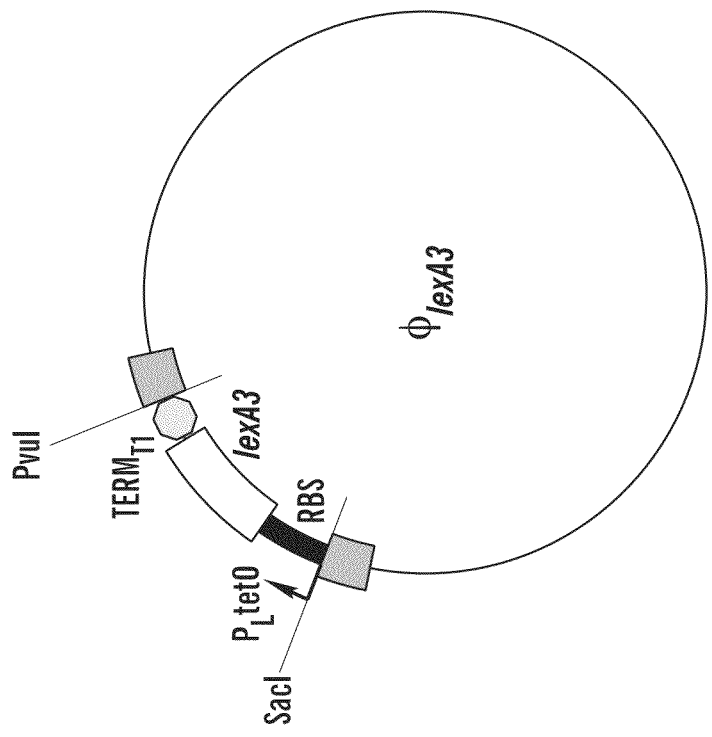
FIGS. 9A-9F show genomes of unmodified M13mp18 bacteriophage and engineered bacteriophage. Engineered bacteriophage were constructed by inserting genetic modules under the control of a synthetic promoter ($P_L$tetO) and ribosome-binding sequence (RBS) in between Sad and PvuI restriction sites. A terminator (Term$_{T1}$) ends transcription of the respective gene(s).
Figure 9A:
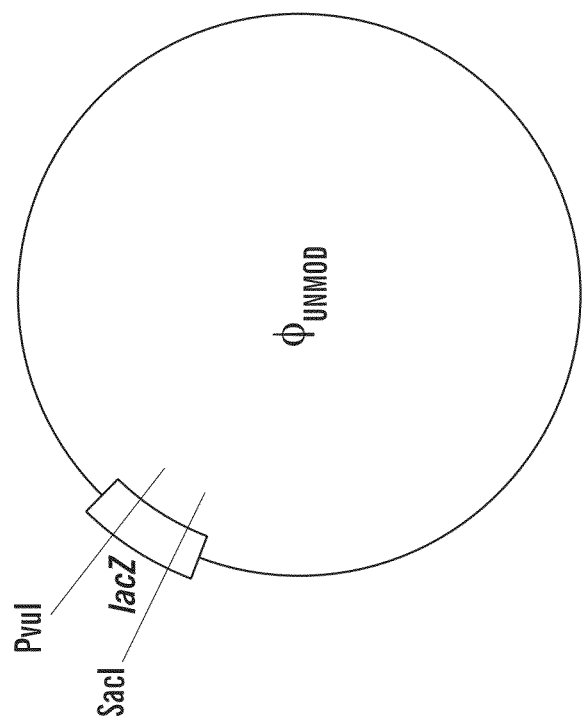
Figure 9D:
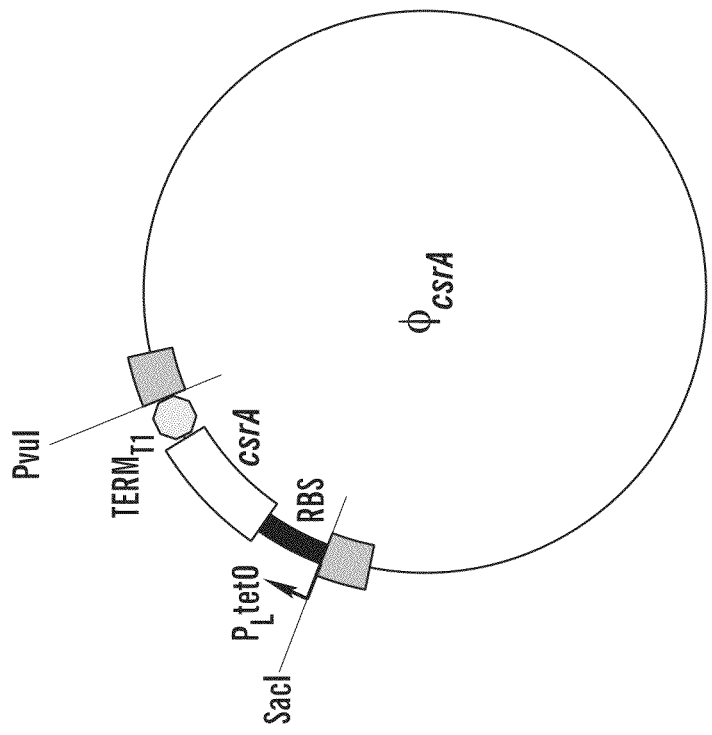
Figure 9C:
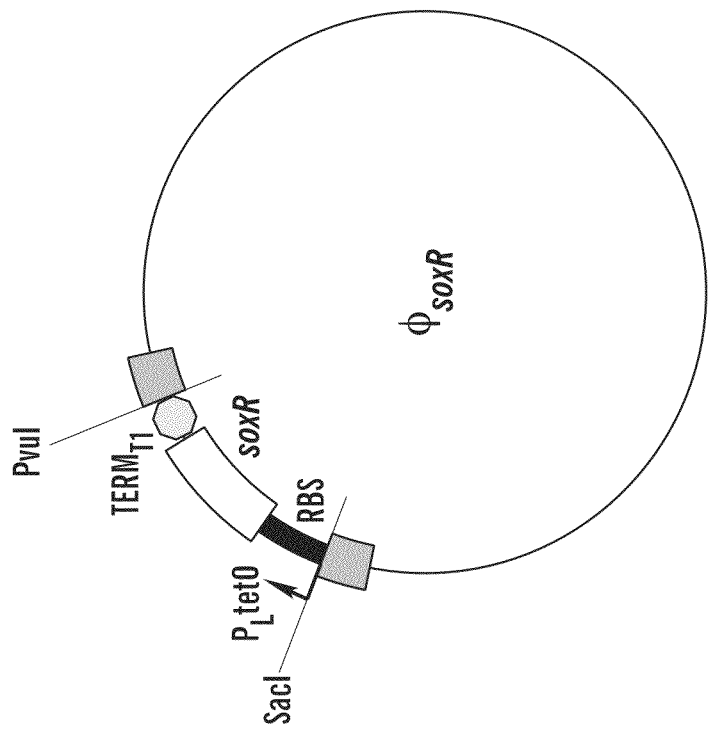

To show that other targets can be found to enhance the efficacy of combination therapy with bacteriophage and antibiotic, the inventors screened M13mp18 bacteriophage which expressed proteins that could modulate sensitivity to antibiotics or that control regulatory networks, such as soxR, fur, crp, marR, icdA, csrA, and ompF. The inventors did this by obtaining viable cell counts after 6 hours of treatment with ofloxacin. Phage expressing soxR, csrA, or ompF yielded the greatest improvements in killing by ofloxacin (See FIG. 1). Like $\phi_{LexA3}$, these phage expressed their respective proteins under the control of $P_L$tetO and a synthetic RBS (FIGS. 9C, 9D, and 9E)[50]. Since SoxR regulates a cellular response to superoxide stress and quinolones stimulate superoxide-based oxidative attack, the inventors surmised that overproducing SoxR could affect this response and improve ofloxacin's bactericidal activity[43,52]. As shown in FIG. 6A, soxR-expressing M13mp18 ($\phi_{SoxR}$) enhanced killing by ofloxacin by about 3.8 $\log_{10}$ (CFU/mL) compared with no phage and by about 1.9 $\log_{10}$ (CFU/mL) compared with unmodified $\phi_{unmod}$ after 6 hours of treatment.

CsrA is a global regulator of glycogen synthesis and catabolism, gluconeogenesis, glycolysis, and biofilm formation[53]. Since biofilm formation has been linked to antibiotic resistance, the inventors assessed if overexpressing csrA might increase susceptibility to antibiotic treatment[54-56]. OmpF is a porin which is used by quinolones to enter bacteria and therefore, the inventors determined that overproducing OmpF would increase killing by ofloxacin[57]. The inventors discovered that csrA-expressing M13mp18 ($\phi_{csrA}$) and ompF-expressing M13mp18 ($\phi_{ompF}$) both increased ofloxacin's bactericidal effect by about 2.7 $\log_{10}$ (CFU/mL) compared with no phage and 0.8 $\log_{10}$ (CFU/mL) compared with unmodified $\phi_{unmod}$ after 6 hours of treatment (FIG. 6B).

Figure 6D:
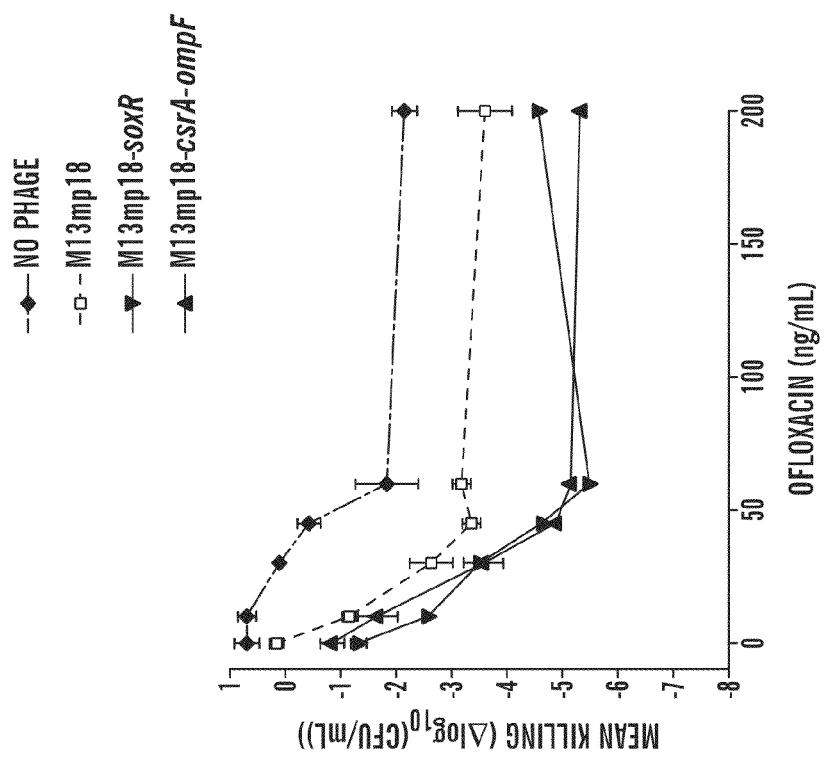
Figure 6C:
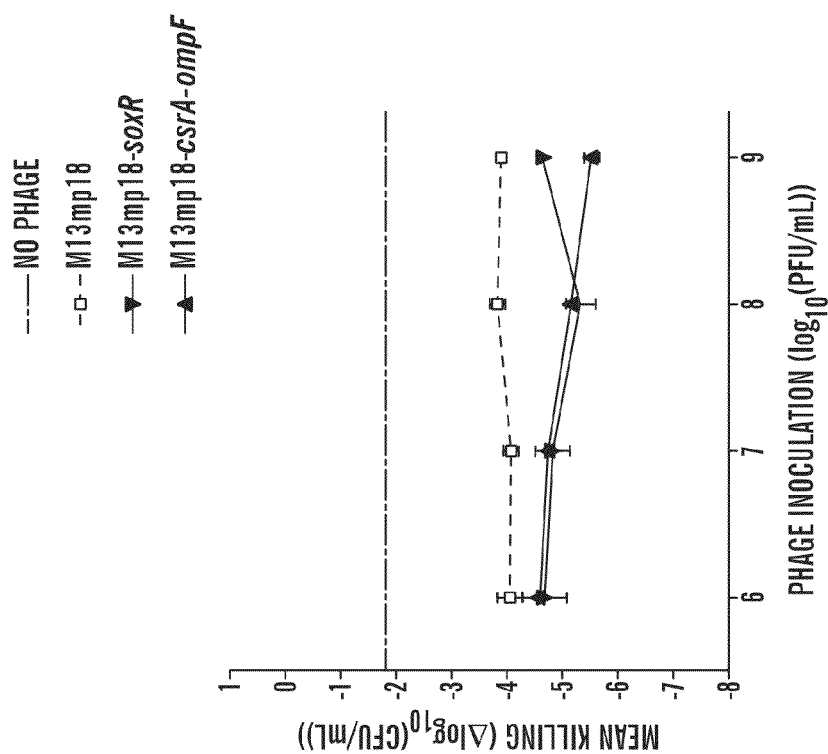
Figure 9F:
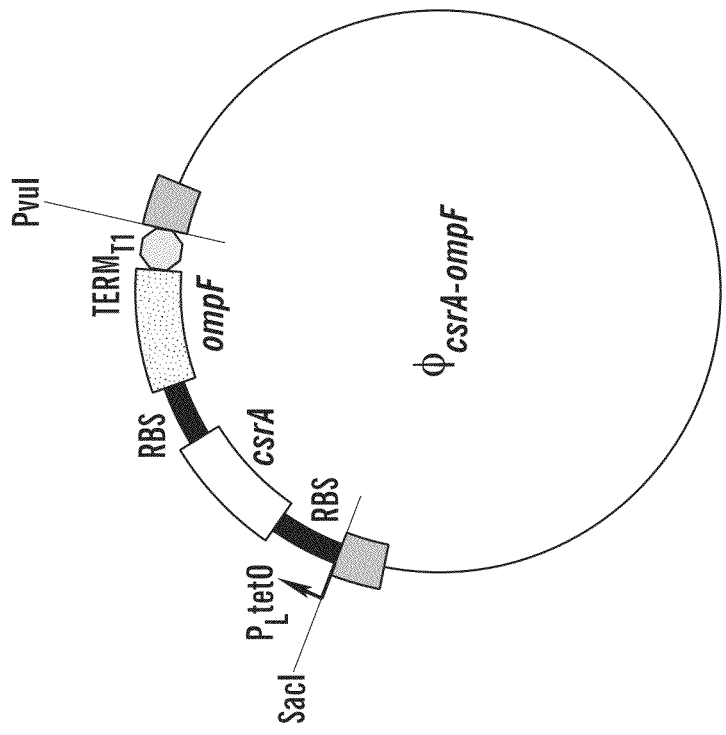
Figure 9E:
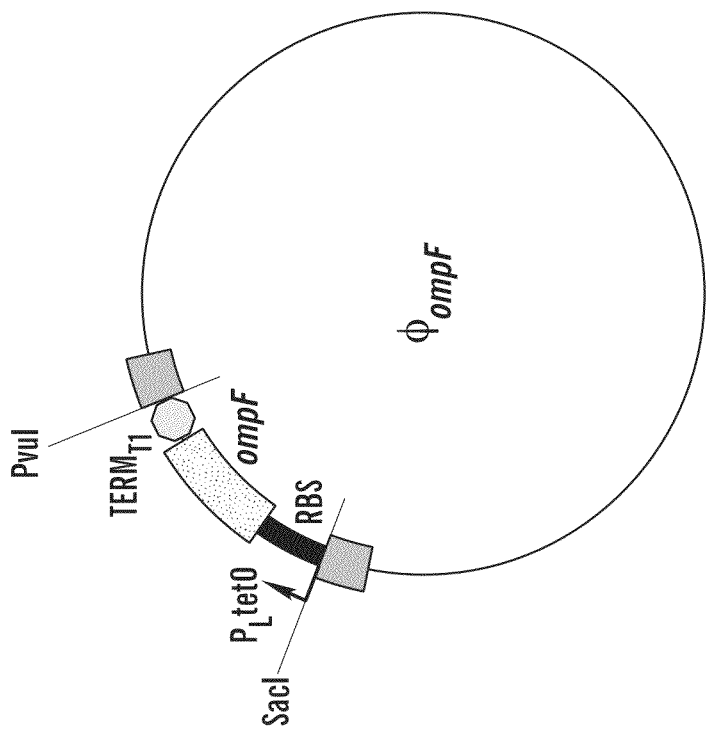
Figure 10B:
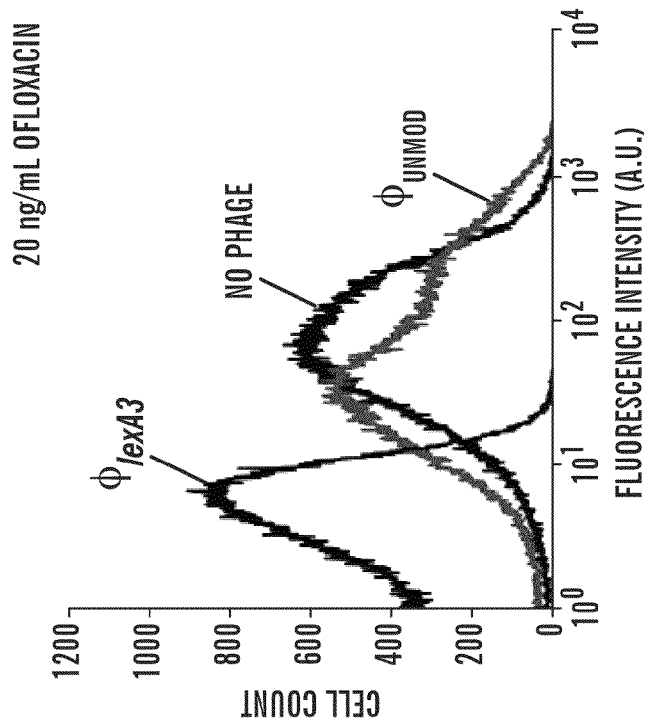
FIGS. 10A-10E show flow cytometry of cells with an SOS-responsive GFP plasmid exposed to no phage (black lines), unmodified phage $\phi_{unmod}$ (red lines), or engineered phage $\phi_{lexA3}$ (blue lines) for 6 hours with varying doses of ofloxacin. $10^8$ plaque forming units per mL (PFU/mL) of phage were applied. Cells exposed to no phage or φunmod showed similar SOS induction profiles, whereas cells with $\phi_{lexA3}$ exhibited significantly suppressed SOS responses.
Figure 10A:
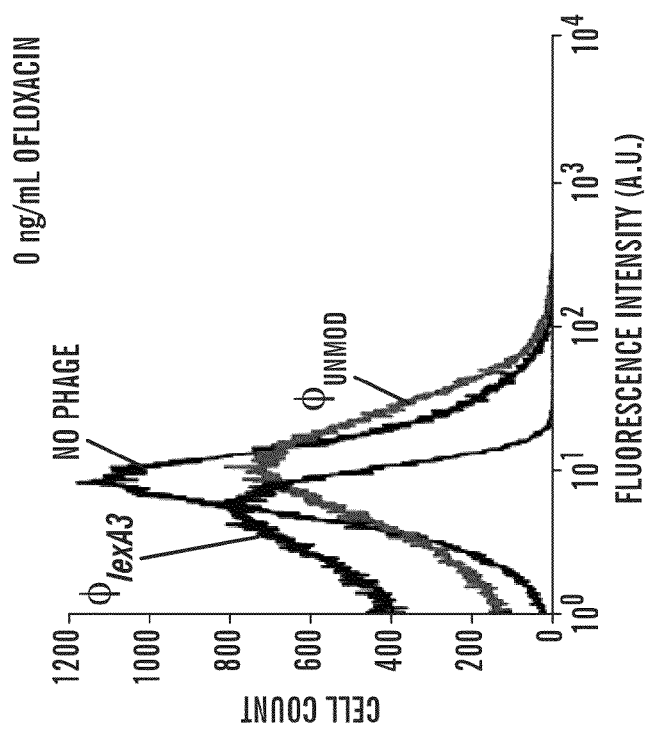
Figure 10D:
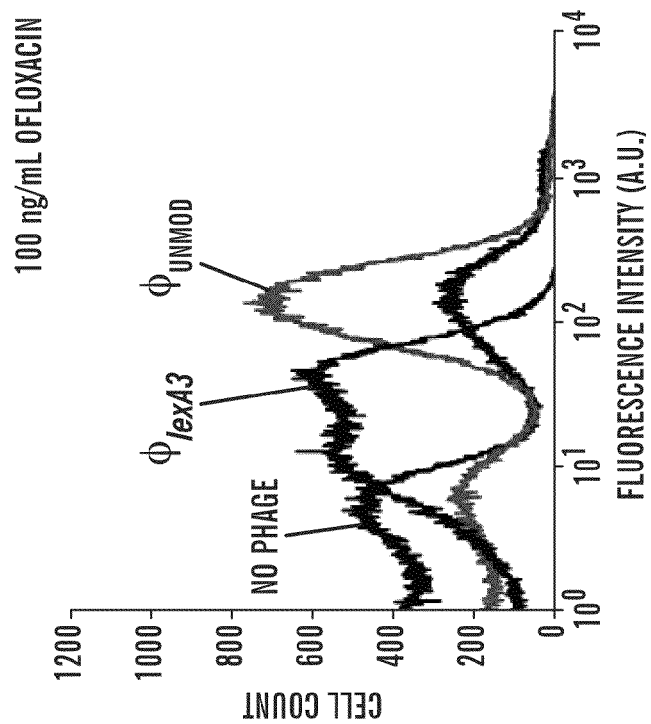
Figure 10C:
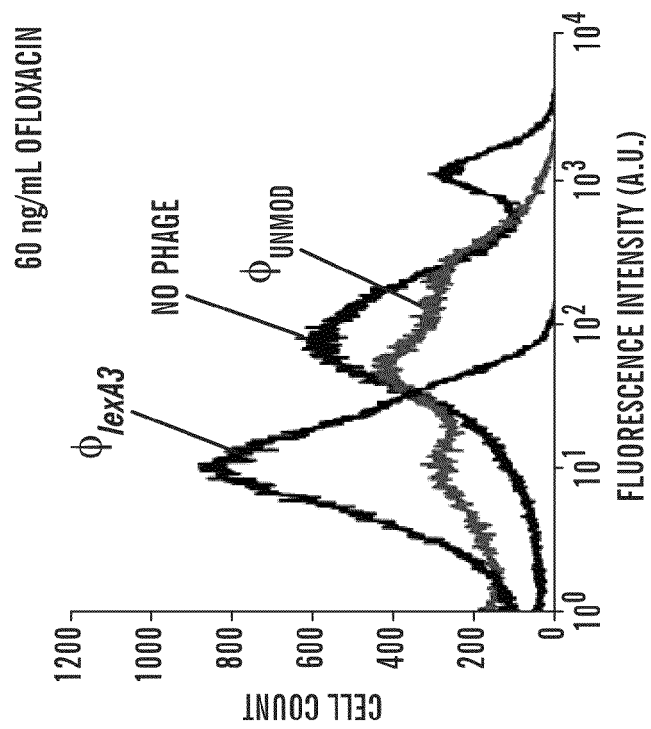
Figure 10E:
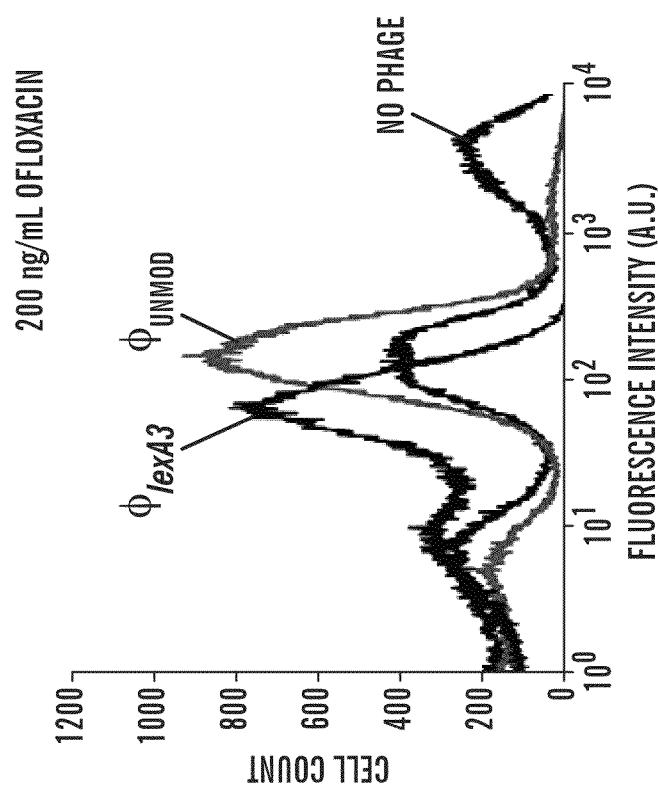

In order to enhance the effectiveness of engineered phage with csrA or ompF alone as antibiotic adjuvants, the inventors designed an M13mp18 phage to express csrA and ompF simultaneously ($\phi_{csrA\text{-}ompF}$) (FIG. 9F). The combination phage was constructed by modifying $\phi_{csrA}$ to carry an RBS and ompF immediately downstream of csrA[50]. $\phi_{csrA\text{-}ompF}$ improved killing by ofloxacin by over 0.7 $\log_{10}$ (CFU/mL) compared with $\phi_{csrA}$ and $\phi_{ompF}$ after 6 hours of treatment (FIG. 6B). The dual-target $\phi_{csrA}$-ompF phage performed comparably with $\phi_{SoxR}$ at various initial phage inoculations with 60 ng/mL ofloxacin (FIG. 6C) and at various concentrations of ofloxacin with $10^8$ PFU/mL phage (FIG. 6D). Both phages were more effective than no phage or $\phi_{unmod}$ at increasing killing by ofloxacin. These results demonstrate that targeting other non-SOS genetic networks and overexpressing multiple factors, i.e. multiple repressors can result in engineered bacteriophage which are good adjuvants for antibiotics.

Exposure to subinhibitory concentrations of antibiotics can lead to initial mutations which confer low-level antibiotic resistance and eventually more mutations that yield high-level antibiotic resistance[17]. By enhancing ofloxacin's bactericidal effect, engineered bacteriophage can reduce the number of antibiotic-resistant mutants that survive in a bacterial population exposed to antimicrobial drugs. To demonstrate this effect, the inventors grew *E. coli* in media with no ofloxacin (FIG. 7A) or 30 ng/mL ofloxacin for 12 hours (FIG. 7B, FIG. 7C, and FIG. 7D) to produce antibiotic-resistant mutants. Then, the inventors divided the cells which grew under no ofloxacin into 60 individual wells with no ofloxacin (FIG. 7A). The inventors also divided the cells which grew under 30 ng/mL ofloxacin into 60 individual wells for each of the following treatments: no phage and 30 ng/mL ofloxacin (FIG. 7B), $10^9$ PFU/mL $\phi_{unmod}$ and 30 ng/mL ofloxacin (FIG. 7C), and $10^9$ PFU/mL $\phi_{lexA3}$ with 30 ng/mL ofloxacin (FIG. 7D). After 12 hours of additional growth, the inventors determined the number of antibiotic-resistant mutants by plating and counting the number of cells that grew on LB agar containing 100 ng/mL ofloxacin. FIG. 7A shows that growth in the absence of ofloxacin yielded very few resistant cells. However, growth in the presence of a subinhibitory level of ofloxacin resulted in a very high number of antibiotic-resistant bacteria (FIG. 7B). Although treatment with $\phi_{unmod}$ reduced the number of resistant cells, all of the 60 individual wells tested contained at least one resistant CFU and over half of the wells had more than 20 resistant CFUs (FIG. 7C). In contrast to treatment with no phage or unmodified $\phi_{unmod}$, $\phi_{lexA3}$ treatment suppressed the level of resistant cells dramatically, resulting in a majority of wells with either no observable resistant CFUs or less than 20 CFUs (FIG. 3d). These results demonstrate that engineered $\phi_{lexA3}$ is efficacious at reducing the number of antibiotic-resistant cells which can develop in the presence of subinhibitory drug concentrations.

Example 9

Figure 8B:
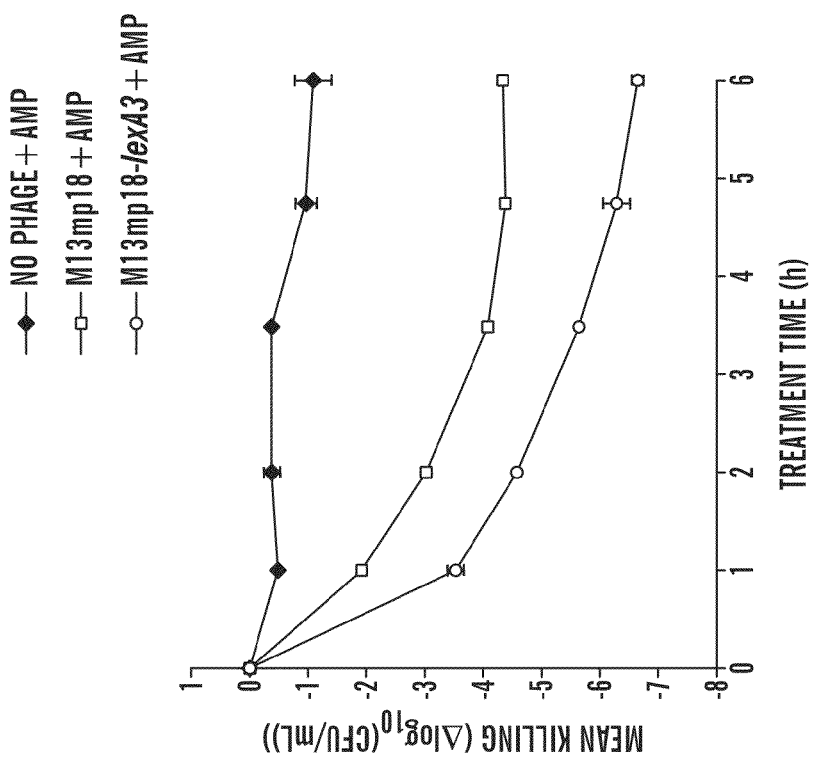
FIGS. 8A-8B shows engineered M13mp18-lexA3 bacteriophage enhances killing by other bactericidal drugs.
Figure 8A:
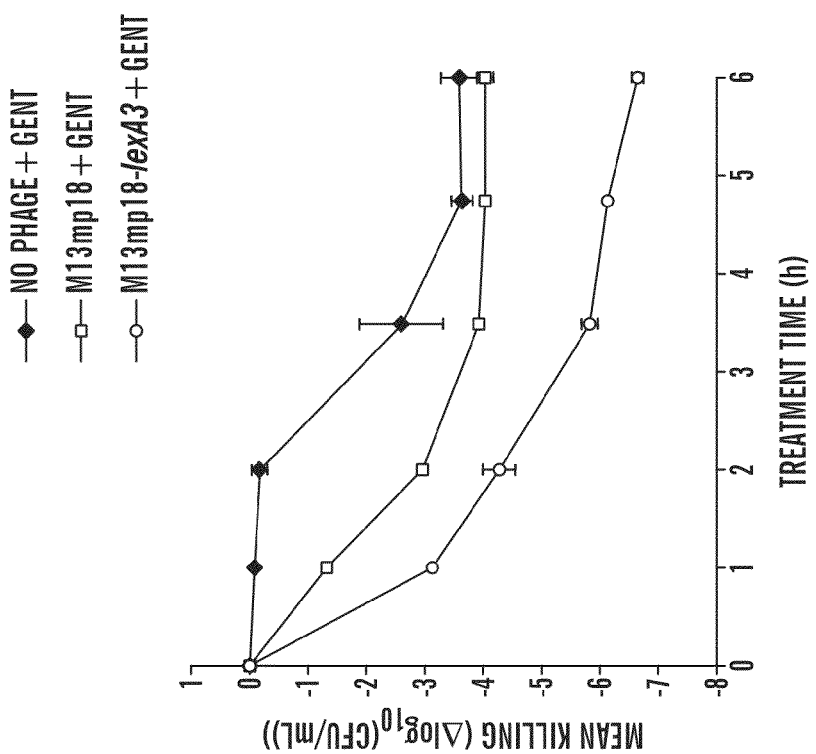

The inventors also sought to determine whether the engineered phage could be applied to different classes of antibiotics other than the quinolones. Since $\phi_{lexA3}$ was the most effective adjuvant for ofloxacin, the inventors tested its adjuvant effect for gentamicin, an aminoglycoside, and ampicillin, a β-lactam antibiotic. For 5 µg/mL gentamicin, $\phi_{unmod}$ was slightly more effective at enhancing bactericidal cells by ofloxacin compared with no phage (FIG. 8A). $\phi_{lexA3}$ increased gentamicin's bactericidal action by over 2.5 $\log_{10}$ (CFU/mL) compared with $\phi_{unmod}$ and by over 3 $\log_{10}$ (CFU/mL) compared with no phage after 6 hours of treatment (FIG. 8A). For 5 µg/mL ampicillin, control $\phi_{unmod}$ alone increased killing by ofloxacin by more than 3 orders of magnitude compared to no phage (FIG. 4b). $\phi_{lexA3}$ improved ampicillin's bactericidal effect by over 2.2 $\log_{10}$ (CFU/mL) compared with unmodified $\phi_{unmod}$ and by over 5.5 $\log_{10}$ (CFU/mL) compared to no phage (FIG. 8B). For both gentamicin and ampicillin, $\phi_{lexA3}$'s strong adjuvant effect was noticeable after 1 hour of treatment (FIG. 8A and FIG. 8B). These results are consistent with previous observations that ΔrecA mutants exhibit increased susceptibility to quinolone, aminoglycoside, and β-lactam drugs[44]. Therefore, engineered bacteriophage such as $\phi_{lexA3}$ can act as general adjuvants for the three major classes of bactericidal drugs.

Using phage, the inventors have demonstrated that targeting genetic networks to potentiate killing by existing antimicrobial drugs is a highly effective strategy for enhancing the usefulness of antibiotics. The host specificity of phage avoids the side effects associated with broad-spectrum antibiotics such as *Clostridium difficile* overgrowth but requires a library of phage to be maintained to cover a range of infections[58,59].

In some embodiments, libraries of existing phage could be modified to overexpress other genes, such as for example but not limited to lexA3 to suppress the SOS response in different bacterial species[60,61].

Example 10

A direct method of attacking antibiotic-resistant bacteria is to express asRNAs to knockdown genes that either confer antibiotic resistance or promote cell repair and the SOS response. Thus, the inventors expressed an antisense RNA (asRNAs) against the cat gene and other antibiotic-resistance genes (genes that inactivate antibiotics or pump out antibiotics or genetic circuits that confer persistence or any other antibiotic resistance phenotype such as vanA, mecA, and others) as well as recA, recB, recC, spoT, relA, and other genes necessary for cell repair or survival. These vectors should sensitize cells to antibiotics since they will target genes that inactivate or pump out antibiotics and those that are necessary for cell repair from damage caused by antibiotics (Dwyer et al., (2007) Mol Syst Biol 3: 91). Inhibiting the SOS response may also reduce the spread of antibiotic resistance genes (Beaber, et al., (2004) Nature 427: 72-74; Ubeda, et al., (2005) Mol Microbiol 56: 836-844).

Figure 12:
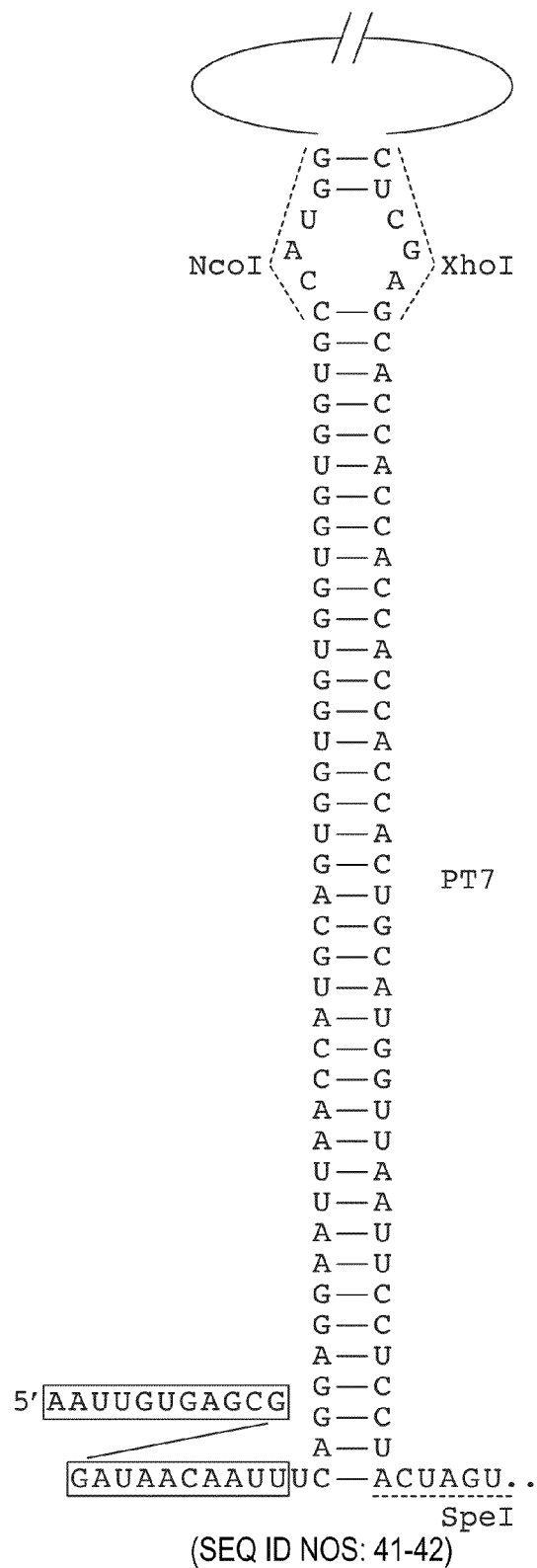
FIG. 12 shows paired-termini design from Nakashima, et al (2006) Nucleic Acids Res 34: e138, in which the antisense RNA is cloned between the flanking restriction sites at the top of the stem. Reprinted from Nakashima, et al (2006) Nucleic Acids Res 34: e138.

The designs that have been currently experimented with extend the paired-termini (PT7) design described in Nakashima et al., (2006) Nucleic Acids Res 34: e138, which produces an RNA similar to that shown in FIG. 12. The PT7 construct produces antisense RNA with longer half-lives in vivo, allowing for greater antisense effect (Nakashima et al., (2006) Nucleic Acids Res 34: e138). Using the PT system, we have constructed antisense RNAs targeting cat, recA, recB, and recC (Nakashima et al., (2006) Nucleic Acids Res 34: e138). These asRNA constructs have been placed under inducible control by aTc by cloning into pZE21s1-cat in place of cat (Lutz et al., (1997) Nucleic Acids Res 25: 1203-1210). The inventors also created all pairwise combinations of asRNAs to recA, recB, and recC by placing one asRNA construct under the control of $P_L$tetO and the other under the control of $P_L$lacO on the same plasmid (Lutz et al., (1997) Nucleic Acids Res 25: 1203-1210).

All the plasmids described thereafter have been introduced into wild-type *E. coli* EMG2 cells and have been assayed for survival with antibiotic treatment. All cells and suitable controls were grown for 8 hours at 37° C. in LB media (with appropriate inducers) and challenged with antibiotics such as ofloxacin at 5 µg/mL. Cell counts were plated after 8 hours of exposure to antibiotic and counted to assess persistence levels. Cells will also be assayed for resistance to specific antibiotics (for example, chloramphenicol in the presence of cat-expressing plasmids).

Figure 14:
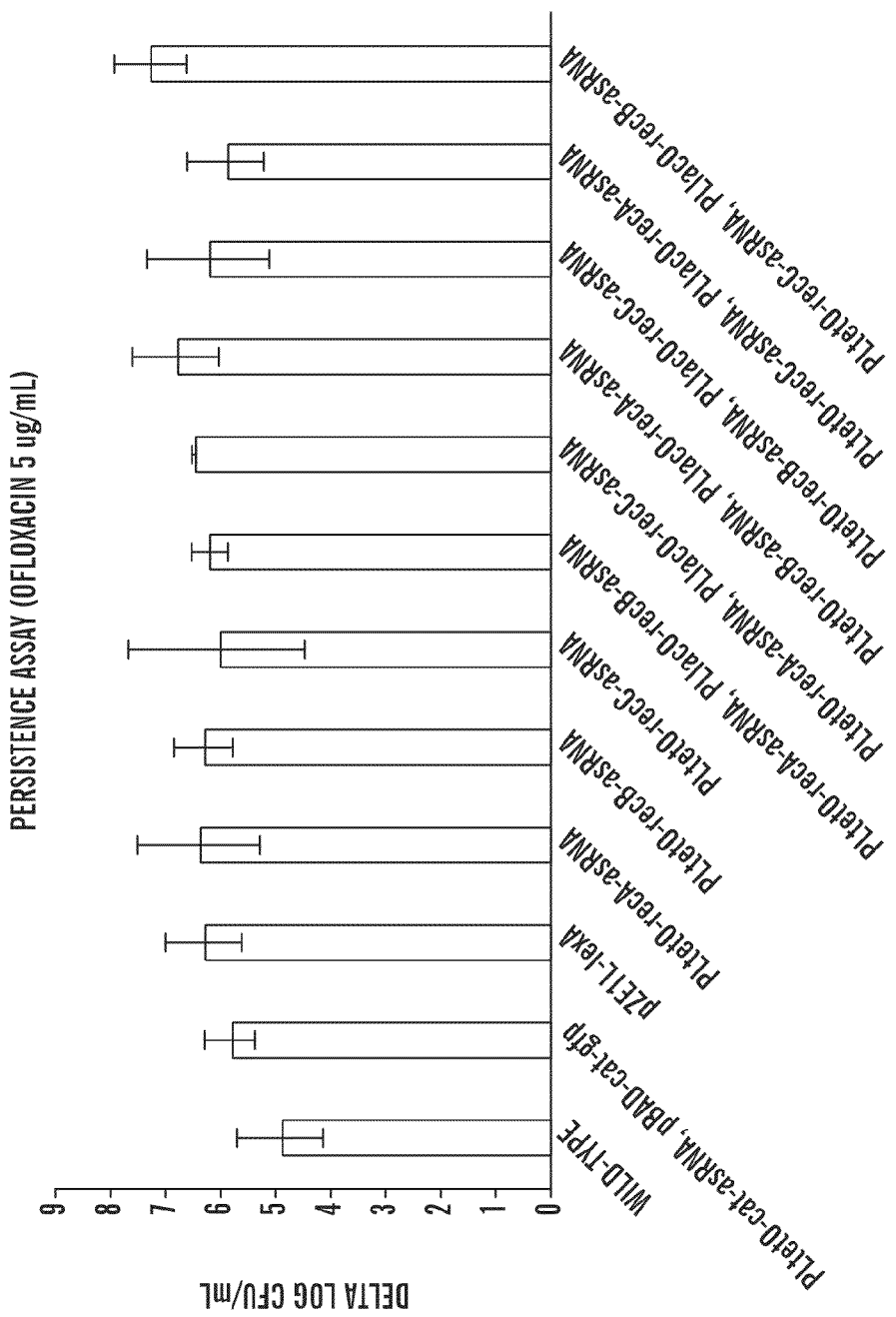
FIG. 14 shows persistence assay for various constructs in wild-type E. coli EMG2 cells after 8 hours of growth in the presence of 1 mM IPTG followed by 8 hours of treatment with 5 µg/mL ofloxacin. Greatly improved cell killing was generated by the double knockouts, especially $P_L$tetO-recB-asRNA/$P_L$lacO-recA-asRNA and $P_L$tetO-recC-asRNA/$P_L$lacO-recB-asRNA. pZE1L-lexA also reduced the number of surviving cells compared with wild-type E. coli EMG2.

The inventors constructed asRNA targeting cat and have expressed the asRNA in a ColE1-type plasmid. With the cat-asRNA vector, the inventors assessed if the chloramphenicol MIC of target bacteria is effectively reduced. The inventors constructed vectors with recA-asRNA, recB-asRNA, recC-asRNA and all pairwise recA, recB, and recC combinations and assayed for persistence levels with ofloxacin (5 µg/mL) with 8 hours of growth followed by 8 hours of treatment. The vectors which demonstrated the strongest phenotypes were the $P_L$tetO-recB-asRNA/$P_L$lacO-recA-asRNA and $P_L$tetO-recC-asRNA/$P_L$lacO-recB-asRNA plasmids (FIG. 14). These constructs displayed 1.87 and 2.37 $\log_{10}$ (CFU/mL) less persisters, respectively, compared with wild-type *E. coli* EMG2.

Example 11

The inventors have demonstrated herein that combination therapy which couples antibiotics with antibiotic-enhancing phage has the potential to be an effective antimicrobial strategy. Moreover, the inventors have demonstrated that antibiotic-enhancing phage are effective in vivo in rescuing bacterially infected mice, and thus have clinical relevance for their use in vivo, in mammalian models of bacterial infections, as well as in human treatment, both for therapeutic and prophylactic treatment. Thus, the inventors have demonstrated a method to modify phage (i.e. bacteriophage) to be engineered to act as effective antibiotic adjuvants in vitro and in vivo and can be used in methods for antimicrobial target identification as well as for therapeutic use and implementation. The inventors have also demonstrated that by targeting non-essential gene networks, a diverse set of engineered bacteriophage can be developed to supplement other antimicrobial strategies.

While use of phages in clinical practice is not widely accepted due to a number of issues such as phage immunogenicity, efficacy, target bacteria identification and phage selection, host specificity, and toxin release (Merril et al., (2003) *Nat. Rev. Drug Discov.* 2, 489-497; Hagens et al., (2003) *Lett. Appl. Microbiol.* 37, 318-323; Hagens et al., (2004) *Antimicrob. Agents Chemother.* 48, 3817-3822; Boratynski et al., (2004) *Cell. Mol. Biol. Lett.* 9, 253-259; Merril et al., (1996) *Proc Natl Acad Sci USA* 93, 3188-3192), the inventors indicate that one way to reduce the risk of leaving lysogenic particles in patients after treatment, the inventors engineered adjuvant phages could be further modified to be non-replicative, as has been previously described (Hagens et al., (2004) *Antimicrob* 11). The inventors have demonstrated an antibiotic-enhancing phage as a prototype phage as proof of-concept antibiotic adjuvants. The inventors indicate that in some embodiments, a combination of antibiotic-enhancing phages or phage cocktails can be used for in vivo and in vitro use, as well as in clinical settings for effective efficacy and/or the ability to treat non-F-plasmid containing bacteria. In particular, in some embodiments phage cocktails which target different, multiple bacterial receptors can be used, which can have a benefit of reducing the development of phage resistance by invading bacteria through multiple different means and pathways. Thus, in another embodiment, phage cocktails can be used with one or more different antibiotics to also enhance bacterial killing as well as reduce resistance to both the phages and antibiotics.

The inventors have demonstrated use of engineered antibiotic-enhancing phages as a phage platform for the development of effective antibiotic adjuvants, and is a practical example of how synthetic biology can be applied to important real-world biomedical issues. Synthetic biology is focused on the rational and modular engineering of organisms to create novel behaviors. The field has produced many reports of synthetic gene circuits and systems with interesting characteristics (Andrianantoandro et al., (2006) *Mol Syst Biol,* 2, 2006.0028; Hasty et al., (2002) in *Nature,* pp. 224-230; McDaniel et al., (2005) in *Curr. Opin. Biotechnol.,* pp. 476-483.; Chan et al., (2005) in *Mol Syst Biol,* p. 2005.0018). More recently, synthetic biologists have begun to address important industrial and medical problems (Lu et al., (2007) *Proc Natl Acad Sci USA* 104, 11197-216; Anderson et al., (2006) *J. Mol. Biol.* 355, 619-627; Loose et al., (2006) *Nature* 443, 867-869; Ro et al, (2006) *Nature* 440, 940-943).

In some embodiments, the present invention also encompasses production and use of libraries of natural phage which have been modified to target gene networks and pathways, such as the SOS response, in different bacterial species (Hickman-Brenner et al., (1991) *J. Clin. Microbiol.* 29, 2817-2823). One of ordinary skill in the art could generate and use such libraries by using routine methods in the art, such as isolation and genetic modification of natural phage with the ability to infect the bacterial species being targeted. With current DNA sequencing and synthesis technology, an entire engineered bacteriophage genome carrying multiple constructs to target different gene networks could be synthesized (Baker et al, (2006) *Sci. Am.* 294, 44-51). Thus, one of ordinary skill in the art, using such technologies could carry out large-scale modifications of phage libraries to produce antibiotic-enhancing phage that can be applied with different antibiotic drugs against a wide range of bacterial infections. Targeting clinical bacterial strains with libraries of engineered phage, which can be carried out by routine testing by one of ordinary skill in the art to identify which engineered phage from the libraries is effective as an antibiotic-enhancing phage to clinically relevant bacterial strains and has important uses in developing treatments against real-world infections.

In some embodiments, the engineered phages as described herein can also be used in industrial, agricultural, and food processing settings where bacterial biofilms and other difficult-to-clear bacteria are present (Lu et al., (2007) *Proc Natl Acad Sci USA* 104, 11197-216). Accordingly, some embodiments as described herein encompass applying the engineered phage as described herein as antibiotic adjuvants in non-medical settings. This could be economically advantageous, reduce community-acquired antibiotic resistance, and be also be useful in testing efficacy of the particular engineered phage prior to its use as a treatment and/or in clinical use (Morens et al., (2004) *Nature* 430, 242-24949).

Figure 13:
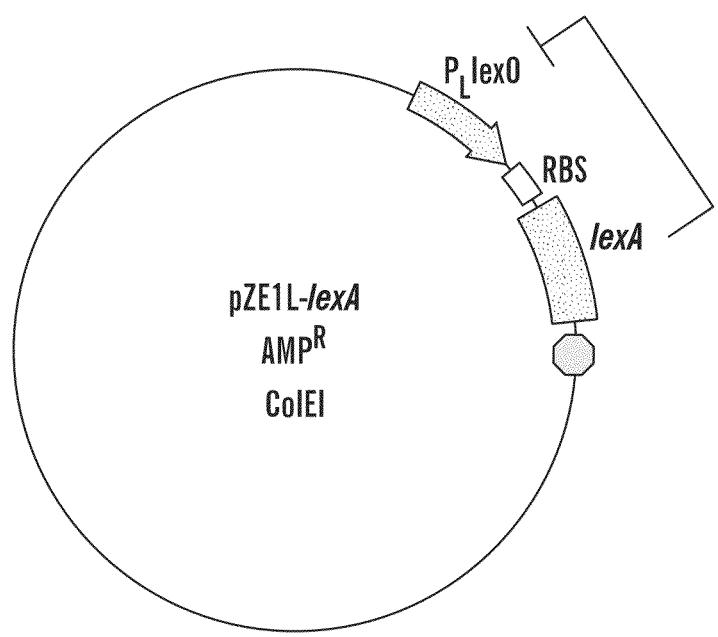
FIG. 13 shows autoregulated negative-feedback module with lexA repressing $P_L$lexO from Morens, et al., (2004) Nature 430: 242-249, can increase the level of lexA expression when lexA is cleaved by recA in response to DNA damage by agents such as ofloxacin.

Another strategy to combat antibiotic resistance is to take advantage of the numerous autoregulated repressors inherent in bacteria that regulate resistance genes or cell repair pathways (Okusu, et al., (1996) J Bacteriol 178: 306-308). For example, lexA represses the SOS response until it is cleaved by recA in response to DNA damage (Dwyer et al., (2007) Mol Syst Biol 3: 91). In addition, marR represses the marRAB operon and acrR represses the acrAB operon; both operons confer resistance to a range of antibiotics (Okusu, et al., (1996) J Bacteriol 178: 306-308). To increase repression of the SOS response or antibiotic-resistance-conferring operons, we propose to overexpress the responsible repressors. However, simple overexpression may impose a high metabolic cost on the cells leading to rejection of the introduced constructs. Therefore, as an alternative to simple overexpression, the inventors created an autoregulated negative-feedback modules with lexA and other repressors and determine whether cells are sensitized to antibiotic treatment with these constructs (FIG. 13). The net effect of this strategy should be to increase the loop gain of inherent autoregulated negative-feedback loops so that any perturbations in the level of repressors will be more rapidly restored, hopefully preventing successful activation of survival pathways.

The inventors produced and assessed the pZE1L-lexA plasmid for persistence levels with ofloxacin (5 µg/mL) with 8 hours of growth followed by 8 hours of treatment. The inventors constructed the pZE1L-lexA plasmid by utilizing the $P_L$lexO promoter described in (Dwyer et al., (2007) Mol Syst Biol 3: 91). Cells containing the pZE1L-lexA construct produced about 1.44 $\log_{10}$ (CFU/mL) less persisters compared with wild-type *E. coli* EMG2 (FIG. 10). The inventors also made changes in the design of pZE1L-lexA by using non-cleavable lexA variants.

The inventors demonstrated, in lytic phage such as T7 or lysogenic phage such as M13 and using synthetic biology, construction of engineered phage by inserting the vector constructs simply into optimal regions in the phage genome to be expressed during infection (Lu et al., (2007) Proc Natl Acad Sci USA 104: 11197-11202). M13 is a filamentous, male-specific phage with a single-stranded, circular DNA genome that infects *E. coli*. During infection, the genome adopts a double-stranded replicative form (RF) which can be stably maintained in lysogeny. M13 subsequently replicates and secretes mature phage particles into the surrounding environment that can infect other cells. M13 is a commonly used phage for peptide display and DNA sequencing and has been modified for genetic manipulation. In some embodiments, M13 and other lysogenic phage can be used as carriers for asRNAs or other genetic modules because they allow propagation of the introduced constructs throughout a bacterial population without massive lysis, which can lead to release of toxic products such as endotoxin or lead to the development of phage resistant bacteria due to strong evolutionary pressure. As the constructs need to be able to reach a large population of cells, have the desired effects, and then be subsequently killed by antibiotic therapy, lysogenic phages were used by the inventors. For example, the gene constructs could be cloned in place of the lacZ gene in the already modified M13mp18 bacteriophage under the control of a strong bacterial-species-specific promoter or phage-specific promoter.

Herein, the inventors have demonstrated that building effective bacteriophage adjuvants that target different factors individually or in combination can be achieved in a modular fashion. As the cost of DNA sequencing and synthesis technologies continues to be reduced, large-scale modifications of phage libraries should become feasible[62-64]. With current technology, an entire engineered M13mp18 genome carrying multiple constructs to target genetic networks could be synthesized for less than $10,000, a price which is sure to decrease in the future[65]. Furthermore, systems biology techniques can be employed to more rapidly identify new targets to be used in engineered bacteriophage[43,44]. Antisense RNA could also be delivered by bacteriophage to enhance killing of bacteria. Cocktails of engineered phage such as those described here could be combined with biofilm-dispersing bacteriophage and antibiotics to increase the removal of harmful biofilms[38].

Since the FDA recently approved the use of bacteriophage against *Listeria monocytogenes* in food products, it is likely that the engineered phages as disclosed herein can be readily adopted for medical, industrial, agricultural, and food processing settings where bacterial biofilms and other difficult-to-clear bacteria are present[38,69]. Potentiating bacterial killing in non-medical settings should have economic advantages in addition to reducing community-acquired antibiotic resistance[12].

Conventional drugs typically achieve their therapeutic effect by reducing protein function. In contrast, the bacteriophage and selective gene targeting approach as described herein potentiates killing by antibiotics by overexpressing proteins that affect genetic networks, such as lexA3, soxR, and csrA, or that act on their own to modulate antibiotic sensitivity, such as ompF. By reducing the SOS response with engineered M13mp18-lexA3 bacteriophage, the inventors have potentiated ofloxacin's bactericidal effect by over 4.5 orders of magnitude and reduced the number of persister cells (FIG. 1b). The inventors have also demonstrated that other factors such as soxR, csrA, and ompF could be targeted for overexpression individually or in combination to enhance killing (FIG. 6). The inventors demonstrated that the number of mutants which acquired antibiotic resistance was significantly decreased by the use of engineered M13mp18-lexA3 bacteriophage in combination with ofloxacin (FIG. 7). In addition, the inventors confirmed that our engineered bacteriophage could be used as antibiotic adjuvants for other drugs such as aminoglycosides and β-lactams (FIG. 8). Combination therapy with antibiotics and engineered phage resulted in no noticeable development of phage resistance. The inventors demonstrated that targeting genetic networks in bacteria which are not primary antibiotic targets yield substantial improvements in killing by antimicrobial drugs. Advances in systems biology and synthetic biology should enable the practical application of engineered bacteriophage with antibiotics as a new combination therapy for combating bacterial infections.

TABLE 2A

Example of a genes which can be inhibited by an repressor-engineered bacteriophage, and in some embodiments, such repressor-engineered bacteriophages which inhibit one or more of the following non-SOS defense genes are useful in combination with a Ciprofloxacin antimicrobial agent. Code: [a]Accession Number (from world-wide web "ecocyc.org"), [b]Categories are as follows: 1-DNA replication, recombination and repair, 1A-functions indirectly affecting category 1, 2-transport, efflux, cell wall and cell membrane synthesis, 2A-chaperones and functions related to 2, 3-protein synthesis, 4-central metabolic reactions, 5-regulation, 6-prophage encoded genes; cell adhesion, or 7-unassigned genes. [c]Gene knockout(s) from KEIO collection (3) using BW25113 (10) as the starting strain.
Table 2A: Example of a genes which can be inhibited by an repressor-engineered bacteriophage, and in some embodiments, such repressor-engineered bacteriophages which inhibit one or more of the following non-SOS defense genes are useful in combination with a Ciprofloxacin antimicrobial agent

| Locus Tag[a] | Gene | Gene Product | Category[b] | MIC (ng/mL) E-Test | MIC (ng/mL) Plating |
|---|---|---|---|---|---|
| | BW25113[c] | | — | 16 | 20 |
| b1413 | hrpA | ATP-dependent helicase | 1 | — | 8.75 |
| b2699 | recA | DNA strand exchange and recombination protein with protease and nuclease activity | 1 | 2 | >8.75 |
| b2820 | recB | DNA helicase, ATP-dependent dsDNA/ssDNA exonuclease | 1 | — | 7.5 |
| b2822 | recC | DNA helicase, ATP-dependent dsDNA/ssDNA exonuclease | 1 | 8 | >8.75 |
| b3652 | recG | ATP-dependent DNA helicase, resolution of Holliday junctions, branch migrations | 1 | 6 | 6 |
| b2616 | recN | Recombination and repair protein | 1 | — | 10 |
| b1861 | ruvA | Holliday junction DNA helicase | 1 | — | 10 |
| b1863 | ruvC | Holliday junction nuclease; resolution of structures; repair | 1 | 8 | >8.75 |
| b3813 | uvrD | DNA-dependent ATPase I and helicase II | 1 | 5 | 6 |
| b2509 | xseA | Exodeoxyribonuclease VII large subunit | 1 | 6 | 6 |
| b0422 | xseB | Exodeoxyribonuclease VII small subunit | 1 | — | 8 |
| b3261 | fis | DNA-binding protein - chromosome compaction | 1A | 6 | >8.75 |
| b1712 | ihfA | Integration host factor alpha-subunit (IHF-alpha). | 1A | — | 7.5 |
| b0464 | acrA | AcrAB-TolC Multidrug Efflux Transport System | 2 | — | 7.5 |
| b0462 | acrB | AcrAB-TolC Multidrug Efflux Transport System | 2 | — | 8 |
| b3035 | tolC | AcrAB-TolC Multidrug Efflux Transport System | 2 | 4 | 5 |
| b0742 | ybgF | Predicted plasma protein | 2 | — | 7.5 |
| b0489 | qmcA | Putative protease | 3 | — | >8.75 |
| b0852 | rimK | Ribosomal protein S6 modification protein. | 3 | — | >8.75 |
| b1317 | pgmB | β-phosphoglucomutase | 4 | — | 10 |
| b0736 | ybgC | Acyl-CoA thioesterase - cytoplasm | 4 | — | 7.5 |
| b2767 | ygcO | Predicted 4Fe-4S cluster-containing protein | 4 | — | 7.5 |
| b1284 | deoT | DNA-binding transcriptional regulator | 5 | — | 7.5 |
| b0145 | dksA | RNA polymerase-binding transcription factor | 5 | — | 10 |
| b4172 | hfq | HF-I, host factor for RNA phage Q β replication | 5 | — | 7.5 |
| b2572 | rseA | Sigma-E factor negative regulatory protein. | 5 | — | >8.75 |
| b1280 | yciM | Putative heat shock protein | 5 | — | 7.5 |
| b1233 | ychJ | Conserved protein YchJ | 7 | — | 7.5 |
| b4402 | yjjY | Predicted protein YjjY | 7 | — | 8.75 |

TABLE 2B

Example of a genes which can be inhibited by an repressor-engineered bacteriophage, and in some embodiments, such repressor-engineered bacteriophages which inhibit one or more of the following non-SOS defense genes are useful in combination with a Vancomycin antimicrobial agent, or analogue or varient thereof.
Table 2B: Example of a genes which can be inhibited by an repressor-engineered bacteriophage, and in some embodiments, such repressor-engineered bacteriophages which inhibit one or more of the following non-SOS defense genes are useful in combination with a Vancomycin antimicrobial agent, or analogue or varient thereof

| Locus Tag | Gene | Gene Product | Category | MIC (µg/mL) Plating | E Test |
|---|---|---|---|---|---|
|  | BW25113 |  |  | 500 | — |
| b3613 | envC | Cytokinesis - murein hydrolase | 2 | 150 | — |
| b3404 | envZ | Osmolarity sensor protein | 2 | 150 | — |
| b0588 | fepC | Ferric enterobactin transport ATP-binding protein | 2 | 150 | — |
| b3201 | lptB | ATP-binding LptAB-YrbK ABC transporter | 2 | 150 | 2.0 |
| b1855 | msbB | Myristoyl-acyl carrier acyltransferase | 2 | 150 | — |
| b0741 | pal | Peptidoglycan-associated lipoprotein precursor. | 2 | 100 | 96 |
| b2678 | proW | Glycine betaine/L-proline transport/permease | 2 | 150 | — |
| b2617 | smpA | Outer membrane lipoprotein | 2 | 100 | 70 |
| b1252 | tonB | Cytoplasmic membrane protein; energy transducer | 2 | 125 | — |
| b2512 | yfgL | Lipoprotein-outer membrane protein assembly | 2 | 150 | — |
| b3245 | yhdP | Transporter activity, membrane protein | 2 | 125 | — |
| b2527 | hscB | Hsc20 co-chaperone, with Hsc66 IscU iron-sulfur cluster | 2A | 150 | — |
| b0178 | skp | Periplasmic chaperone | 2A | 75 | — |
| b0053 | surA | Peptidyl-prolyl cis-trans isomerase PPIase and chaperone | 2A | 8 | 4 |
| b0939 | ycbR | Predicted periplasmic pilin chaperone | 2A | 150 | — |
| b0742 | ybgF | Predicted periplasmic protein | 2 | 100 | — |
| b2269 | elaD | Deubiquitinase | 3 | 150 | — |
| b0852 | rimK | Ribosomal protein S6 modification protein. | 3 | 150 | — |
| b3299 | rpmJ | 50S ribosomal protein L36 (Ribosomal protein B). | 3 | 150 | — |
| b3179 | rrmJ | 23S rRNA m2U2552 methyltransferase | 3 | 150 | — |
| b3344 | tusC | tRNA modification - sulfur transfer protein complex | 3 | 150 | — |
| b3345 | tusD | tRNA modification - sulfur transfer protein complex | 3 | 150 | — |
| b2494 | yfgC | Predicted peptidase | 3 | 150 | — |
| b1317 | pgmB | Putative beta-phosphoglucomutase | 4 | 100 | — |
| b1773 | ydjI | Predicted adolase | 4 | 100 | — |
| b0145 | dksA | RNA polymerase-binding transcription factor | 5 | 125 | — |
| b1237 | hns | DNA-binding protein H-NS | 5 | 150 | — |
| b3961 | oxyR | OxyR transcriptional dual regulator | 5 | 150 | — |
| b2405 | xapR | Xanthosine operon regulatory protein. | 5 | 100 | — |
| b1280 | yciM | Putative heat shock protein | 5 | 100 | — |
| b1553 | ydfP | Qin prophage; conserved protein | 6 | 150 | — |

TABLE 2C

Example of a genes which can be inhibited by an repressor-engineered bacteriophage, and in some embodiments, such repressor-engineered bacteriophages which inhibit one or more of the following non-SOS defense genes are useful in combination with a Rifampicin antimicrobial agent, or analogue or varient thereof
Table 2C: Example of a genes which can be inhibited by an repressor-engineered bacteriophage, and in some embodiments, such repressor-engineered bacteriophages which inhibit one or more of the following non-SOS defense genes are useful in combination with a Rifampicin antimicrobial agent, or analogue or varient thereof

| Locus Tag | Gene | Gene Product | Category | MIC (µg/mL) Plating |
|---|---|---|---|---|
|  | BW25113 |  |  | 16 |
| b2822 | recC | DNA helicase, ATP-dependent dsDNA/ssDNA exonuclease | 1 | 7.5 |
| b2616 | recN | Recombination and repair protein | 1 | 7.5 |
| b1652 | rnt | Ribonuclease T | 1 | >10 |

TABLE 2C-continued

Example of a genes which can be inhibited by an repressor-engineered bacteriophage, and in some embodiments, such repressor-engineered bacteriophages which inhibit one or more of the following non-SOS defense genes are useful in combination with a Rifampicin antimicrobial agent, or analogue or varient thereof Table 2C: Example of a genes which can be inhibited by an repressor-engineered bacteriophage, and in some embodiments, such repressor-engineered bacteriophages which inhibit one or more of the following non-SOS defense genes are useful in combination with a Rifampicin antimicrobial agent, or analogue or varient thereof

| Locus Tag | Gene | Gene Product | Category | MIC (μg/mL) Plating |
|---|---|---|---|---|
| b4058 | uvrA | Excision nuclease subunit A | 1 | 7.5 |
| b3781 | trxA | Thioredoxin electron transfer protein | 1A | 5 |
| b0464 | acrA | AcrAB-TolC Multidrug Efflux Transport System | 2 | >10 |
| b0462 | acrB | AcrAB-TolC Multidrug Efflux Transport System | 2 | 10 |
| b3613 | envC | Cytokinesis - murein hydrolase | 2 | 10 |
| b3404 | envZ | Osmolarity sensor protein | 2 | 10 |
| b0588 | fepC | Ferric enterobactin transport ATP-binding protein | 2 | 10 |
| b1677 | lpp | Major outer membrane lipoprotein precursor | 2 | 5 |
| b3201 | lptB | ATP-binding LptAB-YrbK ABC transporter | 2 | 10 |
| b1855 | msbB | Lipid A biosynthesis (KDO)2-(lauroyl)-lipid IVA acyltransferase | 2 | 7.5 |
| b0741 | pal | Peptidoglycan-associated lipoprotein precursor. | 2 | 5 |
| b1090 | plsX | Fatty acid/phospholipid synthesis protein plsX. | 2 | 10 |
| b0525 | ppiB | Peptidyl-prolyl cis-trans isomerase B | 2 | 5 |
| b3726 | pstA | Phosphate transport system permease protein | 2 | 5 |
| b3728 | pstS | Phosphate-binding periplasmic protein precursor | 2 | 7.5 |
| b3619 | rfaD | ADP-L-glycero-D-manno-heptose-6-epimerase | 2 | 10 |
| b3052 | rfaE | Heptose 1-phosphate adenyltransferase | 2 | 7.5 |
| b3631 | rfaG | Lipopolysaccharide core biosynthesis protein | 2 | 2 |
| b2617 | smpA | Outer membrane lipoprotein | 2 | 5 |
| b3838 | tatB | Sec-independent protein translocase TatB | 2 | 10 |
| b3839 | tatC | Sec-independent protein translocase TatC | 2 | 10 |
| b0738 | tolR | Colicin import; Tolerance to group A colicins | 2 | 3.5 |
| b1252 | tonB | Cytoplasmic membrane protein; energy transducer | 2 | >10 |
| b0742 | ybgF | Predicted periplasmic protein | 2 | >10 |
| b2512 | yfgL | Lipoprotein-outer membrane protein assembly | 2 | >10 |
| b2807 | ygdD | Conserved inner membrane protein | 2 | 10 |
| b3245 | yhdP | Transporter activity, membrane protein | 2 | 10 |
| b0161 | degP | Periplasmic serine protease and chaperone | 2A | 10 |
| b0014 | dnaK | Chaperone protein - chaperone Hsp70; DNA biosynthesis | 2A | 7.5 |
| b0178 | skp | Periplasmic chaperone | 2A | 5 |
| b0053 | surA | Peptidyl-prolyl cis-trans isomerase PPIase and chaperone | 2A | 2 |
| b0939 | ycbR | Predicted periplasmic pilin chaperone | 2A | 10 |
| b2269 | elaD | Deubiquitinase | 3 | >10 |
| b4375 | prfC | Peptide chain release factor 3 (RF-3). | 3 | 10 |
| b0489 | qmcA | Putative protease | 3 | 10 |
| b0852 | rimK | Ribosomal protein S6 modification protein. | 3 | 10 |
| b1269 | rluB | 23s rRNA pseudouridine synthase | 3 | 10 |
| b3984 | rplA | 50S ribosomal protein L1. | 3 | 7.5 |
| b3936 | rpmE | 50S ribosomal protein L31. | 3 | 5 |
| b1089 | rpmF | 50S ribosomal protein L32. | 3 | 7.5 |
| b3299 | rpmJ | 50S ribosomal protein L36 (Ribosomal protein B). | 3 | 7.5 |
| b2494 | yfgC | Predicted peptidase | 3 | 5 |
| b1095 | fabF | β-ketoacyl-ACP synthase | 4 | 5 |
| b3058 | folB | Dihydroneopterin aldolase | 4 | >10 |
| b4395 | gpmB | Probable phosphoglycerate mutase gpmB | 4 | 10 |
| B3612 | gpmM | phosphoglycerate mutase, cofactor independent | 4 | >10 |
| b0677 | nagA | N-acetylglucosamine-6-phosphate deacetylase | 4 | 5 |
| b1317 | pgmB | β-phosphoglucomutase | 4 | 10 |
| b3386 | rpe | Ribulose-phosphate 3-epimerase | 4 | 10 |
| b1731 | cedA | Cell division activator | 5 | 10 |
| b4172 | hfq | HF-I, host factor for RNA phage Q β replication | 5 | 10 |
| b1237 | hns | DNA-binding protein H-NS | 5 | 7.5 |
| b3842 | rfaH | Transcriptional activator rfaH. | 5 | 7.5 |

TABLE 2C-continued

Example of a genes which can be inhibited by an repressor-engineered bacteriophage, and in some embodiments, such repressor-engineered bacteriophages which inhibit one or more of the following non-SOS defense genes are useful in combination with a Rifampicin antimicrobial agent, or analogue or varient thereof
Table 2C: Example of a genes which can be inhibited by an repressor-engineered bacteriophage, and in some embodiments, such repressor-engineered bacteriophages which inhibit one or more of the following non-SOS defense genes are useful in combination with a Rifampicin antimicrobial agent, or analogue or varient thereof

| Locus Tag | Gene | Gene Product | Category | MIC (μg/mL) Plating |
|---|---|---|---|---|
| b2572 | rseA | Sigma-E factor negative regulatory protein. | 5 | 7.5 |
| b2405 | xapR | Xanthosine operon regulatory protein. | 5 | >10 |
| b1280 | yciM | Putative heat shock protein | 5 | 7.5 |
| b0547 | ybcN | Hypothetical protein in lambdoid DLP12 prophage region | 6 | 7.5 |
| b0550.1 | ylcG | DLP12 prophage; predicted protein | 6 | 5 |
| b0659 | ybeY | Hypothetical protein | 7 | 10 |
| b1088 | yceD | Hypothetical protein | 7 | 5 |
| b1233 | ychJ | Hypothetical protein | 7 | 7.5 |
| b4402 | yjjY | Hypothetical protein yjjY. | 7 | >10 |

TABLE 2D

Example of a genes which can be inhibited by an repressor-engineered bacteriophage, and in some embodiments, such repressor-engineered bacteriophages which inhibit one or more of the following non-SOS defense genes are useful in combination with an Ampicillin antimicrobial agent, or analogue or varient thereof
Table 2D: Example of a genes which can be inhibited by an repressor-engineered bacteriophage, and in some embodiments, such repressor-engineered bacteriophages which inhibit one or more of the following non-SOS defense genes are useful in combination with an Ampicillin antimicrobial agent, or analogue or varient thereof

| Locus Tag | Gene | Gene Description | Category | MIC (μg/mL) E test | MIC (μg/mL) Plating |
|---|---|---|---|---|---|
| | BW25113 | | | 5.0 | 6.0 |
| b3017 | sufI | Suppressor of essential cell division protein FtsI | 1A, 2 | — | 2.0 |
| b0464 | acrA | AcrAB-TolC Multidrug Efflux Transport System | 2 | — | 1.5 |
| b0462 | acrB | AcrAB-TolC Multidrug Efflux Transport System | 2 | — | 2.0 |
| b3035 | tolC | AcrAB-TolC Multidrug Efflux Transport System | 2 | 1.0 | 2.0 |
| b0632 | dacA | Penicillin-binding protein 5 precursor | 2 | 1.5 | 1.5 |
| b0092 | ddlB | Subunit of D-alanine:D-alanine ligase B, ADP-forming | 2 | — | 1.0 |
| b2314 | dedD | Putative lipoprotein - inner membrane | 2 | — | 2.0 |
| b1193 | emtA | :ytic murein transglycosylase E | 2 | — | 2.0 |
| b3613 | envC | Cytokinesis - murein hydrolase | 2 | — | 1.5 |
| b3201 | lptB | ATP-binding LptAB-YrbK ABC transporter | 2 | — | 2.0 |
| b0149 | mrcB | Subunit of 5-methylcytosine restriction system | 2 | — | 2.0 |
| b0741 | pal | Peptidoglycan-associated lipoprotein precur. | 2 | 2.0 | 1.5 |
| b3838 | tatB | Sec-independent protein translocase TatB | 2 | 1.5 | 1.5 |
| b3839 | tatC | Sec-independent protein translocase TatC | 2 | 3.0 | 2.0 |
| b0738 | tolR | Colicin import; Tol-pal system component | 2 | — | 2.0 |
| b0742 | ybgF | Hypothetical protein ybgF precursor. | 2 | — | 1.5 |
| b0028 | fkpB | FKBP-type 16 kDa peptidyl-prolyl cis-trans isomerase | 2A | — | 2.5 |
| b2526 | hscA | Chaperone, member of Hsp70 protein family | 2A | — | 2.0 |
| b2527 | hscB | Hsc20 co-chaperone that acts with Hsc66 in IscU iron-sulfur cluster | 2A | — | 2.5 |
| b0178 | skp | Periplasmic chaperone | 2A | — | 2.0 |
| b0053 | surA | Peptidyl-prolyl cis-trans isomerase PPIase and chaperone | 2A | — | 2.0 |
| b0489 | qmcA | Putative protease | 3 | — | 2.5 |
| b0852 | rimK | Ribosomal protein S6 modification protein. | 3 | — | 2.0 |
| b3984 | rplA | 50S ribosomal protein L1. | 3 | 2.0 | 2.0 |
| b1089 | rpmF | 50S ribosomal protein L32. | 3 | — | 1.5 |
| b4200 | rpsF | 30S ribosomal protein S6. | 3 | — | 2.0 |
| b3179 | rrmJ | 23S rRNA m2U2552 methyltransferase | 3 | — | 1.5 |
| b2494 | yfgC | Hypothetical protein yfgC precursor. | 3 | — | 1.5 |
| b2512 | yfgL | Lipoprotein component of outer membrane protein assembly complex | 3 | — | 2.0 |

TABLE 2D-continued

Example of a genes which can be inhibited by an repressor-engineered bacteriophage, and in some embodiments, such repressor-engineered bacteriophages which inhibit one or more of the following non-SOS defense genes are useful in combination with an Ampicillin antimicrobial agent, or analogue or varient thereof
Table 2D: Example of a genes which can be inhibited by an repressor-engineered bacteriophage, and in some embodiments, such repressor-engineered bacteriophages which inhibit one or more of the following non-SOS defense genes are useful in combination with an Ampicillin antimicrobial agent, or analogue or varient thereof

| Locus Tag | Gene | Gene Description | Category | MIC (µg/mL) E test | MIC (µg/mL) Plating |
|---|---|---|---|---|---|
| b3734 | atpA | ATP synthase alpha chain | 4 | — | 2.5 |
| b3809 | dapF | Diaminopimelate epimerase | 4 | 2.0 | 1.0 |
| b2065 | dcd | Deoxycytidine triphosphate deaminase (dTP) | 4 | — | 2.5 |
| b3612 | gpmM | Phosphoglycerate mutase, cofactor independent | 4 | — | 1.5 |
| b1317 | pgmB | β-phosphoglucomutase | 4 | — | 1.5 |
| b2232 | ubiG | 3-demethylubiquinone-9 3-methyltransferase | 4 | — | 2.0 |
| b2767 | ygcO | Predicted 4Fe-4S cluster-containing protein | 4 | — | 2.0 |
| b1284 | deoT | DNA-binding transcriptional regulator | 5 | — | 2.0 |
| b0145 | dksA | RNA polymerase-binding transcription factor | 5 | — | 2.0 |
| b1130 | phoP | Transcriptional regulatory protein | 5 | — | 2.0 |
| b2405 | xapR | Xanthosine operon regulatory protein. | 5 | — | 1.5 |
| b1280 | yciM | Putative heat shock proteins | 5 | — | 1.5 |
|  | JW5115 | Hypothetical protein | 7 | — | 2.0 |
| b0631 | ybeD | conserved protein YbeD | 7 | — | 2.0 |
| b0659 | ybeY | conserved protein Ybey | 7 | — | 2.0 |
| b0762 | ybhT | Hypothetical protein YbhT precursor | 7 | — | 2.0 |
| b4402 | yjjY | predicted protein YjjY | 7 | — | 1.5 |

TABLE 2E

Example of a genes which can be inhibited by an repressor-engineered bacteriophage, and in some embodiments, such repressor-engineered bacteriophages which inhibit one or more of the following non-SOS defense genes are useful in combination with a Sulfamethaxazone antimicrobial agent, or analogue or varient thereof.
Table 2E: Example of a genes which can be inhibited by an repressor-engineered bacteriophage, and in some embodiments, such repressor-engineered bacteriophages which inhibit one or more of the following non-SOS defense genes are useful in combination with a Sulfamethaxazone antimicrobial agent, or analogue or varient thereof

| Locus Tag | Gene | Gene Product | Category | MIC (µg/mL) Plating |
|---|---|---|---|---|
|  | BW25113 |  |  | 1000 |
| b1865 | nudB | dATP pyrophosphohydrolase | 1 | 350 |
| b2699 | recA | DNA strand exchange and recombination protein | 1 | 400 |
| b2820 | recB | DNA helicase, ATP-dependent dsDNA/ssDNA exonuclease | 1 | 350 |
| b2822 | recC | DNA helicase, ATP-dependent dsDNA/ssDNA exonuclease | 1 | 350 |
| b3652 | recG | ATP-dependent DNA helicase, resolution of Holliday junctions | 1 | 500 |
| b3261 | fis | DNA-binding protein - chromosome compaction | 1A | 600 |
| b3613 | envC | Cytokinesis - murein hydrolase | 2 | 400 |
| b3201 | lptB | ATP-binding LptAB-YrbK ABC transporter | 2 | 500 |
| b3726 | pstA | Phosphate transport system permease | 2 | 550 |
| b3728 | pstS | Phosphate-binding periplasmic protein | 2 | 550 |
| b3052 | rfaE | Heptose 1-phosphate adenyltransferase | 2 | 550 |
| b3035 | tolC | AcrAB-TolC Multidrug Efflux Transport System | 2 | 400 |
| b0742 | ybgF | Predicted plasma protein | 2 | >550 |
| b1279 | yciS | Conserved inner membrane protein | 2 | 550 |
| b2512 | yfgL | Lipoprotein component of outer membrane protein assembly complex | 2 | 400 |
| b1520 | yneE | Conserved inner membrane protein | 2 | 550 |
| b0161 | degP | Periplasmic serine protease and chaperone | 2A | 500 |
| b0014 | dnaK | Chaperone protein - chaperone Hsp70; DNA biosynthesis | 2A | 300 |
| b0489 | qmcA | Putative protease | 3 | 550 |
| b0852 | rimK | Ribosomal protein S6 modification protein. | 3 | 350 |
| b3984 | rplA | 50S ribosomal protein L1. | 3 | 500 |

TABLE 2E-continued

Example of a genes which can be inhibited by an repressor-engineered bacteriophage, and in some embodiments, such repressor-engineered bacteriophages which inhibit one or more of the following non-SOS defense genes are useful in combination with a Sulfamethaxazone antimicrobial agent, or analogue or varient thereof.

Table 2E: Example of a genes which can be inhibited by an repressor-engineered bacteriophage, and in some embodiments, such repressor-engineered bacteriophages which inhibit one or more of the following non-SOS defense genes are useful in combination with a Sulfamethaxazone antimicrobial agent, or analogue or varient thereof

| Locus Tag | Gene | Gene Product | Category | MIC (µg/mL) Plating |
|---|---|---|---|---|
| b1089 | rpmF | 50S ribosomal protein L32. | 3 | 550 |
| b3065 | rpsU | 30S ribosomal protein S21. | 3 | 500 |
| b3809 | dapF | Diaminopimelate epimerase | 4 | 300 |
| b2065 | dcd | Deoxycytidine triphosphate deaminase (dTP) | 4 | >550 |
| b3612 | gpmM | Phosphoglycerate mutase, cofactor independent | 4 | 400 |
| b0116 | lpdA | Dihydrolipoamide dehydrogenase (Glycine cleavage) | 4 | 400 |
| b1317 | pgmB | β-phosphoglucomutase | 4 | 500 |
| b1773 | ydjI | Predicted adolase | 4 | >550 |
| b2767 | ygcO | Predicted 4Fe-4S cluster-containing protein | 4 | 550 |
| b1284 | deoT | DNA-binding transcriptional regulator | 5 | 550 |
| b0145 | dksA | Transcription initiation factor | 5 | 550 |
| b1237 | hns | DNA-binding protein H-NS | 5 | 550 |
| b2572 | resA | Sigma-E factor negative regulatory protein. | 5 | >550 |
| b2405 | xapR | Xanthosine operon regulatory protein. | 5 | >550 |
| b1280 | yciM | Putative heat shock protein | 5 | >550 |
| b0550.1 | ylcG | DLP12 prophage; predicted protein | 6 | 500 |
| b1143 | ymfI | Prophage genes - e14 prophage; predicted protein | 6 | 500 |
| | JW5115 | Hypothetical protein | 7 | 400 |
| | JW5474 | Hypothetical protein | 7 | 500 |
| b0659 | ybeY | Hypothetical protein | 7 | 500 |
| b3928 | yiiU | Conserved protein YiiU | 7 | 550 |
| b4402 | yjjY | Predicted protein YjjY | 7 | >550 |

TABLE 2F

Example of a genes which can be inhibited by an repressor-engineered bacteriophage, and in some embodiments, such repressor-engineered bacteriophages which inhibit one or more of the following non-SOS defense genes are useful in combination with a gentamicin antimicrobial agent, or analogue or varient thereof Table 2F: Example of a genes which can be inhibited by an repressor-engineered bacteriophage, and in some embodiments, such repressor-engineered bacteriophages which inhibit one or more of the following non-SOS defense genes are useful in combination with a gentamicin antimicrobial agent, or analogue or varient thereof

| Locus Tag | Gene | Gene Product | Category | MIC (µg/mL) Plating |
|---|---|---|---|---|
| | BW25113 | | | 0.8 |
| b1652 | rnt | Ribonuclease T | 1 | 0.7 |
| b3613 | envC | Cytokinesis - murein hydrolase | 2 | >0.5 |
| b3621 | rfaC | Lipopolysaccharide heptosyltransferase-1 | 2 | 0.7 |
| b3791 | rffA | dTDP-4-oxo-6-deoxy-D-glucose transaminase | 2 | 0.7 |
| b1292 | sapC | Peptide transport system permease protein | 2 | 0.5 |
| b3175 | secG | Protein-export membrane - Sec Protein Secretion Complex | 2 | 0.5 |
| b3839 | tatC | Sec-independent protein translocase TatC | 2 | 0.5 |
| b3035 | tolC | AcrAB-TolC Multidrug Efflux Transport System | 2 | 0.5 |
| b4174 | hflK | Regulator of FtsH protease | 3 | 0.5 |
| b4203 | rplI | 50S ribosomal protein L9. | 3 | 0.7 |
| b3936 | rpmE | 50S ribosomal protein L31. | 3 | 0.6 |
| b3344 | tusC | tRNA modification - sulfur transfer protein complex | 3 | 0.5 |
| b3345 | tusD | tRNA modification - sulfur transfer protein complex | 3 | 0.5 |

TABLE 2F-continued

Example of a genes which can be inhibited by an repressor-engineered bacteriophage, and in some embodiments, such repressor-engineered bacteriophages which inhibit one or more of the following non-SOS defense genes are useful in combination with a gentamicin antimicrobial agent, or analogue or varient thereof Table 2F: Example of a genes which can be inhibited by an repressor-engineered bacteriophage, and in some embodiments, such repressor-engineered bacteriophages which inhibit one or more of the following non-SOS defense genes are useful in combination with a gentamicin antimicrobial agent, or analogue or varient thereof

| Locus Tag | Gene | Gene Product | Category | MIC (µg/mL) Plating |
|---|---|---|---|---|
| b2494 | yfgC | Predicted peptidase | 3 | >0.5 |
| b3809 | dapF | Diaminopimelate epimerase | 4 | 0.7 |
| b3612 | gpmM | Phosphoglycerate mutase, cofactor independent | 4 | 0.7 |
| b3202 | rpoN | RNA polymerase sigma-54 factor. | 5 | 0.5 |
| b2405 | xapR | Xanthosine operon regulatory protein. | 5 | >0.5 |
| b1280 | yciM | Putative heat shock protein | 5 | >0.7 |
|  | JW5360 | Hypothetical protein | 7 | >0.8 |
| b4557 | yidD | Predicted protein YidD | 7 | 0.5 |

TABLE 5

Examples of bacteriophages which can be engineered to be an inhibitor-engineered bacteriophage, or a repressor-engineered bacteriophage or a susceptibility-engineered bacteriophage as disclosed herein.

Table 5: Examples of bacteriophages which can be engineered to be an inhibitor-engineered bacteriophage, or a repressor-engineered bacteriophage or a susceptibility-engineered bacteriophage as disclosed herein.

| organism | accession | length | proteins | RNAs | genes |
|---|---|---|---|---|---|
| *Acholeplasma* phage L2 | NC_001447 | 11965 nt | 14 | 0 | 14 |
| *Acholeplasma* phage MV-L1 | NC_001341 | 4491 nt | 4 | 0 | 4 |
| *Acidianus* bottle-shaped virus | NC_009452 | 23814 nt | 57 | 0 | 57 |
| *Acidianus* filamentous virus 1 | NC_005830 | 20869 nt | 40 | 0 | 40 |
| *Acidianus* filamentous virus 2 | NC_009884 | 31787 nt | 52 | 1 | 53 |
| *Acidianus* filamentous virus 3 | NC_010155 | 40449 nt | 68 | 0 | 68 |
| *Acidianus* filamentous virus 6 | NC_010152 | 39577 nt | 66 | 0 | 66 |
| *Acidianus* filamentous virus 7 | NC_010153 | 36895 nt | 57 | 0 | 57 |
| *Acidianus* filamentous virus 8 | NC_010154 | 38179 nt | 61 | 0 | 61 |
| *Acidianus* filamentous virus 9 | NC_010537 | 41172 nt | 73 | 0 | 73 |
| *Acidianus* rod-shaped virus 1 | NC_009965 | 24655 nt | 41 | 0 | 41 |
| *Acidianus* two-tailed virus | NC_007409 | 62730 nt | 72 | 0 | 72 |
| *Acinetobacter* phage AP205 | NC_002700 | 4268 nt | 4 | 0 | 4 |
| *Actinomyces* phage Av-1 | NC_009643 | 17171 nt | 22 | 1 | 23 |
| *Actinoplanes* phage phiAsp2 | NC_005885 | 58638 nt | 76 | 0 | 76 |
| Acyrthosiphon pisum secondary endosymbiont phage 1 | NC_000935 | 36524 nt | 54 | 0 | 54 |
| *Aeromonas* phage 25 | NC_008208 | 161475 nt | 242 | 13 | 242 |
| *Aeromonas* phage 31 | NC_007022 | 172963 nt | 247 | 15 | 262 |
| *Aeromonas* phage 44RR2.8t | NC_005135 | 173591 nt | 252 | 17 | 269 |
| *Aeromonas* phage Aeh1 | NC_005260 | 233234 nt | 352 | 23 | 375 |
| *Aeromonas* phage phiO18P | NC_009542 | 33985 nt | 45 | 0 | 45 |
| Archaeal BJ1 virus | NC_008695 | 42271 nt | 70 | 1 | 71 |
| *Azospirillum* phage Cd | NC_010355 | 62337 nt | 95 | 0 | 95 |
| *Bacillus* phage 0305phi8-36 | NC_009760 | 218948 nt | 246 | 0 | 246 |
| *Bacillus* phage AP50 | NC_011523 | 14398 nt | 31 | 0 | 31 |
| *Bacillus* phage B103 | NC_004165 | 18630 nt | 17 | 0 | 17 |
| *Bacillus* phage BCJA1c | NC_006557 | 41092 nt | 58 | 0 | 58 |
| *Bacillus* phage Bam35c | NC_005258 | 14935 nt | 32 | 0 | 32 |
| *Bacillus* phage Cherry | NC_007457 | 36615 nt | 51 | 0 | 51 |
| *Bacillus* phage Fah | NC_007814 | 37974 nt | 50 | 0 | 50 |
| *Bacillus* phage GA-1 | NC_002649 | 21129 nt | 35 | 1 | 52 |
| *Bacillus* phage GIL16c | NC_006945 | 14844 nt | 31 | 0 | 31 |
| *Bacillus* phage Gamma | NC_007458 | 37253 nt | 53 | 0 | 53 |
| *Bacillus* phage IEBH | NC_011167 | 53104 nt | 86 | 0 | 86 |
| *Bacillus* phage SPBc2 | NC_001884 | 134416 nt | 185 | 0 | 185 |
| *Bacillus* phage SPO1 | NC_011421 | 132562 nt | 204 | 5 | 209 |
| *Bacillus* phage SPP1 | NC_004166 | 44010 nt | 101 | 0 | 101 |
| *Bacillus* phage TP21-L | NC_011645 | 37456 nt | 56 | 0 | 56 |
| *Bacillus* phage WBeta | NC_007734 | 40867 nt | 53 | 0 | 53 |
| *Bacillus* phage phBC6A51 | NC_004820 | 61395 nt | 75 | 0 | 75 |

TABLE 5-continued

Examples of bacteriophages which can be engineered to be an inhibitor-engineered bacteriophage, or a repressor-engineered bacteriophage or a susceptibility-engineered bacteriophage as disclosed herein.
Table 5: Examples of bacteriophages which can be engineered to be an inhibitor-engineered bacteriophage, or a repressor-engineered bacteriophage or a susceptibility-engineered bacteriophage as disclosed herein.

| organism | accession | length | proteins | RNAs | genes |
|---|---|---|---|---|---|
| *Bacillus* phage phBC6A52 | NC_004821 | 38472 nt | 49 | 0 | 49 |
| *Bacillus* phage phi105 | NC_004167 | 39325 nt | 51 | 0 | 51 |
| *Bacillus* phage phi29 | NC_011048 | 19282 nt | 27 | 0 | 27 |
| *Bacillus* virus 1 | NC_009737 | 35055 nt | 54 | 0 | 54 |
| Bacteriophage APSE-2 | NC_011551 | 39867 nt | 41 | 1 | 42 |
| *Bacteroides* phage B40-8 | NC_011222 | 44929 nt | 46 | 0 | 46 |
| *Bdellovibrio* phage phiMH2K | NC_002643 | 4594 nt | 11 | 0 | 11 |
| *Bordetella* phage BIP-1 | NC_005809 | 42638 nt | 48 | 0 | 48 |
| *Bordetella* phage BMP-1 | NC_005808 | 42663 nt | 47 | 0 | 47 |
| *Bordetella* phage BPP-1 | NC_005357 | 42493 nt | 49 | 0 | 49 |
| *Burkholderia ambifaria* phage BcepF1 | NC_009015 | 72415 nt | 127 | 0 | 127 |
| *Burkholderia* phage Bcep1 | NC_005263 | 48177 nt | 71 | 0 | 71 |
| *Burkholderia* phage Bcep176 | NC_007497 | 44856 nt | 81 | 0 | 81 |
| *Burkholderia* phage Bcep22 | NC_005262 | 63879 nt | 81 | 1 | 82 |
| *Burkholderia* phage Bcep43 | NC_005342 | 48024 nt | 65 | 0 | 65 |
| *Burkholderia* phage Bcep781 | NC_004333 | 48247 nt | 66 | 0 | 66 |
| *Burkholderia* phage BcepB1A | NC_005886 | 47399 nt | 73 | 0 | 73 |
| *Burkholderia* phage BcepC6B | NC_005887 | 42415 nt | 46 | 0 | 46 |
| *Burkholderia* phage BcepGomr | NC_009447 | 52414 nt | 75 | 0 | 75 |
| *Burkholderia* phage BcepMu | NC_005882 | 36748 nt | 53 | 0 | 53 |
| *Burkholderia* phage BcepNY3 | NC_009604 | 47382 nt | 70 | 1 | 70 |
| *Burkholderia* phage BcepNazgul | NC_005091 | 57455 nt | 73 | 0 | 73 |
| *Burkholderia* phage KS10 | NC_011216 | 37635 nt | 49 | 0 | 49 |
| *Burkholderia* phage phi1026b | NC_005284 | 54865 nt | 83 | 0 | 83 |
| *Burkholderia* phage phi52237 | NC_007145 | 37639 nt | 47 | 0 | 47 |
| *Burkholderia* phage phi644-2 | NC_009235 | 48674 nt | 71 | 0 | 71 |
| *Burkholderia* phage phiE12-2 | NC_009236 | 36690 nt | 50 | 0 | 50 |
| *Burkholderia* phage phiE125 | NC_003309 | 53373 nt | 71 | 0 | 71 |
| *Burkholderia* phage phiE202 | NC_009234 | 35741 nt | 48 | 0 | 48 |
| *Burkholderia* phage phiE255 | NC_009237 | 37446 nt | 55 | 0 | 55 |
| *Chlamydia* phage 3 | NC_008355 | 4554 nt | 8 | 0 | 8 |
| *Chlamydia* phage 4 | NC_007461 | 4530 nt | 8 | 0 | 8 |
| *Chlamydia* phage CPAR39 | NC_002180 | 4532 nt | 7 | 0 | 7 |
| *Chlamydia* phage Chp1 | NC_001741 | 4877 nt | 12 | 0 | 12 |
| *Chlamydia* phage Chp2 | NC_002194 | 4563 nt | 8 | 0 | 7 |
| *Chlamydia* phage phiCPG1 | NC_001998 | 4529 nt | 9 | 0 | 9 |
| *Clostridium* phage 39-O | NC_011318 | 38753 nt | 62 | 0 | 62 |
| *Clostridium* phage c-st | NC_007581 | 185683 nt | 198 | 0 | 198 |
| *Clostridium* phage phi CD119 | NC_007917 | 53325 nt | 79 | 0 | 79 |
| *Clostridium* phage phi3626 | NC_003524 | 33507 nt | 50 | 0 | 50 |
| *Clostridium* phage phiC2 | NC_009231 | 56538 nt | 82 | 0 | 82 |
| *Clostridium* phage phiCD27 | NC_011398 | 50930 nt | 75 | 0 | 75 |
| *Clostridium* phage phiSM101 | NC_008265 | 38092 nt | 53 | 1 | 54 |
| *Corynebacterium* phage BFK20 | NC_009799 | 42969 nt | 54 | 0 | 54 |
| *Corynebacterium* phage P1201 | NC_009816 | 70579 nt | 97 | 4 | 101 |
| *Enterobacteria* phage 13a | NC_011045 | 38841 nt | 55 | 0 | 55 |
| *Enterobacteria* phage 933W | NC_000924 | 61670 nt | 80 | 4 | 84 |
| *Enterobacteria* phage BA14 | NC_011040 | 39816 nt | 52 | 0 | 52 |
| *Enterobacteria* phage BP-4795 | NC_004813 | 57930 nt | 85 | 0 | 85 |
| *Enterobacteria* phage BZ13 | NC_001426 | 3466 nt | 4 | 0 | 4 |
| *Enterobacteria* phage EPS7 | NC_010583 | 111382 nt | 170 | 0 | 171 |
| *Enterobacteria* phage ES18 | NC_006949 | 46900 nt | 79 | 0 | 79 |
| *Enterobacteria* phage EcoDS1 | NC_011042 | 39252 nt | 53 | 0 | 53 |
| *Enterobacteria* phage FI sensu lato | NC_004301 | 4276 nt | 4 | 0 | 4 |
| *Enterobacteria* phage Felix 01 | NC_005282 | 86155 nt | 131 | 22 | 153 |
| *Enterobacteria* phage Fels-2 | NC_010463 | 33693 nt | 47 | 0 | 48 |
| *Enterobacteria* phage G4 sensu lato | NC_001420 | 5577 nt | 11 | 0 | 13 |
| *Enterobacteria* phage HK022 | NC_002166 | 40751 nt | 57 | 0 | 57 |
| *Enterobacteria* phage HK620 | NC_002730 | 38297 nt | 58 | 0 | 58 |
| *Enterobacteria* phage HK97 | NC_002167 | 39732 nt | 61 | 0 | 62 |
| *Enterobacteria* phage I2-2 | NC_001332 | 6744 nt | 9 | 0 | 9 |
| *Enterobacteria* phage ID18 sensu lato | NC_007856 | 5486 nt | 11 | 0 | 11 |
| *Enterobacteria* phage ID2 Moscow/ID/2001 | NC_007817 | 5486 nt | 11 | 0 | 11 |
| *Enterobacteria* phage If1 | NC_001954 | 8454 nt | 10 | 0 | 10 |
| *Enterobacteria* phage Ike | NC_002014 | 6883 nt | 10 | 0 | 10 |
| *Enterobacteria* phage JK06 | NC_007291 | 46072 nt | 82 | 0 | 82 |
| *Enterobacteria* phage JS98 | NC_010105 | 170523 nt | 266 | 3 | 269 |
| *Enterobacteria* phage K1-5 | NC_008152 | 44385 nt | 52 | 0 | 52 |
| *Enterobacteria* phage K1E | NC_007637 | 45251 nt | 62 | 0 | 62 |
| *Enterobacteria* phage K1F | NC_007456 | 39704 nt | 43 | 0 | 41 |

TABLE 5-continued

Examples of bacteriophages which can be engineered to be an inhibitor-engineered bacteriophage, or a repressor-engineered bacteriophage or a susceptibility-engineered bacteriophage as disclosed herein.
Table 5: Examples of bacteriophages which can be engineered to be an inhibitor-engineered bacteriophage, or a repressor-engineered bacteriophage or a susceptibility-engineered bacteriophage as disclosed herein.

| organism | accession | length | proteins | RNAs | genes |
|---|---|---|---|---|---|
| *Enterobacteria* phage M13 | NC_003287 | 6407 nt | 10 | 0 | 10 |
| *Enterobacteria* phage MS2 | NC_001417 | 3569 nt | 4 | 0 | 4 |
| *Enterobacteria* phage Min27 | NC_010237 | 63395 nt | 83 | 3 | 86 |
| *Enterobacteria* phage Mu | NC_000929 | 36717 nt | 55 | 0 | 55 |
| *Enterobacteria* phage N15 | NC_001901 | 46375 nt | 60 | 0 | 60 |
| *Enterobacteria* phage N4 | NC_008720 | 70153 nt | 72 | 0 | 72 |
| *Enterobacteria* phage P1 | NC_005856 | 94800 nt | 110 | 4 | 117 |
| *Enterobacteria* phage P2 | NC_001895 | 33593 nt | 43 | 0 | 43 |
| *Enterobacteria* phage P22 | NC_002371 | 41724 nt | 72 | 2 | 74 |
| *Enterobacteria* phage P4 | NC_001609 | 11624 nt | 14 | 5 | 19 |
| *Enterobacteria* phage PRD1 | NC_001421 | 14927 nt | 31 | 0 | 31 |
| *Enterobacteria* phage Phi1 | NC_009821 | 164270 nt | 276 | 0 | 276 |
| *Enterobacteria* phage PsP3 | NC_005340 | 30636 nt | 42 | 0 | 42 |
| *Enterobacteria* phage Qbeta | NC_001890 | 4215 nt | 4 | 0 | 4 |
| *Enterobacteria* phage RB32 | NC_008515 | 165890 nt | 270 | 8 | 270 |
| *Enterobacteria* phage RB43 | NC_007023 | 180500 nt | 292 | 1 | 292 |
| *Enterobacteria* phage RB49 | NC_005066 | 164018 nt | 279 | 0 | 279 |
| *Enterobacteria* phage RB69 | NC_004928 | 167560 nt | 273 | 2 | 275 |
| *Enterobacteria* phage RTP | NC_007603 | 46219 nt | 75 | 0 | 75 |
| *Enterobacteria* phage SP6 | NC_004831 | 43769 nt | 52 | 0 | 52 |
| *Enterobacteria* phage ST104 | NC_005841 | 41391 nt | 63 | 0 | 63 |
| *Enterobacteria* phage ST64T | NC_004348 | 40679 nt | 65 | 0 | 65 |
| *Enterobacteria* phage Sf6 | NC_005344 | 39043 nt | 66 | 2 | 70 |
| *Enterobacteria* phage SfV | NC_003444 | 37074 nt | 53 | 0 | 53 |
| *Enterobacteria* phage T1 | NC_005833 | 48836 nt | 78 | 0 | 78 |
| *Enterobacteria* phage T3 | NC_003298 | 38208 nt | 55 | 0 | 56 |
| *Enterobacteria* phage T4 | NC_000866 | 168903 nt | 278 | 10 | 288 |
| *Enterobacteria* phage T5 | NC_005859 | 121750 nt | 162 | 33 | 195 |
| *Enterobacteria* phage T7 | NC_001604 | 39937 nt | 60 | 0 | 60 |
| *Enterobacteria* phage TLS | NC_009540 | 49902 nt | 87 | 0 | 87 |
| *Enterobacteria* phage VT2-Sakai | NC_000902 | 60942 nt | 83 | 3 | 86 |
| *Enterobacteria* phage WA13 sensu lato | NC_007821 | 6068 nt | 10 | 0 | 10 |
| *Enterobacteria* phage YYZ-2008 | NC_011356 | 54896 nt | 75 | 0 | 75 |
| *Enterobacteria* phage alpha3 | NC_001330 | 6087 nt | 10 | 0 | 10 |
| *Enterobacteria* phage epsilon15 | NC_004775 | 39671 nt | 51 | 0 | 51 |
| *Enterobacteria* phage lambda | NC_001416 | 48502 nt | 73 | 0 | 92 |
| *Enterobacteria* phage phiEco32 | NC_010324 | 77554 nt | 128 | 1 | 128 |
| *Enterobacteria* phage phiEcoM-GJ1 | NC_010106 | 52975 nt | 75 | 1 | 76 |
| *Enterobacteria* phage phiP27 | NC_003356 | 42575 nt | 58 | 2 | 60 |
| *Enterobacteria* phage phiV10 | NC_007804 | 39104 nt | 55 | 0 | 55 |
| *Enterobacteria* phage phiX174 sensu lato | NC_001422 | 5386 nt | 11 | 0 | 11 |
| *Enterococcus* phage phiEF24C | NC_009904 | 142072 nt | 221 | 5 | 226 |
| *Erwinia* phage Era103 | NC_009014 | 45445 nt | 53 | 0 | 53 |
| *Erwinia* phage phiEa21-4 | NC_011811 | 84576 nt | 118 | 26 | 144 |
| *Escherichia* phage rv5 | NC_011041 | 137947 nt | 233 | 6 | 239 |
| *Flavobacterium* phage 11b | NC_006356 | 36012 nt | 65 | 0 | 65 |
| *Geobacillus* phage GBSV1 | NC_008376 | 34683 nt | 54 | 0 | 54 |
| *Geobacillus* virus E2 | NC_009552 | 40863 nt | 71 | 0 | 71 |
| *Haemophilus* phage Aaphi23 | NC_004827 | 43033 nt | 66 | 0 | 66 |
| *Haemophilus* phage HP1 | NC_001697 | 32355 nt | 42 | 0 | 42 |
| *Haemophilus* phage HP2 | NC_003315 | 31508 nt | 37 | 0 | 37 |
| *Haloarcula* phage SH1 | NC_007217 | 30889 nt | 56 | 0 | 56 |
| *Halomonas* phage phiHAP-1 | NC_010342 | 39245 nt | 46 | 0 | 46 |
| *Halorubrumv* phage HF2 | NC_003345 | 77670 nt | 114 | 5 | 119 |
| *Halovirus* HF1 | NC_004927 | 75898 nt | 102 | 4 | 106 |
| His1 virus | NC_007914 | 14462 nt | 35 | 0 | 35 |
| His2 virus | NC_007918 | 16067 nt | 35 | 0 | 35 |
| *Iodobacteriophage* phiPLPE | NC_011142 | 47453 nt | 84 | 0 | 84 |
| *Klebsiella* phage K11 | NC_011043 | 41181 nt | 51 | 0 | 51 |
| *Klebsiella* phage phiKO2 | NC_005857 | 51601 nt | 64 | 0 | 63 |
| *Kluyvera* phage Kvp1 | NC_011534 | 39472 nt | 47 | 1 | 48 |
| *Lactobacillus johnsonii* prophage Lj771 | NC_010179 | 40881 nt | 56 | 0 | 56 |
| *Lactobacillus* phage A2 | NC_004112 | 43411 nt | 61 | 0 | 64 |
| *Lactobacillus* phage KC5a | NC_007924 | 38239 nt | 61 | 0 | 61 |
| *Lactobacillus* phage LL-H | NC_009554 | 34659 nt | 51 | 0 | 51 |
| *Lactobacillus* phage LP65 | NC_006565 | 131522 nt | 165 | 14 | 179 |
| *Lactobacillus* phage Lc-Nu | NC_007501 | 36466 nt | 51 | 0 | 51 |
| *Lactobacillus* phage Lrm1 | NC_011104 | 39989 nt | 54 | 0 | 54 |
| *Lactobacillus* phage Lv-1 | NC_011801 | 38934 nt | 47 | 0 | 47 |

TABLE 5-continued

Examples of bacteriophages which can be engineered to be an inhibitor-engineered bacteriophage, or a repressor-engineered bacteriophage or a susceptibility-engineered bacteriophage as disclosed herein.
Table 5: Examples of bacteriophages which can be engineered to be an inhibitor-engineered bacteriophage, or a repressor-engineered bacteriophage or a susceptibility-engineered bacteriophage as disclosed herein.

| organism | accession | length | proteins | RNAs | genes |
|---|---|---|---|---|---|
| *Lactobacillus* phage phiAT3 | NC_005893 | 39166 nt | 55 | 0 | 55 |
| *Lactobacillus* phage phiJL-1 | NC_006936 | 36674 nt | 46 | 0 | 46 |
| *Lactobacillus* phage phiadh | NC_000896 | 43785 nt | 63 | 0 | 63 |
| *Lactobacillus* phage phig1e | NC_004305 | 42259 nt | 50 | 0 | 62 |
| *Lactobacillus* prophage Lj928 | NC_005354 | 38384 nt | 50 | 1 | 50 |
| *Lactobacillus* prophage Lj965 | NC_005355 | 40190 nt | 46 | 4 | 46 |
| *Lactococcus* phage 1706 | NC_010576 | 55597 nt | 76 | 0 | 76 |
| *Lactococcus* phage 712 | NC_008370 | 30510 nt | 55 | 0 | 55 |
| *Lactococcus* phage BK5-T | NC_002796 | 40003 nt | 63 | 0 | 63 |
| *Lactococcus* phage KSY1 | NC_009817 | 79232 nt | 130 | 3 | 131 |
| *Lactococcus* phage P008 | NC_008363 | 28538 nt | 58 | 0 | 58 |
| *Lactococcus* phage P335 sensu lato | NC_004746 | 36596 nt | 49 | 0 | 49 |
| *Lactococcus* phage Q54 | NC_008364 | 26537 nt | 47 | 0 | 47 |
| *Lactococcus* phage TP901-1 | NC_002747 | 37667 nt | 56 | 0 | 56 |
| *Lactococcus* phage Tuc2009 | NC_002703 | 38347 nt | 56 | 0 | 56 |
| *Lactococcus* phage asccphi28 | NC_010363 | 18762 nt | 28 | 0 | 27 |
| *Lactococcus* phage bIBB29 | NC_011046 | 29305 nt | 54 | 0 | 54 |
| *Lactococcus* phage bIL170 | NC_001909 | 31754 nt | 64 | 0 | 64 |
| *Lactococcus* phage bIL285 | NC_002666 | 35538 nt | 62 | 0 | 62 |
| *Lactococcus* phage bIL286 | NC_002667 | 41834 nt | 61 | 0 | 61 |
| *Lactococcus* phage bIL309 | NC_002668 | 36949 nt | 56 | 0 | 56 |
| *Lactococcus* phage bIL310 | NC_002669 | 14957 nt | 29 | 0 | 29 |
| *Lactococcus* phage bIL311 | NC_002670 | 14510 nt | 22 | 0 | 22 |
| *Lactococcus* phage bIL312 | NC_002671 | 15179 nt | 27 | 0 | 27 |
| *Lactococcus* phage bIL67 | NC_001629 | 22195 nt | 37 | 0 | 0 |
| *Lactococcus* phage c2 | NC_001706 | 22172 nt | 39 | 2 | 41 |
| *Lactococcus* phage jj50 | NC_008371 | 27453 nt | 49 | 0 | 49 |
| *Lactococcus* phage phiLC3 | NC_005822 | 32172 nt | 51 | 0 | 51 |
| *Lactococcus* phage r1t | NC_004302 | 33350 nt | 50 | 0 | 50 |
| *Lactococcus* phage sk1 | NC_001835 | 28451 nt | 56 | 0 | 56 |
| *Lactococcus* phage ul36 | NC_004066 | 36798 nt | 61 | 0 | 61 |
| *Leuconostoc* phage L5 | NC_009534 | 2435 nt | 0 | 0 | 0 |
| *Listeria* phage 2389 | NC_003291 | 37618 nt | 59 | 1 | 58 |
| *Listeria* phage A006 | NC_009815 | 38124 nt | 62 | 0 | 62 |
| *Listeria* phage A118 | NC_003216 | 40834 nt | 72 | 0 | 72 |
| *Listeria* phage A500 | NC_009810 | 38867 nt | 63 | 0 | 63 |
| *Listeria* phage A511 | NC_009811 | 137619 nt | 199 | 16 | 215 |
| *Listeria* phage B025 | NC_009812 | 42653 nt | 65 | 0 | 65 |
| *Listeria* phage B054 | NC_009813 | 48172 nt | 80 | 0 | 80 |
| *Listeria* phage P35 | NC_009814 | 35822 nt | 56 | 0 | 56 |
| *Listeria* phage P40 | NC_011308 | 35638 nt | 62 | 0 | 62 |
| *Listonella* phage phiHSIC | NC_006953 | 37966 nt | 47 | 0 | 47 |
| *Mannheimia* phage phiMHaA1 | NC_008201 | 34525 nt | 49 | 0 | 50 |
| *Methanobacterium* phage psiM2 | NC_001902 | 26111 nt | 32 | 0 | 32 |
| *Methanothermobacter* phage psiM100 | NC_002628 | 28798 nt | 35 | 0 | 35 |
| *Microbacterium* phage Min1 | NC_009603 | 46365 nt | 77 | 0 | 77 |
| *Microcystis* phage Ma-LMM01 | NC_008562 | 162109 nt | 184 | 2 | 186 |
| *Morganella* phage MmP1 | NC_011085 | 38233 nt | 47 | 0 | 47 |
| *Mycobacterium* phage 244 | NC_008194 | 74483 nt | 142 | 2 | 144 |
| *Mycobacterium* phage Adjutor | NC_010763 | 64511 nt | 86 | 0 | 86 |
| *Mycobacterium* phage BPs | NC_010762 | 41901 nt | 63 | 0 | 63 |
| *Mycobacterium* phage Barnyard | NC_004689 | 70797 nt | 109 | 0 | 109 |
| *Mycobacterium* phage Bethlehem | NC_009878 | 52250 nt | 87 | 0 | 87 |
| *Mycobacterium* phage Boomer | NC_011054 | 58037 nt | 105 | 0 | 105 |
| *Mycobacterium* phage Brujita | NC_011291 | 47057 nt | 74 | 0 | 74 |
| *Mycobacterium* phage Butterscotch | NC_011286 | 64562 nt | 86 | 0 | 86 |
| *Mycobacterium* phage Bxb1 | NC_002656 | 50550 nt | 86 | 0 | 86 |
| *Mycobacterium* phage Bxz1 | NC_004687 | 156102 nt | 225 | 28 | 253 |
| *Mycobacterium* phage Bxz2 | NC_004682 | 50913 nt | 86 | 3 | 89 |
| *Mycobacterium* phage Cali | NC_011271 | 155372 nt | 222 | 35 | 257 |
| *Mycobacterium* phage Catera | NC_008207 | 153766 nt | 218 | 34 | 253 |
| *Mycobacterium* phage Chah | NC_011284 | 68450 nt | 104 | 0 | 104 |
| *Mycobacterium* phage Che12 | NC_008203 | 52047 nt | 98 | 3 | 101 |
| *Mycobacterium* phage Che8 | NC_004680 | 59471 nt | 112 | 0 | 112 |
| *Mycobacterium* phage Che9c | NC_004683 | 57050 nt | 84 | 1 | 85 |
| *Mycobacterium* phage Che9d | NC_004686 | 56276 nt | 111 | 0 | 111 |
| *Mycobacterium* phage Cjw1 | NC_004681 | 75931 nt | 141 | 1 | 142 |
| *Mycobacterium* phage Cooper | NC_008195 | 70654 nt | 99 | 0 | 99 |
| *Mycobacterium* phage Corndog | NC_004685 | 69777 nt | 122 | 0 | 122 |
| *Mycobacterium* phage D29 | NC_001900 | 49136 nt | 79 | 5 | 84 |
| *Mycobacterium* phage DD5 | NC_011022 | 51621 nt | 87 | 0 | 87 |

TABLE 5-continued

Examples of bacteriophages which can be engineered to be an inhibitor-engineered bacteriophage, or a repressor-engineered bacteriophage or a susceptibility-engineered bacteriophage as disclosed herein.
Table 5: Examples of bacteriophages which can be engineered to be an inhibitor-engineered bacteriophage, or a repressor-engineered bacteriophage or a susceptibility-engineered bacteriophage as disclosed herein.

| organism | accession | length | proteins | RNAs | genes |
|---|---|---|---|---|---|
| *Mycobacterium* phage Fruitloop | NC_011288 | 58471 nt | 102 | 0 | 102 |
| *Mycobacterium* phage Giles | NC_009993 | 54512 nt | 79 | 1 | 80 |
| *Mycobacterium* phage Gumball | NC_011290 | 64807 nt | 88 | 0 | 88 |
| *Mycobacterium* phage Halo | NC_008202 | 42289 nt | 65 | 0 | 65 |
| *Mycobacterium* phage Jasper | NC_011020 | 50968 nt | 94 | 0 | 94 |
| *Mycobacterium* phage KBG | NC_011019 | 53572 nt | 89 | 0 | 89 |
| *Mycobacterium* phage Konstantine | NC_011292 | 68952 nt | 95 | 0 | 95 |
| *Mycobacterium* phage Kostya | NC_011056 | 75811 nt | 143 | 2 | 145 |
| *Mycobacterium* phage L5 | NC_001335 | 52297 nt | 85 | 3 | 88 |
| *Mycobacterium* phage Llij | NC_008196 | 56852 nt | 100 | 0 | 100 |
| *Mycobacterium* phage Lockley | NC_011021 | 51478 nt | 90 | 0 | 90 |
| *Mycobacterium* phage Myrna | NC_011273 | 164602 nt | 229 | 41 | 270 |
| *Mycobacterium* phage Nigel | NC_011044 | 69904 nt | 94 | 1 | 95 |
| *Mycobacterium* phage Omega | NC_004688 | 110865 nt | 237 | 2 | 239 |
| *Mycobacterium* phage Orion | NC_008197 | 68427 nt | 100 | 0 | 100 |
| *Mycobacterium* phage PBI1 | NC_008198 | 64494 nt | 81 | 0 | 81 |
| *Mycobacterium* phage PG1 | NC_005259 | 68999 nt | 100 | 0 | 100 |
| *Mycobacterium* phage PLot | NC_008200 | 64787 nt | 89 | 0 | 89 |
| *Mycobacterium* phage PMC | NC_008205 | 56692 nt | 104 | 0 | 104 |
| *Mycobacterium* phage Pacc40 | NC_011287 | 58554 nt | 101 | 0 | 101 |
| *Mycobacterium* phage Phaedrus | NC_011057 | 68090 nt | 98 | 0 | 98 |
| *Mycobacterium* phage Pipefish | NC_008199 | 69059 nt | 102 | 0 | 102 |
| *Mycobacterium* phage Porky | NC_011055 | 76312 nt | 147 | 2 | 149 |
| *Mycobacterium* phage Predator | NC_011039 | 70110 nt | 92 | 0 | 92 |
| *Mycobacterium* phage Pukovnik | NC_011023 | 52892 nt | 88 | 1 | 89 |
| *Mycobacterium* phage Qyrzula | NC_008204 | 67188 nt | 81 | 0 | 81 |
| *Mycobacterium* phage Ramsey | NC_011289 | 58578 nt | 108 | 0 | 108 |
| *Mycobacterium* phage Rizal | NC_011272 | 153894 nt | 220 | 35 | 255 |
| *Mycobacterium* phage Rosebush | NC_004684 | 67480 nt | 90 | 0 | 90 |
| *Mycobacterium* phage ScottMcG | NC_011269 | 154017 nt | 221 | 36 | 257 |
| *Mycobacterium* phage Solon | NC_011267 | 49487 nt | 86 | 0 | 86 |
| *Mycobacterium* phage Spud | NC_011270 | 154906 nt | 222 | 35 | 257 |
| *Mycobacterium* phage TM4 | NC_003387 | 52797 nt | 89 | 0 | 89 |
| *Mycobacterium* phage Troll4 | NC_011285 | 64618 nt | 84 | 0 | 84 |
| *Mycobacterium* phage Tweety | NC_009820 | 58692 nt | 109 | 0 | 109 |
| *Mycobacterium* phage U2 | NC_009877 | 51277 nt | 81 | 0 | 81 |
| *Mycobacterium* phage Wildcat | NC_008206 | 78441 nt | 148 | 23 | 171 |
| *Mycoplasma* phage MAV1 | NC_001942 | 15644 nt | 15 | 0 | 15 |
| *Mycoplasma* phage P1 | NC_002515 | 11660 nt | 11 | 0 | 11 |
| *Mycoplasma* phage phiMFV1 | NC_005964 | 15141 nt | 15 | 0 | 17 |
| *Myxococcus* phage Mx8 | NC_003085 | 49534 nt | 86 | 0 | 85 |
| *Natrialba* phage PhiCh1 | NC_004084 | 58498 nt | 98 | 0 | 98 |
| *Pasteurella* phage F108 | NC_008193 | 30505 nt | 44 | 0 | 44 |
| Phage Gifsy-1 | NC_010392 | 48491 nt | 58 | 1 | 59 |
| Phage Gifsy-2 | NC_010393 | 45840 nt | 55 | 0 | 56 |
| Phage cdtI | NC_009514 | 47021 nt | 60 | 0 | 60 |
| Phage phiJL001 | NC_006938 | 63649 nt | 90 | 0 | 90 |
| *Phormidium* phage Pf-WMP3 | NC_009551 | 43249 nt | 41 | 0 | 41 |
| *Phormidium* phage Pf-WMP4 | NC_008367 | 40938 nt | 45 | 0 | 45 |
| *Prochlorococcus* phage P-SSM2 | NC_006883 | 252401 nt | 329 | 1 | 330 |
| *Prochlorococcus* phage P-SSM4 | NC_006884 | 178249 nt | 198 | 0 | 198 |
| *Prochlorococcus* phage P-SSP7 | NC_006882 | 44970 nt | 53 | 0 | 53 |
| *Propionibacterium* phage B5 | NC_003460 | 5804 nt | 10 | 0 | 10 |
| *Propionibacterium* phage PA6 | NC_009541 | 29739 nt | 48 | 0 | 48 |
| *Pseudoalteromonas* phage PM2 | NC_000867 | 10079 nt | 22 | 0 | 22 |
| *Pseudomonas* phage 119X | NC_007807 | 43365 nt | 53 | 0 | 53 |
| *Pseudomonas* phage 14-1 | NC_011703 | 66235 nt | 90 | 0 | 90 |
| *Pseudomonas* phage 201phi2-1 | NC_010821 | 316674 nt | 461 | 1 | 462 |
| *Pseudomonas* phage 73 | NC_007806 | 42999 nt | 52 | 0 | 52 |
| *Pseudomonas* phage B3 | NC_006548 | 38439 nt | 59 | 0 | 59 |
| *Pseudomonas* phage D3 | NC_002484 | 56425 nt | 95 | 4 | 99 |
| *Pseudomonas* phage D3112 | NC_005178 | 37611 nt | 55 | 0 | 55 |
| *Pseudomonas* phage DMS3 | NC_008717 | 36415 nt | 52 | 0 | 52 |
| *Pseudomonas* phage EL | NC_007623 | 211215 nt | 201 | 0 | 201 |
| *Pseudomonas* phage F10 | NC_007805 | 39199 nt | 63 | 0 | 63 |
| *Pseudomonas* phage F116 | NC_006552 | 65195 nt | 70 | 0 | 70 |
| *Pseudomonas* phage F8 | NC_007810 | 66015 nt | 91 | 0 | 91 |
| *Pseudomonas* phage LBL3 | NC_011165 | 64427 nt | 87 | 0 | 87 |
| *Pseudomonas* phage LKA1 | NC_009936 | 41593 nt | 56 | 0 | 56 |
| *Pseudomonas* phage LKD16 | NC_009935 | 43200 nt | 53 | 0 | 53 |
| *Pseudomonas* phage LMA2 | NC_011166 | 66530 nt | 93 | 0 | 93 |

TABLE 5-continued

Examples of bacteriophages which can be engineered to be an inhibitor-engineered bacteriophage, or a repressor-engineered bacteriophage or a susceptibility-engineered bacteriophage as disclosed herein.
Table 5: Examples of bacteriophages which can be engineered to be an inhibitor-engineered bacteriophage, or a repressor-engineered bacteriophage or a susceptibility-engineered bacteriophage as disclosed herein.

| organism | accession | length | proteins | RNAs | genes |
|---|---|---|---|---|---|
| *Pseudomonas* phage LUZ19 | NC_010326 | 43548 nt | 54 | 0 | 54 |
| *Pseudomonas* phage LUZ24 | NC_010325 | 45625 nt | 68 | 0 | 68 |
| *Pseudomonas* phage M6 | NC_007809 | 59446 nt | 85 | 0 | 85 |
| *Pseudomonas* phage MP22 | NC_009818 | 36409 nt | 51 | 0 | 51 |
| *Pseudomonas* phage MP29 | NC_011613 | 36632 nt | 51 | 0 | 51 |
| *Pseudomonas* phage MP38 | NC_011611 | 36885 nt | 51 | 0 | 51 |
| *Pseudomonas* phage PA11 | NC_007808 | 49639 nt | 70 | 0 | 70 |
| *Pseudomonas* phage PAJU2 | NC_011373 | 46872 nt | 79 | 0 | 79 |
| *Pseudomonas* phage PB1 | NC_011810 | 65764 nt | 93 | 0 | 94 |
| *Pseudomonas* phage PP7 | NC_001628 | 3588 nt | 4 | 0 | 4 |
| *Pseudomonas* phage PRR1 | NC_008294 | 3573 nt | 4 | 0 | 4 |
| *Pseudomonas* phage PT2 | NC_011107 | 42961 nt | 54 | 0 | 54 |
| *Pseudomonas* phage PT5 | NC_011105 | 42954 nt | 52 | 0 | 52 |
| *Pseudomonas* phage PaP2 | NC_005884 | 43783 nt | 58 | 0 | 58 |
| *Pseudomonas* phage PaP3 | NC_004466 | 45503 nt | 71 | 4 | 75 |
| *Pseudomonas* phage Pf1 | NC_001331 | 7349 nt | 14 | 0 | 14 |
| *Pseudomonas* phage Pf3 | NC_001418 | 5833 nt | 9 | 0 | 9 |
| *Pseudomonas* phage SN | NC_011756 | 66390 nt | 92 | 0 | 92 |
| *Pseudomonas* phage YuA | NC_010116 | 58663 nt | 77 | 0 | 77 |
| *Pseudomonas* phage gh-1 | NC_004665 | 37359 nt | 42 | 0 | 42 |
| *Pseudomonas* phage phi12 | NC_004173 | 6751 nt | 6 | 0 | 6 |
| *Pseudomonas* phage phi12 | NC_004175 | 4100 nt | 5 | 0 | 5 |
| *Pseudomonas* phage phi12 | NC_004174 | 2322 nt | 4 | 0 | 4 |
| *Pseudomonas* phage phi13 | NC_004172 | 6458 nt | 4 | 0 | 4 |
| *Pseudomonas* phage phi13 | NC_004171 | 4213 nt | 5 | 0 | 5 |
| *Pseudomonas* phage phi13 | NC_004170 | 2981 nt | 4 | 0 | 4 |
| *Pseudomonas* phage phi6 | NC_003715 | 6374 nt | 4 | 0 | 4 |
| *Pseudomonas* phage phi6 | NC_003716 | 4063 nt | 4 | 0 | 4 |
| *Pseudomonas* phage phi6 | NC_003714 | 2948 nt | 5 | 0 | 5 |
| *Pseudomonas* phage phi8 | NC_003299 | 7051 nt | 7 | 0 | 7 |
| *Pseudomonas* phage phi8 | NC_003300 | 4741 nt | 6 | 0 | 6 |
| *Pseudomonas* phage phi8 | NC_003301 | 3192 nt | 6 | 0 | 6 |
| *Pseudomonas* phage phiCTX | NC_003278 | 35580 nt | 47 | 0 | 47 |
| *Pseudomonas* phage phiKMV | NC_005045 | 42519 nt | 49 | 0 | 49 |
| *Pseudomonas* phage phiKZ | NC_004629 | 280334 nt | 306 | 0 | 306 |
| *Pyrobaculum* spherical virus | NC_005872 | 28337 nt | 48 | 0 | 48 |
| *Pyrococcus abyssi* virus 1 | NC_009597 | 18098 nt | 25 | 0 | 25 |
| *Ralstonia* phage RSB1 | NC_011201 | 43079 nt | 47 | 0 | 47 |
| *Ralstonia* phage RSL1 | NC_010811 | 231256 nt | 345 | 2 | 346 |
| *Ralstonia* phage RSM1 | NC_008574 | 8999 nt | 15 | 0 | 15 |
| *Ralstonia* phage RSM3 | NC_011399 | 8929 nt | 14 | 0 | 14 |
| *Ralstonia* phage RSS1 | NC_008575 | 6662 nt | 12 | 0 | 12 |
| *Ralstonia* phage p12J | NC_005131 | 7118 nt | 9 | 0 | 9 |
| *Ralstonia* phage phiRSA1 | NC_009382 | 38760 nt | 51 | 0 | 51 |
| *Rhizobium* phage 16-3 | NC_011103 | 60195 nt | 110 | 0 | 109 |
| *Rhodothermus* phage RM378 | NC_004735 | 129908 nt | 146 | 0 | 146 |
| *Roseobacter* phage SIO1 | NC_002519 | 39898 nt | 34 | 0 | 34 |
| *Salmonella* phage E1 | NC_010495 | 45051 nt | 51 | 0 | 52 |
| *Salmonella* phage Fels-1 | NC_010391 | 42723 nt | 52 | 0 | 52 |
| *Salmonella* phage KS7 | NC_006940 | 40794 nt | 59 | 0 | 59 |
| *Salmonella* phage SE1 | NC_011802 | 41941 nt | 67 | 0 | 67 |
| *Salmonella* phage SETP3 | NC_009232 | 42572 nt | 53 | 0 | 53 |
| *Salmonella* phage ST64B | NC_004313 | 40149 nt | 56 | 0 | 56 |
| *Salmonella* phage phiSG-JL2 | NC_010807 | 38815 nt | 55 | 0 | 55 |
| *Sinorhizobium* phage PBC5 | NC_003324 | 57416 nt | 83 | 0 | 83 |
| *Sodalis* phage phiSG1 | NC_007902 | 52162 nt | 47 | 0 | 47 |
| *Spiroplasma kunkelii* virus SkV1_CR2-3x | NC_009987 | 7870 nt | 13 | 0 | 13 |
| *Spiroplasma* phage 1-C74 | NC_003793 | 7768 nt | 13 | 0 | 13 |
| *Spiroplasma* phage 1-R8A2B | NC_001365 | 8273 nt | 12 | 0 | 12 |
| *Spiroplasma* phage 4 | NC_003438 | 4421 nt | 9 | 0 | 9 |
| *Spiroplasma* phage SVTS2 | NC_001270 | 6825 nt | 13 | 0 | 13 |
| Sputnik virophage | NC_011132 | 18343 nt | 21 | 0 | 21 |
| *Staphylococcus aureus* phage P68 | NC_004679 | 18227 nt | 22 | 0 | 22 |
| *Staphylococcus* phage 11 | NC_004615 | 43604 nt | 53 | 0 | 53 |
| *Staphylococcus* phage 187 | NC_007047 | 39620 nt | 77 | 0 | 77 |
| *Staphylococcus* phage 2638A | NC_007051 | 41318 nt | 57 | 0 | 57 |
| *Staphylococcus* phage 29 | NC_007061 | 42802 nt | 67 | 0 | 67 |
| *Staphylococcus* phage 37 | NC_007055 | 43681 nt | 70 | 0 | 70 |
| *Staphylococcus* phage 3A | NC_007053 | 43095 nt | 67 | 0 | 67 |
| *Staphylococcus* phage 42E | NC_007052 | 45861 nt | 79 | 0 | 79 |

TABLE 5-continued

Examples of bacteriophages which can be engineered to be an inhibitor-engineered bacteriophage, or a repressor-engineered bacteriophage or a susceptibility-engineered bacteriophage as disclosed herein.
Table 5: Examples of bacteriophages which can be engineered to be an inhibitor-engineered bacteriophage, or a repressor-engineered bacteriophage or a susceptibility-engineered bacteriophage as disclosed herein.

| organism | accession | length | proteins | RNAs | genes |
| --- | --- | --- | --- | --- | --- |
| *Staphylococcus* phage 44AHJD | NC_004678 | 16784 nt | 21 | 0 | 21 |
| *Staphylococcus* phage 47 | NC_007054 | 44777 nt | 65 | 0 | 65 |
| *Staphylococcus* phage 52A | NC_007062 | 41690 nt | 60 | 0 | 60 |
| *Staphylococcus* phage 53 | NC_007049 | 43883 nt | 74 | 0 | 74 |
| *Staphylococcus* phage 55 | NC_007060 | 41902 nt | 77 | 0 | 77 |
| *Staphylococcus* phage 66 | NC_007046 | 18199 nt | 27 | 0 | 27 |
| *Staphylococcus* phage 69 | NC_007048 | 42732 nt | 69 | 0 | 69 |
| *Staphylococcus* phage 71 | NC_007059 | 43114 nt | 67 | 0 | 67 |
| *Staphylococcus* phage 77 | NC_005356 | 41708 nt | 69 | 0 | 69 |
| *Staphylococcus* phage 80alpha | NC_009526 | 43864 nt | 73 | 0 | 73 |
| *Staphylococcus* phage 85 | NC_007050 | 44283 nt | 71 | 0 | 71 |
| *Staphylococcus* phage 88 | NC_007063 | 43231 nt | 66 | 0 | 66 |
| *Staphylococcus* phage 92 | NC_007064 | 42431 nt | 64 | 0 | 64 |
| *Staphylococcus* phage 96 | NC_007057 | 43576 nt | 74 | 0 | 74 |
| *Staphylococcus* phage CNPH82 | NC_008722 | 43420 nt | 65 | 0 | 65 |
| *Staphylococcus* phage EW | NC_007056 | 45286 nt | 77 | 0 | 77 |
| *Staphylococcus* phage G1 | NC_007066 | 138715 nt | 214 | 0 | 214 |
| *Staphylococcus* phage K | NC_005880 | 127395 nt | 115 | 0 | 115 |
| *Staphylococcus* phage PH15 | NC_008723 | 44041 nt | 68 | 0 | 68 |
| *Staphylococcus* phage PT1028 | NC_007045 | 15603 nt | 22 | 0 | 22 |
| *Staphylococcus* phage PVL | NC_002321 | 41401 nt | 62 | 0 | 62 |
| *Staphylococcus* phage ROSA | NC_007058 | 43155 nt | 74 | 0 | 74 |
| *Staphylococcus* phage SAP-2 | NC_009875 | 17938 nt | 20 | 0 | 20 |
| *Staphylococcus* phage Twort | NC_007021 | 130706 nt | 195 | 0 | 195 |
| *Staphylococcus* phage X2 | NC_007065 | 43440 nt | 77 | 0 | 77 |
| *Staphylococcus* phage phi 12 | NC_004616 | 44970 nt | 49 | 0 | 49 |
| *Staphylococcus* phage phi13 | NC_004617 | 42722 nt | 49 | 0 | 49 |
| *Staphylococcus* phage phi2958PVL | NC_011344 | 47342 nt | 60 | 0 | 59 |
| *Staphylococcus* phage phiETA | NC_003288 | 43081 nt | 66 | 0 | 66 |
| *Staphylococcus* phage phiETA2 | NC_008798 | 43265 nt | 69 | 0 | 69 |
| *Staphylococcus* phage phiETA3 | NC_008799 | 43282 nt | 68 | 0 | 68 |
| *Staphylococcus* phage phiMR11 | NC_010147 | 43011 nt | 67 | 0 | 67 |
| *Staphylococcus* phage phiMR25 | NC_010808 | 44342 nt | 70 | 0 | 70 |
| *Staphylococcus* phage phiN315 | NC_004740 | 44082 nt | 65 | 0 | 64 |
| *Staphylococcus* phage phiNM | NC_008583 | 43128 nt | 64 | 0 | 64 |
| *Staphylococcus* phage phiNM3 | NC_008617 | 44061 nt | 65 | 0 | 65 |
| *Staphylococcus* phage phiPVL108 | NC_008689 | 44857 nt | 59 | 0 | 59 |
| *Staphylococcus* phage phiSLT | NC_002661 | 42942 nt | 61 | 0 | 61 |
| *Staphylococcus* phage phiSauS-IPLA35 | NC_011612 | 45344 nt | 62 | 0 | 62 |
| *Staphylococcus* phage phiSauS-IPLA88 | NC_011614 | 42526 nt | 60 | 0 | 61 |
| *Staphylococcus* phage tp310-1 | NC_009761 | 41407 nt | 59 | 0 | 59 |
| *Staphylococcus* phage tp310-2 | NC_009762 | 45710 nt | 67 | 0 | 67 |
| *Staphylococcus* phage tp310-3 | NC_009763 | 41966 nt | 58 | 0 | 58 |
| *Staphylococcus* prophage phiPV83 | NC_002486 | 45636 nt | 65 | 0 | 65 |
| *Stenotrophomonas* phage S1 | NC_011589 | 40287 nt | 48 | 0 | 48 |
| *Stenotrophomonas* phage phiSMA9 | NC_007189 | 6907 nt | 7 | 0 | 7 |
| *Streptococcus* phage 2972 | NC_007019 | 34704 nt | 44 | 0 | 44 |
| *Streptococcus* phage 7201 | NC_002185 | 35466 nt | 46 | 0 | 46 |
| *Streptococcus* phage 858 | NC_010353 | 35543 nt | 46 | 0 | 46 |
| *Streptococcus* phage C1 | NC_004814 | 16687 nt | 20 | 0 | 20 |
| *Streptococcus* phage Cp-1 | NC_001825 | 19343 nt | 25 | 0 | 25 |
| *Streptococcus* phage DT1 | NC_002072 | 34815 nt | 45 | 0 | 45 |
| *Streptococcus* phage EJ-1 | NC_005294 | 42935 nt | 73 | 0 | 73 |
| *Streptococcus* phage MM1 | NC_003050 | 40248 nt | 53 | 0 | 53 |
| *Streptococcus* phage O1205 | NC_004303 | 43075 nt | 57 | 0 | 57 |
| *Streptococcus* phage P9 | NC_009819 | 40539 nt | 53 | 0 | 53 |
| *Streptococcus* phage PH15 | NC_010945 | 39136 nt | 60 | 0 | 60 |
| *Streptococcus* phage SM1 | NC_004996 | 34692 nt | 56 | 0 | 56 |
| *Streptococcus* phage SMP | NC_008721 | 36216 nt | 48 | 0 | 48 |
| *Streptococcus* phage Sfi11 | NC_002214 | 39807 nt | 53 | 0 | 53 |
| *Streptococcus* phage Sfi19 | NC_000871 | 37370 nt | 45 | 0 | 45 |
| *Streptococcus* phage Sfi21 | NC_000872 | 40739 nt | 50 | 0 | 50 |
| *Streptococcus* phage phi3396 | NC_009018 | 38528 nt | 64 | 0 | 64 |
| *Streptococcus pyogenes* phage 315.1 | NC_004584 | 39538 nt | 56 | 0 | 56 |
| *Streptococcus pyogenes* phage 315.2 | NC_004585 | 41072 nt | 60 | 1 | 61 |
| *Streptococcus pyogenes* phage 315.3 | NC_004586 | 34419 nt | 52 | 0 | 52 |
| *Streptococcus pyogenes* phage 315.4 | NC_004587 | 41796 nt | 64 | 0 | 64 |
| *Streptococcus pyogenes* phage 315.5 | NC_004588 | 38206 nt | 55 | 0 | 55 |
| *Streptococcus pyogenes* phage 315.6 | NC_004589 | 40014 nt | 51 | 0 | 51 |

TABLE 5-continued

Examples of bacteriophages which can be engineered to be an inhibitor-engineered bacteriophage, or a repressor-engineered bacteriophage or a susceptibility-engineered bacteriophage as disclosed herein.
Table 5: Examples of bacteriophages which can be engineered to be an inhibitor-engineered bacteriophage, or a repressor-engineered bacteriophage or a susceptibility-engineered bacteriophage as disclosed herein.

| organism | accession | length | proteins | RNAs | genes |
| --- | --- | --- | --- | --- | --- |
| *Streptomyces* phage VWB | NC_005345 | 49220 nt | 61 | 0 | 61 |
| *Streptomyces* phage mu1/6 | NC_007967 | 38194 nt | 52 | 0 | 52 |
| *Streptomyces* phage phiBT1 | NC_004664 | 41831 nt | 55 | 1 | 56 |
| *Streptomyces* phage phiC31 | NC_001978 | 41491 nt | 53 | 1 | 54 |
| Stx1 converting phage | NC_004913 | 59866 nt | 167 | 0 | 166 |
| Stx2 converting phage I | NC_003525 | 61765 nt | 166 | 0 | 166 |
| Stx2 converting phage II | NC_004914 | 62706 nt | 170 | 0 | 169 |
| Stx2-converting phage 1717 | NC_011357 | 62147 nt | 77 | 0 | 81 |
| Stx2-converting phage 86 | NC_008464 | 60238 nt | 81 | 3 | 80 |
| *Sulfolobus islandicus* filamentous virus | NC_003214 | 40900 nt | 73 | 0 | 73 |
| *Sulfolobus islandicus* rod-shaped virus 1 | NC_004087 | 32308 nt | 45 | 0 | 45 |
| *Sulfolobus islandicus* rod-shaped virus 2 | NC_004086 | 35450 nt | 54 | 0 | 54 |
| *Sulfolobus* spindle-shaped virus 4 | NC_009986 | 15135 nt | 34 | 0 | 34 |
| *Sulfolobus* spindle-shaped virus 5 | NC_011217 | 15330 nt | 34 | 0 | 34 |
| *Sulfolobus* turreted icosahedral virus | NC_005892 | 17663 nt | 36 | 0 | 36 |
| *Sulfolobus* virus 1 | NC_001338 | 15465 nt | 32 | 0 | 33 |
| *Sulfolobus* virus 2 | NC_005265 | 14796 nt | 34 | 0 | 34 |
| *Sulfolobus* virus Kamchatka 1 | NC_005361 | 17385 nt | 31 | 0 | 31 |
| *Sulfolobus* virus Ragged Hills | NC_005360 | 16473 nt | 37 | 0 | 37 |
| *Sulfolobus* virus STSV1 | NC_006268 | 75294 nt | 74 | 0 | 74 |
| *Synechococcus* phage P60 | NC_003390 | 47872 nt | 80 | 0 | 80 |
| *Synechococcus* phage S-PM2 | NC_006820 | 196280 nt | 236 | 1 | 238 |
| *Synechococcus* phage Syn5 | NC_009531 | 46214 nt | 61 | 0 | 61 |
| *Synechococcus* phage syn9 | NC_008296 | 177300 nt | 226 | 6 | 232 |
| Temperate phage phiNIH1.1 | NC_003157 | 41796 nt | 55 | 0 | 55 |
| *Thalassomonas* phage BA3 | NC_009990 | 37313 nt | 47 | 0 | 47 |
| *Thermoproteus tenax* spherical virus 1 | NC_006556 | 20933 nt | 38 | 0 | 38 |
| *Thermus* phage IN93 | NC_004462 | 19603 nt | 40 | 0 | 32 |
| *Thermus* phage P23-45 | NC_009803 | 84201 nt | 117 | 0 | 117 |
| *Thermus* phage P74-26 | NC_009804 | 83319 nt | 116 | 0 | 116 |
| *Thermus* phage phiYS40 | NC_008584 | 152372 nt | 170 | 3 | 170 |
| *Vibrio* phage K139 | NC_003313 | 33106 nt | 44 | 0 | 44 |
| *Vibrio* phage KSF-1phi | NC_006294 | 7107 nt | 12 | 0 | 12 |
| *Vibrio* phage KVP40 | NC_005083 | 244834 nt | 381 | 29 | 415 |
| *Vibrio* phage VGJphi | NC_004736 | 7542 nt | 13 | 0 | 13 |
| *Vibrio* phage VHML | NC_004456 | 43198 nt | 57 | 0 | 57 |
| *Vibrio* phage VP2 | NC_005879 | 39853 nt | 47 | 0 | 47 |
| *Vibrio* phage VP5 | NC_005891 | 39786 nt | 48 | 0 | 48 |
| *Vibrio* phage VP882 | NC_009016 | 38197 nt | 71 | 0 | 71 |
| *Vibrio* phage VSK | NC_003327 | 6882 nt | 14 | 0 | 14 |
| *Vibrio* phage Vf12 | NC_005949 | 7965 nt | 7 | 0 | 7 |
| *Vibrio* phage Vf33 | NC_005948 | 7965 nt | 7 | 0 | 7 |
| *Vibrio* phage VfO3K6 | NC_002362 | 8784 nt | 10 | 0 | 10 |
| *Vibrio* phage VfO4K68 | NC_002363 | 6891 nt | 8 | 0 | 8 |
| *Vibrio* phage fs1 | NC_004306 | 6340 nt | 15 | 0 | 15 |
| *Vibrio* phage fs2 | NC_001956 | 8651 nt | 9 | 0 | 9 |
| *Vibrio* phage kappa | NC_010275 | 33134 nt | 45 | 0 | 45 |
| *Vibrio* phage VP4 | NC_007149 | 39503 nt | 31 | 0 | 31 |
| *Vibrio* phage VpV262 | NC_003907 | 46012 nt | 67 | 0 | 67 |
| *Xanthomonas* phage Cf1c | NC_001396 | 7308 nt | 9 | 0 | 9 |
| *Xanthomonas* phage OP1 | NC_007709 | 43785 nt | 59 | 0 | 59 |
| *Xanthomonas* phage OP2 | NC_007710 | 46643 nt | 62 | 0 | 62 |
| *Xanthomonas* phage Xop411 | NC_009543 | 44520 nt | 58 | 0 | 58 |
| *Xanthomonas* phage Xp10 | NC_004902 | 44373 nt | 60 | 0 | 60 |
| *Xanthomonas* phage Xp15 | NC_007024 | 55770 nt | 84 | 0 | 84 |
| *Yersinia pestis* phage phiA1122 | NC_004777 | 37555 nt | 50 | 0 | 50 |
| *Yersinia* phage Berlin | NC_008694 | 38564 nt | 45 | 0 | 45 |
| *Yersinia* phage L-413C | NC_004745 | 30728 nt | 40 | 0 | 40 |
| *Yersinia* phage PY54 | NC_005069 | 46339 nt | 67 | 0 | 66 |
| *Yersinia* phage Yepe2 | NC_011038 | 38677 nt | 46 | 0 | 46 |
| *Yersinia* phage phiYeO3-12 | NC_001271 | 39600 nt | 59 | 0 | 59 |

TABLE 6

Examples of promoters which can be operatively linked to the nucleic acid in the engineered bacteriophages.
Table 6: Examples of promoters which can be operatively linked to the nucleic acid in the engineered bacteriophages.

| Name | Description | Length |
| --- | --- | --- |
| BBa_I0500 | Inducible pBad/araC promoter | 1210 |
| BBa_I13453 | Pbad promoter | 130 |
| BBa_I712004 | CMV promoter | 654 |
| BBa_I712074 | T7 promoter (strong promoter from T7 bacteriophage) | 46 |
| BBa_I714889 | OR21 of PR and PRM | 101 |
| BBa_I714924 | RecA_DlexO_DLacO1 | 862 |
| BBa_I714927 | RecA_S_WTlexO_DLacO | 862 |
| BBa_I714929 | RecA_S_WTlexO_DLacO3 | 862 |
| BBa_I714930 | RecA_D_consenLexO_lacO1 | 862 |
| BBa_I714933 | WT_sulA_Single_LexO_double_LacO1 | 884 |
| BBa_I714935 | WT_sulA_Single_LexO_double_LacO2 | 884 |
| BBa_I714936 | WT_sulA_Single_LexO_double_LacO3 | 884 |
| BBa_I714937 | sluA_double_lexO_LacO1 | 884 |
| BBa_I714938 | sluA_double_lexO_LacO2 | 884 |
| BBa_I714939 | sluA_double_lexO_LacO3 | 884 |
| BBa_I715038 | pLac-RBS-T7 RNA Polymerase | 2878 |
| BBa_I716014 | yfbE solo trial 2 | 302 |
| BBa_I716102 | pir (Induces the R6K Origin) | 918 |
| BBa_I719005 | T7 Promoter | 23 |
| BBa_I732205 | NOT Gate Promoter Family Member (D001O55) | 124 |
| BBa_J13002 | TetR repressed POPS/RIPS generator | 74 |
| BBa_J13023 | 3OC6HSL + LuxR dependent POPS/RIPS generator | 117 |
| BBa_J23100 | constitutive promoter family member | 35 |
| BBa_J23101 | constitutive promoter family member | 35 |
| BBa_J23102 | constitutive promoter family member | 35 |
| BBa_J23103 | constitutive promoter family member | 35 |
| BBa_J23104 | constitutive promoter family member | 35 |
| BBa_J23105 | constitutive promoter family member | 35 |
| BBa_J23106 | constitutive promoter family member | 35 |
| BBa_J23107 | constitutive promoter family member | 35 |
| BBa_J23108 | constitutive promoter family member | 35 |
| BBa_J23109 | constitutive promoter family member | 35 |
| BBa_J23110 | constitutive promoter family member | 35 |
| BBa_J23111 | constitutive promoter family member | 35 |
| BBa_J23112 | constitutive promoter family member | 35 |
| BBa_J23113 | constitutive promoter family member | 35 |
| BBa_J23114 | constitutive promoter family member | 35 |
| BBa_J23115 | constitutive promoter family member | 35 |
| BBa_J23116 | constitutive promoter family member | 35 |
| BBa_J23117 | constitutive promoter family member | 35 |
| BBa_J23118 | constitutive promoter family member | 35 |
| BBa_J44002 | pBAD reverse | 130 |
| BBa_J52010 | NFkappaB-dependent promoter | 814 |
| BBa_J52034 | CMV promoter | 654 |
| BBa_J61043 | [fdhF2] Promoter | 269 |
| BBa_J63005 | yeast ADH1 promoter | 1445 |
| BBa_J63006 | yeast GAL1 promoter | 549 |
| BBa_K082017 | general recombine system | 89 |
| BBa_K091110 | LacI Promoter | 56 |
| BBa_K091111 | LacIQ promoter | 56 |
| BBa_K094120 | pLacI/ara-1 | 103 |
| BBa_K100000 | Natural Xylose Regulated Bi-Directional Operator | 303 |
| BBa_K100001 | Edited Xylose Regulated Bi-Directional Operator 1 | 303 |
| BBa_K100002 | Edited Xylose Regulated Bi-Directional Operator 2 | 303 |
| BBa_K118011 | PcstA (glucose-repressible promoter) | 131 |
| BBa_K135000 | pCpxR (CpxR responsive promoter) | 55 |
| BBa_K137029 | constitutive promoter with (TA)10 between −10 and −35 elements | 39 |
| BBa_K137030 | constitutive promoter with (TA)9 between −10 and −35 elements | 37 |
| BBa_K137046 | 150 bp inverted tetR promoter | 150 |
| BBa_K137047 | 250 bp inverted tetR promoter | 250 |
| BBa_K137048 | 350 bp inverted tetR promoter | 350 |
| BBa_K137049 | 450 bp inverted tetR promoter | 450 |
| BBa_K137050 | 650 bp inverted tetR promoter | 650 |
| BBa_K137051 | 850 bp inverted tetR promoter | 850 |
| BBa_R0010 | promoter (lacI regulated) | 200 |
| BBa_R0011 | Promoter (lacI regulated, lambda pL hybrid) | 55 |
| BBa_R0053 | Promoter (p22 cII regulated) | 54 |
| BBa_I1010 | cI(1) fused to tetR promoter | 834 |
| BBa_I1051 | Lux cassette right promoter | 68 |
| BBa_I12006 | Modified lamdba Prm promoter (repressed by 434 cI) | 82 |

TABLE 6-continued

Examples of promoters which can be operatively linked to the nucleic acid in the engineered bacteriophages.
Table 6: Examples of promoters which can be operatively linked to the nucleic acid in the engineered bacteriophages.

| Name | Description | Length |
| --- | --- | --- |
| BBa_I12036 | Modified lamdba Prm promoter (cooperative repression by 434 cI) | 91 |
| BBa_I12040 | Modified lambda P(RM) promoter: −10 region from P(L) and cooperatively repressed by 434 cI | 91 |
| BBa_I13005 | Promoter R0011 w/ YFP (−LVA) TT | 920 |
| BBa_I13006 | Promoter R0040 w/ YFP (−LVA) TT | 920 |
| BBa_I14015 | P(Las) TetO | 170 |
| BBa_I14016 | P(Las) CIO | 168 |
| BBa_I14017 | P(Rhl) | 51 |
| BBa_I14018 | P(Bla) | 35 |
| BBa_I14033 | P(Cat) | 38 |
| BBa_I14034 | P(Kat) | 45 |
| BBa_I714890 | OR321 of PR and PRM | 121 |
| BBa_I714925 | RecA_DlexO_DLacO2 | 862 |
| BBa_I714926 | RecA_DlexO_DLacO3 | 862 |
| BBa_I714928 | RecA_S_WTlexO_DLacO2 | 862 |
| BBa_I714931 | RecA_D_consenLexO_lacO2 | 862 |
| BBa_I718018 | dapAp promoter | 81 |
| BBa_I720001 | AraBp->rpoN | 1632 |
| BBa_I720002 | glnKp->lacI | 1284 |
| BBa_I720003 | NifHp->cI (lambda) | 975 |
| BBa_I720005 | NifA lacI RFP | 3255 |
| BBa_I720006 | GFP glnG cI | 2913 |
| BBa_I720007 | araBp->rpoN (leucine landing pad) | 51 |
| BBa_I720008 | Ara landing pad (pBBLP 6) | 20 |
| BBa_I720009 | Ara landing pad (pBBLP 7) | 23 |
| BBa_I720010 | Ara landing pad (pBBLP 8) | 20 |
| BBa_I721001 | Lead Promoter | 94 |
| BBa_I723020 | Pu | 320 |
| BBa_I728456 | MerRT: Mercury-Inducible Promoter + RBS (MerR + part of MerT) | 635 |
| BBa_I741018 | Right facing promoter (for xylF) controlled by xylR and CRP-cAMP | 221 |
| BBa_I742124 | Reverse complement Lac promoter | 203 |
| BBa_I746104 | P2 promoter in agr operon from *S. aureus* | 96 |
| BBa_I746360 | PF promoter from P2 phage | 91 |
| BBa_I746361 | PO promoter from P2 phage | 92 |
| BBa_I746362 | PP promoter from P2 phage | 92 |
| BBa_I746364 | Psid promoter from P4 phage | 93 |
| BBa_I746365 | PLL promoter from P4 phage | 92 |
| BBa_I748001 | Putative Cyanide Nitrilase Promoter | 271 |
| BBa_I752000 | Riboswitch(theophylline) | 56 |
| BBa_I761011 | CinR, CinL and glucose controlled promotor | 295 |
| BBa_I761014 | cinr + cinl (RBS) with double terminator | 1661 |
| BBa_I764001 | Ethanol regulated promoter AOX1 | 867 |
| BBa_I765000 | Fe promoter | 1044 |
| BBa_I765001 | UV promoter | 76 |
| BBa_I765007 | Fe and UV promoters | 1128 |
| BBa_J13210 | pOmpR dependent POPS producer | 245 |
| BBa_J22106 | rec A (SOS) Promoter | 192 |
| BBa_J23119 | constitutive promoter family member | 35 |
| BBa_J24669 | Tri-Stable Toggle (Arabinose induced component) | 3100 |
| BBa_J3902 | PrFe (PI + PII rus operon) | 272 |
| BBa_J58100 | AND-type promoter synergistically activated by cI and CRP | 106 |
| BBa_J61051 | [PsaI1] | 1268 |
| BBa_K085005 | (lacI)promoter->key3c->Terminator | 405 |
| BBa_K088007 | GlnRS promoter | 38 |
| BBa_K089004 | phaC Promoter (−663 from ATG) | 663 |
| BBa_K089005 | −35 to Tc start site of phaC | 49 |
| BBa_K089006 | −663 to Tc start site of phaC | 361 |
| BBa_K090501 | Gram-Positive IPTG-Inducible Promoter | 107 |
| BBa_K090504 | Gram-Positive Strong Constitutive Promoter | 239 |
| BBa_K091100 | pLac_lux hybrid promoter | 74 |
| BBa_K091101 | pTet_Lac hybrid promoter | 83 |
| BBa_K091104 | pLac/Mnt Hybrid Promoter | 87 |
| BBa_K091105 | pTet/Mnt Hybrid Promoter | 98 |
| BBa_K091106 | LsrA/cI hybrid promoter | 141 |
| BBa_K091107 | pLux/cI Hybrid Promoter | 57 |
| BBa_K091114 | LsrAR Promoter | 248 |
| BBa_K091115 | LsrR Promoter | 100 |
| BBa_K091116 | LsrA Promoter | 126 |
| BBa_K091117 | pLas promoter | 126 |
| BBa_K091143 | pLas/cI Hybrid Promoter | 164 |

TABLE 6-continued

Examples of promoters which can be operatively linked to the nucleic acid in the engineered bacteriophages.
Table 6: Examples of promoters which can be operatively linked to the nucleic acid in the engineered bacteriophages.

| Name | Description | Length |
| --- | --- | --- |
| BBa_K091146 | pLas/Lux Hybrid Promoter | 126 |
| BBa_K091184 | pLux/cI + RBS + LuxS + RBS + Mnt + TT + pLac/Mnt + RBS + LuxS + RBS + cI + TT | 2616 |
| BBa_K093000 | pRecA with LexA binding site | 48 |
| BBa_K101017 | MioC Promoter (DNAa-Repressed Promoter) | 319 |
| BBa_K101018 | MioC Promoter (regulating tetR) | 969 |
| BBa_K105020 | tetR - operator | 29 |
| BBa_K105021 | cI - operator | 27 |
| BBa_K105022 | lex A - operator | 31 |
| BBa_K105023 | lac I - operator | 25 |
| BBa_K105024 | Gal4 - operator | 27 |
| BBa_K105026 | Gal1 promoter | 549 |
| BBa_K105027 | cyc100 minimal promoter | 103 |
| BBa_K105028 | cyc70 minimal promoter | 103 |
| BBa_K105029 | cyc43 minimal promoter | 103 |
| BBa_K105030 | cyc28 minimal promoter | 103 |
| BBa_K105031 | cyc16 minimal promoter | 103 |
| BBa_K108014 | PR | 234 |
| BBa_K108016 | PP | 406 |
| BBa_K108025 | Pu | 200 |
| BBa_K109200 | AraC and TetR promoter (hybrid) | 132 |
| BBa_K110005 | Alpha-Cell Promoter MF(ALPHA)2 | 500 |
| BBa_K110006 | Alpha-Cell Promoter MF(ALPHA)1 | 501 |
| BBa_K110016 | A-Cell Promoter STE2 (backwards) | 500 |
| BBa_K112118 | rrnB P1 promoter | 503 |
| BBa_K112318 | {<bolA promoter>} in BBb format | 436 |
| BBa_K112319 | {<ftsQ promoter>} in BBb format | 434 |
| BBa_K112320 | {<ftsAZ promoter>} in BBb format | 773 |
| BBa_K112322 | {Pdps} in BBb format | 348 |
| BBa_K112323 | {H-NS!} in BBb format | 414 |
| BBa_K112400 | Promoter for grpE gene - Heat Shock and Ultrasound Sensitive | 98 |
| BBa_K112401 | Promoter for recA gene - SOS and Ultrasound Sensitive | 286 |
| BBa_K112402 | promoter for FabA gene - Membrane Damage and Ultrasound Senstitive | 256 |
| BBa_K112405 | Promoter for CadA and CadB genes | 370 |
| BBa_K112406 | cadC promoter | 2347 |
| BBa_K112407 | Promoter for ygeF psuedogene | 494 |
| BBa_K113009 | pBad/araC | 1210 |
| BBa_K116001 | nhaA promoter, that can be regulated by pH and nhaR protein. | 274 |
| BBa_K116401 | external phosphate sensing promoter | 506 |
| BBa_K116500 | OmpF promoter that is activated or repressesed by OmpR according to osmolarity. | 126 |
| BBa_K116603 | pRE promoter from λ phage | 48 |
| BBa_K117002 | LsrA promoter (indirectly activated by AI-2) | 102 |
| BBa_K117004 | pLacI-GFP | 1086 |
| BBa_K117005 | pLacI-RBS | 220 |
| BBa_K119002 | RcnR operator (represses RcnA) | 83 |
| BBa_K122000 | pPGK1 | 1497 |
| BBa_K122002 | pADH1 (truncated) | 701 |
| BBa_K123002 | LacIQ ERE TetR | 742 |
| BBa_K123003 | ER | 1849 |
| BBa_K125110 | nir promoter + rbs (0.6) | 111 |
| BBa_K128006 | *L. bulgaricus* LacS Promoter | 197 |
| BBa_K133044 | TetR(RBS) | 35 |
| BBa_K136006 | flgA promoter followed by its natural RBS | 202 |
| BBa_K136008 | flhB promoter followed by its natural RBS | 203 |
| BBa_K136009 | fliL promoter followed by its natural RBS | 154 |
| BBa_K136010 | fliA promoter | 345 |
| BBa_K137031 | constitutive promoter with (C)10 between −10 and −35 elements | 62 |
| BBa_K137032 | constitutive promoter with (C)12 between −10 and −35 elements | 64 |
| BBa_K137125 | LacI-repressed promoter B4 | 103 |
| BBa_K145150 | Hybrid promoter: HSL-LuxR activated, P22 C2 repressed | 66 |
| BBa_K149001 | Prp22 promoter | 1006 |
| BBa_K165001 | pGAL1 + w/XhoI sites | 672 |
| BBa_K165011 | Zif268-HIV binding sites (3) | 46 |
| BBa_K165012 | Gli1 binding sites | 127 |
| BBa_K165013 | YY1 binding sites | 51 |
| BBa_K165016 | mCYC1 minimal yeast promoter | 245 |
| BBa_K165030 | mCYC promoter plus Zif268-HIV binding sites | 307 |
| BBa_K165031 | mCYC promoter plus LexA binding sites | 403 |
| BBa_K165032 | mCYC promoter plus Gli1 binding sites | 411 |
| BBa_K165033 | YY1 binding sites + mCYC promoter | 304 |
| BBa_K165034 | Zif268-HIV bs + LexA bs + mCYC promoter | 457 |

TABLE 6-continued

Examples of promoters which can be operatively linked to the nucleic acid in the engineered bacteriophages.
Table 6: Examples of promoters which can be operatively linked to the nucleic acid in the engineered bacteriophages.

| Name | Description | Length |
| --- | --- | --- |
| BBa_K165035 | Gli1 bs + Zif268-HIV bs + mCYC promoter | 442 |
| BBa_K165036 | Gli1 bs + LexA bs + mCYC promoter | 538 |
| BBa_K165038 | Gli1 binding sites + ADH1 constitutive yeast promoter | 1580 |
| BBa_K165039 | Zif268-HIV binding sites + ADH1 yeast promoter | 1499 |
| BBa_K165040 | Gli1 binding sites + TEF constitutive yeast promoter | 538 |
| BBa_K165041 | Zif268-HIV binding sites + TEF constitutive yeast promoter | 457 |
| BBa_K165042 | Gli1 binding sites + MET25 inducible yeast promoter | 522 |
| BBa_K165043 | Zif268-HIV binding sites + MET25 constitutive yeast promoter | 441 |
| BBa_K165045 | pGAL1 + LexA bindingsites | 785 |
| BBa_K165048 | LexA op8 mCYC1 | 393 |
| BBa_R0050 | Promoter (HK022 cI regulated) | 55 |
| BBa_R0052 | Promoter (434 cI regulated) | 46 |
| BBa_R0061 | Promoter (HSL-mediated luxR repressor) | 30 |
| BBa_R0063 | Promoter (luxR & HSL regulated -- lux pL) | 151 |
| BBa_R0065 | Promoter (lambda cI and luxR regulated -- hybrid) | 97 |
| BBa_R0071 | Promoter (RhlR & C4-HSL regulated) | 53 |
| BBa_R0073 | Promoter (Mnt regulated) | 67 |
| BBa_R0074 | Promoter (PenI regulated) | 77 |
| BBa_R0075 | Promoter (TP901 cI regulated) | 117 |
| BBa_R0077 | Promoter (cinR and HSL regulated, RBS+) | 231 |
| BBa_R0078 | Promoter (cinR and HSL regulated) | 225 |
| BBa_R0081 | Inhibitor (AraC loop attachment with O2 site) | 183 |
| BBa_R0082 | Promoter (OmpR, positive) | 108 |
| BBa_R0083 | Promoter (OmpR, positive) | 78 |
| BBa_R0084 | Promoter (OmpR, positive) | 108 |
| BBa_R1050 | Promoter, Standard (HK022 cI regulated) | 56 |
| BBa_R1051 | Promoter, Standard (lambda cI regulated) | 49 |
| BBa_R1052 | Promoter, Standard (434 cI regulated) | 46 |
| BBa_R1053 | Promoter, Standard (p22 cII regulated) | 55 |
| BBa_R1062 | Promoter, Standard (luxR and HSL regulated -- lux pR) | 56 |
| BBa_R2000 | Promoter, Zif23 regulated, test: between | 45 |
| BBa_R2001 | Promoter, Zif23 regulated, test: after | 52 |
| BBa_R2002 | Promoter, Zif23 regulated, test: between and after | 52 |
| BBa_R2109 | Promoter with operator site for C2003 | 72 |
| BBa_R2114 | Promoter with operator site for C2003 | 72 |
| BBa_I10498 | Oct-4 promoter | 1417 |
| BBa_I12001 | Promoter (PRM+) | 96 |
| BBa_I12003 | Lambda Prm Promoter | 88 |
| BBa_I12005 | lambda Prm Inverted Antisense (No start codon) | 85 |
| BBa_I12008 | Barkai-Leibler design experiment part A (p22cII) | 1154 |
| BBa_I12010 | Modified lamdba Prm promoter (repressed by p22 cII) | 78 |
| BBa_I12014 | Repressor, 434 cI (RBS- LVA-) | 636 |
| BBa_I12021 | Inducible Lambda cI Repressor Generator (Controlled by IPTG and LacI) | 2370 |
| BBa_I12031 | Barkai-Leibler design experiment Part A (Lambda cI) wth cooperativity | 1159 |
| BBa_I12032 | Modified lamdba Prm promoter (repressed by p22 cI with cooperativity) RBS+ | 106 |
| BBa_I12034 | Modified lamdba Prm promoter (repressed by 434 cI with cooperativity) RBS+ | 102 |
| BBa_I12035 | Modified lamdba Prm promoter (repressed by p22 cI without cooperativity) RBS+ | 106 |
| BBa_I12037 | Reporter 3 for Barkai-Leibler oscillator | 1291 |
| BBa_I12044 | Activator for BL oscillator with reporter protein, (cooperativity) | 2112 |
| BBa_I12045 | BL oscillator, cooperativity, reporter protein, kickstart | 4139 |
| BBa_I12046 | Activator for BL oscillator with reporter protein, (cooperativity and L-strain −10 region) | 2112 |
| BBa_I12047 | BL oscillator, cooperativity + replaced −10 region (Llac), reporter protein, kickstart | 4139 |
| BBa_I12210 | plac Or2-62 (positive) | 70 |
| BBa_I12212 | TetR - TetR-4C heterodimer promoter (negative) | 61 |
| BBa_I12219 | Wild-type TetR(B) promoter (negative) | 71 |
| BBa_I13062 | LuxR QPI | 822 |
| BBa_I13267 | Intermediate part from assembly 317 | 1769 |
| BBa_I13406 | Pbad/AraC with extra REN sites | 1226 |
| BBa_I14021 | plTetO1.RBS.CinI | 810 |
| BBa_I20255 | Promoter-RBS | 57 |
| BBa_I20256 | Promoter-RBS | 56 |
| BBa_I20258 | Promoter-RBS | 56 |
| BBa_I1714932 | RecA_D_consenLexO_lacO3 | 862 |
| BBa_I1715003 | hybrid pLac with UV5 mutation | 55 |

TABLE 6-continued

Examples of promoters which can be operatively linked to the nucleic acid in the engineered bacteriophages.
Table 6: Examples of promoters which can be operatively linked to the nucleic acid in the engineered bacteriophages.

| Name | Description | Length |
| --- | --- | --- |
| BBa_I715052 | Trp Leader Peptide and anti-terminator/terminator | 134 |
| BBa_I715053 | Trp Leader Peptide and anti-terminator/terminator with hixC insertion | 159 |
| BBa_I717002 | Pr from lambda switch | 177 |
| BBa_I723011 | pDntR (estimated promoter for DntR) | 26 |
| BBa_I723013 | pDntA (estimated promoter for DntA) | 33 |
| BBa_I723018 | Pr (promoter for XylR) | 410 |
| BBa_I731004 | FecA promoter | 90 |
| BBa_I732021 | Template for Building Primer Family Member | 159 |
| BBa_I732200 | NOT Gate Promoter Family Member (D001O1wt1) | 125 |
| BBa_I732201 | NOT Gate Promoter Family Member (D001O11) | 124 |
| BBa_I732202 | NOT Gate Promoter Family Member (D001O22) | 124 |
| BBa_I732203 | NOT Gate Promoter Family Member (D001O33) | 124 |
| BBa_I732204 | NOT Gate Promoter Family Member (D001O44) | 124 |
| BBa_I732206 | NOT Gate Promoter Family Member (D001O66) | 124 |
| BBa_I732207 | NOT Gate Promoter Family Member (D001O77) | 124 |
| BBa_I732270 | Promoter Family Member with Hybrid Operator (D001O12) | 124 |
| BBa_I732271 | Promoter Family Member with Hybrid Operator (D001O16) | 124 |
| BBa_I732272 | Promoter Family Member with Hybrid Operator (D001O17) | 124 |
| BBa_I732273 | Promoter Family Member with Hybrid Operator (D001O21) | 124 |
| BBa_I732274 | Promoter Family Member with Hybrid Operator (D001O24) | 124 |
| BBa_I732275 | Promoter Family Member with Hybrid Operator (D001O26) | 124 |
| BBa_I732276 | Promoter Family Member with Hybrid Operator (D001O27) | 124 |
| BBa_I732277 | Promoter Family Member with Hybrid Operator (D001O46) | 124 |
| BBa_I732278 | Promoter Family Member with Hybrid Operator (D001O47) | 124 |
| BBa_I732279 | Promoter Family Member with Hybrid Operator (D001O61) | 124 |
| BBa_I732301 | NAND Candidate (U073O26D001O16) | 120 |
| BBa_I732302 | NAND Candidate (U073O27D001O17) | 120 |
| BBa_I732303 | NAND Candidate (U073O22D001O46) | 120 |
| BBa_I732304 | NAND Candidate (U073O22D001O47) | 120 |
| BBa_I732305 | NAND Candidate (U073O22D059O46) | 178 |
| BBa_I732306 | NAND Candidate (U073O11D002O22) | 121 |
| BBa_I732351 | NOR Candidate (U037O11D002O22) | 85 |
| BBa_I732352 | NOR Candidate (U035O44D001O22) | 82 |
| BBa_I732400 | Promoter Family Member (U097NUL + D062NUL) | 165 |
| BBa_I732401 | Promoter Family Member (U097O11 + D062NUL) | 185 |
| BBa_I732402 | Promoter Family Member (U085O11 + D062NUL) | 173 |
| BBa_I732403 | Promoter Family Member (U073O11 + D062NUL) | 161 |
| BBa_I732404 | Promoter Family Member (U061O11 + D062NUL) | 149 |
| BBa_I732405 | Promoter Family Member (U049O11 + D062NUL) | 137 |
| BBa_I732406 | Promoter Family Member (U037O11 + D062NUL) | 125 |
| BBa_I732407 | Promoter Family Member (U097NUL + D002O22) | 125 |
| BBa_I732408 | Promoter Family Member (U097NUL + D014O22) | 137 |
| BBa_I732409 | Promoter Family Member (U097NUL + D026O22) | 149 |
| BBa_I732410 | Promoter Family Member (U097NUL + D038O22) | 161 |
| BBa_I732411 | Promoter Family Member (U097NUL + D050O22) | 173 |
| BBa_I732412 | Promoter Family Member (U097NUL + D062O22) | 185 |
| BBa_I732413 | Promoter Family Member (U097O11 + D002O22) | 145 |
| BBa_I732414 | Promoter Family Member (U097O11 + D014O22) | 157 |
| BBa_I732415 | Promoter Family Member (U097O11 + D026O22) | 169 |
| BBa_I732416 | Promoter Family Member (U097O11 + D038O22) | 181 |
| BBa_I732417 | Promoter Family Member (U097O11 + D050O22) | 193 |
| BBa_I732418 | Promoter Family Member (U097O11 + D062O22) | 205 |
| BBa_I732419 | Promoter Family Member (U085O11 + D002O22) | 133 |
| BBa_I732420 | Promoter Family Member (U085O11 + D014O22) | 145 |
| BBa_I732421 | Promoter Family Member (U085O11 + D026O22) | 157 |
| BBa_I732422 | Promoter Family Member (U085O11 + D038O22) | 169 |
| BBa_I732423 | Promoter Family Member (U085O11 + D050O22) | 181 |
| BBa_I732424 | Promoter Family Member (U085O11 + D062O22) | 193 |
| BBa_I732425 | Promoter Family Member (U073O11 + D002O22) | 121 |
| BBa_I732426 | Promoter Family Member (U073O11 + D014O22) | 133 |
| BBa_I732427 | Promoter Family Member (U073O11 + D026O22) | 145 |
| BBa_I732428 | Promoter Family Member (U073O11 + D038O22) | 157 |
| BBa_I732429 | Promoter Family Member (U073O11 + D050O22) | 169 |
| BBa_I732430 | Promoter Family Member (U073O11 + D062O22) | 181 |
| BBa_I732431 | Promoter Family Member (U061O11 + D002O22) | 109 |
| BBa_I732432 | Promoter Family Member (U061O11 + D014O22) | 121 |
| BBa_I732433 | Promoter Family Member (U061O11 + D026O22) | 133 |
| BBa_I732434 | Promoter Family Member (U061O11 + D038O22) | 145 |
| BBa_I732435 | Promoter Family Member (U061O11 + D050O22) | 157 |
| BBa_I732436 | Promoter Family Member (U061O11 + D062O22) | 169 |
| BBa_I732437 | Promoter Family Member (U049O11 + D002O22) | 97 |
| BBa_I732438 | Promoter Family Member (U049O11 + D014O22) | 109 |

TABLE 6-continued

Examples of promoters which can be operatively linked to the nucleic acid in the engineered bacteriophages.
Table 6: Examples of promoters which can be operatively linked to the nucleic acid in the engineered bacteriophages.

| Name | Description | Length |
| --- | --- | --- |
| BBa_I732439 | Promoter Family Member (U049O11 + D026O22) | 121 |
| BBa_I732440 | Promoter Family Member (U049O11 + D038O22) | 133 |
| BBa_I732441 | Promoter Family Member (U049O11 + D050O22) | 145 |
| BBa_I732442 | Promoter Family Member (U049O11 + D062O22) | 157 |
| BBa_I732443 | Promoter Family Member (U037O11 + D002O22) | 85 |
| BBa_I732444 | Promoter Family Member (U037O11 + D014O22) | 97 |
| BBa_I732445 | Promoter Family Member (U037O11 + D026O22) | 109 |
| BBa_I732446 | Promoter Family Member (U037O11 + D038O22) | 121 |
| BBa_I732447 | Promoter Family Member (U037O11 + D050O22) | 133 |
| BBa_I732448 | Promoter Family Member (U037O11 + D062O22) | 145 |
| BBa_I732450 | Promoter Family Member (U073O26 + D062NUL) | 161 |
| BBa_I732451 | Promoter Family Member (U073O27 + D062NUL) | 161 |
| BBa_I732452 | Promoter Family Member (U073O26 + D062O61) | 181 |
| BBa_I735008 | ORE1X Oleate response element | 273 |
| BBa_I735009 | ORE2X oleate response element | 332 |
| BBa_I735010 | This promoter encoding for a thiolase involved in beta-oxidation of fatty acids. | 850 |
| BBa_I739101 | Double Promoter (constitutive/TetR, negative) | 83 |
| BBa_I739102 | Double Promoter (cI, negative/TetR, negative) | 97 |
| BBa_I739103 | Double Promoter (lacI, negative/P22 cII, negative) | 87 |
| BBa_I739104 | Double Promoter (LuxR/HSL, positive/P22 cII, negative) | 101 |
| BBa_I739105 | Double Promoter (LuxR/HSL, positive/cI, negative) | 99 |
| BBa_I739106 | Double Promoter (TetR, negative/P22 cII, negative) | 84 |
| BBa_I739107 | Double Promoter (cI, negative/LacI, negative) | 78 |
| BBa_I741015 | two way promoter controlled by XylR and Crp-CAmp | 301 |
| BBa_I741017 | dual facing promoter controlled by xylR and CRP-cAMP (I741015 reverse complement) | 302 |
| BBa_I741019 | Right facing promoter (for xylA) controlled by xylR and CRP-cAMP | 131 |
| BBa_I741020 | promoter to xylF without CRP and several binding sites for xylR | 191 |
| BBa_I741021 | promoter to xylA without CRP and several binding sites for xylR | 87 |
| BBa_I741109 | Lambda Or operator region | 82 |
| BBa_I742126 | Reverse lambda cI-regulated promoter | 49 |
| BBa_I746363 | PV promoter from P2 phage | 91 |
| BBa_I746665 | Pspac-hy promoter | 58 |
| BBa_I751500 | pcI (for positive control of pcI-lux hybrid promoter) | 77 |
| BBa_I751501 | plux-cI hybrid promoter | 66 |
| BBa_I751502 | plux-lac hybrid promoter | 74 |
| BBa_I756002 | Kozak Box | 7 |
| BBa_I756014 | LexAoperator-MajorLatePromoter | 229 |
| BBa_I756015 | CMV Promoter with lac operator sites | 663 |
| BBa_I756016 | CMV-tet promoter | 610 |
| BBa_I756017 | U6 promoter with tet operators | 341 |
| BBa_I756018 | Lambda Operator in SV-40 intron | 411 |
| BBa_I756019 | Lac Operator in SV-40 intron | 444 |
| BBa_I756020 | Tet Operator in SV-40 intron | 391 |
| BBa_I756021 | CMV promoter with Lambda Operator | 630 |
| BBa_I760005 | Cu-sensitive promoter | 16 |
| BBa_I761000 | cinr + cinI (RBS) | 1558 |
| BBa_I761001 | OmpR binding site | 62 |
| BBa_I766200 | pSte2 | 1000 |
| BBa_I766214 | pGal1 | 1002 |
| BBa_I766555 | pCyc (Medium) Promoter | 244 |
| BBa_I766556 | pAdh (Strong) Promoter | 1501 |
| BBa_I766557 | pSte5 (Weak) Promoter | 601 |
| BBa_I766558 | pFig1 (Inducible) Promoter | 1000 |
| BBa_I9201 | lambda cI operator/binding site | 82 |
| BBa_J01005 | pspoIIE promoter (spo0A J01004, positive) | 206 |
| BBa_J01006 | Key Promoter absorbs 3 | 59 |
| BBa_J03007 | Maltose specific promotor | 206 |
| BBa_J03100 | -- No description -- | 847 |
| BBa_J04700 | Part containing promoter, riboswitch mTCT8-4 theophylline aptamer (J04705), and RBS | 258 |
| BBa_J04705 | Riboswitch designed to turn "ON" a protein | 38 |
| BBa_J04800 | J04800 (RevAptRibo) contains a theophylline aptamer upstream of the RBS that should act as a riboswi | 258 |
| BBa_J04900 | Part containing promoter, 8 bp, RBS, and riboswitch mTCT8-4 theophylline aptamer (J04705) | 258 |
| BBa_J05209 | Modifed Pr Promoter | 49 |
| BBa_J05210 | Modifed Prm+ Promoter | 82 |
| BBa_J05215 | Regulator for R1-CREBH | 41 |

TABLE 6-continued

Examples of promoters which can be operatively linked to the nucleic acid in the engineered bacteriophages.
Table 6: Examples of promoters which can be operatively linked to the nucleic acid in the engineered bacteriophages.

| Name | Description | Length |
| --- | --- | --- |
| BBa_J05216 | Regulator for R3-ATF6 | 41 |
| BBa_J05217 | Regulator for R2-YAP7 | 41 |
| BBa_J05218 | Regulator for R4-cMaf | 41 |
| BBa_J05221 | Tripple Binding Site for R3-ATF6 | 62 |
| BBa_J05222 | ZF-2*e2 Binding Site | 37 |
| BBa_J05500 | Sensing Device A (cI) | 2371 |
| BBa_J05501 | Sensing Device B (cI + LVA) | 2337 |
| BBa_J06403 | RhIR promoter repressible by CI | 51 |
| BBa_J07007 | ctx promoter | 145 |
| BBa_J07010 | ToxR_inner (aa's 1-198; cytoplasm + TM) | 594 |
| BBa_J07019 | FecA Promoter (with Fur box) | 86 |
| BBa_J07041 | POPS/RIPS generator (R0051::B0030) | 72 |
| BBa_J07042 | POPS/RIPS generator (R0040::B0030) | 77 |
| BBa_J11003 | control loop for PI controller with BBa_J11002 | 961 |
| BBa_J13211 | R0040.B0032 | 75 |
| BBa_J13212 | R0040.B0033 | 73 |
| BBa_J15301 | Pars promoter from *Escherichia coli* chromosomal ars operon. | 127 |
| BBa_J15502 | copA promoter | 287 |
| BBa_J16101 | BanAp - Banana-induced Promoter | 19 |
| BBa_J16105 | HelPp - "Help" Dependant promoter | 26 |
| BBa_J16400 | Iron sensitive promoter (test delete later) | 26 |
| BBa_J21002 | Promoter + LuxR | 998 |
| BBa_J21003 | Promoter + TetR | 904 |
| BBa_J21004 | Promoter + LacL | 1372 |
| BBa_J21006 | LuxR, TetR Generator | 1910 |
| BBa_J21007 | LuxR, TetR, LacL Generator | 3290 |
| BBa_J22052 | Pcya | 65 |
| BBa_J22086 | pX (DnaA binding site) | 125 |
| BBa_J22126 | Rec A (SOS) promoter | 186 |
| BBa_J23150 | 1bp mutant from J23107 | 35 |
| BBa_J23151 | 1bp mutant from J23114 | 35 |
| BBa_J24000 | CafAp (Cafeine Dependant promoter) | 14 |
| BBa_J24001 | WigLp (Wiggle-dependent Promotor) | 46 |
| BBa_J24670 | Tri-Stable Toggle (Lactose induced component) | 1877 |
| BBa_J24671 | Tri-Stable Toggle (Tetracycline induced component) | 2199 |
| BBa_J24813 | URA3 Promoter from *S. cerevisiae* | 137 |
| BBa_J26003 | Mushroom Activated Promoter | 23 |
| BBa_J31013 | pLac Backwards [cf. BBa_R0010] | 200 |
| BBa_J31014 | crRNA | 38 |
| BBa_J3102 | pBad:RBS | 153 |
| BBa_J31020 | produces taRNA | 295 |
| BBa_J31022 | comK transcription activator from *B. subtilis* | 578 |
| BBa_J33100 | ArsR and Ars Promoter | 472 |
| BBa_J34800 | Promoter tetracyclin inducible | 94 |
| BBa_J34806 | promoter lac induced | 112 |
| BBa_J34809 | promoter lac induced | 125 |
| BBa_J34814 | T7 Promoter | 28 |
| BBa_J45503 | hybB Cold Shock Promoter | 393 |
| BBa_J45504 | htpG Heat Shock Promoter | 405 |
| BBa_J45992 | Full-length stationary phase osmY promoter | 199 |
| BBa_J45993 | Minimal stationary phase osmY promoter | 57 |
| BBa_J45994 | Exponential phase transcriptional control device | 1109 |
| BBa_J48103 | Iron promoter | 140 |
| BBa_J48104 | NikR promoter, a protein of the ribbon helix-helix family of trancription factors that repress expre | 40 |
| BBa_J48106 | vnfH | 891 |
| BBa_J48107 | UGT008-3 Promoter/Met32p | 588 |
| BBa_J48110 | Fe Promoter+ mRFP1 | 1009 |
| BBa_J48111 | *E. coli* NikR | 926 |
| BBa_J48112 | vnfH: vanadium promoter | 1816 |
| BBa_J49000 | Roid Rage | 4 |
| BBa_J49001 | Testosterone dependent promoter for species *Bicyclus Bicyclus* | 89 |
| BBa_J49006 | Nutrition Promoter | 3 |
| BBa_J4906 | WrooHEAD2 (Wayne Rooney's Head dependent promoter) | 122 |
| BBa_J54015 | Protein Binding Site_LacI | 42 |
| BBa_J54016 | promoter_lacq | 54 |
| BBa_J54017 | promoter_always | 98 |
| BBa_J54018 | promoter_always | 98 |
| BBa_J54101 | deltaP-GFP(A) | |
| BBa_J54102 | DeltaP-GFP(A) | 813 |
| BBa_J54110 | MelR_regulated promoter | 76 |
| BBa_J54120 | EmrR_regulated promoter | 46 |
| BBa_J54130 | BetI_regulated promoter | 46 |

TABLE 6-continued

Examples of promoters which can be operatively linked to the nucleic acid in the engineered bacteriophages.
Table 6: Examples of promoters which can be operatively linked to the nucleic acid in the engineered bacteriophages.

| Name | Description | Length |
| --- | --- | --- |
| BBa_J54200 | lacq_Promoter | 50 |
| BBa_J54210 | RbsR_Binding_Site | 37 |
| BBa_J54220 | FadR_Binding_Site | 34 |
| BBa_J54230 | TetR_regulated | 38 |
| BBa_J54250 | LacI_Binding_Site | 42 |
| BBa_J56012 | Invertible sequence of dna includes Ptrc promoter | 409 |
| BBa_J56015 | lacIQ - promoter sequence | 57 |
| BBa_J61045 | [spv] spv operon (PoPS out) | 1953 |
| BBa_J61054 | [HIP-1] Promoter | 53 |
| BBa_J61055 | [HIP-1fnr] Promoter | 53 |
| BBa_J64000 | rhlI promoter | 72 |
| BBa_J64001 | psicA from *Salmonella* | 143 |
| BBa_J64010 | lasI promoter | 53 |
| BBa_J64065 | cI repressed promoter | 74 |
| BBa_J64067 | LuxR + 3OC6HSL independent R0065 | 98 |
| BBa_J64068 | increased strength R0051 | 49 |
| BBa_J64069 | R0065 with lux box deleted | 84 |
| BBa_J64700 | Trp Operon Promoter | 616 |
| BBa_J64712 | LasR/LasI Inducible & RHLR/RHLI repressible Promoter | 157 |
| BBa_J64750 | SPI-1 TTSS secretion-linked promoter from *Salmonella* | 167 |
| BBa_J64800 | RHLR/RHLI Inducible & LasR/LasI repressible Promoter | 53 |
| BBa_J64804 | The promoter region (inclusive of regulator binding sites) of the B. subtilis RocDEF operon | 135 |
| BBa_J64931 | glnKp promoter | 147 |
| BBa_J64951 | E. Coli CreABCD phosphate sensing operon promoter | 81 |
| BBa_J64979 | glnAp2 | 151 |
| BBa_J64980 | OmpR-P strong binding, regulatory region for Team Challenge03-2007 | |
| BBa_J64981 | OmpR-P strong binding, regulatory region for Team Challenge03-2007 | 82 |
| BBa_J64982 | OmpR-P strong binding, regulatory region for Team Challenge 03-2007 | 25 |
| BBa_J64983 | Strong OmpR Binding Site | 20 |
| BBa_J64986 | LacI Consensus Binding Site | 20 |
| BBa_J64987 | LacI Consensus Binding Site in sigma 70 binding region | 32 |
| BBa_J64991 | TetR | 19 |
| BBa_J64995 | Phage −35 site | 6 |
| BBa_J64997 | T7 consensus −10 and rest | 19 |
| BBa_J64998 | consensus −10 and rest from SP6 | 19 |
| BBa_J70025 | Promoter for tetM gene, from pBOT1 plasmid, pAMbeta1 | 345 |
| BBa_J72005 | {Ptet} promoter in BBb | 54 |
| BBa_K076017 | Ubc Promoter | 1219 |
| BBa_K078101 | aromatic compounds regulatory pcbC promoter | 129 |
| BBa_K079017 | Lac symmetric - operator library member | 20 |
| BBa_K079018 | Lac 1 - operator library member | 21 |
| BBa_K079019 | Lac 2 - operator library member | 21 |
| BBa_K079036 | Tet O operator library member | 15 |
| BBa_K079037 | TetO-4C - operator library member | 15 |
| BBa_K079038 | TetO-wt/4C5G - operator library member | 15 |
| BBa_K079039 | LexA 1 - operaor library member | 16 |
| BBa_K079040 | LexA 2 - opeartor library member | 16 |
| BBa_K079041 | Lambda OR1 - operator library member | 17 |
| BBa_K079042 | Lambda OR2 - operator library member | 17 |
| BBa_K079043 | Lambda OR3 - operator library member | 17 |
| BBa_K079045 | Lac operator library | 78 |
| BBa_K079046 | Tet operator library | 61 |
| BBa_K079047 | Lambda operator library | 67 |
| BBa_K079048 | LexA operator library | 40 |
| BBa_K080000 | TCFbs-BMP4 | 1582 |
| BBa_K080001 | A20/alpha cardiac actin miniPro-BMP4 | 1402 |
| BBa_K080003 | CMV-rtTA | 1413 |
| BBa_K080005 | TetO (TRE)-nkx2.5-fmdv2A-dsRed | 2099 |
| BBa_K080006 | TetO (TRE)-gata4-fmdv2A-dsRed | 2447 |
| BBa_K080008 | TetO (TRE)-nkx-2.5-fmdv2A-gata4-fmdv2A-dsRed | 3497 |
| BBa_K085004 | riboswitch system with GFP | 1345 |
| BBa_K085006 | pTet->lock3d->GFP->Ter | 932 |
| BBa_K086017 | unmodified Lutz-Bujard LacO promoter | 55 |
| BBa_K086018 | modified Lutz-Bujard LacO promoter, with alternative sigma factor σ24 | 55 |
| BBa_K086019 | modified Lutz-Bujard LacO promoter, with alternative sigma factor σ24 | 55 |
| BBa_K086020 | modified Lutz-Bujard LacO promoter, with alternative sigma factor σ24 | 55 |

TABLE 6-continued

Examples of promoters which can be operatively linked to the nucleic acid in the engineered bacteriophages.
Table 6: Examples of promoters which can be operatively linked to the nucleic acid in the engineered bacteriophages.

| Name | Description | Length |
| --- | --- | --- |
| BBa_K086021 | modified Lutz-Bujard LacO promoter, with alternative sigma factor σ24 | 55 |
| BBa_K086022 | modified Lutz-Bujard LacO promoter, with alternative sigma factor σ28 | 55 |
| BBa_K086023 | modified Lutz-Bujard LacO promoter, with alternative sigma factor σ28 | 55 |
| BBa_K086024 | modified Lutz-Bujard LacO promoter, with alternative sigma factor σ28 | 55 |
| BBa_K086025 | modified Lutz-Bujard LacO promoter, with alternative sigma factor σ28 | 55 |
| BBa_K086026 | modified Lutz-Bujard LacO promoter, with alternative sigma factor σ32 | 55 |
| BBa_K086027 | modified Lutz-Bujard LacO promoter, with alternative sigma factor σ32 | 55 |
| BBa_K086028 | modified Lutz-Bujard LacO promoter, with alternative sigma factor σ32 | 55 |
| BBa_K086029 | modified Lutz-Bujard LacO promoter, with alternative sigma factor σ32 | 55 |
| BBa_K086030 | modified Lutz-Bujard LacO promoter, with alternative sigma factor σ38 | 55 |
| BBa_K086031 | modified Lutz-Bujard LacO promoter, with alternative sigma factor σ38 | 55 |
| BBa_K086032 | modified Lutz-Bujard LacO promoter, with alternative sigma factor σ38 | 55 |
| BBa_K086033 | modified Lutz-Bujard LacO promoter, with alternative sigma factor σ38 | 55 |
| BBa_K090502 | Gram-Positive Xylose-Inducible Promoter | 126 |
| BBa_K090503 | Gram-Positive General Constitutive Promoter | 91 |
| BBa_K091112 | pLacIQ1 promoter | 56 |
| BBa_K091156 | pLux | 55 |
| BBa_K091157 | pLux/Las Hybrid Promoter | 55 |
| BBa_K093008 | reverse BBa_R0011 | 55 |
| BBa_K094002 | plambda P(O-R12) | 100 |
| BBa_K094140 | pLacIq | 80 |
| BBa_K100003 | Edited Xylose Regulated Bi-Directional Operator 3 | 303 |
| BBa_K101000 | Dual-Repressed Promoter for p22 mnt and TetR | 61 |
| BBa_K101001 | Dual-Repressed Promoter for LacI and LambdacI | 116 |
| BBa_K101002 | Dual-Repressed Promoter for p22 cII and TetR | 66 |
| BBa_K102909 | TA11 gate from synthetic algorithm v1.1 | 134 |
| BBa_K102910 | TA12 gate from synthetic algorithm v1.1 | 107 |
| BBa_K102911 | TA13 gate from synthetic algorithm v1.2 | 90 |
| BBa_K102912 | TA12 plus pause sequence | 108 |
| BBa_K102950 | TA0In null anti-sense input | 175 |
| BBa_K102951 | TA1In anti-sense input to TA1 (BBa_K102901) | 157 |
| BBa_K102952 | TA2In anti-sense input to BBa_K102952 | 168 |
| BBa_K102953 | TA13n anti-sense input to TA3 (BBa_K102903) | 168 |
| BBa_K102954 | TA6In anti-sense input to BBa_K102904 | 169 |
| BBa_K102955 | TA7In anti-sense input to BBa_K102905 | 168 |
| BBa_K102956 | TA8In anti-sense input to BBa_K102906 | 168 |
| BBa_K102957 | TA9In anti-sense input to BBa_K102907 | 173 |
| BBa_K102958 | TA10In anti-sense input to BBa_K102908 | 183 |
| BBa_K102959 | TA11In anti-sense input to BBa_K102909 | 178 |
| BBa_K102960 | TA12In anti-sense input to anti-terminator BBa_K102910 | 173 |
| BBa_K102961 | TA13In anti-sense input to BBa_K102911 | 171 |
| BBa_K102962 | TA14In anti-sense input to BBa_K102912 | 180 |
| BBa_K103021 | modified T7 promoter with His-Tag | 166 |
| BBa_K103022 | Plac with operator and RBS | 279 |
| BBa_K106673 | 8xLexAops-Cyc1p | 418 |
| BBa_K106680 | 8xLexAops-Fig1P | 1169 |
| BBa_K106694 | Adh1P! (Adh1 Promoter, A! end) | 1511 |
| BBa_K106699 | Gal1 Promoter | 686 |
| BBa_K109584 | this is a test part, disregard it | |
| BBa_K110004 | Alpha-Cell Promoter Ste3 | 501 |
| BBa_K110007 | A-Cell Promoter MFA2 | 501 |
| BBa_K110008 | A-Cell Promoter MFA1 | 501 |
| BBa_K110009 | A-Cell Promoter STE2 | 501 |
| BBa_K110014 | A-Cell Promoter MFA2 (backwards) | 550 |
| BBa_K110015 | A-Cell Promoter MFA1 (RtL) | 436 |
| BBa_K112139 | oriR6K conditional replication origin | 408 |
| BBa_K112148 | phoPp1 magnesium promoter | 81 |
| BBa_K112149 | PmgtCB Magnesium promoter from *Salmonella* | 280 |
| BBa_K112321 | {H-NS!} using MG1655 reverse oligo in BBb format | 414 |
| BBa_K112701 | hns promoter | 669 |

TABLE 6-continued

Examples of promoters which can be operatively linked to the nucleic acid in the engineered bacteriophages.
Table 6: Examples of promoters which can be operatively linked to the nucleic acid in the engineered bacteriophages.

| Name | Description | Length |
| --- | --- | --- |
| BBa_K112706 | Pspv2 from *Salmonella* | 474 |
| BBa_K112707 | Pspv from *Salmonella* | 1956 |
| BBa_K112708 | PfhuA | 210 |
| BBa_K112711 | rbs.spvR! | 913 |
| BBa_K112900 | Pbad | 1225 |
| BBa_K112904 | PconB5 | 41 |
| BBa_K112905 | PconC5 | 41 |
| BBa_K112906 | PconG6 | 41 |
| BBa_K112907 | Pcon | 41 |
| BBa_K113010 | overlapping T7 promoter | 40 |
| BBa_K113011 | more overlapping T7 promoter | 37 |
| BBa_K113012 | weaken overlapping T7 promoter | 40 |
| BBa_K116201 | ureD promoter from *P mirabilis* | |
| BBa_K119000 | Constitutive weak promoter of lacZ | 38 |
| BBa_K119001 | Mutated LacZ promoter | 38 |
| BBa_K120010 | Triple_lexO | 114 |
| BBa_K120023 | lexA_DBD | 249 |
| BBa_K121011 | promoter (lacI regulated) | 232 |
| BBa_K121014 | promoter (lambda cI regulated) | 90 |
| BBa_K124000 | pCYC Yeast Promoter | 288 |
| BBa_K124002 | Yeast GPD (TDH3) Promoter | 681 |
| BBa_K125100 | nir promoter from *Synechocystis* sp. PCC6803 | 88 |
| BBa_K131017 | p_qrr4 from *Vibrio harveyi* | 275 |
| BBa_K137085 | optimized (TA) repeat constitutive promoter with 13 bp between −10 and −35 elements | 31 |
| BBa_K137086 | optimized (TA) repeat constitutive promoter with 15 bp between −10 and −35 elements | 33 |
| BBa_K137087 | optimized (TA) repeat constitutive promoter with 17 bp between −10 and −35 elements | 35 |
| BBa_K137088 | optimized (TA) repeat constitutive promoter with 19 bp between −10 and −35 elements | 37 |
| BBa_K137089 | optimized (TA) repeat constitutive promoter with 21 bp between −10 and −35 elements | 39 |
| BBa_K137090 | optimized (A) repeat constitutive promoter with 17 bp between −10 and −35 elements | 35 |
| BBa_K137091 | optimized (A) repeat constitutive promoter with 18 bp between −10 and −35 elements | 36 |
| BBa_K137124 | LacI-repressed promoter A81 | 103 |
| BBa_K143010 | Promoter ctc for *B. subtilis* | 56 |
| BBa_K143011 | Promoter gsiB for *B. subtilis* | 38 |
| BBa_K143012 | Promoter veg a constitutive promoter for *B. subtilis* | 97 |
| BBa_K143013 | Promoter 43 a constitutive promoter for *B. subtilis* | 56 |
| BBa_K143014 | Promoter Xyl for *B. subtilis* | 82 |
| BBa_K143015 | Promoter hyper-spank for *B. subtilis* | 101 |
| BBa_K145152 | Hybrid promoter: P22 c2, LacI NOR gate | 142 |
| BBa_K157042 | Eukaryotic CMV promoter | 654 |
| BBa_K165000 | MET 25 Promoter | 387 |
| BBa_K165015 | pADH1 yeast constitutive promoter | 1445 |
| BBa_K165017 | LexA binding sites | 393 |
| BBa_K165037 | TEF2 yeast constitutive promoter | 403 |
| BBa_M13101 | M13K07 gene I promoter | 47 |
| BBa_M13102 | M13K07 gene II promoter | 48 |
| BBa_M13103 | M13K07 gene III promoter | 48 |
| BBa_M13104 | M13K07 gene IV promoter | 49 |
| BBa_M13105 | M13K07 gene V promoter | 50 |
| BBa_M13106 | M13K07 gene VI promoter | 49 |
| BBa_M13108 | M13K07 gene VIII promoter | 47 |
| BBa_M13110 | M13110 | 48 |
| BBa_M31201 | Yeast CLB1 promoter region, G2/M cell cycle specific | 500 |
| BBa_M31232 | Redesigned M13K07 Gene III Upstream | 79 |
| BBa_M31252 | Redesigned M13K07 Gene V Upstream | 72 |
| BBa_M31272 | Redesigned M13K07 Gene VII Upstream | 50 |
| BBa_M31282 | Redesigned M13K07 Gene VIII Upstream | 146 |
| BBa_M31292 | Redesigned M13K07 Gene IX Upstream | 69 |
| BBa_M31302 | Redesigned M13K07 Gene X Upstream | 115 |
| BBa_M31370 | tacI Promoter | 68 |
| BBa_M31519 | Modified promoter sequence of g3. | 60 |
| BBa_R0001 | HMG-CoA Dependent RBS Blocking Segment | 53 |
| BBa_R00100 | Tet promoter and sRBS | 67 |
| BBa_R00101 | VM1.0 to RiPS converter | 36 |
| BBa_R0085 | T7 Consensus Promoter Sequence | 23 |
| BBa_R0180 | T7 RNAP promoter | 23 |
| BBa_R0181 | T7 RNAP promoter | 23 |

TABLE 6-continued

Examples of promoters which can be operatively linked to the nucleic acid in the engineered bacteriophages.
Table 6: Examples of promoters which can be operatively linked to the nucleic acid in the engineered bacteriophages.

| Name | Description | Length |
| --- | --- | --- |
| BBa_R0182 | T7 RNAP promoter | 23 |
| BBa_R0183 | T7 RNAP promoter | 23 |
| BBa_R0184 | T7 promoter (lacI repressible) | 44 |
| BBa_R0185 | T7 promoter (lacI repressible) | 44 |
| BBa_R0186 | T7 promoter (lacI repressible) | 44 |
| BBa_R0187 | T7 promoter (lacI repressible) | 44 |
| BBa_R1028 | Randy Rettberg Standardillator | |
| BBa_R1074 | Constitutive Promoter I | 49 |
| BBa_R1075 | Constitutive Promoter II | 49 |
| BBa_R2108 | Promoter with operator site for C2003 | 72 |
| BBa_R2110 | Promoter with operator site for C2003 | 72 |
| BBa_R2111 | Promoter with operator site for C2003 | 72 |
| BBa_R2112 | Promoter with operator site for C2003 | 72 |
| BBa_R2113 | Promoter with operator site for C2003 | 72 |
| BBa_R2182 | RiPS generator | 44 |
| BBa_R2201 | C2006-repressible promoter | 45 |
| BBa_R6182 | RiPS generator | 36 |
| BBa_S03331 | --Specify Parts List-- | 30 |
| BBa_S03385 | Cold-sensing promoter (hybB) | |
| BBa_Z0251 | T7 strong promoter | 35 |
| BBa_Z0252 | T7 weak binding and processivity | 35 |
| BBa_Z0253 | T7 weak binding promoter | 35 |
| BBa_Z0294 | A1, A2, A3, boxA | 435 |

REFERENCES

The references cited herein and throughout the application are incorporated herein by reference in their entirety.

1. Walsh, C. Where will new antibiotics come from? Nat Rev Microbiol 1, 65-70 (2003).
2. Shah, D. et al. Persisters: a distinct physiological state of *E. coli*. BMC Microbiol. 6, 53 (2006).
3. Wise, R. The relentless rise of resistance? J. Antimicrob. Chemother. 54, 306-310 (2004).
4. Hall-Stoodley, L., Costerton, J. W. & Stoodley, P. Bacterial biofilms: from the natural environment to infectious diseases. Nat Rev Microbiol 2, 95-108 (2004).
5. Levin, B. R. & Bonten, M. J. M. Cycling antibiotics may not be good for your health. Proc Natl Acad Sci USA 101, 13101-13102 (2004).
6. Projan, S. Phage-inspired antibiotics? Nat. Biotechnol. 22, 167-168 (2004).
7. Schoolnik, G K, Summers, W. C. & Watson, J. D. Phage offer a real alternative. Nat. Biotechnol. 22, 505-506; author reply 506-507 (2004).
8. Vandenesch, F. et al. Community-acquired methicillin-resistant *Staphylococcus aureus* carrying Panton-Valentine leukocidin genes: worldwide emergence. Emerg. Infect. Dis. 9, 978-984 (2003).
9. From the Centers for Disease Control and Prevention. Four pediatric deaths from community-acquired methicillin-resistant *Staphylococcus aureus*—Minnesota and North Dakota, 1997-1999. JAMA 282, 1123-1125 (1999).
10. Hall, B. G. Predicting the evolution of antibiotic resistance genes. Nat Rev Microbiol 2, 430-435 (2004).
11. Alekshun, M. N. & Levy, S. B. Molecular mechanisms of antibacterial multidrug resistance. Cell 128, 1037-1050 (2007).
12. Morens, D. M., Folkers, G. K. & Fauci, A. S. The challenge of emerging and re-emerging infectious diseases. Nature 430, 242-249 (2004).
13. Salyers, A. A., Gupta, A. & Wang, Y. Human intestinal bacteria as reservoirs for antibiotic resistance genes. Trends Microbiol. 12, 412-416 (2004).
14. Chang, S. et al. Infection with vancomycin-resistant *Staphylococcus aureus* containing the vanA resistance gene. N. Engl. J. Med. 348, 1342-1347 (2003).
15. Beaber, J. W., Hochhut, B. & Waldor, M. K. SOS response promotes horizontal dissemination of antibiotic resistance genes. Nature 427, 72-74 (2004).
16. Ubeda, C. et al. Antibiotic-induced SOS response promotes horizontal dissemination of pathogenicity island-encoded virulence factors in staphylococci. Mol. Microbiol. 56, 836-844 (2005).
17. Martinez, J. L. & Baquero, F. Mutation frequencies and antibiotic resistance. Antimicrob. Agents Chemother. 44, 1771-1777 (2000).
18. Klevens, R. M. et al. Invasive methicillin-resistant *Staphylococcus aureus* infections in the United States. JAMA 298, 1763-1771 (2007).
19. Balaban, N. Q., Merrin, J., Chait, R., Kowalik, L. & Leibler, S. Bacterial persistence as a phenotypic switch. Science 305, 1622-1625 (2004).
20. Lewis, K. Persister cells, dormancy and infectious disease. Nat Rev Microbiol (2006).
21. Wiuff, C. et al. Phenotypic tolerance: antibiotic enrichment of noninherited resistance in bacterial populations. Antimicrob. Agents Chemother. 49, 1483-1494 (2005).
22. Lewis, K. Persister cells and the riddle of biofilm survival. Biochemistry (Mosc). 70, 267-274 (2005).
23. Korch, S. B. & Hill, T. M. Ectopic overexpression of wild-type and mutant hipA genes in *Escherichia coli*: effects on macromolecular synthesis and persister formation. J. Bacteriol. 188, 3826-3836 (2006).
24. Vázquez-Laslop, N., Lee, H. & Neyfakh, A. A. Increased persistence in *Escherichia coli* caused by controlled expression of toxins or other unrelated proteins. J. Bacteriol. 188, 3494-3497 (2006).

25. Avery, S. V. Microbial cell individuality and the underlying sources of heterogeneity. Nat Rev Microbiol 4, 577-587 (2006).

26. Wang, J. et al. Platensimycin is a selective FabF inhibitor with potent antibiotic properties. Nature 441, 358-361 (2006).

27. Bergstrom, C. T., Lo, M. & Lipsitch, M. Ecological theory suggests that antimicrobial cycling will not reduce antimicrobial resistance in hospitals. Proc Natl Acad Sci USA 101, 13285-13290 (2004).

28. Brown, E. M. & Nathwani, D. Antibiotic cycling or rotation: a systematic review of the evidence of efficacy. J. Antimicrob. Chemother. 55, 6-9 (2005).

29. Soulsby, E. J. Resistance to antimicrobials in humans and animals. BMJ 331, 1219-1220 (2005).

30. Soulsby, L. Antimicrobials and animal health: a fascinating nexus. J. Antimicrob. Chemother. 60 Suppl 1, i77-i78 (2007).

31. Hagens, S. & Blasi, U. Genetically modified filamentous phage as bactericidal agents: a pilot study. Lett. Appl. Microbiol. 37, 318-323 (2003).

32. Hagens, S., Habel, A. v. A. U., von Gabain, A. & Blasi, U. Therapy of experimental pseudomonas infections with a nonreplicating genetically modified phage. Antimicrob. Agents Chemother. 48, 3817-3822 (2004).

33. Westwater, C. et al. Use of genetically engineered phage to deliver antimicrobial agents to bacteria: an alternative therapy for treatment of bacterial infections. Antimicrob. Agents Chemother. 47, 1301-1307 (2003).

34. Heitman, J., Fulford, W. & Model, P. Phage Trojan horses: a conditional expression system for lethal genes. Gene 85, 193-197 (1989).

35. Brüssow, H. Phage therapy: the *Escherichia coli* experience. Microbiology 151, 2133-2140 (2005).

36. Summers, W. C. Bacteriophage therapy. Annu. Rev. Microbiol. 55, 437-451 (2001).

37. Loose, C., Jensen, K., Rigoutsos, I. & Stephanopoulos, G. A linguistic model for the rational design of antimicrobial peptides. Nature 443, 867-869 (2006).

38. Lu, T. K. & Collins, J. J. Dispersing biofilms with engineered enzymatic bacteriophage. Proc Natl Acad Sci USA 104, 11197-11202 (2007).

39. Bonhoeffer, S., Lipsitch, M. & Levin, B. R. Evaluating treatment protocols to prevent antibiotic resistance. Proc Natl Acad Sci USA 94, 12106-12111 (1997).

40. Chait, R., Craney, A. & Kishony, R. Antibiotic interactions that select against resistance. Nature 446, 668-671 (2007).

41. Levy, S. B. & Marshall, B. Antibacterial resistance worldwide: causes, challenges and responses. Nat. Med. 10, 5122-5129 (2004).

42. Hagens, S., Habel, A. & Bläsi, U. Augmentation of the antimicrobial efficacy of antibiotics by filamentous phage. Microb Drug Resist 12, 164-168 (2006).

43. Dwyer, D. J., Kohanski, M. A., Hayete, B. & Collins, J. J. Gyrase inhibitors induce an oxidative damage cellular death pathway in *Escherichia coli*. Mol Syst Biol 3, 91 (2007).

44. Kohanski, M. A., Dwyer, D. J., Hayete, B., Lawrence, C. A. & Collins, J. J. A common mechanism of cellular death induced by bactericidal antibiotics. Cell 130, 797-810 (2007).

45. Miller, C. et al. SOS response induction by beta-lactams and bacterial defense against antibiotic lethality. Science 305, 1629-1631 (2004).

46. Lewin, C. S., Howard, B. M., Ratcliffe, N. T. & Smith, J. T. 4-quinolones and the SOS response. J. Med. Microbiol. 29, 139-144 (1989).

47. Little, J. W. & Harper, J. E. Identification of the lexA gene product of *Escherichia coli* K-12. Proc Natl Acad Sci USA 76, 6147-6151 (1979).

48. Yanisch-Perron, C., Vieira, J. & Messing, J. Improved M13 phage cloning vectors and host strains: nucleotide sequences of the M13mp18 and pUC19 vectors. Gene 33, 103-119 (1985).

49. Walker, G. C. Mutagenesis and inducible responses to deoxyribonucleic acid damage in *Escherichia coli*. Microbiol. Rev. 48, 60-93 (1984).

50. Lutz, R. & Bujard, H. Independent and tight regulation of transcriptional units in *Escherichia coli* via the LacR/O, the TetR/O and AraC/I1-I2 regulatory elements. Nucleic Acids Res 25, 1203-1210 (1997).

51. Little, J. W., Edmiston, S. H., Pacelli, L. Z. & Mount, D. W. Cleavage of the *Escherichia coli* lexA protein by the recA protease. Proc Natl Acad Sci USA 77, 3225-3229 (1980).

52. Hidalgo, E., Ding, H. & Demple, B. Redox signal transduction via iron-sulfur clusters in the SoxR transcription activator. Trends Biochem. Sci. 22, 207-210 (1997).

53. Jackson, D. W. et al. Biofilm formation and dispersal under the influence of the global regulator CsrA of *Escherichia coli*. J. Bacteriol. 184, 290-301 (2002).

54. Lewis, K. Riddle of biofilm resistance. Antimicrob. Agents Chemother. 45, 999-1007 (2001).

55. Stewart, P. S. & Costerton, J. W. Antibiotic resistance of bacteria in biofilms. Lancet 358, 135-138 (2001).

56. Lynch, S. V. et al. Role of the rapA gene in controlling antibiotic resistance of *Escherichia coli* biofilms. Antimicrob. Agents Chemother. 51, 3650-3658 (2007).

57. Hirai, K., Aoyama, H., Irikura, T., Iyobe, S. & Mitsuhashi, S. Differences in susceptibility to quinolones of outer membrane mutants of *Salmonella typhimurium* and *Escherichia coli*. Antimicrob. Agents Chemother. 29, 535-538 (1986).

58. Aslam, S., Hamill, R. J. & Musher, D. M. Treatment of *Clostridium difficile*-associated disease: old therapies and new strategies. Lancet Infect. Dis. 5, 549-557 (2005).

59. Bartlett, J. G. Narrative review: the new epidemic of *Clostridium difficile*-associated enteric disease. Ann. Intern. Med. 145, 758-764 (2006).

60. Hickman-Brenner, F. W., Stubbs, A. D. & Farmer, J. J. Phage typing of *Salmonella enteritidis* in the United States. J. Clin. Microbiol. 29, 2817-2823 (1991).

61. Wentworth, B. B. Bacteriophage Typing of the Staphylococci. Bacteriol. Rev. 27, 253-272 (1963).

62. Andrianantoandro, E., Basu, S., Karig, D. K. & Weiss, R. Synthetic biology: new engineering rules for an emerging discipline. Mol Syst Biol 2, 2006.0028 (2006).

63. Baker, D. et al. Engineering life: building a fab for biology. Sci. Am. 294, 44-51 (2006).

64. Tian, J. et al. Accurate multiplex gene synthesis from programmable DNA microchips. Nature 432, 1050-1054 (2004).

65. Newcomb, J., Carlson, R. & Aldrich, S. Genome Synthesis and Design Futures: Implications for the U.S. Economy. (Bio Economic Research Associates, 2007).

66. Merril, C. R., Scholl, D. & Adhya, S. L. The prospect for bacteriophage therapy in Western medicine. Nat. Rev. Drug Discov. 2, 489-497 (2003).

67. Boratynski, J. et al. Preparation of endotoxin-free bacteriophages. Cell. Mol. Biol. Lett. 9, 253-259 (2004).

68. Merril, C. R. et al. Long-circulating bacteriophage as antibacterial agents. Proc Natl Acad Sci USA 93, 3188-3192 (1996).

69. Shuren, J., Vol. 71. (ed. H. U.S. Food and Drug Administration) 47729-47732 (Federal Register, 2006).

Wise R (2004) J. Antimicrob. Chemother. 54, 306-310.

Hall-Stoodley L, Costerton JW, & Stoodley P (2004) Nat Rev Microbiol 2, 95-108.

Hall B G (2004) Nat Rev Microbiol 2, 430-435.

Balaban N Q, Merrin J, Chait R, Kowalik L, & Leibler S (2004) Science 305, 1622-1625.

Lewis K (2007) Nat Rev Microbiol 5, 48-56.

Walsh C (2003) Nat Rev Microbiol 1, 65-70.

Dwyer D J, Kohanski Mass., Hayete B, & Collins J J (2007) Mol Syst Biol 3, 91.

Kohanski M A, Dwyer D J, Hayete B, Lawrence C A, & Collins J J (2007) Cell 130, 797-810.

Merril C R, Scholl D, & Adhya S L (2003) Nat. Rev. Drug Discov. 2, 489-497.

Hagens S & Blasi U (2003) Lett. Appl. Microbiol. 37, 318-323.

Hagens S, et al., (2004) Antimicrob. Agents Chemother. 48, 3817-3822.

Westwater et al., (2003) Antimicrob. Agents Chemother. 47, 1301-1307.

Heitman J, Fulford W, & Model P (1989) Gene 85, 193-197.

Brüssow H (2005) Microbiology 151, 2133-2140.

Summers W C (2001) Annu. Rev. Microbiol. 55, 437-451.

Lu T K & Collins J J (2007) Proc Natl Acad Sci USA 104, 11197-11202.

Bonhoeffer S, Lipsitch M, & Levin BR (1997) Proc Natl Acad Sci USA 94, 12106-12111.

Chait R, Craney A, & Kishony R (2007) Nature 446, 668-671.

Levy S B & Marshall B (2004) Nat. Med. 10, 5122-5129.

Hagens S, Habel A, & Bläsi U (2006) Microb Drug Resist 12, 164-168.

Miller et al., (2004) Science 305, 1629-1631.

Lewin C S, Howard B M, Ratcliffe N T, & Smith J T (1989) J. Med. Microbiol. 29, 139-144.

Little J W & Harper J E (1979) Proc Natl Acad Sci USA 76, 6147-6151.

Cirz R T, et al., (2005) in PLoS Biol, p. e176.

Yanisch-Perron C, Vieira J, & Messing J (1985) Gene 33, 103-119.

Walker G C (1984) Microbiol. Rev. 48, 60-93.

Lutz R & Bujard H (1997) Nucleic Acids Res 25, 1203-1210.

Karlsson et al., (2005) Can J Microbiol 51, 29-35.

Schleif R (1972) Proc Natl Acad Sci USA 69, 3479-3484.

Martinez J L & Baquero F (2000) Antimicrob. Agents Chemother. 44, 1771-1777.

Hidalgo E, Ding H, & Demple B (1997) Cell 88, 121-129.

Hidalgo E, Leautaud V, & Demple B (1998) EMBO J. 17, 2629-2636.

Zheng M, Doan B, Schneider TD, & Storz G (1999) J Bacteriol 181, 4639-4643.

Gaudu P & Weiss B (1996) Proc Natl Acad Sci USA 93, 10094-10098.

Jackson et al., (2002) J. Bacteriol. 184, 90-301.

Stewart P S & Costerton J W (2001) Lancet 358, 135-138.

Hirai K, et al., (1986) Antimicrob. Agents Chemother. 29, 535-538.

Boratynski J, et al., (2004) Cell. Mol. Biol. Lett. 9, 253-259.

Merril C R, et al., (1996) Proc Natl Acad Sci USA 93, 3188-3192.

Andrianantoandro, et al., (2006) Mol Syst Biol 2, 2006.0028.

Hasty J, McMillen D, & Collins J J (2002) in Nature, pp. 224-230.

McDaniel R & Weiss R (2005) in Curr. Opin. Biotechnol., pp. 476-483.

Chan L Y, Kosuri S, & Endy D (2005) in Mol Syst Biol, p. 2005.0018.

Anderson J C, Clarke E J, Arkin A P, & Voigt C A (2006) J. Mol. Biol. 355, 619-627.

Loose C, Jensen K, Rigoutsos I, & Stephanopoulos G (2006) Nature 443, 867-869.

Ro D-K, et al., (2006) Nature 440, 940-943.

Hickman-Brenner, et al., (1991) J. Clin. Microbiol. 29, 2817-2823.

Baker et al., (2006) Sci. Am. 294, 44-51.

Morens et al., (2004) Nature 430, 242-249.

Stewart et al., (2008) PLoS Biol 6, e10.

The invention claimed is:

1. An engineered bacteriophage comprising a nucleic acid operatively linked to a promoter, wherein the nucleic acid encodes:
 a bacterial porin or porin-like protein of the OMP superfamily.

2. The bacteriophage of claim 1, wherein the porin is ompF.

3. A method to inhibit or eliminate a bacterial infection comprising administering to a surface infected with bacteria, the engineered bacteriophage of claim 1 and at least one antimicrobial agent.

4. The method of claim 3, wherein the administration of the bacteriophage occurs simultaneously or prior to, or after administration of the antimicrobial agent.

5. The method of claim 3, wherein the antimicrobial agent is selected from a group consisting of: quinolone, ampicillin, aminoglycoside, ciproflaxacin, levofloxacin, ofloxacin, gatifloxacin, norfloxacin, lomefloxacin, trovafloxacin, moxifloxacin, sparfloxacin, gemifloxacin, pazufloxacin, amikacin, gentamycin, gentamicin, tobramycin, netromycin, streptomycin, kanamycin, paromomycin, neomycin, β-lactam, penicillin, ampicillin, penicillin derivatives, cephalosporins, monobactams, carbapenems, β-lactamase inhibitors and variants or analogues thereof.

6. The method of claim 3, wherein the bacteria is present in a subject.

7. The method of claim 6, wherein the subject is a mammal.

8. The method of claim 7, wherein the mammal is a human.

9. The method of claim 3, wherein the bacteria is in a biofilm.

10. A composition comprising the engineered bacteriophage of claim 1 and at least one antimicrobial agent.

11. A kit comprising an engineered bacteriophage of claim 1, and at least one antimicrobial agent.

12. The composition of claim 10, wherein the antimicrobial agent is selected from a group consisting of: quinolone, ampicillin, aminoglycoside, ciproflaxacin, levofloxacin, ofloxacin, gatifloxacin, norfloxacin, lomefloxacin, trovafloxacin, moxifloxacin, sparfloxacin, gemifloxacin, pazufloxacin, amikacin, gentamycin, gentamicin, tobramycin, netromycin, streptomycin, kanamycin, paromomycin, neomycin, β-lactam, penicillin, ampicillin, penicillin derivatives, cephalosporins, monobactams, carbapenems, β-lactamase inhibitors and variants or analogues thereof.

13. The kit of claim 11, wherein the antimicrobial agent is selected from a group consisting of: quinolone, ampicillin, aminoglycoside, ciproflaxacin, levofloxacin, ofloxacin, gatifloxacin, norfloxacin, lomefloxacin, trovafloxacin, moxifloxacin, sparfloxacin, gemifloxacin, pazufloxacin, amikacin, gentamycin, gentamicin, tobramycin, netromycin, streptomycin, kanamycin, paromomycin, neomycin, β-lactam, penicillin, ampicillin, penicillin derivatives, cephalosporins, monobactams, carbapenems, β-lactamase inhibitors and variants or analogues thereof.

14. The engineered bacteriophage of claim 1, wherein the engineered bacteriophage infects one or more of *Escherichia coli, Pseudomonas aeruginosa, Staphylococcus aureus,* or *Enterococcus faecalis.*

15. The engineered phage of claim 1, wherein the phage is lysogenic.

16. The engineered phage of claim 1, wherein the phage is lytic.

17. The engineered phage of claim 1, wherein the phage is an engineered lambda phage, M13 phage, T7 phage, T3 phage, T2 phage, T4 phage, RB69 phage, Pf1 phage, Pf4 phage, phage B40-8, or coliphage MS-2.

18. The engineered phage of claim 1, wherein the engineered phage increases susceptibility of the bacteria to one or more antibiotic agents selected from a glycopeptide, carbapenum, cephalosporin, fluoroquinolone, quinolone, amino glycoside, β-lactam, sulphonamide, oxazolidinone, and tetracyclines.

19. The engineered phage of claim 18, wherein the engineered phage increases susceptibility of the bacteria to one or more of an aminoglycoside, quinolone, and β-lactam.

20. The engineered phage of claim 1, wherein the nucleic acid encodes a bacterial porin or porin-like protein of the OMP superfamily selected from the group consisting of ompA, ompC, ompF, ompG, ompL, ompN, ompW, pgaA, phoE, tolE, tolC, tsx or yncD.

* * * * *

SEQUENCE LISTING

```
<160> NUMBER OF SEQ ID NOS: 42

<210> SEQ ID NO 1
<211> LENGTH: 1434
<212> TYPE: DNA
<213> ORGANISM: Escherichia coli

<400> SEQUENCE: 1
atgtttaaga atgcatttgc taacctgcaa aaggtcggta aatcgctgat gctgccggta      60
tccgtactgc ctatcgcagg tattctgctg ggcgtcggtt ccgcgaattt cagctggctg     120
cccgccgttg tatcgcatgt tatggcagaa gcaggcggtt ccgtctttgc aaacatgcca     180 ctgattttg cgatcggtgt cgccctcggc tttaccaata acgatggcgt atccgcgctg     240
gccgcagttg ttgcctatgg catcatggtt aaaaccatgg ccgtggttgc gccactggta     300
ctgcatttac ctgctgaaga aatcgcctct aaacacctgg cggatactgg cgtactcgga     360
gggattatct ccggtgcgat cgcagcgtac atgttaacc gtttctaccg tattaagctg     420
cctgagtatc ttggcttctt tgccggtaaa cgctttgtgc cgatcatttc tggcctggct     480
gccatcttta ctggcgttgt gctgtccttc atttggccgc cgattggttc tgcaatccag     540
```

-continued

```
accttctctc agtgggctgc ttaccagaac ccggtagttg cgtttggcat ttacggtttc    600
atcgaacgtt gcctggtacc gtttggtctg caccacatct ggaacgtacc tttccagatg    660
cagattggtg aatacaccaa cgcagcaggt caggttttcc acggcgacat tccgcgttat    720
atggcgggtg acccgactgc gggtaaactg tctggtggct tcctgttcaa aatgtacggt    780
ctgccagctg ccgcaattgc tatctggcac tctgctaaac cagaaaaccg cgcgaaagtg    840
ggcggtatta tgatctccgc ggcgctgacc tcgttcctga ccggtatcac cgagccgatc    900
gagttctcct tcatgttcgt tgcgccgatc ctgtacatca tccacgcgat tctggcaggc    960
ctggcattcc caatctgtat tcttctgggg atgcgtgacg gtacgtcgtt ctcgcacggt   1020
ctgatcgact tcatcgttct gtctggtaac agcagcaaac tgtggctgtt cccgatcgtc   1080
ggtatcggtt atgcgattgt ttactacacc atcttccgcg tgctgattaa agcactggat   1140
ctgaaaacgc cgggtcgtga agacgcgact gaagatgcaa aagcgacagg taccagcgaa   1200
atggcaccgg ctctggttgc tgcatttggt ggtaaagaaa acattactaa cctcgacgca   1260
tgtattaccc gtctgcgcgt cagcgttgct gatgtgtcta aagtggatca ggccggcctg   1320
aagaaactgg gcgcagcggg cgtagtggtt gctggttctg tgttcaggc gattttcggt    1380
actaaatccg ataacctgaa aaccgagatg gatgagtaca tccgtaacca ctaa           1434
```

<210> SEQ ID NO 2
<211> LENGTH: 10851
<212> TYPE: DNA
<213> ORGANISM: Enterococcus faecium

<400> SEQUENCE: 2

```
ggggtagcgt caggaaaatg cggatttaca acgctaagcc tatttttcctg acgaatccct    60
cgttttttaac aacgttaaga aagttttagt ggtcttaaag aatttaatga gactactttc   120
tctgagttaa aatggtattc tcctagtaaa ttaatatgtt cccaacctaa gggcgacata    180
tggtgtaaca aatcttcatt aaagctacct gtccgttttt tatattcaac tgctgttgtt    240
aggtggagag tattccaaat acttatagca ttgataatta tgtttaaagc actggctctt    300
tgcaattgat gctgtatggt gcgttctcta agctcacctt gttttccgaa gaaaatagct    360
cttgccaatc cattcatggc ttctcctta ttcaatcctc tttgtatttt tcttcttaat    420
gattcatccg atatataatt caaaataaag atcgtttttt ctattcggcc catctcacgt    480
aaggctgtag ctaagctgtt ttgtcttgaa taggaaccta gcttccccat aataagggat    540
gctgaaactg ttccctccct tatagaatga gctaatcgca aaacatcctc ataattttct    600
ttaatgacct ttgtatttat ttgtccacgt aaaatggctt ctagttttgg atactcactt    660
gctttatcta tcgtaaataa ttttgagtcc gataaatccc ttattcttgg ggcaaattta    720
aatcctaata aatgagtcag tccgaatatt tggtcagtgt aaccggcagt gtctgtataa    780
tgttcctcta tgtttagatc cgtctcatga tgtaacaaac catccaaaac atgaatcgca    840
tctcttgaat tagtatgaat aatctttgtg tagtaagaag agaattgatc acttgtaaat    900
cggtagatgg tggctccttt tccagttcca taatgtggat ttgcatctgc atgtagtgat    960
gaaacaccta gctgcattct cataccatct gacgaagatt tgtaccgtc gccccaatag  1020
aaaggcaatt gtaatttatg atgaaagttt actaatatgg cttgggcttt attcatggca  1080
tcttcataca tgcgccattg agatacattg gctagttgct tatatgtaag tccgggtgtg  1140
gcttcggcca tcttgctcaa gccaatattc attcccattc ctaaaagggc agccatgata  1200
```

-continued

```
atgattgttt cttccttatc tggttttcga ttattggaag catgagtgaa ttgctcatga    1260
aatcctgtta tatgggccac atccatgagt aaatcagtta attttattct tggtagcatc    1320
tgataaaggc ttgcactaaa ttttttgct tcttctggaa catcttttc taagcgtgca      1380 agtgatagct ttcctttttc aagagaaacc ccatctaact tattggaatt ggcagctaac    1440
cactttaacc tttcattaaa gctgctggtt ctctccgtta tataatcttc gaatgataaa    1500
ctaactgata atctcgtatt ccccttcgat tgattccatg tatcttccga aaacaaatat    1560
tcctcaaaat ccctatattg tctgctgcca acaatggaaa catctcctgc ccgaacatgc    1620
tcccgaagtt ctgttaaaac agccatttca tagtaatgac gattaattgt tgtaccatca    1680
tcctcgtata aatgtctttt ccatcgtttt gaaataaaat ccacaggtga gtcatcaggc    1740
acttttcgct ttccagattc gttcattcct cggataatct caacagcttg taaaagtggc    1800
tcatttgcct ttgtagaatg aaattccaat actcttaata gcgttggcgt atattttctt    1860
agtgaataaa accgttttg cagtaagtct aaataatcat agtcggcagg acgtgcaagt    1920
tcctgagcct cttctactga agagacaaag gtattccatt caataaccga ttctaaaacc    1980
ttaaaaacgt ctaattttc ctctcttgct ttaattaatg cttgtccgat gttcgtaaag    2040
tgtataactt tctcatttag ctttttaccg ttttgtttct ggatttcctc ttgagcctta    2100
cgaccttttg ataacaaact aagtatttgc ctatcatgaa tttcaaacgc tttatccgtt    2160
agctcctgag taagttgtaa taaatagatg gttaatatcg ataacgtttt attttcttga    2220
aagtcacgga atgcatacgg ctcgtatctt gagcctaagc gagacagctg caacaggcgg    2280
ttacggtgca aatgactaat ttgcactgtt tctaaatcca ttcctcgtat gtattcgagt    2340
cgttctatta ttttagaaa agtttcgggt gaaggatgac ccggtggctc ttttaaccaa    2400
cccaatatcg ttttattgga ttcggatgga tgctgcgagg taataatccc ttcaagcttt    2460 tcttttgct catttgttag agatttacta accgtattaa atagcttctt ttcagccatt    2520
gcccttgctt cccacaccat tctttcaagt gtagtgatag caggcagtat aattttgttt    2580
tttcttagaa aatctatgca ttcatgcagt agatgaatgg catcaccatt ttccaaagct    2640
aattgatgaa ggtacttaaa tgtcattcga tattcactca gggtaaaagt tacaaagtcg    2700
tattcacttc gaatttcttt caaatgatcc caaagtgtat tttccctttg aggataatga    2760
tcaagcgagg atggactaac accaatctgt ttcgatatat attgtatgac cgaatctggg    2820
atgcttttga tatgagtgta tggccaaccg ggataccgaa gaacagctaa ttgaacagca    2880
aatcctaaac ggttttcttc cctccttcgc ttattaacta tttctaaatc ccgtttggaa    2940
aaagtgaagt aggtccccag tatccattca tcttcaggga tttgcataaa agcctgtctc    3000
tgttccggtg taagcaattc tctacctctc gcaattttca ttcagtatca ttccatttct    3060
gtattttcaa tttattagtt caattatata tcaatagagt gtactctatt gatacaaatg    3120
tagtagactg ataaaatcat agttaagagc gtctcataag acttgtctca aaatgaggt    3180 gatattttgc ggaaaatcgg ttatattcgt gtcagttcga ctaaccagaa tccttcaaga    3240
caatttcagc agttgaacga gatcggaatg gatattatat atgaagagaa agtttcagga    3300
gcaacaaagg atcgcgagca acttcaaaaa gtgttagacg atttacagga agatgacatc    3360
atttatgtta cagacttaac tcgaatcact cgtagtacac aagatctatt tgaattaatc    3420
gataacatac gagataaaaa ggcaagttta aaatcactaa aagatacatg gcttgattta    3480
tcagaagata atccatacag ccaattctta attactgtaa tggctggtgt taaccaatta    3540
gagcgagatc ttattcggat gagacaacgt gaagggattg aattggctaa gaagaagga    3600
```

```
aagtttaaaag gtcgattaaa gaagtatcat aaaaatcacg caggaatgaa ttatgcggta   3660
aagctatata aagaaggaaa tatgactgta aatcaaattt gtgaaattac taatgtatct   3720
agggcttcat tatacaggaa attatcagaa gtgaataatt agccattctg tattccgcta   3780
atgggcaata tttttaaaga agaaaaggaa actataaaat attaacagcc tcctagcgat   3840
gccgaaaagc cctttgataa aaaaagaatc atcatcttaa gaaattctta gtcatttatt   3900
atgtaaatgc ttataaattc ggccctataa tctgataaat tattaagggc aaacttatgt   3960
gaaagggtga taactatgag cgataaaata cttattgtgg atgatgaaca tgaaattgcc   4020
gatttggttg aattatactt aaaaaacgag aattatacgg ttttcaaata ctataccgcc   4080
aaagaagcat tggaatgtat agacaagtct gagattgacc ttgccatatt ggacatcatg   4140
cttcccggca aagcggcct tactatctgt caaaaaataa gggacaagca cacctatccg   4200
attatcatgc tgaccgggaa agatacagag gtagataaaa ttacagggtt aacaatcggc   4260
gcggatgatt atataacgaa gccctttcgc ccactggagt taattgctcg ggtaaaggcc   4320
cagttgcgcc gatacaaaaa attcagtgga gtaaaggagc agaacgaaaa tgttatcgtc   4380
cactccggcc ttgtcattaa tgttaacacc catgagtgtt atctgaacga aagcagtta   4440 tcccttactc ccaccgagtt ttcaatactg cgaatcctct gtgaaaacaa ggggaatgtg   4500
gttagctccg agctgctatt tcatgagata tggggcgacg aatatttcag caagagcaac   4560
aacaccatca ccgtgcatat ccggcatttg cgcgaaaaaa tgaacgacac cattgataat   4620
ccgaaatata taaaaacggt atgggggggtt ggttataaaa ttgaaaaata aaaaaaacga   4680
ctattccaaa ctagaacgaa aactttacat gtatatcgtt gcaattgttg tggtagcaat   4740
tgtattcgtg ttgtatattc gttcaatgat ccgaggaaa cttggggatt ggatcttaag   4800
tattttggaa aacaaatatg acttaaatca cctggacgcg atgaaattat atcaatattc   4860
catacggaac aatatagata tctttatttta tgtggcgatt gtcattagta ttcttattct   4920
atgtcgcgtc atgctttcaa aattcgcaaa atactttgac gagataaata ccggcattga   4980
tgtacttatt cagaacgaag ataaacaaat tgagctttct gcggaaatgg atgttatgga   5040
acaaaagctc aacacattaa aacggactct ggaaaagcga gagcaggatg caaagctggc   5100
cgaacaaaga aaaatgacg ttgttatgta cttggcgcac gatattaaaa cgccccttac   5160
atccattatc ggttatttga gcctgcttga cgaggctcca gacatgccgg tagatcaaaa   5220
ggcaaagtat gtgcatatca cgttggacaa agcgtatcga ctcgaacagc taatcgacga   5280 gtttttttgag attacacggt ataacctaca aacgataacg ctaacaaaaa cgcacataga   5340
cctatactat atgctggtgc agatgaccga tgaatttttat cctcagcttt ccgcacatgg   5400
aaaacaggcg ttattcacg cccccgagga tctgaccgtg tccggcgacc ctgataaact   5460
cgcgagagtc tttaacaaca ttttgaaaaa cgccgctgca tacagtgagg ataacagcat   5520
cattgacatt accgcgggcc tctccgggga tgtggtgtca atcgaattca gaacactgg   5580 aagcatccca aaagataagc tagctgccat atttgaaaag ttctataggc tggacaatgc   5640
tcgttcttcc gatacgggtg gcgcgggact tggattggcg attgcaaaag aaattattgt   5700
tcagcatgga gggcagattt acgcggaaag caatgataac tatacgacgt ttagggtaga   5760
gcttccagcg atgccagact tggttgataa aaggaggtcc taagagatgt atataatttt   5820
ttaggaaaat ctcaaggtta tctttacttt ttcttaggaa attaacaatt taatattaag   5880
aaacggctcg ttcttacacg gtagacttaa taccgtaaga acgagccgtt ttcgttcttc   5940
```

```
agagaaagat ttgacaagat taccattggc atccccgttt tatttggtgc ctttcacaga   6000
aagggttggt cttaattatg aataacatcg gcattactgt ttatggatgt gagcaggatg   6060
aggcagatgc attccatgct ctttcgcctc gctttggcgt tatggcaacg ataattaacg   6120
ccaacgtgtc ggaatccaac gccaaatccg cgcctttcaa tcaatgtatc agtgtgggac   6180
ataaatcaga gatttccgcc tctattcttc ttgcgctgaa gagagccggt gtgaaatata   6240
tttctacccg aagcatcggc tgcaatcata tagatacaac tgctgctaag agaatgggca   6300
tcactgtcga caatgtggcg tactcgccgg atagcgttgc cgattatact atgatgctaa   6360
ttcttatggc agtacgcaac gtaaaatcga ttgtgcgctc tgtggaaaaa catgatttca   6420
ggttggacag cgaccgtggc aaggtactca gcgacatgac agttggtgtg gtgggaacgg   6480
gccagatagg caaagcggtt attgagcggc tgcgaggatt tggatgtaaa gtgttggctt   6540
atagtcgcag ccgaagtata gaggtaaact atgtaccgtt tgatgagttg ctgcaaaata   6600
gcgatatcgt tacgcttcat gtgccgctca atacggatac gcactatatt atcagccacg   6660
aacaaataca gagaatgaag caaggagcat tccttatcaa tactgggcgc ggtccacttg   6720
tagataccta tgagttggtt aaagcattag aaaacgggaa actgggcggt gccgcattgg   6780
atgtattgga aggagaggaa gagttttcct actctgattg cacccaaaaa ccaattgata   6840
atcaatttt acttaaactt caaagaatgc ctaacgtgat aatcacaccg catacggcct   6900
attataccga gcaagcgttg cgtgataccg ttgaaaaaac cattaaaaac tgtttggatt   6960
ttgaaaggag acaggagcat gaatagaata aagttgcaa tactgtttgg gggttgctca   7020
gaggagcatg acgtatcggt aaaatctgca atagagatag ccgctaacat taataaagaa   7080
aaatacgagc cgttatacat tggaattacg aaatctggtg tatggaaaat gtgcgaaaaa   7140
ccttgcgcgg aatgggaaaa cgacaattgc tattcagctg tactctcgcc ggataaaaaa   7200
atgcacggat tacttgttaa aaagaaccat gaatatgaaa tcaaccatgt tgatgtagca   7260
ttttcagctt tgcatggcaa gtcaggtgaa gatggatcca tacaaggtct gtttgaattg   7320
tccggtatcc cttttgtagg ctgcgatatt caaagctcag caatttgtat ggacaaatcg   7380
ttgacataca tcgttgcgaa aaatgctggg atagctactc ccgccttttg ggttattaat   7440
aaagatgata ggccggtggc agctacgttt acctatcctg ttttttgttaa gccggcgcgt   7500
tcaggctcat ccttcggtgt gaaaaaagtc aatagcgcgg acgaattgga ctacgcaatt   7560
gaatcggcaa gacaatatga cagcaaaatc ttaattgagc aggctgtttc gggctgtgag   7620
gtcggttgtg cggtattggg aaacagtgcc gcgttagttg ttggcgaggt ggaccaaatc   7680
aggctgcagt acggaatctt tcgtattcat caggaagtcg agccggaaaa aggctctgaa   7740
aacgcagtta taaccgttcc cgcagacctt tcagcagagg agcgaggacg gatacaggaa   7800
acggcaaaaa aaatatataa agcgctcggc tgtagaggtc tagcccgtgt ggatatgttt   7860
ttacaagata acggccgcat tgtactgaac gaagtcaata ctctgcccgg tttcacgtca   7920
tacagtcgtt atccccgtat gatggccgct gcaggtattg cacttcccga actgattgac   7980
cgcttgatcg tattagcgtt aaaggggtga taagcatgga aataggattt acttttttag   8040
atgaaatagt acacggtgtt cgttgggacg ctaaatatgc cacttgggat aatttcaccg   8100
gaaaaccggt tgacggttat gaagtaaatc gcattgtagg gacatacgag ttggctgaat   8160
cgcttttgaa ggcaaaagaa ctggctgcta cccaagggta cggattgctt ctatgggacg   8220
gttaccgtcc taagcgtgct gtaaactgtt ttatgcaatg ggctgcacag ccggaaaata   8280
acctgacaaa ggaaagttat tatcccaata ttgaccgaac tgagatgatt tcaaaaggat   8340
```

```
acgtggcttc aaaatcaagc catagccgcg gcagtgccat tgatcttacg ctttatcgat   8400
tagacacggg tgagcttgta ccaatgggga gccgatttga ttttatggat gaacgctctc   8460
atcatgcggc aaatggaata tcatgcaatg aagcgcaaaa tcgcagacgt ttgcgctcca   8520
tcatggaaaa cagtgggttt gaagcatata gcctcgaatg gtggcactat gtattaagag   8580
acgaaccata ccccaatagc tattttgatt tccccgttaa ataaactttt aaccgttgca   8640
cggacaaact atataagcta actctttcgg caggaaaccc gacgtatgta actggttctt   8700
agggaattta tatatagtag atagtattga agatgtaagg cagagcgata ttgcggtcat   8760
tatctgcgtg cgctgcggca agatagcctg ataataagac tgatcgcata gagggtggt   8820 atttcacacc gcccattgtc aacaggcagt tcagcctcgt taaattcagc atgggtatca   8880
cttatgaaaa ttcatctaca ttggtgataa tagtaaatcc agtagggcga ataattgac    8940 tgtaatttac ggggcaaaac ggcacaatct caaacgagat tgtgccgttt aaggggaaga   9000
ttctagaaat atttcatact tccaactata tagttaagga ggagactgaa aatgaagaag   9060
ttgttttttt tattgttatt gttattctta atatacttag gttatgacta cgttaatgaa   9120
gcactgtttt ctcaggaaaa agtcgaattt caaaattatg atcaaaatcc caagaaacat   9180
ttagaaaata gtgggacttc tgaaaatacc caagagaaaa caattacaga agaacaggtt   9240
tatcaaggaa atctgctatt aatcaatagt aaatatcctg ttcgccaaga aagtgtgaag   9300
tcagatatcg tgaatttatc taaacatgac gaattaataa atggatacgg gttgcttgat   9360
agtaatattt atatgtcaaa agaaatagca caaaatttt cagagatggt caatgatgct    9420
gtaaagggtg gcgttagtca ttttattatt aatagtggct atcgagactt tgatgagcaa   9480
agtgtgcttt accaagaaat gggggctgag tatgccttac cagcaggtta tagtgagcat   9540
aattcaggtt tatcactaga tgtaggatca agcttgacga aaatggaacg agcccctgaa   9600
ggaaagtgga tagaagaaaa tgcttggaaa tacgggttca ttttacgtta tccagaggac   9660
aaaacagagt taacaggaat tcaatatgaa ccatggcata ttcgctatgt tggtttacca   9720
catagtgcga ttatgaaaga aaagaatttc gttctcgagg aatatatgga ttacctaaaa   9780
gaagaaaaaa ccatttctgt tagtgtaaat ggggaaaaat atgagatctt ttattatcct   9840
gttactaaaa ataccaccat tcatgtgccg actaatcttc gttatgagat atcaggaaac   9900
aatatagacg gtgtaattgt gacagtgttt cccggatcaa cacatactaa ttcaaggagg   9960
taaggatggc ggaatgaaac caacgaaatt aatgaacagc attattgtac tagcactttt  10020
ggggtaacgt tagcttttta atttaaaacc cacgttaact aggacattgc tatactaatg  10080
atacaactta aacaaagaa ttagaggaaa ttatattggg aaaaatatta tctagaggat   10140
tgctagcttt atatttagtg acactaatct ggttagtgtt attcaaatta caatacaata  10200
ttttatcagt atttaattat catcaaagaa gtcttaactt gactccattt actgctactg  10260
ggaatttcag agagatgata gataatgtta aatctttat tccatttggc ttgcttttga   10320
atgtcaattt taaagaaatc ggatttttac ctaagtttgc ttttgtactg gttttaagtc  10380
ttacttttga aataattcaa tttatcttcg ctattggagc gacagacata acagatgtaa  10440
ttacaaatac tgttggaggc tttcttggac tgaaattata tggtttaagc aataagcata  10500
tgaatcaaaa aaaattagac agagttatta tttttgtagg tatactttg ctcgtattat    10560 tgctcgttta ccgtacccat ttaagaataa attacgtgta agatgtctaa atcaagcaat  10620
ctgatctttc atacacataa agatattgaa tgaattggat tagatggaaa acgggatgtg  10680
```

```
gggaaactcg cccgtaggtg tgaagtgagg ggaaaaccgg tgataaagta aaaagcttac   10740
ctaacactat agtaacaaag aaagcccaat tatcaatttt agtgctgagg aattggtctc   10800
tttaataaat ttccttaacg ttgtaaatcc gcatttcct gacggtaccc c            10851
```

<210> SEQ ID NO 3
<211> LENGTH: 2456
<212> TYPE: DNA
<213> ORGANISM: Staphylococcus aureus
<400> SEQUENCE: 3

```
atgaactgat tatacttaac attaaaaaag atgataacac cttctacacc tccatatcac     60
aaaaaattat aacattattt tgacataaat actacatttg taatatacta caaatgtagt    120
cttatataag gaggatattg atgaaaaaga taaaaattgt tccacttatt ttaatagttg    180
tagttgtcgg gtttggtata tattttttatg cttcaaaaga taaagaaatt aataatacta   240
ttgatgcaat tgaagataaa aatttcaaac aagtttataa agatagcagt tatatttcta   300
aaagcgataa tggtgaagta gaaatgactg aacgtccgat aaaaatatat aatagtttag   360
gcgttaaaga tataaacatt caggatcgta aaataaaaaa agtatctaaa aataaaaaac   420
gagtagatgc tcaatataaa attaaaacaa actacgtaa cattgatcgc aacgttcaat   480
ttaattttgt taaagaagat ggtatgtgga agttagattg ggatcatagc gtcattattc   540
caggaatgca gaaagaccaa agcatacata ttgaaaattt aaaatcagaa cgtggtaaaa   600
ttttagaccg aaacaatgtg gaattggcca atacaggaac acatatgaga ttaggcatcg   660
ttccaaagaa tgtatctaaa aaagattata agcaatcgc taaagaacta agtatttctg   720
aagactatat caacaacaaa tggatcaaaa ttgggtacaa gatgatacct tcgttccact   780
ttaaaaccgt taaaaaatg gatgaatatt taagtgattt cgcaaaaaaa tttcatctta   840
caactaatga aacagaaagt cgtaactatc ctctagaaaa agcgacttca catctattag   900
gttatgttgg tcccattaac tctgaagaat taaaacaaaa agaatataaa ggctataaag   960
atgatgcagt tattggtaaa aagggactcg aaaaacttta cgataaaaag ctccaacatg   1020
aagatggcta tcgtgtcaca atcgttgacg ataatagcaa tacaatcgca catacattaa   1080
tagagaaaaa gaaaaagat ggcaaagata ttcaactaac tattgatgct aaagttcaaa   1140 agagtatttta taacaacatg aaaaatgatt atggctcagg tactgctatc caccctcaaa   1200
caggtgaatt attagcactt gtaagcacac cttcatatga cgtctatcca tttatgtatg   1260
gcatgagtaa cgaagaatat aataaattaa ccgaagataa aaaagaacct ctgctcaaca   1320
agttccagat tacaacttca ccaggttcaa ctcaaaaaat attaacagca atgattgggt   1380
taaataacaa acattagac gataaaacaa gttataaaat cgatggtaaa ggttggcaaa   1440
aagataaatc ttggggtggt tacaacgtta caagatatga agtggtaaat ggtaatatcg   1500
acttaaaaca agcaatagaa tcatcagata acatttctt tgctagagta gcactcgaat   1560
taggcagtaa gaaattgaa aaaggcatga aaaaactagg tgttggtgaa gatataccaa   1620
gtgattatcc attttataat gctcaaattt caaacaaaaa tttagataat gaaatattat   1680
tagctgattc aggttacgga caaggtgaaa tactgattaa cccagtacag atccttttcaa   1740 tctatagcgc attagaaaat aatggcaata ttaacgcacc tcacttatta aaagacacga   1800 aaacaaagt ttggaagaaa atattattt ccaaagaaaa tatcaatcta ttaaatgatg   1860
gtatgcaaca agtcgtaaat aaaacacata agaagatat ttatagatct tatgcaaact   1920
taattggcaa atccggtact gcagaactca aaatgaaaca aggagaaagt ggcagacaaa   1980
```

-continued

```
ttgggtggtt tatatcatat gataaagata atccaaacat gatgatggct attaatgtta    2040
aagatgtaca agataaagga atggctagct acaatgccaa atctcaggt aaagtgtatg     2100 atgagctata tgagaacggt aataaaaaat acgatataga tgaataacaa aacagtgaag    2160
caatccgtaa cgatggttgc ttcactgttt tattatgaat tattaataag tgctgttact    2220
tctcccttaa atacaatttc ttcattttca ttgtatgttg aaagtgacac tgtaacgagt    2280
ccattttctt tttttatgga tttcttattt gtaatttcag cgataacgta caatgtatta    2340
cctggtatac agtttaataa atttaacgtt attcatttgt gttcctgcta caacttcttc    2400
tccgtattta ccttcttcta cccataattt aaatgatatt gaaagtgtat gcatgc        2456
```

<210> SEQ ID NO 4
<211> LENGTH: 1062
<212> TYPE: DNA
<213> ORGANISM: Escherichia coli

<400> SEQUENCE: 4

```
ttaaaaatct tcgttagttt ctgctacgcc ttcgctatca tctacagaga aatccggcgt     60
tgagttcggg ttgctcagca gcaactcacg tactttcttc tcgatctctt tcgcggtttc    120
cgggttatct ttcagccagg cagtcgcatt cgctttaccc tgaccgatct tctcacctttt  180 gtagctgtac cacgcgcctg cttttctgat cagcttctct tttacgccca ggtcaaccag   240
ttcgccgtag aagttgatac cttcgccgta gaggatctgg aattcagcct gtttaaacgg   300
cgcagcgatt tgttcttca ccactttcac gcgggtttcg ctaccacca cgttttcgcc    360 ctctttcacc gcgccgatac gacggatgtc gagacgaaca gaggcgtaga atttcagcgc   420
gttaccaccg gtagtggttt ccgggttacc gaacatcaca ccaattttca tacggatctg   480
gttgatgaag atcagcagcg tgttggactg cttcaggtta cccgccagct tacgcatcgc   540
ctggctcatc atacgtgccg caaggcccat gtgagagtcg ccgatttcgc cttcgatttc   600
cgctttcggc gtcagtgccg ccacggagtc aacgacgata acgtctactg cgccagaacg   660
cgccagggcg tcacagattt ccagtgcctg ctcgccggtg tccggctggg agcacagcag   720
gttgtcgata tcgacgccca gtttacgtgc gtagattggg tccagcgcgt gttcagcatc   780
gataaacgca caggttttac cttcacgctg cgctgcggcg atcacctgca gcgtcagcgt   840
ggttttaccg gaagattccg gtccgtagat ttcgacgata cggcccatcg gcagaccacc   900
tgccccaagc gcgatatcca gtgaaagcga accggtagag atggtttcca catccatgga   960
acggtcttca cccaggcgca tgatggagcc tttaccaaat tgtttctcaa tctggcccag  1020
tgctgccgcc aacgctttct gtttgttttc gtcgatagcc at                      1062
```

<210> SEQ ID NO 5
<211> LENGTH: 3543
<212> TYPE: DNA
<213> ORGANISM: Escherichia coli

<400> SEQUENCE: 5

```
ttacgcctcc tccagggtca taccggcaaa catctcatcc atcagggcaa tcaacccggc     60
gttgggtcgg gttgtgtaaa tcccctgttg cggatgttct ttatcaacgc cacgcaggaa    120 cagataaaata acgccgccaa agtggtgctc atagtcgtaa tcagcaatgc gatggcgcag   180
ataacgatgc agcgccaggg tataaagctg atattgcaga tcatagcggt gtgcctgcat    240
tgccgctgcc atagcctgtt gggtgtaagc cgaactgtct tcacccaacc agttggattt    300
```

```
atagtcgagc aggtaataac gcccttcgtg gcggaacacc aggtcgataa agccttttaa    360
catgccacgt acctgcatga actccagcgg cgggcagcct gcggatagcg ggtcaaactg    420
gcggattaac gtatcaagct gactggcgat aagcggttca ctaatcggca gataaaactc    480
catctccacc tgtttattgc gggcggaaag ttgactcagg cttacgccgg tttcattgag    540
aggtgcctgg aggacagccg tgatccactc ggtcaatacc ggttcccact gcgattcaaa    600
gccgccgagt tccagttttt cccgcaccca gttcgggtca accggctggg taaaatccag    660
gtcttcaaac aaactgtgca agaacgtccc cggtgacgca ccgcgcggaa actgatgtgg    720
tgttaacgtc ggttcttcaa cgacgctggc aacgcctgca gcatcgacat ccagccgagg    780
catcaaatcc tgggcgatac cgtgaccacg ctgttgcaaa ccagagtagc tggtgacgcg    840
ccagttatcg ccgggcaatc gttgtaacgt cttcgcattc agctctgctg tagaaacatc    900
attaacctgc cagggttggt tatcaccagt ttgtgccgtt tgccaggcaa tatcatcatc    960
gcataacgct tcaatacagg tgcgaagccc tgccgcatct tgcggttccc cttttttgcag   1020
caaacgcccg agcgcacttt ggtggacgtc ggtgtcacct tttttatcgc cacgacggcg   1080
caccagcggt gcaacgccga gactgcaatg ccaaaccgaa cgtgtcagcg ccacgtaaag   1140
caaacgcaga tcttccgcca gacgttcggc ctccgcgagg tcgacgcttt ctggcgcagc   1200
attaagatcc agaactgcct caaacgagtg gcgatcgtga taaaacgcct gctcctggac   1260
gcggaaattg tgataaacg gcagccagac caatggatat tccagccctt tcgatttgtg    1320
gatcgtgaca atctgcacca gatgtttatc actttcgaga cgcatttgtt ggctggaggc   1380
attactgtct ggctcgagga tatgttgcga taaccagcgt accagcgcat gttcactttc   1440
cagctgcgtt ccggcttctt gtagcagttc gctgatatgc aagatatcgg taagacgccg   1500
ctcaccgcct gccgttgcca gcaagttttc agcaatgtta cgcgccgaca tcagcgcccg   1560
cagcatcggc ataacgccac gtttgcgcca gatttgccga taaccatcga actcttcgac   1620
taccacatcc cacgcatgtt cgtcattgtt cagcgtttcg atatccagcg cgttcagccc   1680
catcattgac gttgccagcg cactacgcag ggtgttctca cgttcgggcg tcatcaccgc   1740
ctgcaacaac caaagcattt cctgcgcttc cagagtttca aaaacactgt cgcggttcga   1800
aaggtaaacg gaagggattt ccagcaacgt taaggcatcg cgcacctggg cggcctcctg   1860
gcggctgcgc accagcacac tgatgtccga agcacgcacc ggacgcgcgt cgtcgccgtt   1920
catcagcaac gcttcgcccc gctgtccggc ttgtagccag tcgcggattt gcgcagcaca   1980
tacctgcgcc atggtacttt gataatcgcc aacgccgcag ctttcgcctt ccatcagcca   2040
cattttcatc gcaggctgtg tttcaccttt aaatacaaaa cgtaacgcct gattttccc    2100
ggctgatttc actggaataa acggtatttc gcgaaacatg aacgcgtcat cagtctggct   2160
gaaaagctta ttcacgctgt tcaccattcc tggtgcggaa cgccagttgg tgtctaaagt   2220
gtagtgggcg tgaacttcgc tacgcgcctt catataagtg aagatatccg caccccggaa   2280
tgcatatatg gcctgcttcg ggtcgccaat tagcaacaat gcggtttccg gctgatggtg   2340
ccagatacgg cgaaaaattc ggtactgctg ggggtcggta tcctgaaatt catcgatcat   2400
tgccaccgga atcgcgtac ggatcgccgc tgccaacacc tcaccgcttt cgctacgcag   2460
cgcggaatcg agccgactta acatgtcatc aaaacccaat tcgccacggc ggcgttttc    2520
acgcgctact gtttcgcgga tctcagccaa tgcgcgggtg atcaccagat cgcggatcga   2580
caatggttct gcaagcagtt gatcgatcgc tcaaacagt ggatgtcgcg gggtttcccc    2640
cccggccttc gtgcgatctt ctaagaaacg ctgggagaat ttttccagcg actccggcaa   2700
```

-continued

```
ctgataactg tttgtctctt cttctgccca ggcgctgatc ttgtcgatcc atttagcctg    2760
attgctacgg ttaaacttgc gtcgatcaat accagaagat tcgatcagcg catccagttc    2820
acccactgcg tcgcgccact gctgttttac cgtatcaata cgcgccacaa tttgcgcgtg    2880
acgggaagcc agcgtttcat catcggcgg cggtgctttg ataaccggcg cttcgccttg     2940
cagataacga ttaatatcgc gcagcaacgc ctgcggccct ttccaggttt caaagacgac    3000
ctgggctatt tcacgcggca gcgggtagca gtggcgacgc cagaaatcgg cgcaggcctg    3060
gtagcgtagc agagactcat cttcaatcag ctgctgctca aacagcatgc cggattcaaa    3120
ggcattcagg ttgagcatgc gctggcaaaa gccgtgaata gtaaagactg ccgcttcatc    3180
catctgccgt tcggctaaca acaaccactg cgcggcttgc gctttatcgt cgatctcttc    3240
cagcaggcgt tcgtacagtg gattgtcggt ggtttcacgc agacaggcga tgcgcaactc    3300
gtggatattg ctacggatac gaccgcgcaa ttctgccgtg gcagcctcgg taaaggtgac    3360
caccagcagt tcttcaacgg tcagcgggcg gggaaaggcg gcggaaccgc ctagtccaag    3420
taacaggcgc aaatagagcg ccgcaatcgt aaaggttttg cctgtgccgg cagaggcttc    3480
aatcaggcgc tcaccctgta agggcaagcg caaaggatct agtgtctcgg cgacatcact    3540
cat                                                                 3543
```

<210> SEQ ID NO 6
<211> LENGTH: 3369
<212> TYPE: DNA
<213> ORGANISM: Escherichia coli

<400> SEQUENCE: 6

```
tcatgactga ttaaagcgaa acagcggtaa caggaaacgt tgcgactgtt caacgatggc      60
ctccattgtc tctggtgtta attgccgcca gagcctttga taccagatat catcaccttc     120
gccacgcacc atcatgttgc cttcgtaagc ctgaaggaat tcgtacggg cttttttgcaa     180 cgtggaatcg tcatccagca tggcatcgtt ttgcgcgtca taacaggttt ttagccacgc    240
gccgccactt tcaggtaaca ccagcaatgg cgcggacatt ccttcacgat accctcaat    300 cagttgtgag aggtaatgca aagcctgttc ggctgcaagc ggcggaaaac gccactcgcc    360 gtcttgcgt agaaaaaggc gactttcacc attaccaccg ctggcacagt agacaaggtg     420
ttccagccaa agttgcattc cctgggccac acttaataaa gagggacgcc agcgcaacag    480
gccatccggc tgcacctgcg gcaaccagcc agttatctgc acaccgttgc aggcgagatc    540
aatttccata ctctgccccg gctggcgaca ggcaatgact ctgtcggcaa gctgctgcat    600
ctcctggcac tgtgtttccc agaaaatttc accaaaagcg ccatacggta aatcccctgc    660
cgctcggaag cggcggaaca agcgttcggc atcatcctgc tcaaccagtg cattcaataa    720
ctgctgattg atttgataac ggctaagtcc ttccagaata aatggctcgg tgtcggggat    780
ttcgctgtct tcagtacgga agttcacctg caaacgcatc tggaaaaatg cccgcaccgg    840
atgtgcccag aatcgttgta gcgtttccag cggcacggtt tccggtaagg taaacggcag    900
cggctgaaca aattcagaat gtgctttacc agcctggctg gccgcaggta gccattcacg    960
agcatagctt tgtcgttcgc ctggctggta gttttgtgga tcaaacggca tccgggtatg   1020
gaggcaagta agatgcgctt ttaccccttgc ctcgctttca tcacagttga gcgcttcatc   1080
gcccggtaga taatgacttt gcccgatgta gtcgatcagt tcctgcacca gtaccgacgg   1140
gaaacgctca ctgttatcct gaatggaacg accgatatag ctgatataga gttttgctg    1200
```

```
cgcggaaatt aacgcttcca ggaacagata gcggtcgtca tcgcgacggc tacggtcgcc    1260
acgcttcggt ttctggctca tcaggtcaaa gcccaatggc gcaagctgac gtggataaac    1320
gccgtcgttc attcccagca ggcaaaccac tttgaacgga attgaacgca ttggcatcag    1380
agtacaaatg ttaaccggtc cggcgagaaa acgctggctg atacgttctt gatccagacg    1440
ctgtgccagt tcatcacgca atagtgacag cggcaccgcg tcgccatact gcgcacctaa    1500
accttcggcg ataatcgcct gccattgttg ttcgatcagc gtcatcgccg cttcggtttc    1560
cgcatccggc aggaagaagg cgttgagcat atcgcgacaa accggcaacc actcttccag    1620
cggacgctcc tgtgccagcc cgcgacgcca gatgtttagc tgcattagca gtgaagccag    1680
atgccccacc agttctgcaa ttaagccgct cgattcatca taaggtagaa ccgattgcca    1740
ctcgccctgc gcgctctcca tcgcgtagcc aacaacata cgcgtcaggc caaatcgcca    1800
ggtgtgttgt ccggtggcgg ggagttccag ctcgcgaacg ttgtcgtcat ctatgcccca    1860
acgaatgccg gattcgttga cccactggcg taaataacgc agcccttctt cggtgatgtc    1920
aaaccgcgcc gccagcaccg gcacatccag caacgccagc acatcctctg acacaaaacg    1980
actgtcaggc agtgataaca ggctgataaa cgcttccagt accggatgtg actgccgcgc    2040
acgacggtcg gaaatggcgt aaggtaggta acgatccgca ggtgcgctac caaacacagc    2100
ctgaataaac ggactgtagc tgtcgatatc agccaccatc acgatgatgt cgcgcggagt    2160
aagtgtcggt tcttcctcca gcatcgccag caggcgatcg tgtaaaactt caacttcacg    2220
ctgcgggcta tggcaaacgt ggaaggtgat actgctatcc agtggatcaa gcgggcgttt    2280
gttatcgcta cgggaaaact cttcgatgtt cacaccagca acggcgcggt tttccagttc    2340
cagaatgtca gactgaatgt tatgcagcag gttatctggc gtgacatcga caaaggcgtc    2400
cagctcctgc tgctctcca ggtcagaaag gagataaatg tagtcgcgcc caagcttacc    2460
ccatgaagcc agcagcgggt tgccgacatc ctgttcacca tcgctgttaa agagctgccc    2520
ggcatttcg ctatcacgaa atagcggcaa ttcgcgatct tcaaaactgt gtcgacgctg    2580
acgggtcagc agtttcgcca gataagcagg atctttaata tcgccccagt aataacggca    2640
ggggttggta acaggagat ggatttcaat atgtttaccc agcgcctgta gcgcctggag    2700
ataaacaggc ggtaacgcgg aaataccgca tataaagacg cgcgaaggta accccggcgg    2760
gcaggtcgtc gcggactcca gcgtttcgat aaagcgctga tagagattgg cgcggtgcca    2820
gcgcggttgc ccgagttgat gggtatattc caccagcgcc ttccacaacg gggcttgcca    2880
ggcctgtgct tctcccagcc cttcaaccaa atgtcctgtt tcccactgtg ccagccagtc    2940
cggacgatag accagatact ggtcaaacag gtccgccgct tttgaggaaa gctggaacag    3000
ttttcgcttg tcgctatcgt cagtcagata atgccgcaac agggtaaagt cttcgcgctc    3060
cagcaattgc ggcagcagag tcatcagttt ccagctcatg ctctgtttgt taaaggcgct    3120
ctctttgggg atttccggta acacccggac gaacatatcc cagataaagc tcgctggcag    3180
cggaaaatca atgtttgccg caataccaaa cttttgcgac agggtcattt gcagccactg    3240
tgccataccg gtactttgca ccagaatcat ctctggttcg aaaggatcgt ccagccgttc    3300
gcgttcgaca ataaactcca tcaacgcttc cagcacgtcc agacgattgg aatggtagac    3360
ccttaacat                                                             3369

<210> SEQ ID NO 7
<211> LENGTH: 2109
<212> TYPE: DNA
<213> ORGANISM: Escherichia coli
```

<400> SEQUENCE: 7

```
ttgtatctgt tgaaagcct gaatcaactg attcaaacct acctgccgga agaccaaatc      60
aagcgtctgc ggcaggcgta tctcgttgca cgtgatgctc acgagggggca aacacgttca    120
agcggtgaac cctatatcac gcacccggta gcggttgcct gcattctggc cgagatgaaa    180
ctcgactatg aaacgctgat ggcggcgctg ctgcatgacg tgattgaaga tactcccgcc    240
acctaccagg atatggaaca gcttttttggt aaaagcgtcg ccgagctggt agaggggggtg   300
tcgaaacttg ataaactcaa gttccgcgat aagaagagg cgcaggccga aaactttcgc     360
aagatgatta tggcgatggt gcaggatatc cgcgtcatcc tcatcaaact tgccgaccgt    420
acccacaaca tgcgcacgct gggctcactt cgcccggaca aacgtcgccg catcgcccgt    480
gaaactctcg aaatttatag cccgctggcg caccgtttag gtatccacca cattaaaacc    540
gaactcgaag agctgggttt tgaggcgctg tatcccaacc gttatcgcgt aatcaaagaa    600
gtggtgaaag ccgcgcgcgg caaccgtaaa gagatgatcc agaagattct ttctgaaatc    660
gaagggcgtt tgcaggaagc gggaataccg tgccgcgtca gtggtcgcga aagcatctt     720
tattcgattt actgcaaaat ggtgctcaaa gagcagcgtt ttcactcgat catggacatc    780
tacgctttcc gcgtgatcgt caatgattct gacacctgtt atcgcgtgct gggccagatg    840
cacagcctgt acaagccgcg tccgggccgc gtgaaagact atatcgccat tccaaaagcg    900
aacggctatc agtctttgca cacctcgatg atcggcccgc acggtgtgcc ggttgaggtc    960
cagatccgta ccgaagatat ggaccagatg gcggagatgg tgttgccgc gcactgggct   1020
tataaagagc acggcgaaac cagtactacc gcacaaatcc gcgcccagcg ctggatgcaa   1080
agcctgctgg agctgcaaca gagcgccggt agttcgtttg aatttatcga gagcgttaaa   1140
tccgatctct tcccggatga gatttacgtt ttcacaccgg aagggcgcat tgtcgagctg   1200
cctgccggtg caacgcccgt cgacttcgct tatgcagtgc ataccgatat cggtcatgcc   1260
tgcgtgggcg cacgcgttga ccgccagcct tacccgctgt cgcagccgct taccagcggt   1320
caaaccgttg aaatcattac cgctccgggc gctcgcccga atgccgcttg gctgaacttt   1380
gtcgttagct cgaaagcgcg cgccaaaatt cgtcagttgc tgaaaaacct caagcgtgat   1440
gattctgtaa gcctgggccg tcgtctgctc aaccatgctt tgggtggtag ccgtaagctg   1500
aatgaaatcc gcaggaaaa tattcagcgc gagctggatc gcatgaagct ggcaacgctt   1560
gacgatctgc tggcagaaat cggacttggt aacgcaatga gcgtggtggt cgcgaaaaat   1620
ctgcaacatg gggacgcctc cattccaccg gcaacccaaa gccacggaca tctgcccatt   1680
aaaggtgccg atggcgtgct gatcacccttt gcgaaatgct gccgcccttat tcctggcgac   1740
ccgattatcg cccacgtcag ccccggtaaa ggtctggtga tccaccatga atcctgccgt   1800
aatatccgtg gctaccagaa agagccagag aagtttatgg ctgtggaatg ggataaagag   1860
acggcgcagt tcatcac cgaaatcaag gtggagatgt caatcatca gggtgcgctg   1920
gcaaacctga cggcggcaat taacaccacg acttcgaata ttcaaagttt gaatacggaa   1980
gagaaagatg tcgcgtctcta cagcgccttt attcgtctga ccgctcgtga ccgtgtgcat   2040
ctggcgaata tcatgcgcaa aatccgcgtg atgccagacg tgattaaagt cacccgaaac   2100
cgaaattaa                                                           2109
```

<210> SEQ ID NO 8
<211> LENGTH: 2235
<212> TYPE: DNA

<213> ORGANISM: Escherichia coli

<400> SEQUENCE: 8

| | | | | | |
|---|---|---|---|---|---|
| ctaactcccg | tgcaaccgac | gcgcgtcgat | aacatccggc | acctggttga | gtttacccag | 60 |
| cacgcgcccc | agcacttgca | ggttgtaaat | ctcaatggtc | atgtcgatgg | tcgccagttg | 120 |
| ctgtttggtg | tcgctacggc | tggcaacgcc | aagcacgttc | accttctcgt | tggcgagaat | 180 |
| ggtcgtgata | tcacgtaaca | acccactacg | atcattagct | accacgcgga | ccaccagcga | 240 |
| atatccggcg | gagtagctct | caccccatac | cgcgtcaaca | atgcgttctg | gcgcatggga | 300 |
| gcgcagttcc | gccagttgtt | cgcaatcggc | gcggtgtact | gaaataccgc | gcccctgggt | 360 |
| aatgaagccg | acaatctcat | ctccaggaat | cggctggcag | cagcgcgcga | tgtggtgcat | 420 |
| caggttgcca | acaccttcga | ctaccacgcg | accgttatct | ttactgcggt | tttgcggcgt | 480 |
| gtagcttttt | tgctgaagtt | gcttcagcgc | ggcggcgtcc | tgctcttcgg | cactcggctt | 540 |
| attaaattgc | gattgcagga | agttcaccat | ctgattgaga | cggatatccc | cgccaccaat | 600 |
| cgccgccagc | aactcgtcga | catcattgaa | gttgtaacgc | ggcagcagat | gttttctgc | 660 |
| ttctttcagg | ctgatcccca | gatgttccag | ctcgtcgtca | aggatttgcc | gcccagccag | 720 |
| aatgttttg | tcacggtcct | gtttacggaa | ccaggcgtga | attttcgaac | gcccacggct | 780 |
| ggttgtgacg | taaccgaggt | ttgggtttaa | ccagtcacgg | ctggggttcg | gctgtttctg | 840 |
| ggtgataatt | tcaatctggt | cgcccatctg | cagctggtag | gtgaacggca | caatgcgccc | 900 |
| gccaattttt | gccccgatgc | agcggtgtcc | gacatcactg | tggatgtggt | aagcgaagtc | 960 |
| cagcggcgtt | gatcccgcag | gcaaatcaac | gacatcacct | tcggcgtaa | agacgtacac | 1020 |
| ccggtcgtca | aagacctgac | tacgtacttc | gtcgagcatt | cgccggaat | cagccatctc | 1080 |
| ttcctgccac | gcaatcagtt | tacgcagcca | ggcaatccgg | tcttcatgtc | ccgaacgtgc | 1140 |
| gccgccagca | gccgcgccct | ctttatattt | ccagtgcgca | gcaacaccca | actctgcatc | 1200 |
| ttcatgcatc | tgtttggtgc | ggatttggat | ctcaacggtt | tttccacccg | gccccagaac | 1260 |
| cacggtatga | atagactgat | aaccgtttgg | tttcgggtta | gcgacgtaat | cgtcaaactc | 1320 |
| atccggcagg | tggcgatagt | gagtgtgcac | tatccccagt | gcggcatagc | aatcctgtaa | 1380 |
| acgctcggcg | acaatacgta | ccgcacgcac | atcaaacagc | tcatcaaagg | cgaggttctt | 1440 |
| tttctgcatt | ttacgccaga | tgctgtagat | gtgtttcgga | cgaccataca | cttccgcttt | 1500 |
| aacgccttca | gctttcatct | cagcgcgcag | atgaccaacg | aactcttcga | tgtagtgttc | 1560 |
| gcggtcgaga | cgccgttcat | gcagcagttt | ggcaattcgt | ttgtattcgg | ttggatggag | 1620 |
| gtaacggaag | cagtaatctt | ccagttccca | tttcagttgt | ccgattccga | gacggttagc | 1680 |
| cagcggtgcg | tagatgttgg | tacactcttt | tgccgccagt | acacgttcat | cttccggcgc | 1740 |
| atcttttact | tcgcgcagat | gagcaatacg | ctccgccagt | ttgatgacta | cgcagcgaaa | 1800 |
| atcatcgacc | atcgccaata | acatccggcg | aacgttatcg | acctgttcgg | aggaaacaga | 1860 |
| atcagtgtgc | gtcgctttca | gctggcggat | cgccgccata | tcacgcacgc | cgtgaataag | 1920 |
| gttaacgacc | gacttaccga | cgctctcacg | cagcacatct | tcgctgacta | cgttggcatc | 1980 |
| cgccagaggg | aaaagcagcg | ccgccgcag | cgtgtcaatg | tccatactta | atgtcgagag | 2040 |
| gatctccacc | atctcaacac | cacgccacaa | taacagactg | gcatccggat | gcccctgcgt | 2100 |
| ctgttgcaga | caatacgccc | aggtttcggc | taagcactca | cacgacttct | ggctggtaat | 2160 |
| acccagactt | gcgatccatt | tttccggatc | aaattcacca | gccttattga | tatgtgcact | 2220 |
| tcttaccgca | accat | | | | | 2235 |

<210> SEQ ID NO 9
<211> LENGTH: 609
<212> TYPE: DNA
<213> ORGANISM: Escherichia coli

<400> SEQUENCE: 9

```
atgaaagcgt taacggccag gcaacaagag gtgtttgatc tcatccgtga tcacatcagc      60
cagacaggta tgccgccgac gcgtgcggaa atcgcgcagc gtttgggggtt ccgttccccca    120
aacgcggctg aagaacatct gaaggcgctg gcacgcaaag gcgttattga aattgtttcc     180
ggcgcatcac gcgggattcg tctgttgcag gaagaggaag aagggttgcc gctggtaggt     240
cgtgtggctg ccggtgaacc acttctggcg caacagcata ttgaaggtca ttatcaggtc     300
gatccttcct tattcaagcc gaatgctgat ttcctgctgc gcgtcagcgg gatgtcgatg     360
aaagatatcg gcattatgga tggtgacttg ctggcagtgc ataaaactca ggatgtacgt     420
aacggtcagg tcgttgtcgc acgtattgat gacgaagtta ccgttaagcg cctgaaaaaa     480
cagggcaata aagtcgaact gttgccagaa aatagcgagt ttaaaccaat tgtcgttgac     540
cttcgtcagc agagcttcac cattgaaggg ctggcggttg gggttattcg caacggcgac     600
tggctgtaa                                                              609
```

<210> SEQ ID NO 10
<211> LENGTH: 435
<212> TYPE: DNA
<213> ORGANISM: Escherichia coli

<400> SEQUENCE: 10

```
gtgaaaagta ccagcgatct gttcaatgaa attattccat gggtcgctt aatccatatg       60
gttaatcaga agaaagatcg cctgcttaac gagtatctgt ctccgctgga tattaccgcg     120
gcacagttta aggtgctctg ctctatccgc tgcgcggcgt gtattactcc ggttgaactg     180
aaaaaggtat tgtcggtcga cctggagca ctgacccgta tgctggatcg cctggtctgt      240
aaaggctggg tggaaaggtt gccgaacccg aatgacaagc gcggcgtact ggtaaaactt     300
accaccggcg gcgcggcaat atgtgaacaa tgccatcaat tagttggcca ggacctgcac     360
caagaattaa caaaaaacct gacggcggac gaagtggcaa cacttgagta tttgcttaag     420
aaagtcctgc cgtaa                                                       435
```

<210> SEQ ID NO 11
<211> LENGTH: 41724
<212> TYPE: DNA
<213> ORGANISM: Enterobacteria phage P22 virus

<400> SEQUENCE: 11

```
agagaagatt tatctgaagt cgttacgcga gcagaacagg tcatctacga ccagaaattc       60
tctggcgcag ccgctgacct tctcaacgct aacatcatcg cccgtgattt gggcctcaaa     120
gagcagtcgc aagttgaaga cgtgacacct gataagggag atcgcgataa gcgacgctct     180
cgtatcaagg agctattcaa ccgtggaact ggacgcgatt cttgataacc tgagcgatga     240
agagcaaatc gaattgctcg agctactcga agaagagag aactaccgaa atacacactt      300
gctatatgag tttgcgccat acagcaaaca gcgtgagttc atcgacgcag gtcatgacta     360
tccagagcga tgttttatgg ctggtaacca gcttggtaag tcatttactg cgctgctga      420
agtcgcgttt caccttaccg ggcgataccc gggaacgaaa ggttatccgg ctgatggtaa     480
```

```
atatggcggg gagtggaaag gtaagcgttt ctatgagcct gttgtcttct ggattggtgg    540
cgagacaaac gagactgtaa ccaaaacgac tcaacgcatc ctgtgcggtc gtatcgaaga    600
gaatgatgag cctggctatg ggtcaatccc gaaagaggac atcattagct ggaagaagtc    660
tccgttcttc cctaatcttg ttgatcatct tctggttaag catcacacgg ctgatggtgt    720
tgaagatggc atttcaatct gctacttcaa gccatactcg caaggccgtg cacgctggca    780
gggtgacaca atccacggcg tgtggtttga cgaagagcca ccatacagca tttatggcga    840
aggtcttacc cgtacaaaca aatacgggca attctcaatt ctaacgttta ccccgctgat    900
ggggatgtct gacgttgtta ccaagttcct gaagaatccc agcaagtcgc agaaagtggt    960
caacatgacc atctatgacg ctgagcacta caccgacgag cagaaagagc aaatcatcgc   1020
atcctatcct gagcatgaga gagaggcgcg tgctcgcggt attcctacga tgggtagcgg   1080
tcgaatattc cagataccgg aagagacgat taagtgccag ccattcgaat gcccggatca   1140
cttctatgtt atcgacgctc aggacttcgg ctggaaccac ccgcaagctc acattcagct   1200
ttggtgggac aaagacgcag atgttttcta tctggcgcgt gtgtggaaga atcagagaa    1260 caccgcagtt caggcatggg gtgctgttaa gtcgtgggct aacaaaatac ctgtcgcgtg   1320
gcctcatgac ggtcaccaac acgaaaaggg cggtggtgag caacttaaaa cccaatatgc   1380
ggatgccggg ttctctatgc ttcccgatca cgcaacgttc ccggatggcg gtaactcagt   1440
agagtcaggc attagtgagc ttcgtgacct gatgcttgaa ggaagattca agtattcaa    1500 cacatgcgaa ccattctttg aagagttccg cctctatcat cgcgacgaga acggcaagat   1560
cgtcaagacc aacgatgatg tgctcgatgc tactcgctac ggctacatga tgcgccgctt   1620
cgccaggatg atgcgcgata tcagaaagcc gaaagaaaag aaaattcccg caccgattag   1680
accagtacgc agaggacgat aatggccgac aatgaaaaca ggctggagag catcctgtcg   1740
cgctttgatg cggactggac agccagtgat gaagccagac gagaggcaaa gaatgatctc   1800
ttcttctccc gcgtatctca gtgggatgac tggctatcac aatacacaac cctgcagtat   1860
cgcgggcagt tcgatgttgt acgtccagtg gtgcgcaagc tcgtttctga gatgcgtcag   1920
aaccctattg atgttctgta tcgtccaaag gacggagcaa gacctgatgc cgctgatgtg   1980
cttatgggta tgtatcgcac agacatgcgg cataacacgg ctaaaatcgc ggttaacatc   2040
gctgttcgtg agcagattga agctggagtt ggtgcgtggc gtctggtcac tgactacgaa   2100
gaccaaagtc cgacgagcaa caatcaggtt atccgtcgag agcctatcca tagtgcctgc   2160
tcccatgtta tctgggacag caacagcaaa ctgatggata gtctgacgc ccgtcactgc   2220 acagttatcc actcaatgag ccagaatggt tgggaggatt tcgcagaaaa atacgacctc   2280
gatgcggatg atattccatc attccagaac cccaacgatt gggtatttcc atggctgacg   2340
caggacacaa ttcagatcgc tgagttttac gaagtggtcg agaagaaaga gacggcgttt   2400
atctaccaag cccggttac gggtgagccg gtaagctact ttaagcgcga tattaaagac   2460
gtcatcgatg acctggctga tagtggattt atcaaaattg cagagcgcca gattaagcgt   2520
cgccgggtat acaaatcgat tatcacctgc actgctgtac tcaaagacaa gcagctcatt   2580
gctggcgagc atatccccat tgttccggtg ttcgagagt ggggcttcgt tgaagataaa    2640
gaagtgtatg agggtgtcgt ccgcctgaca aaagacggcc agcgtctgcg caacatgatt   2700
atgtcgttca acgccgacat cgtggcccgc actccgaaga agaagccgtt cttctggcct   2760
gagcagattg caggctttga gcatatgtac gacggtaacg acgattaccc atactacctg   2820
ctcaatcgca ctgacgaaaa tagtggagac cttccgactc agccgctggc atattatgaa   2880
```

```
aacccggaag tgccgcaagc caacgcctac atgctggaag cagcaaccag cgcagtaaaa    2940
gaggttgcca ctctcggagt tgatacagaa gcggtaaatg gcggacaggt tgcgtttgat    3000
accgtcaatc aactgaatat gagggctgac cttgagacat acgtgtttca ggataatctg    3060
gctaccgcca tgcgccgtga cggagagatt taccagtcga tagttaatga catctacgat    3120
gttcctcgca acgttacgat tacccttgag gatggcagcg agaaagatgt tcagctaatg    3180
gctgaggttg ttgaccttgc tactggagaa aagcaggtac taaacgatat caggggcgc    3240 tatgagtgct acacggatgt tggaccatca ttccagtcca tgaagcagca aaaccgcgca    3300
gaaattcttg agttgctcgg caagacgcca cagggaacgc cagaatatca actgctgttg    3360
cttcagtact tcaccctgct tgatggtaaa ggtgttgaga tgatgcgtga ctatgccaac    3420
aagcagctta ttcagatggg cgttaagaag ccagaaacgc ccgaagagca gcaatggtta    3480
gtagaggcgc aacaagccaa acaaggtcaa caagacccgg caatggttca ggctcagggc    3540
gtactcctgc aggggcaggc tgaactggct aaagctcaga accagacgct gtccctgcaa    3600
atcgatgcag ctaaagtcga agcgcagaac cagcttaacg ctgccagaat cgcagaaatc    3660
ttcaacaaca tggaccctcag taaacaatct gagtttagag agttccttaa aaccgttgct    3720
tcattccagc aggaccgcag cgaagacgct cgcgcaaatg ctgagttact ccttaaaggc    3780
gatgaacaga cgcacaagca gcgaatggac attgccaaca tcctgcaatc gcagagacaa    3840
aatcaacctt ccggcagtgt agccgagaca cctcaataag agagagttaa tcatggaacc    3900
aaccaccgaa attcaggcaa ctgaagactt aaccctgtcc ggcgatcatg cagcggcatc    3960
tgctgatagc ttagttgtcg ataatgccaa cgacaatgca ggtcaggaag agggctttga    4020
gattgtcctg aaggacgatg agacagcacc aaaacaagac ccggcaaaga acgcagaatt    4080
cgcccgccgc cgcatcgagc gcaaacgaca gcgcgagctt gagcagcaga tggaggcagt    4140
taaacgcgga gaattgccgg agagtttacg ggtaaaccct gaccttcctc ctcagccaga    4200
cattaacgcc tatctgtcag aagaaggcct ggctaaaatat gactacgaca acagccgtgc    4260
gcttgccgct ttcaatgctg ctaataccga atggctaatg aaagcgcagg acgcccgcag    4320
caatgccgta gcagaacagg gccgcaagac tcaggagttt acccagcaat cagcgcaata    4380
cgtcgaagct gcccgcaaac actatgacgc ggcggaaaag ctcaacatcc ctgactatca    4440
ggagaaagaa gacgcatttta tgcaactggt tccgcctgcg gttggggccg acattatgcg    4500
cctgttcccg gaaaagtccg ccgcgctcat gtatcacctg ggggcaaacc cggagaaagc    4560
ccgccagtta ctggcgatgg atgggcagtc cgcgctgatt gaactcactc gactatccga    4620
acgcttaact ctcaagcctc gcggtaaaca aatctcttcc gctcccctg ctgaccagcc    4680 tattaccggt gatgtcagcg cagcaaataa agatgccatt cgtaaacaaa tggatgctgc    4740
tgcgagcaag ggagatgtgg aaacctaccg caagctaaag gcaaaactta aggaatccg    4800 ataatggctt tgaacgaagg tcaaattgtt acactggcgg tagatgaaat catcgaaacc    4860
atctccgcaa tcactccaat ggcgcagaaa gccaagaaat acaccccgcc tgctgcttct    4920
atgcagcgct ccagcaatac catctggatg cctgtagagc aagagtcacc cactcaggag    4980
ggctgggatt taactgataa agcgacaggg ttactggaac ttaacgtcgc ggtaaacatg    5040
ggagagccgg ataacgactt cttccagttg cgtgctgatg acttgcgaga cgaaactgcg    5100
tatcgtcgcc gcatccagtc tgccgctcgc aagctggcga acaacgttga gttgaaagtc    5160
gcaaacatgg ccgccgagat gggttcgctg gttatcacct cccctgatgc catcggcact    5220
```

```
aataccgcag acgcctggaa ctttgtggcc gacgcagaag aaatcatgtt ctcccgcgaa      5280
cttaaccgcg acatggggac atcgtacttc ttcaaccctc aggactacaa aaaagcgggt      5340
tacgacctga ccaagcgtga catcttcggg cgtattcctg aagaagcata ccgagatggc      5400
accattcagc gtcaggtcgc tggcttcgat gatgtcctgc gctctccgaa acttcctgtg      5460
ctgaccaaat ccaccgcaac tggcatcact gtatccggtg cgcagtcctt caagcctgtc      5520
gcatggcaac tggataacga tggcaacaaa gttaacgttg ataaccgttt tgctaccgtc      5580
accctgtctg caactaccgg catgaaacgc ggcgacaaaa tttcgtttgc tggcgttaag      5640
ttccttggtc agatggctaa gaacgtactg gctcaggatg cgactttctc cgtagtccgc      5700
gttgttgacg gtactcatgt tgaaatcacg ccgaagccgg tagcgctgga tgatgtttcc      5760
ctgtctccgg agcagcgtgc ctacgccaac gttaacacct cgctggctga tgcaatggca      5820
gtgaacattc tgaacgttaa agacgctcgc actaatgtgt tctgggctga cgatgctatt      5880
cgtatcgtgt ctcagccgat tccggctaac catgaacttt ttgcaggtat gaaaactacc      5940
tcattcagca tccctgatgt tggcctgaac ggtatcttcg ctacgcaggg tgatatttcc      6000
accctgtccg gcctgtgccg tattgcgctg tggtacggcg taaacgcgac acgaccggag      6060
gcaatcggtg ttggcctgcc tggtcagact gcgtaactaa caggggctgc ggccccttc       6120 tttatggagt ggctatgaaa atagcaatct ataagcccgg tggaagcatc atggtatggg      6180
gcgtcatggc tcagatgaag gtcatcgact ccagcgaact tccggaatat gtcaaagatg      6240
gctggcttga tcatccatca aagctgctgc ccgtggaagc agatgatgtt aagccacgca      6300
aaggccgcaa gcctaaggcg gtaagcgatg cagataaaga ctaaaggcga tctggtcagg      6360
gctgcgcttc gtaagttggg cgtggcatca gatgcaaccc ttaccgatgt cgaacctcag      6420
tctatgcagg atgccgttga tgatctggaa gcgatgatgg cggagtggta tcaggacggg      6480
aaaggcatca ttaccggtta tgtattctca gatgatgaga atcctcccgc tgaaggtgat      6540
gatcacggcc ttcgctcaag cgcagtcagc gcggtattcc acaatcttgc ctgccgcatt      6600
gctcctgatt atgcgcttga ggctactgcc aaaattatcg ccactgctaa atacggaaaa      6660
gagcttctct ataagcaaac cgccatttcc agagcaaaaa gagcgcctta cccatcacgt      6720
atgccaactg gcagtggaaa cagtttcgcc aatctgaacg aatggcatta ttccccggga      6780
gaacagaatg ccgattcaac aactcccat gatgaaggga atgggtaaag acttcaagaa       6840
cgccgattat atcgactatc tgccagtgaa tatgctggca cacccaaag aaatccttaa       6900 cagcagcggc tatctccgct cattccctgg cattaccaaa cgttatgata tgaacggcgt      6960
atcgcgtgga gttgagtaca acaccgctca gaatgctgtt tatcgtgttt gtggtggcaa      7020
gctctacaaa ggagaaagcg aagttggtga tgttgccgga agtggtcgcg tatcaatggc      7080
acatggtcgg acatcacagg cggtaggcgt taatggccaa ctggtcgagt atcgctatga      7140
tggcacggtt aaaaccgtct caaactggcc tgcagacagc ggattcacgc agtatgagtt      7200
aggttcagtg cgtgacatta cgcgcttacg tgggcgttat gcgtggtcaa aagacggcac      7260
tgattcatgg tttatcactg acctcgaaga tgaatcgcat cctgaccgct acagcgcaca      7320
atatcgcgca gagtcgcagc ctgacggcat catcggcatc ggaacatgga gagacttcat      7380
cgtctgcttt ggttcgtcaa cgatagagta tttctcctg acaggcgcaa ccaccgctgg       7440
cgctgcgttg tatgtcgcac agccatcgtt gatggtacag aagggcattg ccggaacata      7500
ctgtaaaacg ccgttcgctg attcatacgc ctttatcagt catccggcta ctggcgcacc      7560
ttccgtctac atcatcggtt cagggcaggc atcgccaatt gcgaccgcca gtattgagaa      7620
```

```
aattatccgc tcatataccg ctgaagaaat ggcgacgggt gtgatggaga ctttgcgctt    7680
cgattctcat gagcttctga ttattcatct ccctcgccat gttctggttt acgacgcatc    7740
gtccagccag aacggacctc agtggtgtgt gctgaaaacc gggctttacg atgatgtata    7800
tcgcggcgtc gacttcatgt acgaaggaaa ccagataacg tgcggcgaca atcagaagc     7860 ggtggtcgga caattgcaat tcgacatcag cagccagtac gacaaacaac aagaacacct    7920
actgtttacg cccctttca aagcagataa cgccagatgc ttcgaccttg aggttgaatc     7980
atccactggt gttgctcaat acgctgaccg cctgttcctg tctgcaacaa ctgacggcat    8040
caattacggt cgtgaacaga tgattgagca gaacgagccg tttgtgtacg acaagcgcgt    8100
tttatggaaa cgtgttgggc gcattcgtcg attaatcgga ttcaaactgc gagtaatcac    8160
caaatcacca gtaacactat ccgggtgtca aattcgtctg gagtaaaata tggcagaccc    8220
gtcacttaat aatcctgtcg ttattcaggc cacccgtctc gacgcttcaa ttcttccccg    8280
taacgtcttt agcaagtctt atctgctcta tgtaatcgcg cagggaactg acgttggtgc    8340
tattgcagga aaggcaaacg aagctggaca gggtgcttat gacgcacagg taaaaaatga    8400
tgagcaggat gtagagcttg cagaccatga agcaagaatt aagcaactgc gcatcgatgt    8460
agatgatcac gaaagtcgca ttactgcgaa cactaaggca attactgcgc tgaatgtcag    8520
ggtaactacc gctgaaggag aaattgcctc cttgcagact aatgttagtg ctcttgatgg    8580
cagggttacg actgccgaga caatatttc ggcattgcag gctgactacg tatctaaaac     8640
cgccactaca tctcaatcgc tggcttcacc cctcaacgtg acaacgtcat attcagtcgg    8700
cggaaagaag gttgtcggcg ctcgccagac tggatggacc gcggcaacag gtacggcgaa    8760
taaaggcgta ttcgatgctg acctgacatt cgccgttagc gatacttaca cgcaatctga    8820
aatccaggct atagccaatg ctctaattac tgagcgtcgg cgcactaagg ctttggaaga    8880
cgccttgcgt gcacatgggt tgattgatta atgattacat tcactccaac acgcaacatc    8940
gacctgatag aaatggttgg caaccacccc gacatcattg ccggaagcaa caacggtgac    9000
ggatacgact acaagcctga gtgtcgttac tttgaagtga acgtacatgg tcagttcggt    9060
ggcatcgtgt attacaacga gattcagccg atgacctttg actgccacgc catgtacctg    9120
cctgagattc gcggattcag taaggaaatc ggactggcgt tctggcgata tattctcacc    9180
aataccaccg ttcagtgcgt tacatcattt gctgcacgca aatttcgcca cggtcagatg    9240
tactgcgcaa tgattggcct taagcgtgtg ggaaccatca agaaatactt caaaggcgta    9300
gatgacgtga cgtttacgc cgccacccga gaagagttaa ccgaattact gaataacggg     9360
agataaacat gttatatgca tttacgctgg gcaggaaact gcgcggtgag gaaccttctt    9420
atcctgaaaa aggcggtaaa ggtggcgcag ataaaagcgc aaagtatgca gcagaagcgc    9480
aaaagtatgc cgcagacctg caaaaccagc agttcaatac catcatgaac aacctgaagc    9540
cgtttactcc tctggcagat aagtatatcg gcagtcttga aggtttatcg tctctcgaag    9600 gtcagggca ggcgcttaat aattactata actcccaaca ataccaggac cttgcggggc     9660
aggctcgcta tcagaatctg gcagcggcag aagcaacagg tggcctgggt tctacagcga    9720
ccagtaacca gctttcagca atcgcccaa cacttggtca gcaatggctg tcaggtcaga     9780
tgaataacta tcagaacctt gcaaatattg gtcttggtgc gcttcagggg caggcaaacg    9840
ccggacagac atatgccaac aatatgagtc agatttcaca gcaaagcgcg gctcttgcag    9900
cggcaaatgc caacagacca tcagctatgc aatctgctat tggcggaggt gcgtctggtg    9960
```

```
cgattgctgg ggctggactt gcgaaattaa ttggttcatc aactccgtgg ggtgctgcca     10020
tcggtggtgg tattggtctg cttggctcgt tgttttaagg ggtaatcaat ggctacgtgg     10080
cagcagggca ttaattcagg tggttttctg gctggcattg gtgcgcaaaa tgagaacgca     10140
ccaaaggcaa gagatattaa cgcaacgctg ggtctgattc gcgaaaacaa tgatttagcc     10200
cgttcaggcg ctaataatgt ggctttaaca gggctgcgtg gtctggctgg cgttgctgat     10260
atttataacc aggaacagca acagaaagcg ctaaacgcat tcaaccaggt tcatgccaac     10320
gcatgggcta ctggtgaccc gtctggcctg tttaagtttg ctcaggaaaa ccctgcgttt     10380
gttgcgcagg cacagcaggc gttttccggt cttaatgagc agcagcgtaa cgatatgggc     10440
gatttagcta tgaaggctaa cgtcgctctt tctcagggc cggaagccta cagtaaattc     10500
attactgata acaaggacag gttaaatcgt gttggcgcta atccggactg gatgatacag     10560
actggagtgc agaatccaga acagctatca cacatgctga ctacgatgtc cctcggtgcg     10620
cttggacccg aaaaggcgtt tgctgttcag gataagatgg ttggccgtga gattgaccga     10680
ggcaggctgg ctgaaacaat ccgcagcaat aaagccggtg aggggcttca ggctcgcggg     10740
cagaatataa caatgcgtgg acaagatatg tcagcggcaa cagcacgacg cggtcaagat     10800
ttggcaacgc aaagagcaaa cgccagaacg atatcaggca gcgaaggaaa tcgggtcgtt     10860
cagcttgcag acgggcgaac agtcagcgtc ggtggaaaac ttcacggcgc aggggcgaat     10920
gcgttttacg aaggtattga cgataacggc aatatggttc gtgtcccggc aagcgccatt     10980
gccgcacctc caacgtctgc ggcaagcgca cagaactacg caatgaagaa agacattgat     11040
gcaatcgcaa atgcagatgc ttctgctctc gatttcatga ctggaatgac tggcggagca     11100
ggaaatccgg caattggtgc agatgttcgc agccgactca caggcaaaga gcaacgccag     11160
ttatataact ccgcacaacg tattcaggga agaatgcaga atcagggcgt ggcagcagca     11220
agagatatgg gcgctagcgg tatcaacacc attgcagaag cgaagatgta ttttcagggg     11280
atgccgcagg ttgactactc aagcccggag gctatgcagc agtctattcg tgagattcag     11340
gaatacacca acaattataa ccagcagtac aacgttaatg ttggtaatgg tgggctgaaa     11400
tcaccaaggc agcagccaga tactcagcaa tcagccggag gaagttacac gtctaaatct     11460
ggcattaaat tcacggtgga ataatgaaag ttaccgctaa tggcaagaca ttcaacttcc     11520
ctgatggaac cagcacagaa gacatcggcg ctgcagttga tgagtatttt gcagggcagg     11580
catcagcagc agaaacacaa ccagcagaac agcaggaaga accacagcag cctgaacaat     11640
ccctgatgca acgggctggt gacttactca ctggcggcca gtcagcaggc cagattgcag     11700
agcaggctgg gcgtgggctc gtaaatatcc cgtttgatgt attgcagggc ggcgcgagtc     11760
tcattaacgc aatcagccaa gggttaggcg gcccgaaagt gctggatgac gtgtatcgcc     11820
cggtagatcg cccgactgac ccatatgcgc aggcaggaga atccattggc gggtatctaa     11880
ttccaggcgc tggcgtcgct ggcaacatgg cgatcggctc agtggctgag gcagccaatc     11940
agcagggaga ttttgctggc aacgttgcga agaatgccgc ggtaaacctc ggcgctcagg     12000
ggctactttc tggcgcagct aaattagtcg ggcgtggcat tactgcagca agaggtgaga     12060
ttgcaccaga ggccagacaa ctgattgata ccgctgagat tatgggtgtt aagcccatga     12120
cgtcagatat gatcaagcct ggcaatgcct ttactcgcag cttaatgcaa ggtggtgaag     12180
gtgcgttgct tggaacggga ggaaaaagag cagaacagta cgctatccgc agcaaacttc     12240
taggcgacta tttcgaccga gtgggaggat acaatcctga tgatatcgtt aagtcaatga     12300
ccagtacagt aggagggcgt aaaaatgcgg caggagcagt aagagatgaa atagtaaata     12360
```

```
gaatgggaag cgctccagtg ggaaccacca attcaattaa tgcaattgat acaaatattg   12420
caagacttga gaagctcggc acatcagcgg accagaggct tttgacagcg cttaaaaatc   12480
taaaggggga attgaatagc gggaatgttg attttgatct cctgcaacag catcgcactg   12540
cattccgcac caatgttcag ggtgatgcga tggtattccc aaatcaggcc aaggctgcaa   12600
ctaacatggt tgaaaatgca atgactcgtg atttgcgcaa tgctgtcggt aaatcactag   12660
ggccacaaga tgcagcaaaa tatctcaaat ccaactcaga cttcgcaaac atttacaata   12720
aggttctgaa taagcgcatc tctaatacgc taaataaagc cagaagcgaa tacacacccg   12780
agcttattaa caccgttgtt ttcagtcgca aaccgtcaga tataaagcgc atatggagct   12840
ccctggataa caaggaaag acgcaatgc gagctgcata catcagcaag attgctgaaa    12900
aaactggtga ttctccagct aagttcataa ccgaagtaaa caaattaaaa gcgcaatccg   12960
gaggtgagat ttacaacacc attttcagcg gacgacacat gaaggaactt gatgcgcttc   13020
atgatgtgct gagacaaaca gctaggtctg attcggcaaa tgttgtcaca cagacggggc   13080
aggcgctggc aaatccggta aggcttggcg ctgcaattcc tactttaggt aagtcactcg   13140
cagcagaggc cggctatggc ttggcaatga gggtgtatga gagcaagcca ataagaaata   13200
tgctactcag gctggctaac accaagccgg gcacacctgc atatgagcgt gcgctgaatc   13260
aggccgctac tgcagtgcgc cctcttttag ctaacgaagc tacccggcag tagcgctata   13320
agccaaggac ggcatttatt ttatagtttt tatgaattct ttattaaatc cattcgcttc   13380
tccggggtat cttccaaaga caattttta aaaaacagaa aaaataaaga tagcaatgct    13440
taacaacaat tgcagtatca ttggaaccca agaacaaca ggctctatat tcatgaaacc    13500
aaatattctt cctgcgatca tggcaaagta ccacactgtt atcagcaaac ttagtggtat   13560
atgaattact gatattatca atccaagggc atcagtaatt ctgttttcaa atctttcagg   13620
ggaaaacttt tctttaaggt aattgagtac gtaggcctca ttctctggat ttttagcatt   13680
tttccctatt gcaatagaaa cctcagatat ccttgattca agtcttttac gtttaataaa   13740
attagaaaaa aacaaccacg caatctgcaa tcctatcccc agaaatagag ttgcggcaac   13800
tagcacagca taactcatag aatcagacac accaacctcc ttagttttgt gcaggatacc   13860
atgaaaaaag ttaacattgg aaacgtacca aagatgctcg ttccgctctt tgagagcggt   13920
acaattgtgt tttgtagaga cttttccgaa tggcaacgcc tgcatcaaaa acttggtgtg   13980
gacgtgcagg actcggatgc caacggagcg tctcatacaa tgagcagcga gatggtgtt    14040 ttgcatgtga taggcgtgtt caatggcaaa ctatctacta ttgcccatga gtgcgctcac   14100
atggcattcg atatctgctc aagggtcggt gttgatgttg aaccaggaag agccaacgag   14160
acttactgct acttaatgag caggcttgtt gagttctgcg agcgacatat caaaaagccg   14220
gagtgacccg gcttgattat tacttttgc tgtctggagt tcgcttatct aatacccagc    14280
cattacctgg ctttgttgtt ggtggaagcc tttcgttgtc cttgacggtg gcaaaattgt   14340 cttttcttacc gcctcgcggg ccaacttctt ggtatattcc gccgtttttt cctgtgttt    14400 cacctggttt tttcgccatg atataccta acatacaccc gttattgggc gattaaatat    14460
tgatctcatt ttataagtag tcaatatggc ccaggtaaat gcaaaaatta acccgccgtc   14520
aggtggtttt tttgtacaaa tccttcagcg tatcaaacac catcttctta acaagctctg   14580
actgctcatc agcgagtcgt tctgcatcgt tgcgatatcc agtcacaggc gatggttttg   14640
atagagcatc ttggacgatt tgtaacaact cggagttcat tgatctccca ttcgcctccg   14700
```

```
ccctgaattt taatttctcc ctgacttcca taggcatacg aagttaaag tgcggatcat    14760 ctctagccat gccatcactc caagttagtg tattgacatg atagaagcac tctactatat    14820
tctcaatagg tccacggtgg acctgtattg tgaggtgaat atgaaaggaa tgagcaaaat    14880
gccgcagttc aatttgcggt ggcctagaga agtattggat ttggtacgca aggtagcgga    14940
agagaatggt cggtctgtta attctgagat ttatcagcga gtaatggaaa gctttaagaa    15000
ggaagggcgc attggcgcgt aaagttgaag ccccaactgc ggtaacagtc agggcttcgg    15060
ttgtcagtaa atccttggag aaaaaccaac atgaatagta tagcaatttt agaagcagtt    15120
aacacctctt acgtgccgtt taatggacag catgttctta ccgctatggt ggctggagtt    15180
gcctatgtag ctatgaagcc agtcgtggat aacattggtc tctcatggtc atctcaggtg    15240
caaaagcttc tgaaaatgaa agataaattc aactatgtcg atatcgacat ggttgctgga    15300
gatatgaaga aacgtctcat gggatgcatc ccactgaaga aacttaacgg ctggctgttc    15360
agcattaacc ctgagaaagt tcgtgcagac atccgtgaca aactgattaa gtaccaggaa    15420
gaatgcttca ccgttctgta tgattactgg acgaaaggta aggctgaaaa cccgcgtaag    15480
aaaacatctg tcgatgagag gacgccgctt cgtgatgctg taaatatgct tgtaagcaaa    15540
aagcatctga tgtacccaga agcttatgca atgatccatc agcgtttcaa tgtggaaagt    15600
attgaagaac tggaggcgtc tcagataccg ctggccgtag agtacatcca cagggtagtg    15660
cttgaaggtg agttcattgg caaacaagag aagaaaacca acgatctttc tgcaaaagaa    15720
gcaaacagcc ttgtatggtt atgggattat gccaaccgct cacaggcgtt attccgcgaa    15780
ctgtatcctg caatgagaca gattcaatct aactattcag gaaagtgcta cgactacggc    15840
catgaattct cgtacatcat tggaatagcg agagacgttt taattaatca cacgcgagat    15900
gttgatatta atgaacctga cgggccaacg aatctttccg catggatgag acttaaggat    15960
aaagagcttc caccttcatt acatcgctac tgacagataa ccaacgcaac gacccagctt    16020
cggctgggtt tttttatgcc caaaattcac cgtagccacg cttaggtaat gagcttgaag    16080
gagagaccta caaaaaaatt gtaggtcgaa aagcgaacaa aataacttcc gaaaaagttg    16140
ttttatcaca aaaaattcac cgtagccatg ctgcggcaat tccttgcatc tggagcaaat    16200
taaatgacag acatcactgc aaacgtagtt gtttctaacc ctcgtccaat cttcactgaa    16260
tcccgttcgt ttaaagctgt tgctaatggg aaaatttaca ttggtcagat tgataccgat    16320
ccggttaatc ctgccaatca gatacccgta tacattgaaa atgaggatgg ctctcacgtc    16380
cagattactc agccgctaat tatcaacgca gccggtaaaa tcgtatacaa cggccaactg    16440
gtgaaaattg tcaccgttca gggtcatagc atggctatct atgatgccaa tggttctcag    16500
gttgactata ttgctaacgt attgaagtac gatccagatc aatattcaat agaagctgat    16560
aaaaaattta agtattcagt aaaattatca gattatccaa cattgcagga tgcagcatct    16620
gctgcggttg atggccttct tatcgatcga gattataatt tttatggtgg agagacagtt    16680
gattttggcg gaaaggttct gactatagaa tgtaaagcta aatttatagg gatggaaat    16740 cttatttta cgaaattagg caaaggttcc cgcattgccg gggttttttat ggaaagcact    16800 acaacaccat gggttatcaa gccttggacg gatgacaatc agtggctaac ggatgccgca    16860
gcggtcgttg ccactttaaa acaatctaaa actgatgggt atcagccaac cgtaagcgat    16920
tacgttaaat tcccaggaat agaaacgtta ctcccaccta atgcaaaagg gcaaaacata    16980
acgtctacgt tagaaattag agaatgtata ggggtcgaag ttcatcggc tagcggtcta    17040 atggctggtt ttttgtttag agggtgtcac ttctgcaaga tggtagacgc caataatcca    17100
```

```
agcggaggta aagatggcat tataaccttc gaaaaccttta gcggcgattg ggggaagggt      17160
aactatgtca ttggcggacg aaccagctat gggtcagtaa gtagcgccca gttttacgt      17220 aataatggtg gctttgaacg tgatggtgga gttattgggt ttacttcata tcgcgctggg      17280
gagagtggcg ttaaaacttg gcaaggtact gtgggctcga caacctctcg caactataat      17340
ctgcaattcc gcgactcggt cgttatttac cccgtatggg acggattcga tttaggtgct      17400
gacactgaca tgaatccgga gttggacagg ccagggact acctataac caataccca      17460 ctgcatcagt taccctaaa tcacctgatt gataatcttc tggttcgcgg ggcgttaggt      17520
gtaggttttg gtatggatgg taagggcatg tatgtgtcta atattaccgt agaagattgc      17580
gctgggtctg gcgcgtacct actcacccac gaatcagtat ttaccaatat agccataatt      17640
gacaccaata ctaaggattt ccaggcgaat cagatttata tatctggggc ttgccgtgtg      17700
aacggtttac gtttaattgg gatccgctca accgatgggc agggtctaac catagacgcc      17760
cctaactcta ccgtaagcgg tataaccggg atggtagacc cctctagaat taatgttgct      17820
aatttggcag aagaagggtt aggtaatatc cgcgctaata gtttcggcta tgatagcgca      17880
gcgattaaac tgcggattca taagttatca aagacattag atagcggagc attgtactcc      17940
cacattaacg gggggccgg ttctggctca gcgtatactc aacttactgc tatttcaggt      18000
agcacacctg acgctgtatc attaaaagtt aaccacaaag attgcagggg ggcagagata      18060
ccatttgttc ctgacatcgc gtcagatgat tttataaagg attcctcatg ttttttgcca      18120
tattgggaaa ataattctac ttctttaaag gctttagtga aaaaacccaa tggagaatta      18180
gttagattaa ccttggcaac actttagata tgtaataaaa atgggtgtaa acacccattt      18240
ttattttatg ttaaatattc tatagctaat taaacctaac aactatggtt tcccctacaa      18300
caccaatatc gtatacgtta ttaccagatt ttttccaccc attttcaagt ttaacctctt      18360
tgtcatatag tctgtaattt ctggaaaaca catttcttg cattaacacc tctgaccaca      18420
tccaatcatt gttaataatg cgtggtatta actctctcat taaaggatgc tttattacta      18480
tgttttcatt tattggtgca tacggttctg tgccaatgaa ttttatattt ttttgtctc      18540 ttccaaatcc aagataatct atgtcttgag atattctatt tacaatgctt tcctcaagct      18600
gaaactgtgc atttatggca ttgtaagcac cataagaaaa tattgttgat attaaaagaa      18660
taaaagaaaa atatattctt gatattaact gtttatcttc aaaagcatag aatacgcata      18720
ggcaacaaaa aaacataaag ccacccatac caatcaatac cctcggtgcg tatattggtg      18780
attttagaaa aatcattggt ccaatgatga agaacattga tgctaataaa attaaaacta      18840
ctagcaataa ctttgttttc ttattttcat ctctttgat tgcttttaaa actatgacta      18900
tcaaagaaat gattagcgca aagaatagcg agtagtagat taagtaatta tcgccattca      18960
agatcgtgct aaacattcta taaaatgata agacgttaga aattatccct tcaaataaac      19020
ttgagtttat ctctataatc ttactatgtt cgatattgta agaacctgtt acaagtctttt     19080 ttgcaataaa gtaagaatag gcaaaatatc ctactattaa accagcgaca gaagatgctg      19140 tatttttgt gatatttgaa attgagtttt tcttaaccac atctgaaatt ataaaggcca      19200
acaagaatat tgcgtaagta ttcagcgcag cctgataaag actaaggaat gcaatggtta      19260
aaatggatga tattatgata tttataggct tgtattgata agcgacatac gatgagataa      19320
tagatattgc cacactcatg cacattgtta atgaatcata tctatatgat agattttcaa      19380
taaagaatgg gtttgccaaa atcatcataa aacaaagaga tgctgtgatg tagtcatctc      19440
```

```
caaacagctt ttccctgatg caggatagtg ccaatgctaa aataactatc cctagcatta    19500
aaggtagcgg agaagcatct ataattgggg ttccaaaatt aatgatatag aaaataaagt    19560
cggaaagtgg gcgaccattg cctgaccaac ccaacccgcc atataaagac ctacccaagt    19620
catcaacgaa aaatgattga tgtgtcaata aaggaaatgt atatataatc gccaatccaa    19680
gaaagattga tataaatatc ctgtcattac tattaaattt cacttttaaa accccttacgc   19740 tttaatatgt atttaggccg ctgtttggtt tctatgtaaa ttctaccaat atattctcca    19800
agaataccta ttcctatcaa ttgaacgcca cccaggaaaa gaacagaaac aagaagagac    19860
gggtagccag gaacattatt tccaaatatt aatttatcaa taatcatcca tgcaccgtaa    19920
aggaatgaca tacctgcaat aaacaatcca atgtaagtcc atatgcggag cggaaatgtt    19980
gagaaagaag ttattccctc cagcgccagg ttccataatt tccagccgtt gaatttcgaa    20040
tcaccggcca cgcgttcggc acgggcatat ttaacaacat ccgttttttcc gccaacccaa   20100 ctgagcacac ccttcataaa caagttgcgt tctggcattt gtttgatgtt ctcgacaacc    20160
gcacggctca ttaaccgaaa gtcgccaaca ttttcttcga tttttggatt gctgatttta    20220
ttgtgcagct tataaaacca ctcagctgtc ttacgcttca tgcgcccgtc agttgagcgg    20280
tctgagcgct tagccagcac catatccgcg ccagcctgcc acttctcaat gagatgaggg    20340
ataacttcta tcggatcctg taaatcgaca tcaataggaa tgaccgcatc cccggttgca    20400
tggtcgagac ccgcgaaaag agcaggttct ttaccgaagt ttcgcgtaaa cgaaagcgga    20460
ataacgagcg gatcagatgc agctattttg ttaattattg attcagtcgc atctttacta    20520
ccatcattaa taaaaacgat ctcaatttca tattctttta gctcattaaa ctcacgtacc    20580
gttttataga aaatcggtat cgtgtcttct tcgttaaaaa ctggaacgac aagagagatt    20640
ttcatcttat atccctgaaa acaatgaatc tggaatagat aaagccgcat accaggctaa    20700
ttgccgagaa agtgataagg gtaatcaatg gtggcaagga acattggtca gccatccagc    20760
caacaacagc gctcagtgtt cccatgaatc ccacatacat catgtagcga agcgtggtgg    20820
tggtggcatt aaaggtgaaa cgcgcattgg catagaagct gaacgatacg gcgataacaa    20880
aaccggaaaa gttcgccagc gcctgatgcg tatgcatccc atacacacaa aaagcaaata    20940
cgccccaatg aataagcgtg ttaagaacac cgatcgatgt gtacttagcg aataacttca    21000
acattatgaa aatcagcgga ttcggaaagg tctgaagtgt agcactacaa attgttttga    21060
tcgatacaag cgatcaataa tgtataattt gatagttttt atctatataa tgcatgttaa    21120
ttgatcgttg ttaccgatca attttttattg ctgattgcta agtggtttgg acaaaaatg    21180 ggacatacaa atctttgcat cggtttgcaa ggctttgcat gtctttcgaa gatgggacgt    21240
gtgagcgcag gtatgacgtg gtatgttgtt gacttaaaag gtagttctta taattcgtaa    21300
tgcgaaggtc gtaggttcga ctcctattat cggcaccagt taaatcaaat acttacgtat    21360
tattcgtgcc ttccttattt ttactgtggg acatatttgg gacagaagta ccaaaaatcg    21420
agtcaatttg tcgagcatgt tcagtcaggt gatttggtgc cagatgagca tatcggcgaa    21480
ccatttcgat agactcccag ccacccattt cctgcaatac cgaaatcgga acgccagcct    21540
gaactaacca acttgcccac gtgtgcctca ggtcatgaaa acggaagtct tcaatgcccg    21600
ctcgttttaa tgctgccctc catgcagtat tagcgtcata gcgcatcttc ctcactacag    21660
gtgatttagt tccgtctggt ttggtgctgc tttccttgta gacgaacacc catttgtgat    21720
gattgccgat ttgcttttc agcacccggc aagcggtatc attcagcgcc actccaatgg    21780
catgattaga cttgctttgt tccgggtgta tccatgccac cttttcgttgc atgtctatct    21840
```

-continued

```
gctgccactc cagattgata atgttagacc gccttaagcc agtagaaagc gcaaactcta  21900
cgactgactt tagcggttcc tggcattcat caatcaacct ttttgcctcg tgaggctcaa  21960
gccagcggat acgcttattt ttcggctgag aactttgat gatcggagcc ttatccagca   22020
tcttccattc gcgttcagca gcccggagga gtgcctaat gaatgaaagg tgagttgctt   22080
ttgtagctac tgctgccggc ttaggcttga ataccggagg ctgcttccca ttcttcctgc  22140
aagcttcatc cattaacttc cagttttcct catgccgccg attagttatc ttctggatgg  22200
cggagtaaat cttcgtctcg gtaatatcct tcaactgcat tcctgcaaaa tgctggagcc  22260
agaatcctat ccgactcttg tcatcatcca gcgacttctt atgcgcctte tcctctaacc  22320
acctgacaca ggcccctca aaagtcatgt caggcgtctc tcctaattta cttaccctcc   22380
atgcttctgc cttcagcttg tcatgaagct ctgtggcctg cctttgtcc tttgtcccaa    22440
gagactgctt aaatctttg ccgttcggca atgtgaaact ggcgtaccag gtttcacctc   22500
tgcggaatag tgacatttca gttcctctgt tatgtcatca cccgcgctca cctggacagt   22560
atgcagcgga gattgaagtg ccgcaatgca ggcttgtcgt gtggtgaggt aagggggatt   22620
cggtttggtg gggtctttac gtgttgcctg tagtcggcct gtgcgaatcc agttggtggc   22680
ggtaggtctg gatatcttga gaaatgcaca ggcctcatca agtgtgaggc tgtgtgattc   22740
catgtttact ccgctgtttc ttcttcgtct tcttttgcgt tagcgatgtc gtagaattgc   22800
ccgtaagtta ttttcttgaa tgcatcaggg ataacaacta cgccatgcct ttcttctttg   22860
ttatttggta ttgcaaaaat aagacaatca tcgcgttgcg ggtgcttgcc gccgtacgtt   22920
gataacataa cgaaaccaaa gccacggccc gattgaccac caattcctgt acgcataatc   22980
ccgtagtggt tggttatgta gtaattccat tcaggcaagg attttagctt ggcgttagcg   23040
ttatgcatga ttgcatccag ctctttgttg tatgcgcggc cttcctttgt gtttccctt    23100
cctcgcgcta tcacaactct cttcccgtcc aaaaaatcct cgcgtttgat tgttatctgg   23160
catgggaatt catatccttt ttcccaaacg aagctttgta gaagtccgcc ttctccaccc   23220
cagctacggg ctgtagtcca tgcgattgcg ccaacctttt cagcggctgt ggttaggatt   23280
gaatttcgtt gatcgttaat ggtgtcgtat gactggataa gctccttaac atcctcaccc   23340
tctaccatgt agtagtcgta atatttgctc tggcctgaca tttattgtct ccaataaaaa   23400
accgccatca ggcggcttgg tgttctttca gttcttcaat tcgaatattg gttacattgt   23460
tttcatatat gaataaataa attagctttt ttcgttgcct ttgcgttcct tattaattct   23520
gacaaactcg ttttaccac gctctccaaa tgcgtcttta gagtcgttgt atccgcaatc    23580
gcagcacaca taatcatcag accatccacg cattgttttt tcttttgcaa tatttccaga   23640
accgcatttt ggacaagaca tgtcactacc tccaaagcat gagtgagatg acaacgtaac   23700
attgattgga gattaacaat agattgctga tgtaaaagat atgtataagc ttcgctatca   23760
aaggggagga tctggtagct gcatccagtg gcttacaccg ataatttcca taccctccca   23820
atagtcaaag aacccatcat cgtcgtatgt agcaacgaac atccctgac ccagacattt    23880
tccggtaaaa attgcgatgg gtttagattc atcattatct ggcattcgct cactacagct   23940
tatccagcca cccggaatta ccggagagtt gcctgccagc gcttcttgca gtcgttcaag   24000
cttcacgtat tcctgaacgc aagttcccga gtagttattt atccagatgg tcgccttttc   24060
tgggtcaggc gtataagtaa ccacttctcc cgactgccag cacagggcgt acaggtcagc   24120
gactgcctta acctgtgcgt atggcaactc ggcagggcat tcctccggca ctaccgactc   24180
```

```
tggctgctct ttgatatgca gtcgtggctc gccgtctttc ggttcaggcc actggcgtgt   24240
tttgtttatc tccagttttt caatcatcgc cctcgtaatg aattcgtcgg aaattcccat   24300
gcgccgctgg gcatcccaca ataaaaactg catatcagcc cattcaagcg gtctgatgg    24360 gtcggcagcg gcttccagcg cttctttcga aagatgttta agcggccga ctggaccaac    24420 atcgccgaac gtcttatctg accactcggc gtgctcacgg cgaatacgtt cgcgttctgg   24480
cactggcggg gcggcgtaga gcggtatata cacggcaaca tcatcagcag catttggctg   24540
ctgctctaat gtcacgcatg taccggaaaa tttattcagg tatcgcacag tctcagcatc   24600
cagcgatgcc agcgcaatcc gtgccagctc catttgttcg ccacgggtaa gcccgttttc   24660
aagcggcgat ttaacgaaca attcaatacg ttctttggta atagtggtca tgggttagtc   24720
ctcaacgctg atatcaacgg ccactttcat tctcccggca gaaacttcaa aaccggtgac   24780
atccgcatta agcatgtatt cagatataac cagcgcaaga agttttaact tcgcgtctgt   24840
atcgttaccg ttcaattctt caagaagctc aataactggc ttcatatgtt caccaatctt   24900
catgctcatt cccccttaac cttgatgcca gcgcgtgtgc tatatgcaga catgcactgc   24960
gtgaacccgg attggtcatc tgtctgccca taactgaacc ctgctttcag gccgtcacgg   25020
aatgcgccat cctgcaactt gtcgtcagtt tcaagcttcg cctccagttc ttgaatacgc   25080
tggcgtaacg ctgtaatttc cacctcagca gcgtctgcgt aatgaacgtt ttcatgctca   25140
agtggtggta aatccggcgt aatgacacca aaaagttttg ccagcgcccg gtaattcagt   25200
tcgctgtgat aacgaccttt gcagcgaacc agttttttcag cagcagctac aatcgcgctt   25260
tgttctgtca tgcgcttttt tgctgcttcc agctcaactc gcagcttccc aaccgtaagc   25320
gcaatatcct cgtcctcctg gtcgcggagt ttgatgtatt gctgtttttt atccagctca   25380
tccagcagcg cctctgcggc gatataaata acctggcgtg cacggtctgc tgggtcgctg   25440
taatggtctt gcatgtactg gaattcttca cgcagcgcct gtttgtcgat gttgctcatt   25500
gggctgtctc cggtggataa caaatatcgt cgaaatattt ttctgcaacg cacatgttga   25560
agtgatcgag attcatctcc tccacctgga gttttgcccc aacaatacccc gtgcatcgat   25620 tgacgtaatc ccgatttcct ggggattccg ctacccactc cataaggtct tcggtgacac   25680
gttttaagca acgtaaggcg cagtccatat cagtaaaatg ctgagcatct gtgatgcagg   25740
agacgacata atacgtggtg atttttggcc cttcagcgcg tcgcttaagt tctctctcta   25800
tatctctttt cagatcaacc agttcatggt cattgagttt gtcgatgttg ctcattgggc   25860
tggccctcgc atttgtgatt ttctggatca tcggctttga aataaccgcc gcagattttg   25920
cagggtatcg tcggcacttc gtcgtaattt gaggttcccg taatcatgac tgcactcctt   25980
tgcgaagctg gcggcgata tcttcgataa cgccatcggc gaatgagcga tcaaaatcgc   26040
cttccggtgc atcagccata aattctgtgg aggtcagtat cattcgtgcg atgtccgcag   26100
cgttctttgc tgtgtcgtcg ataaatcctg catcccatgc ggccagcatt cggttagcaa   26160
caaagtaagc gccttccttg tgagcctgcg cccgcatctc cgccagaaag gcgtctgtcg   26220
ccggggtctc agtgaaatcg tctacccacg tatcgccaac gtcctcgcac tcgtgacgac   26280
aataatcgtt gaattcgacc tctgattttt tcagtgcccc attctccacc accagtgccg   26340
cgcatttcgc ctccagttcc cgataatccg acgccagcac cagatccaca cagaacgatt   26400
cagactgtac cggtggggat aaatctgatg gggatgcggt gtaaattttt acctgttgca   26460
tttatctttc ctcagtatcg cattcaaata tttattctcg ttaatagaag gaatgaatt    26520 gcgctgcaat aattcttcgc gtgtaggcat tggtttaatt ttgtgcctaa taataagttc   26580
```

```
ggctggtaga atgtcgggat tgtatgcaag tcctctcatc gtaaactcct cagttattgc   26640
tgatagctcc gtaacgcgaa cggtaatcac gaagacgcgg gtctatttca atgaatttgg   26700
tgtaagtggc tttgcggaat ggccggatgg ctgtctggta aattcgctcg cgttcttctt   26760
tctctgcaag ccatatacag tggcgaaatt ccttttcctc tttcgtttcc tgcggtagtg   26820
acattatcag gtcgtagttt tttctgaatt tatccagcac ctccgatacg gaattgccgg   26880
aacagcggcg cgggtcatcc gcaccataca aggcgctgg cataatttac tccagggtag    26940
gttatccgaa taatgtggta cgtatagggt tatttctttc gtaaacgtga tagcctgctt   27000
tttaccgact cttcacttcg cccgagaatt tttgctacat ttctttgtgt atagcctgat   27060
gagataagcg tctgcattct tttgtcttcg tcgtcgctcc atcttggctt aatgaatgcc   27120
gttttaatg acagttttt tgctatgtaa taaaactgat ttatgtttag cccagatgt      27180
tctgctgcac ggcaagctac catgcgaccg caaactgact ccatctccgc tgtagttatg   27240
tttaatcttc tcattaagcc acctgtttaa gctcatttat tctgatattc attacctgaa   27300
cgcattttgt ctgctcatca tcgtgaccag tcaataattg ccagtcgtgc tggtatctct   27360
caattagctt tttcttgtcc gtttctgttg ctgcatattc actgaatgcc ttaagaacct   27420
gttcaggagc aggggaggaa ggcgatgatt tagtttgctt agcaggtgct gcattctgct   27480
gctgtttgtg ctcctcagta tcagcgtctt tggcgtcgtc gataccaaac aaaccgttaa   27540
ggcaatattt gcgagcgtaa gagcttgtag cgcccgttac ctgagctgca tccattccct   27600
tcttgttttc ttcttctcgc gctatagcgc ttgctgaatg gctatttca ccatctgtaa    27660
tggtcgctgt ggccttgacg taataacggt cgccaatcag cacgatttca tcactgatag   27720
acaggaacag acctttcagt agtggcttaa caccctcaag aatgtcctca caactgcggt   27780
atttgtattt accaaacgag ttgtactgat tctttggcgc attcagatgc tcctgaattt   27840
cagcaagtct tgcgtaaaac tctttgctca tgagtaatac cccgcaaatt catcccaacc   27900
aataatcgga ttttgccgtt ctgcggctaa gttgatttgt tgctcaacct cttcctcaat   27960
ttcaggagag ataagcgcga taaattcttc gtcactaaat tcatgctgca tgatttcgat   28020
tccagtcttc gtcctgacaa tcttcccagc ccattgcgat tgatgatgcc catgcgtatg   28080
cggcgctgtt accttccttc gtatccggga aggatgcttc gtagagcttg ttaaactcac   28140
gattgccttg ctgcacaagg atggttccgt taacaggcac aatagtcatg gctcggcact   28200
ccaggctgat taaggatgtc tgccagccgt ttccagccag cgcgtaattt gcgggtgatg   28260
cgatctaaaa gtgattcgtg taactgggaa acgcccatgc gagcgcttcc cgcgattgcg   28320
ataatcatgg gagttcctta tgttgtgtgt gattgcatga ggctgagcac ttgaataaat   28380
actcactcag atgcggatat gaaaagccg cactcaggcg gctgtcgttt cttctttcag    28440
gctttcgaga tattcacgcg ggtcgtcgta acactggcac tcgctatacc aatcaatcca   28500
gcgatcatcc agttccatat cttccaaatc ctggtcggta aggctctcgt caaacatctg   28560
taaaccgttg gcgttgcagt aatcaggctt gatgttgttg tcatactgaa aggcgtcata   28620
atcagccagt gcatccatca ttcgtacacc ttcttcaaca ctacccactt ctacaatgaa   28680
tggcttcata gggacttgcg ggatatgcca gacacgtaat ttcatatttc ctccaggcaa   28740
aaagaatgcc gcccatatag agcggcaaga ctatcaaggg atgattctcc aataaccaga   28800
acgagtcttc gtcctcattc ggttacgagc gatattgctc acatagcaga ctcgtaaatc   28860
tgctataggt gcttattcgc ttggtggttc aggtaatggc atccagtgag tcactcgctc   28920
```

```
atgcttgatt aaacgcgtgt cctgctttga gttctttgcc tcaattactg gcttcctcat   28980
ggtgtaaatt cccgagaaat ttgaattgca aacacaatat ccaagcacag taattccgga   29040
ttccggcatc cgctcactac acttaatcca ctccatcact ccttccccag agccttgccg   29100
atggctgcgc gagccgtcgc gtacacagcg tcccactcgc tcacgtcatg ttccatatcg   29160
ataatgctta acagagcctc gagaagctca ggagctgcac ttgccaattt tatttcctgc   29220
ttattggcgt tctcggctga aaacagaatg tgaccttcag taacatcgac aatgtaatct   29280
tcatcaacat cccaatgcgg tatgtctttc atattcacct ctgtggcttg ctgccaaaag   29340
aagacagact atatagcctt tagttttttcc agctctctgg caatcatttc cgtggttctg   29400
attgcccatt tatcgacaat cttttccatct tctctcacca gagccatttc ctcaggcttt   29460
accatacatt cagcatcaag cttgcagcct ttgcatttca caaaacgact acaccattga   29520
tttgtatcaa tagtcgtagt catatgggta gtcctggtat tgttccatca catcctgagg   29580
atgctcttcg aactcttcaa attcttcttc catatctcat ctcaaatagt ggattgcggt   29640
agtaaagatt gtgcctgtct tttaaccacg tcaggctcgg tggttctcgt gtaccoctac   29700 agcgagaaat cggataaact ctattcaccc ctacagagag taaaaagaga atcgccgatg   29760
aacaactcat ggtggcagga gttaatgcgt ttttcctgc aaggaatgac acttaaacag   29820
ttgattcata tgctaatcat cctgatcgta ttgattattg ttatgccggt aagcgtaaaa   29880
gaatggataa acctgcataa tccagaaata cttcctcatt actggatgta ttacatcctg   29940
ttgttctgcg ttagctatgt gcttaacggt gttgttaatt ccgtttatca cgctgttact   30000
gaaagaattg aggcatcaac tgctcagcgg cgtaaggaca gagaagaaaa agtcgttcgg   30060
gatttgtttg attcgttaac tcttggagaa agagcgtatt tggcattcgc tgtagccgct   30120
aataaccagc taaagacaga aaagggaagc cctgaagcaa tttcattgct caaaaaggg   30180 attatcactc gattgccttc tgctattgga tatcctgata ttgaccgttt tattatcccg   30240
gaaaagtatt ttaatgagtg ctacatgaga tttgccggga agtcagacat tcttatgaat   30300
gaacttattg tacaggacga acagctcaaa aaataacgac ttaaccgaca aataccttac   30360
ctcgctgtta tttgtttgct cttacgatga ccagccgcgt aaagtgctac gcctggaaga   30420
agtacagatc ctccttcaac ttccttctga cgcgttccgg caagcgaaat ggctttggtg   30480
acacggtcaa ttcttttggc tttaacttcc tgagaagcat caggagcatc gcagccaaaa   30540
attgaatcga tgatattgca gatggtgtcg cgctctatgg ctagctttct gcgccgctca   30600
tgacggcgag ttttagcatt gcctgcaaac gttgacttcc cgtaggtgat aaccgtcatg   30660
atttaatcct catgtgaaat ggctttggta ctggcgccgg aacctgtctc aatttccgga   30720
tttcaagtgg cttctcagtc cggcccgatc ggtacagcta gaggcctaag ctccaccaca   30780
cgccagtcca aaccaatctc gtttggtatt tgttcgcgct ttgtcagcgc atcatcgaag   30840
ttaaagagcg ttgcctttcc gtttggctac cagcgtcctg ctgatggcta aaatttaaga   30900
cttcttaatt aaatggtcaa gtgtattttt gaagaaaact taaatatttt atcgttactt   30960 aagttttttat ttgattttta aaggaaaatg tagtgtgagg ggcgggtgcc ccttatggaa   31020
gatttgcgag ttttgcgtca acaactacgc caatgatttt gcagtttccg ttgatttcta   31080
tcatcggata ttgtgggttt aatggttttta aaaactttcg gcctgcatcc ataactaatt   31140
ttttgaatgt ggcctcgttt tcaccttcta attttgcaac aaccagcttg ccgtttcttg   31200
gttcgacttc gggatcaacc agaattatca ttccttctgg aatgcttaac cctgccggtg   31260
ctgtcataga gtcaccttgg acatcaagcc aaaatgaatc ttctgaacaa tctacagtgg   31320
```

```
tgtcgtgcca gttctctatc gcgcgcttgt gataaggttc tacagcttcc atccattgcc   31380
ctgcgcttac ccaactgata agagggtatg atcctcttgg ctcatgccta ctatgatagg   31440
caacgtttgt ctggcttaaa tctcctttca gcaaatagtc aggggagcac tgaagagcct   31500
tcgaaagtgc caacaggttc tccccatttg gctcagtctc cgagcgctcc cattgcgata   31560
ttgcaacatt agacactccc accatcttac caagagcggc ttgtctaatc ttgagttttt   31620
ttcttcgagc gcgaatacgc tcacccatca attgtgtatt catagttaag tcatcttaaa   31680
taaacttgac taaagattcc tttagtagat aatttaagtg ttctttaatt tcggagcgag   31740
tctatgtaca agaaagatgt tatcgaccac ttcggaaccc agcgtgcagt agctaaggct   31800
ttaggcatta gcgatgcagc ggtctctcag tggaaggaag ttatcccaga gaaagacgca   31860
taccgattag agatcgttac agctggcgcc ctgaagtacc aagaaaacgc ttatcgccaa   31920
gcggcgtaag caaaacgctc tttaccaatc tgaaccgccg acaacgcggt aaacctattt   31980
caaagcgcat caacgaatgc gcacaactaa ctattaacta caggaatgtt cacatatgga   32040
actcacaagc actcgcaaga aagccaacgc aattaccagc agcatcctta accggatagc   32100
tattcgtgga cagcgtaaag tcgctgatgc gttaggcatt aacgaatctc aaatttcacg   32160
atggaaaggc gatttcattc cgaagatggg gatgttattg gcggttctgg agtggggtgt   32220
cgaggatgag gagttggcag aactggcaaa gaaagttgcg catctgctga caaaagaaaa   32280
gcctcaagac tgcgggaaca gttttgaggc ctgatgtaga aagactggat caatccacag   32340
gagtaattat gccaaaacaa ctcagtcctg accaggacaa attacacaaa acatactac   32400 gtgatcggtt cttatccagc ttcaaacagc ctggtcgatt tcgggctgag ttggagaaag   32460
tgaagctaat actgaagagg aaaggtcatg agtaatcttg caacagttac accgataaaa   32520
cctcatctgg aggttgtgga gcatcgcgtg gcagaactcg acgatggcta cacccggact   32580
gcaaatacac tgctgaagc tgtcatgctt tctgggctta ctcaacatca gctactgatt   32640
gttatggctg tgtggcgcaa gacatacggt tataacaaaa aaatagattg gatcggaaat   32700
gaacagttcg ctgaactcac tggcatggcg ccaaccaaat gttctaccgc caaaaacgag   32760
cttatcagaa tgggggttct cactcaggtg gggcgtcagg ttggtatgaa taaaaatatt   32820
tccgagtgga agacgaaggt taacggattc ggtaaaacat ttaccagatc ggtaaaacta   32880
accttcacca aatcggtaaa aaccaattta ccgaatcagt caaacacaaa agacaatata   32940
caaaagacaa taaatacaaa tacccccttta cccccctaaag ggggatgcga tgaaggttct   33000
aaacctgaaa agcgaaaacc taccaagatt aactacagcg aatatcttgc tgcctacaac   33060
gagattgttg gtgacagact cccacatgca gtggaggtca attctgaacg acaacgcaag   33120
ttgaaaaagc tgattgattc actggcaacc aaaaacatcg acggattccg ggcatacgtc   33180
aaagcgttca tggcagcagc cagaccattc catttcggtg ataacgaccg tgactgggta   33240
gctaattttg attatctgct acgcccgaaa gtactgatag caattcgtga gggaacacta   33300
tgagacagga tatcgaggcg agcgttatcg gtggcttgct gattggcgga ttaacaccaa   33360
ccgccagtga cgttctggca acactggagc ctgaagcatt ctcaattccg ctctaccgga   33420
aagcttttga agttattcga aagcaggcca gaaacaggaa cctgattgat ggactgatgg   33480
tggccgagga gtgcggggat gaatacgcaa cggcggtgat gatgactgcg cggtcatgtc   33540
ccagcgctgc aaacctgaaa ggttatgccg gaatggttgc agacagttat caacggcgtc   33600
aggttttaca gctactggat gagatgcggg agccaatcag taacggcacg ctggacgcat   33660
```

```
caggcagagc gatggacgag cttgtaaagc gcctgtcatc catcaggaag ccgcggaacg   33720
aggttaaacc tgtgcgactg ggtgaaatca tcaatgacta cactgacacg cttgacaggc   33780
gtctgaggaa cggagaagag tcggataccc tgaagaccgg aatcgaagag cttgacgcta   33840
tcaccggagg gatgaacgca gaagaccttg tgattattgc tgctcgtcca ggtatgggta   33900
aaaccgaact ggcgctgaag atagccgaag gcgtggcaag tcgtgttatt cctggttctg   33960
gcgtccggcg cggtgtgttg attttctcga tggaaatgag cgccattcag gttgttgaga   34020
gagggattgc cggcgcagga atgatgtcgg tcagtgtgct gcgtaacccg tcacgtatgg   34080
acgatgaagg atgggcgaga gttgcaagcg ggatgaagtt gctggcagag ctggatgtgt   34140
gggtagttga cgcatcgcgt ttgtctgtcg aagaaatcag gtccatttcc gaacgccaca   34200
agcaggagca tcctaatctg tcactgatta tggctgacta tctcgggcta attgagaaac   34260
caaaagcgga acgtaatgac ctcgccatag cacatatctc cggtagcctg aaagcgatgg   34320
cgaaagacct gaaaactcca gttatctccc taagccagct ctcccgcgat gttgagaagc   34380
ggccaaacaa gcgcccgaca aacgcagatt tgcgggattc aggaagcatt gaacaggacg   34440
cagactcaat catcatgctc tatcgggaag cggtatatga cgagaacagt agcgccgcgc   34500
catttgctga aatcatcgtg acgaaaaacc gttttggctc gcttggtacg gtttaccagc   34560
ggttctgcaa cggacacttt gttgcatgtg accaggacga agccagacag atttgcacgg   34620
catcaaatgc acctgctgga cgcagaaagc gatatgcaca aggggctgac gtatgactat   34680
ttacatcact gagttggtaa caggcctgct ggtaatcgca ggcctttttaa tttgggggag   34740 agggaagaca tgaaaaaact aacctttgaa attcgatctc cagcacatca gcaaaatgcc   34800
attcacgcag tacagcaaat ccttccagac ccaaccaaac caatcgtagt aaccattcag   34860
gaacgcaacc gcagcttaga ccaaaatcgg aagctttggg cttgccttgg tgatgtctca   34920
cgtcaggtaa actggcatgg acgatggctt gacgctgaaa gctggaagtg tgtgtttacc   34980
gcagccttaa agcagcagga tgttgtccct aaccttgccg ggcatggctt cgtggtaata   35040
ggccagtcaa ccagcaggat gcgtgtaagc gagtttgcgg agctattaga gcttatacag   35100
gcattcggta cagagcgcgg cgttaagtgg tcagacgaag cccggttagc actggaatgt   35160
aaagcgaggt ttggagacgc cgcatgaaac actgctaccg ctgcggagaa agcaaagacg   35220
attatcgatt ccggccaaat caaccttatt ggcaccaatg tgtgtatcag atgtgagcggt   35280 cgccagtagg taatttcccg ctgccagaga cgaaggagga cgtatggcac gacagcgacg   35340
aagtatcacc gacataatct gcgaaaactg caaatacctt ccaacgaaac gttccagaaa   35400
taaacgcaag ccaatcccaa aagagtctga cgtaaaaacc ttcaattaca cggctcacct   35460
gtgggatatc cggtggctaa gacatcgtgc gaggaaatga caatggatta ttcacagtta   35520
agtgattttg aaattaacaa gcgagtcgcg atagcgacag ggcataagaa gtttaacggc   35580 ctggatggc aagggacaca agaagacagt tgtagcgcag tgatagtaag aggtccaact   35640
aaaataggcg cgtttgaccc catgtaataac ccggcagacg catggccgat tattgagaaa   35700
tacagaattt ctttcttaga ccagttaact gaatggtgtg tagatgcaaa aggcgtgagt   35760
ccaatatttg atatcagacc tctccgcgcc gccatgattg tctttctcct gatgcaggac   35820
gccaataatg cttagcccat cacaatccct tcaataccag aaagaaagcg tcgagcgggc   35880
tttaacgtgc gctaactgcg gtcagaagct gcatgtgctg gaagttcatg tatgtgaagc   35940
gtgctgcgca gaactgatga gcgatccgaa tagctcaatg tacgaggaag aagacgatgg   36000
ctaaatcagc gcgaagacga tgcaaaaacg aagaatgtag ggaatggttt caccctgcat   36060
```

```
tcgctaatca gtggtggtgc tctccagagt gtggaaccaa gatagcactc gaacgacgaa   36120
gcaaagagcg cgaaaaagca gaaaaagcag cagagaagaa acgacgacga gaggagcaaa   36180
aacagaaaga taaactgaag attcgaaaac tcgccttaaa gccccgcagt tactggatta   36240
aacaagccca acaagccgta aacgccttca tcagagaaag agaccgcgac ttaccatgta   36300
tctcgtgcgg aacgctcacg tctgctcagt gggatgccgg gcattaccga acaaccgctg   36360
cggcacctca gctccgattt gatgaacgca atatccataa gcaatgcgtc gtgtgcaatc   36420
aacacaagag cgggaacctg gttccttatc gcgtgatgct catcgagcgc atagggattg   36480
cagcagtaga cgaaatcgaa tctgaccata agcggcatcg ctggactacc gaagagtgca   36540
aagcgattaa ggcggagtat cagcagaagc ttaaagacct acgtgacagc agaagcgagg   36600
cagcatgagc aaaatccaat acccaatgac cactgcggca attttcgatg atgttgtcta   36660
tccgctgcat ttcgacaatg ccggcaaggt taggcaagaa atggaaggcg ctgttaactg   36720
gttctgcagg tggtgcaacg aagagaaagc cgctgtgaaa gcgagattgt tggtcagttg   36780
ctggggtcaa tatctgagtc atgagcaggt tatccgggag gccgcatgac acacactgtc   36840
aaaaccattc cagacatgct catagagaca tatggaaacc agacagaagt agcacggcgc   36900
ttatcgtgcc accgcaacac agtcaggcgt tatctgtacg acaaagaagc caggtatcac   36960
gccatcgtta acgcgttttt aatgattcat cagggcggga gaggtattta tgaccgtaac   37020
cagcattaac caggcaaaac atcagcgtga acgtgacgag gctgaattac gcagcgtcag   37080
agagatgacg gagcaacacc agaaggcgat ggattatctg catgagcgag agcgtgaact   37140
ggtgaaccgg attggattga acaagccagc gggagacgat gctgcatgag actcgaaagc   37200
gtagctaaat tccattcgcc aaaaagcccg atgatgagtg actcaccacg ggctacggct   37260
tctgactctc tttccggtac tgatgtgatg gctgctatgg gaatggcgca atcacaagcc   37320
ggattcggaa tggctgcatt ctgcggtaag cacgaactca gccagaacga caaacaaaag   37380
gctatcaact atctgatgca atttgcacac aaggtatcgg ggaaatacccc tggtgtggca   37440 aagcttgaag gaaatactaa ggcaaaggta ctgcaagtgc tcgcaacatt tgcttatgcg   37500
gattattgcc gtagtgccgc gacgccggga gcaagatgca gggattgcca cggtacagga   37560
cgggcagttg atatagccaa aacagagcag tgggggagag ttgttgagaa ggtgtgcgga   37620
agatgcaagg gcgtcggcta ttcaaaggtg ccggcaagcg ccgcatatcg cgccataacg   37680
atgctaatcc caaaccttac ccaacccacc tggtcacgca ctgttaagcc gctgtatgac   37740
gctttggtgg tgcaatgcca caaggaagag tcaatcgcag acaatatttt gaatgcggtc   37800
acgcgttaat agcatgattg ccacggatgg caacatatta acagcatgat attgactttt   37860
tgaataaagt tgggtaaatt tgactcaacg atggataaat gcactcgtta aataaagccc   37920
tgagtttaac cgctcgggc tttttgcgtt ttaagcacga catttctgaa agcgccctat   37980
caccaatcac cagaacacat ccagataccc ttgctcattc gtggcgacgg ggtagggcgt   38040
tttacacaaa agaaaaccca gaactatggc tgggcttcgt gaagatgggt ggcaagagac   38100
tgcgctaaca gcctcttgcc tgatctgccc atgctcttaa tcacggacaa accacgttac   38160
cgcaaaatgt atcctggatt tgttctttcc aatatcaacc aattcataac attgaacaaa   38220
tcctcacggt cgtgaggtaa gacatgaaaa agatgccaga aaaacatgat ctgttaaccg   38280
ccatgatggc ggcaaaggaa cagggcatcg gggcaatcct tgcgtttgca atggcgtacc   38340
ttcgcggtcg gtataatggc ggtgcgttta agaaaacact aatagacgca acgatgtgcg   38400
```

```
ccattatcgc ctggttcatt cgtgaccttt tagtcttcgc cggactgagt agcaatcttg    38460
cttacatagc gagtgtgttt atcggctaca tcggcacaga ctcgattggt tcgctaatca    38520
aacgcttcgc tgctaaaaaa gccggagtcg atgatgcaaa tcagcagtaa cggaatcacc    38580
agattaaaac gtgaagaagg tgagagacta aaagcctatt cagatagcag ggggatacca    38640
accattgggg ttgggcatac cggaaaagtg gatggtaatt ctgtcgcatc agggatgaca    38700
atcaccgccg aaaaatcttc tgaactgctt aaagaggatt gcagtgggt tgaagatgcg    38760 ataagtagtc ttgttcgcgt cccgctaaat cagaaccagt atgatgcgct atgtagcctg    38820
atattcaaca taggtaaatc agcatttgcc ggctctaccg ttcttcgcca gttgaattta    38880
aagaattacc aggcagcagc agatgctttc ctgttatgga aaaaagctgg taaagacccct   38940 gatattctcc ttccacggag gcggcgagaa agagcgctgt tcttatcgtg agtcgtatta    39000
aggcaattat tgcgtctgtc attatctgca tcatcgtctg tctttcgtgg gctgttaatc    39060
attatcgtga taacgccatc acctacaaag agcagcgcga taaagccaca tcaatcatcg    39120
ctgatatgca gaagcgtcaa cgagatgtag cagaactcga tgccagatac acaaaggagc    39180
ttgctgatgc taacgcgact atcgaaactc tccgcgctga tgtttctgct gggcgtaagc    39240
gcctgcaagt ctccgccacc tgtccaaagt caacgaccgg agccagcggc atgggcgatg    39300
gagaaagccc aagacttaca gcagatgctg aactcaatta ttaccgtctc gaagtggaa    39360 tcgacaggat aaccgcgcag gttaactacc tgcaggagta catcaggagt cagtgcttaa    39420 aataattta atttcactga aatttaacaa gtgactttca ggaaaatgcc tcgcagatgc    39480
ggggcgtttt tgtataggtg tttcaccgcg caccgcagcg cacaacaacc accgaacctg    39540
accctttgga atgggccttt gaggatacca gttagtgctg gcgagcctcg gtgggctggt    39600
ttcctgtgcg gcaaaggttc atttcaaaga agaaggcaac gccatgaatg aattaattgc    39660
gaatcatgac ttcgactttc gccagttagt taccgcagca gaaggtcaac cggtaactga    39720
caccttccag attgctaagg catttggtaa gcgtcacgcg gacgtattga gggcgctgaa    39780
aaattgtcat tgctctgaag atttccggag agcgcatttt tgcgtttccg aaaaaatcaa    39840
taacttaggg attttcgata agaagcagat ttactaccgc atggacttta gcggattcgt    39900
tatgctggtc atgggattta atggcgcaaa agccgacgcc gttaaagagg cctatataaa    39960
tgcctttaac tggatgtcag cagaactccg taagtacagc gaaagttatg aagcagaacg    40020
caacgccata atgctggagt atatgaaaga gaaggatgtc gccagcatgt ctggccgcct    40080
gctcaatcgc tggggaaaaa ttaagaagcc tcagctactg gcgagaattg gacgccttga    40140
acagcacggg caaaccgtaa tccccgggct cactaattaa cggcaggaca gcgaaacaac    40200
ccaagccagt aagtgggga aaataacact ggcagccact gaaagatgaa cctccagccg    40260
tatggcaaaa aagattcttt gtggtggcgg actgatggaa agacatcggt tattgcagag    40320
gccatttaat gagtggcctc gataatggct tataccatcg actggatatt attcgttta    40380 tcccgtctat gtgggggggg ggataaaaaa gccgcttact tagcggcttg acgtttgaag    40440
aatgattatt gttgcgtgcc cagtagggct gcaaccttct cattcagttt ggctatgtaa    40500
ccatctgaaa ctttattatc aatctcgccg ctatccgcct gagcaatgct gttgagatac    40560
atatcaccta gcttagcatc cttacccatt aagccattta aagaggttga taaaaccgca    40620
atagcaacac gagatgcgtg tgcatccaat tgcatcttct cgataatatc ttcaaggtgg    40680
gcaatttttt gctctatatc tgacatgtcc actcctttgc ataaagtttc ttgtggttga    40740
aaagtggcac tcaccgacaa gcaagaaatg ttctgtcatg agtacctcat cgatttaaac    40800
```

```
gccacgcaag cggcgatttg ggcggagata tctaagattg ctatcacact gcccaagaaa    40860
aaatgtcaaa accttacgtc cagccaagga ttattgttct gtaaacttaa agcaatgatc    40920
tggttggtat aaatgtgaca catgtcatga atcgactagt tgagatagtc cagatgggcg    40980
tgctcggcat catcaccaca accggagcca acaatggcag agattattcc catgactgaa    41040
gaacagaaat tccagttaga gatttacaag ctggtcatga accagaacgc agccgcagag    41100
gaagcatttc aattcattgg cactgacgag ctgaagcttg agctattcaa aattcacttc    41160
cagtcaggcg gagcaaattc ggatatcacg acccgcacta tcgaagcggt gcgtaaatcg    41220
agggaagcgt tagacctgtt cactaccgga gcatgatgtg gtccgcgtaa tcaatttggg    41280
taaggagaag aaattcccaa ttactcaaga actatacgag cggctggaaa gcgtcattca    41340
tgattacgat ggtgaaatca gtttatgcga ggcgattggc acactcgaat tgctaaagca    41400
gtcattgatt gagggcgcga aagagtcctc agcctgaaat aacaactaag tgagatgaat    41460
atggcggcac caaagggcaa ccgatttttgg gaggcccgca gtagtcatgg gcgaaatcct    41520
aaattcgaat cgcctgaggc gctgtgggct gcttgttgtg aatacttcga gtgggtggaa    41580
gctaacccgc tatgggagat gaaggcgttc tcgtatcagg gtgaagtgat acaagagcct    41640
atcgccaaga tgcgagcgat gaccattact ggcctcactc tgttcattga tgtgacgctt    41700
gaaacatggc gcacatatcg cctg                                          41724

<210> SEQ ID NO 12
<211> LENGTH: 465
<212> TYPE: DNA
<213> ORGANISM: Escherichia coli

<400> SEQUENCE: 12
atggaaaaga aattaccccg cattaaagcg ctgctaaccc ccggcgaagt ggcgaaacgc      60
agcggtgtgg cggtatcggc gctgcatttc tatgaaagta aagggttgat taccagtatc    120
cgtaacagcg gcaatcagcg gcgatataaa cgtgatgtgt tgcgatatgt tgcaattatc    180
aaaattgctc agcgtattgg cattccgctg gcgaccattg gtgaagcgtt tggcgtgttg    240
cccgaagggc atacgttaag tgcgaaagag tggaaacagc tttcgtccca atggcgagaa    300
gagttggatc ggcgcattca taccttagtg gcgctgcgtg acgaactgga cggatgtatt    360
ggttgtggct gcctttcgcg cagtgattgc ccgttgcgta acccgggcga ccgcttagga    420
gaagaaggta ccggcgcacg cttgctggaa gatgaacaaa actaa                    465

<210> SEQ ID NO 13
<211> LENGTH: 447
<212> TYPE: DNA
<213> ORGANISM: Escherichia coli

<400> SEQUENCE: 13
ttatttgcct tcgtgcgcat gttcatcttc gcggcaatcg ccttcggcac agtgaccgta     60
aagatagaga ctgtggttag tcaggcgaat gccatgtttt gcggcaattt cacgctgacg    120
cgcttcgatg gaatcatcac taaattcgat aaccttgccg cagtcgaggc agatcaggtg    180
atcgtggtga tgttgctgtg tcagttcaaa tacggattta ccgccttcaa aattgtggcg    240
ggtgacgata ccagcgtcgt caaactggtt cagtacgcga tataccgtag ccagaccaat    300
ttcttcaccc catatcgatca gacgtttgta taaatcttcc gcactgacgt gatggttgtc    360
cggctcctga agaacttcca ggattttttaa acgaggaagc gttactttca ggccagcttt    420
```

```
ctttagggcg gtattgttat cagtcat                                        447
```

```
<210> SEQ ID NO 14
<211> LENGTH: 633
<212> TYPE: DNA
<213> ORGANISM: Escherichia coli

<400> SEQUENCE: 14
atggtgcttg gcaaaccgca aacagacccg actctcgaat ggttcttgtc tcattgccac    60
attcataagt acccatccaa gagcacgctt attcaccagg gtgaaaaagc ggaaacgctg   120
tactacatcg ttaaaggctc tgtggcagtg ctgatcaaag acgaagaggg taaagaaatg   180
atcctctcct atctgaatca gggtgatttt attggcgaac tgggcctgtt tgaagagggc   240
caggaacgta gcgcatgggt acgtgcgaaa accgcctgtg aagtggctga aatttcgtac   300
aaaaaatttc gccaattgat tcaggtaaac ccggacattc tgatgcgttt gtctgcacag   360
atggcgcgtc gtctgcaagt cacttcagag aaagtgggca acctggcgtt cctcgacgtg   420
acgggccgca ttgcacagac tctgctgaat ctggcaaaaa aaccagacgc tatgactcac   480
ccggacggta tgcaaatcaa aattacccgt caggaaattg gtcagattgt cggctgttct   540
cgtgaaaccg tgggacgcat tctgaagatg ctggaagatc agaacctgat ctccgcacac   600
ggtaaaacca tcgtcgtttt acggcactcgt taa                               633
```

```
<210> SEQ ID NO 15
<211> LENGTH: 1251
<212> TYPE: DNA
<213> ORGANISM: Escherichia coli

<400> SEQUENCE: 15
atggaaagta aagtagttgt tccggcacaa ggcaagaaga tcaccctgca aaacggcaaa    60
ctcaacgttc ctgaaaatcc gattatccct tacattgaag gtgatggaat cggtgtagat   120
gtaacccccag ccatgctgaa agtggtcgac gctgcagtcg agaaagccta aaaggcgag   180
cgtaaaatct cctggatgga atttacaccc ggtgaaaaat ccacacaggt ttatggtcag   240
gacgtctggc tgcctgctga aactcttgat ctgattcgtg aatatcgcgt tgccattaaa   300
ggtccgctga ccactccggt tggtggcggt attcgctctc tgaacgttgc cctgcgccag   360
gaactggatc tctacatctg cctgcgtccg gtacgttact atcagggcac tccaagcccg   420
gttaaacacc ctgaactgac cgatatggtt atcttccgtg aaaactcgga agacatttat   480
gcgggtatcg aatggaaagc agactctgcc gacgccgaga agtgattaa attcctgcgt   540
gaagagatgg gggtgaagaa aattcgcttc ccggaacatt gtggtatcgg tattaagccg   600
tgttcggaag aaggcaccaa acgtctggtt cgtcagcga tcgaatacgc aattgctaac   660
gatcgtgact ctgtgactct ggtgcacaaa ggcaacatca tgaagttcac cgaaggagcg   720
tttaaagact ggggctacca gctggcgcgt gaagagtttg gcggtgaact gatcgacggt   780
ggcccgtggc tgaaagttaa aaacccgaac actggcaaag atcgtcat taagacgtg    840
attgctgatg cattcctgca acagatcctg ctgcgtccgg ctgaatatga tgttatcgcc   900
tgtatgaacc tgaacggtga ctacatttct gacgccctgg cagcgcaggt tggcggtatc   960
ggtatcgccc ctggtgcaaa catcggtgac gaatgcgccc tgtttgaagc cacccacggt  1020
actgcgccga aatatgccgg tcaggacaaa gtaaatcctg gctctattat tctctccgct  1080
gagatgatgc tgcgccacat ggggttggacc gaagcggctg acttaattgt taaaggtatg  1140
gaaggcgcaa tcaacgcgaa aaccgtaacc tatgacttcg agcgtctgat ggatggcgct  1200
```

```
aaactgctga aatgttcaga gtttggtgac gcgatcatcg aaaacatgta a            1251
```

<210> SEQ ID NO 16
<211> LENGTH: 186
<212> TYPE: DNA
<213> ORGANISM: Escherichia coli

<400> SEQUENCE: 16

```
ttagtaactg gactgctggg atttttcagc ctggatacgc tggtagatct cttcacggtg    60
aacagaaact tccttcgggg catttacgcc aatacgtacc tggttgccct ttaccctaa    120
aactgtcacg gtgacctcat ccccaatcat gagggtctca ccaactcgac gagtcagaat   180
cagcat                                                              186
```

<210> SEQ ID NO 17
<211> LENGTH: 1041
<212> TYPE: DNA
<213> ORGANISM: Escherichia coli

<400> SEQUENCE: 17

```
ttaagcctgc ggctgagtta caacgtcttt gatacccttta acttcgatct ctacgcgacg    60
atccggagcc aggcagtcga tcagtgcagc acgctgtttc acgttgtcac aggtgttgcc   120
agtaaccggg ttggattcgc ccataccacg tgcggagatc ttgtctgccg ggatacccttt   180
ggagatcagg taatcaacaa cagactgagc acggcgctcg acagaccct ggttgtaagc    240
gtcagaaccg atgcggtcgg tgtaacccag aacaactacg gaaccgtctt tcggatccag   300
gttgctcagc tggctgtaca gctgatccag agcagcctga ccttccggtt tcagggttgc   360
tttgttgaag ttgaacagaa cgtcagactt cagagtgaag tgcttggtct gtacttccgg   420
tgccggagct ggagccggag caactactgg agctgcttcg ccctgaccga aacggtagga   480
aacacccagg ctcagcatgc cgttgtccgg acgagtgccg atggtgtgtg cgtcaccgat   540
gttgttggtc cactggtatt ccagacgggt agcgatttca ggagtgatcg cgtactcaac   600
accgccagcg aagaccggag aaacgccggt gtcgtggttt ttaccataaa cgttggattt   660
agtgtctgca cgccatacca tgccacccag acgagtgtag atgtccaggt cgtcagtgat   720
tgggtaaccc agtttagcgg tcagttgaac gccctgagct ttgtatgcac cgttttcaac   780
gctgcctttg tacggcatac gacctaacca gtcgtaaccc atttcaaagc caacatacgg   840
gttaacctgg taaccaccaa aagcaccagc gcccagttgg ttttcatggg tcgggccatt   900
gttgttgatg aaaccagtgt catggtactg gaccagccc agtttagcac cagtgtacca    960
ggtgttatct ttcggagcgg cctgcgctac ggtagcgaaa ccagccagtg ccactgcaat  1020
cgcgatagct gtcttttttca t                                            1041
```

<210> SEQ ID NO 18
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18

```
ttatcaggta ccatgaaagc gttaacggcc                                      30
```

<210> SEQ ID NO 19

```
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 19
atacataagc ttttacagcc agtcgccg                                          28

<210> SEQ ID NO 20
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
agaggagaaa ggtaccatgg aaaagaaatt accccg                                 36

<210> SEQ ID NO 21
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
atacataagc ttttagtttt gttcatcttc cag                                    33

<210> SEQ ID NO 22
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
agtagagaat tcattaaaga ggagaaaggt accatg                                 36

<210> SEQ ID NO 23
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
atacataagc ttttagtttt gttcatcttc cag                                    33

<210> SEQ ID NO 24
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
```

-continued agaggagaaa ggtaccatgc tgattctgac tcgt                34

<210> SEQ ID NO 25
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 25
atacataagc ttttagtaac tggactgctg g                31

<210> SEQ ID NO 26
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26
agaggagaaa ggtaccatga tgaagcgcaa tattct                36

<210> SEQ ID NO 27
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
atacataagc ttttagaact ggtaaacgat acc                33

<210> SEQ ID NO 28
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
ccagtcaagc ttattaaaga ggagaaaggt acc                33

<210> SEQ ID NO 29
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
atacatggat ccttagaact ggtaaacgat acc                33

<210> SEQ ID NO 30
<211> LENGTH: 38
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 30
aatacagagc tcctaatccc tatcagtgat agagattg                                  38

<210> SEQ ID NO 31
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
taatctcgat cgtctagggc ggcggat                                              27

<210> SEQ ID NO 32
<211> LENGTH: 74
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
tccctatcag tgatagagat tgacatccct atcagtgata gagatactga gcacatcagc          60
aggacgcact gacc                                                            74

<210> SEQ ID NO 33
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
ataaatgtga gcggataaca ttgacattgt gagcggataa caagatactg agcacatcag          60
caggacgcac tgacc                                                           75

<210> SEQ ID NO 34
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
aaaatttatc aaaagagtg ttgacttgtg agcggataac aatgatactt agattcaatt           60
gtgagcggat aacaatttca caca                                                 84

<210> SEQ ID NO 35
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 35
catagcattt ttatccataa gattagcgga tcctaagctt tacaattgtg agcgctcaca      60
attatgatag attcaattgt gagcggataa caatttcaca ca                        102

<210> SEQ ID NO 36
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
gcatgctccc tatcagtgat agagattgac atccctatca gtgatagaga tactgagcac      60
atcagcagga cgcactgacc agga                                             84

<210> SEQ ID NO 37
<211> LENGTH: 286
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 37
aagaaaccaa ttgtccatat tgcatcagac attgccgtca ctgcgtcttt tactggctct      60
tctcgctaac caaaccggta accccgctta ttaaaagcat tctgtaacaa agcgggacca     120
aagccatgac aaaaacgcgt aacaaaagtg tctataatca cggcagaaaa gtccacattg     180
attatttgca cggcgtcaca ctttgctatg ccatagcatt tttatccata agattagcgg     240
atcctacctg acgcttttta tcgcaactct ctactgtttc tccata                    286

<210> SEQ ID NO 38
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
ccatcgaatg gctgaaatga gctgttgaca attaatcatc cggctcgtat aatgtgtgga      60
attgtgagcg gataacaatt tcacacagga                                        90

<210> SEQ ID NO 39
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
gcatgcacag ataaccatct gcggtgataa attatctctg gcggtgttga cataaatacc      60
actggcggtt ataatgagca catcagcagg                                        90

<210> SEQ ID NO 40

```
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
gtatgcaaag ga                                                         12

<210> SEQ ID NO 41
<211> LENGTH: 66
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
aauugugagc ggauaacaau uucaggagga auuaaccaug cagugguggu gguggugguggug    60 ccaugg                                                                66

<210> SEQ ID NO 42
<211> LENGTH: 49
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
cucgagcacc accaccacca ccacugcaug guuaauuccu ccuacuagu                  49
```